Figure 2:
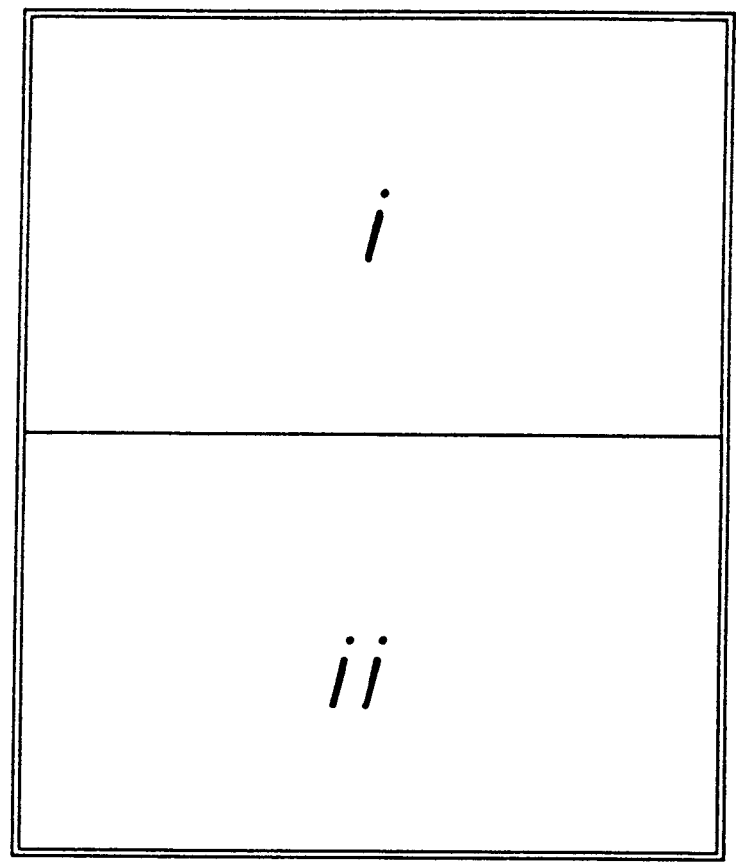

US006010895A

United States Patent [19]
Deacon et al.

[11] Patent Number: 6,010,895
[45] Date of Patent: Jan. 4, 2000

[54] NON-PATHOGENIC STRAINS OF HIV-1 CONTAINING MUTATIONS IN THE NEF GENE OR THE U3 REGION OF THE LONG TERMINAL REPEAT

[75] Inventors: Nicholas John Deacon, Balwyn; Jennifer Catherine Learmont, Patongo; Dale Alan McPhee, Fitzroy; Suzanne Crowe, South Yarra; David Cooper, Bellevue Hill, all of Australia

[73] Assignees: Macfarlane Burnet Centre for Medical Research Limited, Victoria; Australian Red Cross Society, Sidney, both of Australia

[21] Appl. No.: 08/388,353

[22] Filed: Feb. 14, 1995

[51] Int. Cl.[7] .............................. C12N 7/04; C12N 7/00; A61K 39/21

[52] U.S. Cl. .................. 435/236; 435/235.1; 424/188.1; 424/208.1

[58] Field of Search .................................. 435/235, 296; 536/23.22

[56] References Cited

PUBLICATIONS

Kirchoff et al., 1995, New Engl. J. Med. 332:228–232.
Huang et al., 1995, J. Virol. 69:93–100.
Terwilliger et al., 1991, Proc. Natl. Acad. Sci. USA 88:10971–10975.
Michael et al., 1995, J. Virol. 69:6758–6769.
Haynes, B., 1993, Science 260:1279–1286.
Graham et al., 1995, New Engl. J. Med. 333:1331–1339.
Ruprecht et al., 1995, The Lancet 346:177–178.
Baba et al., 1995, Science 267:1820–1825.
Miller et al., 1994, J. Exp. Med. 179:101–113.
Zagury et al., 1990, AIDS Res. Human Retro. 6:1079–1085.
Kestler et al., 1991, Cell 65:651–662.
Binninger et al., 1991, J. Virol. 65:5237–5243.
Desrosiers,R., 1992, AIDS Res. Human Retro. 8:411–421.

*Primary Examiner*—Laurie Scheiner
*Assistant Examiner*—Jeffrey S. Parkin
*Attorney, Agent, or Firm*—Scully, Scott, Murphy & Presser

[57] ABSTRACT

This invention is directed toward non-pathogenic human immunodeficiency virus type 1 (HIV-1) strains containing deletions in the nef gene and U3 region of the long terminal repeat (LTR). A blood donor infected with HIV-1 and a cohort of six blood or blood product recipients infected from this donor were identified. These individuals, who remained free of HIV-1-related disease with stable and normal $CD4^+$ lymphocyte counts 10 to 14 years after infection, were termed long-term nonprogressors (LTNPs). The molecular characterization of HIV-1 sequences obtained from either virus isolates or patient peripheral blood mononuclear cells (PBMCs) of LTNPs identified similar deletions in the nef gene and in the region of overlap of nef and the U3 region of the LTR. Full-length sequencing of one isolate genome and amplification of selected HIV-1 genome regions from other cohort members revealed no other abnormalities of obvious functional significance. These deletions corresponded to amino acids 166–206, or nucleotides 9281 to 9437, of the HIV-$1_{NL43}$ nef/LTR region. These data illustrate the importance of nef or the U3 region of the LTR in determining the pathogenicity of HIV-1. These non-pathogenic strains should prove useful, inter alia, in the development of HIV-1-specific diagnostic reagents.

7 Claims, 47 Drawing Sheets

Diagrammatic sequence alignmet against HIV NL4-3 showing deletetions in HIV-1 asymptomatic cohort. Deletions shown as gaps in sequence blocks.

FIGURE 1

| |
|---|
| i |
| ii |
| iii |
| iv |
| v |
| vi |
| vii |
| viii |
| ix |
| x |
| xi |
| xii |
| xiii |
| xiv |
| xv |
| xvi |
| xvii |
| xviii |

FIGURE 1 (i)

```
          8072                                                                      8121
NL43   GAACAGATTTGGAATAACATGACCTGGATGGAGTGGGACAGAGAAATTAA
       *** ********* * ***************************** *
D36P   GAAGAGATTTGGGAGAACATGACCTGGATGCAGTGGGACAGAGAAATTCA
       *** ********* * *****************************
C18S   GAAACAATTTGGGATAACATGACCTGGATGCAGTGGGAAAGAGAAATTGA
       *** ******** * ****************************** *
C18M   GAAACAATTTGGGATAACATGACCTGGATGCAGTGGGAAAGAGAAATTGA
                                                **********
C98H                                         GAAATTAA

8171
NL43   CAATTACACAAGCTTAATAACACTCCCTTAATTGAAGAATCGCAAACCAGC
       ********** ************ ******** ***************
D36P   CAATCACACAAAATACATATCCCTTACTTGAAAAATCGCAGAACCAAC
       **** ******  * * ***  ******* ****** *** ***** *
C18S   CAATTACACAAAACATAATATACACCTTAATTGAAGAATCGCAGAACCAAC
       ************ * ********  ******* ************
C18M   CAATTACACAAAACATAATATACACCTTAATTGAAGAATCGCAGAACCAAC
       ************  ********** ******* *************
C98H   CAATTACACAAGATTAATATACAACTTAATTGAAGAATCGCAGAACCAAC
```

FIGURE 1(ii)

```
         8221                                                                                    8271
NL43  AAGAAAAAGAATGAACAAGAATTATTGGAATTAGATAAATGGGCAAGTTTG    TGGAATTGGTTTAACATAACAAATTGGCTGTGGTATATAAAATTATTCAT
      **************************************************    **************************************************
D36P  AAGAAAAAGAATGAACAAGAATTATTGGAATTGGATCAATGGGCAAGTTTG    TGGAATTGGTTTGACATAACAAATTGGCTGTGGTATATAAAATATTCAT
      *********************** ******* ******************    ************ ********* ************ **** *******
C18S  AAGAAAAAGAATGAACTAGAACTAGAATTATTGGAATTGGATAAATGGGCAAATTTG    TGGAATTGGTTTAGTATATCAAACTGGCTATGGTATATAAAATTATTCAT
      **************   *** ** *******   *** ********* ***    ************  ****** **** ****** ***************
C18M  AAGAAAAAGAATGAACTAGAATTATTGGAATTGGATAAATGGGCAAATTTG    TGGAATTGGTTTAGTATATCAAACTGGCTATGGTATATAAAATTATTCAT
      ***************  ** ******************** ** ******    ************  ****** **** ****** ***************
C98H  AAGAAAAAGAATGAACAAGACTTATTGGAATTAGATAAATGGGCAAGTTTG    TGGAATTGGTTTGACATAACAAGTGGGCTGTGGTATATAAAATTATTCAT
      ****************  ** ****************************     ************ ****** **   **  ** ****************
```

FIGURE 1 (iii)

```
           8321
NL43  AATGATAGTAGGAGGCTTGGTAGTTTAAGAATAGTTTTTGCTGTACTTT
D36P  ****AATGGTAGTAGGAGGCTTGGTAGTTTAAGAATAGTTTTTGCTGTACTTT
C18S  ****AATGGTAGTAGGAGGCTTGGTAGTTTAAGAATAGTTTTTACTGTACTTT
C18M  ****AATGGTAGTAGGAGGCTTGGTAGTTTAAGAATAGTTTTTACTGTACTTT
C98H  ****AATGATAGTAGGAGGCTTGGTAGTTTAAGAATAGTTTTAGCTGTACTTT

SA8   SA9          SA10
           8371
NL43  CTATAGTGAATAGAGTTAGGCAGGGATATTCACCATTATCGTTTCAGACC
D36P  CTATAGTGAATAGAGTTAGGCAGGGATACTCACCATTGTCGTTTCAGACC
C18S  CTATAGTTAATAGAGTTAGGCAGGGATACTCACCATTATCGTTTCAGACC
C18M  CTATAGTTAATAGAGTTAGGCAGGGATACTCACCATTATCGTTTCAGACC
C98H  CTATAGTGAATAGAGTTAGGCAGGGATACTCACCATTATCGTTTCAGACC
```

FIGURE 1 (iv)

```
                                                    Tat termination NL43
NL43  CACCTTCCCAATCCCCGAGGGGACCCAGGCCCCGAAGGAATAGAAGAAGA 8421
      *******************************************
D36P  CTCCTCCCAACCCCGAGGGGACCCAGGCCCCGAAGGAATCGAAGAAGA
      ***** ************************************
C18S  CACCTCCCAACCCCGAGGGGACCCAGGCCCCGAAGGAATCGAAGAAGA
      ****  ***************************** *******
C18M  CACCTCCCAACCCCGAGGGGACCCAGGCCCCGAAGGAATCGAAGAAGA
      ****  ***************************** *******
C98H  CACCTCCCAACCCCGAGGGGACCCAGGCCCCGAAGGAATCGAAGAAGA
      ****  ***************************** *******

NL43  AGGTGGAGAGAGAGACAGAGACAGATCCATTCGATTAGTGAACGGATCCT 8471
      ************************ *** **** ** *********
D36P  AGGTGGAGAGAGAGACAGAGACAGATCCACTCGATTAGTACACGGATTCT
      ************************ *** *** ** ************
C18S  AGGTGGAGAGAGAGACAGAGACAGGCAGCTCCACTCGATTAGTGCACGGATTCT
      ************************ *** *** ** ************
C18M  AGGTGGAGAGAGAGACAGAGACAGGCAGCTCCACTCGATTAGTGCACGGATTCT
      ************************ *** *** ** ************
C98H  AGGTGGAGAGAGAGACAGAGACAGATCCAGTCGATTAGTGCACGGATTCT
      ********************** **** ***** ***********
            D36P, C18S, C18M & C98H Tat termination
```

FIGURE 1 (v)

```
NL43  TAGCACTTATCTGGGACGATCTGCGGAGCCTGTGCCTCTTCAGCTACCAC  8521
      ************ * ************ *********************
D36P  TAGCACTTTTCTGGGACGACCTGAGGAGCCTGTGCCTCTTCCTCTACCAC
      ************ * ************ ************* *******
C18S  TAGCACTTTTCTGGGACGACCTGAGGAGTCTGTGCCTCTTCAGCTACCAC
      ************ * ************ *********************
C18M  TAGCACTTTTCTGGGTCGACCTGAGGAGTCTGTGCCTCTTCAGCTACCAC
      ************ * ***********   *********************
C98H  TAGCACTTTTCTGGGTCGACCTGAGGAGCCTGTGCCTCTTCAGCTACCAC

NL43  CGCTTGAGAGACTTACTCTTGATTGTAACGAGGATTGTGGAACTTCTGGG  8571
      * ********************** * ***********************
D36P  CACTTGAGAGACTTACTCTTGATTGTAACAAGGATTGTGGAACTTCTGGG
      * ***********************  ***********************
C18S  CACTTGAGAGACTTACTCTTGATTGTAACGAGGATTGTGGAACTTCTGGG
      * ***********************************************
C18M  CGCTTGAGAGACTTACTCTTGATTGTAACGAGGATTGTGGAACTTCTGGG
      **************************************************
C98H  CGCTTGAGAGACTTACTCTTGATTGTAACGAGGATTGTGGAACTTCTGGG
```

FIGURE 1 (vi)

```
NL43  ACGCAGGGGGTGGGAAGCCCTCAAATATTGGTGGAATCTCCTACAGTATT  8621
D36P  ACGCAGGGGATGGGAAGCCCTCAAATATTGGTGGAACCTCCTAAAGTATT
      **** ****** ************************ ******* *****
C18S  ACGCAGGGGATGGGAAGCCCTCAAATACTGGTGGAATCTCCTGCAGTATT
      **** ****** ************** ********* ***** ******
C18M  ACGCGGGGGATGGGAAGCCCTCAAATACTGGTGGAATCTCCTGCAGTATT
      **** ****** ************** ********* ***** ******
C98H  ACGCAGGGGGTGGGAAGCCCTCAAATATTGGTGGAATCTCCTACAATATT
      *********** ***************************** *** ***

NL43 Rev termination

NL43  GGAGTCAGGAACTAAAGAATAGTGCTGTTAACTTGCTCAATGCCACAGCC  8671
D36P  GGAGCCAGGAACTGCAGAAGAGTGCTGTTATCTTGCTCAATGCCACCGCC
      **** ******** * **** ********  ************** ***
C18S  GGAGGCAGGAACTACAGAAGAGTGCTGTTAGCTTGCTTGTTCAATGGCACGGCC
      ****  ******* * **** ********* ****** ** ***** ** ***
C18M  GGAGACAGGAACTACAGAAGAGTGCAGTTAGCTTGCTTGTTCAATGCCATAGCC
      **** ******** * **** **** **** ****** ** ***** ** ***
C98H  GGAGTCAGGAACTCAAGAAGAGTGCTATTAGCTTGTTCAATGCCACCGCC
      **** ******** * **** ****  *** **** ** ***** ** ***
                    C18S, C18M & C98H Rev termination
```

FIGURE 1(vii)

```
NL43   ATAGCAGTAGCTGAGGGGACAGATAGGGTTATAGAAGTATTACAAGCAGC  8721
       **************** ***  *****************  ****  ***
D36P   ATAGCAGTAGCTGAGGGGACAGATAGAGTTTTAGAAGTATTACAAAGAGC
       ****  *  *  ****  ****  *  *  ***  *****  ****  **
C18S   ATAGCAGTAGCTGAGGGGACAGATAGAGTTATAGAAGCTTTACGAAGGC
       ****************************** *  ***  ****  ***
C18M   ATAGCAGTAGCTGAGGGGACAGATAGAGCTATAGAAGGATTACAAAGAGC
       *************************************************
C98H   ATAGCAGTAGCTGAGGGGACAGATAGAGTTATAGAAGTATTACAAAGAGC
                         D36P Rev termination NL43   TTATAGAGCTATTCGCCACATACCTAGAAGAATAAGACAGGGCTTGGAAA  8771
       **************  *  ****************** * **  *
D36P   TTATAGAGCTATCCTCCACATACCTAGAAGAATAAGACAGGGCCTCGAAA
       ****************  *****************************  *
C18S   TTATAGAGCTATTCTCCACATACCTAGAAGAATAAGACAGGGCTTAGAAA
       *  *************************************************
C18M   TTATAGAGCTATTCTCCACATACCTAGAAGAATAAGACAGGGCTTAGAAA
       ** *  ***  *  ****************************  *****
C98H   TTGTAGAGCTGTTCTCCACATACCTAGAAGAATAAGACAGGGCTTCGAAA
```

FIGURE 1 (viii)

```
                Env termination    Nef start
NL43   GGATTTTGCTATAAGATGGGTGGCAAGTGGTCAAAAGTAGTGTGATTGG   8821
       *  ***************************  *************  *  *
D36P   TGGCTTTGCTATAAAAATGGGTGGCAAGTGGTCAAAAAGTAGTGTAGTCAG
       **  ****************************  ************  **  *
C18S   GGGCTTTGCTATAAAAATGGGTGGCAAGTGGTCAGAAAGTAGTGTGGTTAG
       **  ****************************  ******
C18M   GGGCTTTGCTGTGTAAAATGGG-----------------------------
       **  ******  ***  ***
C98H   GGGCTATGCTATAAAAATGGGTGGCAAGTGGTTAAAAAGTAGTATGGTTAG
                                      D36P Nef termination nef duplication region
NL43   ATGGCCTGCTGTAAGGGAAAGAATGAGAGACGAGCTGAGCCAGCAGCAGATG   8871
       **  ***                                       **  ***  *
D36P   ATAGCATG-----------------------------------CATCATAAG
       *  ****  ***
C18S   AAGGCATG---------------------------------------------
       ***  ***
C18M   -----------------------------------------------------
       **  ****************  **  *****************  *******
C98H   ATGGCCTGCTGTAAGGGAAAAATGAAACAAGTGAGCTGAGCCAGCAGCAGAAG
```

FIGURE 1 (ix)

```
NL43  GGGTGGGGAGCAGTATCTCGAGACCTAGAAAAACATGGAGCAATCACAAGT  8921
D36P  ******** ** **
      GGGTGGGGGC----------------------------------------
C18S  --------------------------------------------------
C18M  ------------------------------------------** ******
C98H  **************************************** *********
      GGGTGGGAGCAATATCTCGAGACCTAGGAAAAACATGGAGCAATCCCAAGT

SIVmac239 IPTC

NL43  AGCAATACAGCAGCTAACAATGCTGCTTGTGCCTGGCTAGAAGCACAAGA  8971
D36P  ** ** ******************* * ********** ***********
      ------CAACAACTAACAATGCTGATCGTGCCTGATCGTGCCTAGAAGCACAAGA
C18S  --------------------------------------------------
C18M  ***** ** ***** *********** ***********************
C98H  ***** ****************** * ***********************
      AGCAATACAACAACTAACAATGCTAATTGTGCCTGGCTAGAAGCACAAGA
```

FIGURE 1(x)

```
NL43  GGAGGAAGAGGTGGGTTTTCCAGTCACACCTCAGGTACCTTTAAGACCAA    9021
D36P  *************  **************  ****************
C18S  GAAGGAAGAAGCGGGTTTTCCAGTCAAACCCTCAGGTA------------
                 *  ************* ***********
C18M  -----------------------------------TACCTTTAAGAC---
                                          ************
C98H  -----------------------------  ****  ************
      ******  **  ************* ***  ****  ************
      GGAGGAGGAAGTGGGTTTTCCAGTCAAACCTCAGGTACCTTTAAGACCAA

Poly purine tract

NL43  TGACTTACAAGGCAGCTGTAGATCTTAGCCACTTTTTAAAAGAAAAGGGG    9071
D36P  ------------------GCTGTAGATCTTAGCCACTTTTTAAAAGAAAAGGGG
                       *************************************
C18S  ------------AAGGCAGCTATAGATCTTAGCCGCTTTTAAAAGAAAAGGGG
                  ****************** ********* ************
C18M  ---------------------GATCTTAGCCACTTTTTAAAAGAAAAGGGG
                          * ***************************
C98H  TGACTTACAAG----------------------------------------
      ***********
C54P                   ---GCCACTTTTTAAAAGAAAAGGGG
                         ********************
                AGCCACTTTTTAAAAGAAAAGGGG

C18S & C18F nef termination
              C18M and C98H nef Termination
```

FIGURE 1 (xi)

```
        [   U3
NL43  GGACTGGAAGGGCTAATTCACTCCCAAAGAAGACAAGATATCCTTGATCT    9121
      **************************************************
D36P  GGACTGGAAGGGCTAATTCACTCCCAAAGAAGACAAGATA----------
      ****************************************
C18S  GGACTGGAAGGGCTAATTCACTCCCAAAGAAGACAGAGAAGA--------
      ***********************************  **  ******
C18M  GGACTGGAAGGGCTAATTCACTCCTCACAGAGAAGA--------------
      ************************  ** ** ******
C98H  GGACTGGAAGGGCTAATTCACTCCTAAAGAAGACAAGATATCCTTGATCT
      ************************ *************************
C54P  GGACTGGAAGGGCTAATTCGCTCCCCAAAGAAGACAAGATATCCTTGATCT
      ******************* ***** *************************

SA12
NL43  GTGGATCTACCACACACAAGGCTACTTCCCTGATTGGCAGAACTACACAC    9171
      **************************************************
D36P  --------------------------------------------------
C18S  --------------------------------------------------
C18M  ----------------------------------------*********
                                              *********
C98H  TTGGATCTACCACACACAAGGCTACT------------------------
      * ***********************
C54P  GTGGGTCTACCACACACAAGGCTACTTCCCTGAGTGGCAGAACTACACAC
      *** ********************************* ***********
```

FIGURE 1 (xii)

```
                [   NRE --->
NL43    CAGGGGCCAGGGGTCAGATATCCACTGACCTTTGGATGGTGCTACAAGCTA           9221
              * ****** *** ***
D36P    -------------------------------------CACAGTGCTGCAAACTA
                                              *****  ***
C18S    ---------------------------------------------------
C18M    ---------------------------------------------------
              ***********   ******** *** ** **
C98H    -------------ATCCACTGACTTTTGG,TGGTGCTTCAAATTA
              ************* ********* ** ****** * *
C54P    CAGGGCCAGGGACCAGATATCCCACTGACCTTTGGATGGTGCTGCAAACGA myb                    NF-AT
NL43    GTACCAGTTGAGCCAGATAAGGTAGAAGAGAGGCCAATAAAGGAGAGAACAC           9271
              *  ***** ****  ***  *********  ********* ***
D36P    TTACCAGTGGAGTCAGCGAAGATAGAAGAGAGGCCAATGAGGAGGAAAACCA
              ****** ******  *********  ***** * *** ******
C18S    ---TCAGTTGAACCAGAAGAAGATAGAAGAGAGGCCATGAAGAAGAAACAA
              ****  * *****   * *** *** ****  * ****** ***
C18M    ---TCAGTTGAACCAGAAGAAGATGAAGAGAGGCCATGAAGAAGAAAACAA
              ****  * *****   *  ***** ***** ****** *** ****
C98H    GTACCAGTGGANCCAGA--AGAGAGAAGAGATAGAAGAGGCCAATGGAGGAGAGAACAA-
              ****  ***  ***       *** *    ***
C54P    GTGCCAGTGGAAACAGAGAAGATAGAAGAGGCCAATGGAGGAGAAACAA
              (myb)
```

FIGURE 1 (xiii)

```
                                                                              NF-AT
NL43   CAGCTTGTTACACCCTGTGAGCCTGCATGGAATGGATGACCCTGAGAGAG    9321
       ***  ******
D36P   CAGATTGTT---------------------------------------
       ***  ******
C18S   CAGATTGTT---------------------------------------
       ***  ******
C18M   CAGATTGTT---------------------------------------
             **
C98H   ---------------------------------------------
       ***  ****
C54P   CAGACTGTT---------------------------------------

<-- NRE  ]                         USF
NL43   AAGTGTTAGAGTGGAGGTTTGACAGCCGCCTAGCATTTCATCACGTGGCC    9371
D36P   ---------------------------------------------
                                                    *  *  ----
C18S   --------------------------------------------CCGTTTGTT
                                                    *   *
C18M   -----------------------------------------------CTGCT
C98H   ---------------------------------------------A
C54P   ---------------------------------------------
```

FIGURE 1 (xiv)

```
                             TCF-1α                    Nef termination
NL43  CGAGAGCTGCATCCGGAGTACTTCAAGAACTGCTGACATCGAGCTTGCTA  9421
         *       *        **              *   **    **
D36P  CTGTTGGGACTTTCCATCCGTTGGGGACTTTCCAAGGGCGGTGGCCTG
         *       *        *                           **
C18S  CCGTTGGGACTTTCCA,,,,,,GGAGACGTGGCCTGAGTGATAAGCCG
         *                       *           ****      *
C18M  TGCTCAGCTGGGACTTTCCAAGGGCGGCCCTGAGTGACTAAGCCCCG
         *       **                **      ****
C98H  CAGAGTGTGGGACTCTCCACAACAGAGTGTGGGACTTTCCAAGGAGGC
         **                        **      ****    *
C54P  ----CCGTTGGGACTTTCCAAGGAGGCCGTGGCCTGAGTGACTAAGTTCC D36P, C18S, C18M, & C98H extra NFKB
                   D36P & C98H  extra NFKB
```

FIGURE 1 (XV)

```
        NFKB                                    NFKB               Sp1
NL43    CAAGGGACTTTCCG,,,,,,,,,CTGGGGACTTTCCAG,GGAGGCGTGGC
        *****           ****************  *** ***
D36P    GGTGACTAGTTCCG,,,,,,,,,GTGGGGACTTTCCAA,GAAGGCGCGGC
        * ************* ****************  *    *******
C18S    CTGGGGACTTTCCGAAGAGGCGTGACGGGGACTTTCCAA,GGCGACGTGGC
        ** ***********         *  ************  *  *******
C18M    TTGGGGACTTTCCGAAGAGGCATGAAGTTCCGTTCCAAG,GCAGGCGTGGC
        *  ***********                *******  *  ********
C98H    GTGGCCTGAGTGACTAAGTTCCGTTGGGGACTTTCCAA,AAAGGCGAGGC
        *             ****************  *******  *
C54P    GTTGGGGACTTTCCAAGGAGGC,,GCGGGGACTTTCCAA,GGAGGCGCGGC
        ***************        ****************  ********

NFkB                                    NFκB              Sp1
        C18S & C18M NFKB
        D36P and C98H 3'-half NFκB
```

9461

FIGURE 1 (xvi)

|  | Sp1 | Sp1 | TATA box | 9510 |
|---|---|---|---|---|
| NL43 | CTGGGCGGGACTGGGGAGTGGCGAGCCC, | TCAGATGCTGCATATAAGCAG | | |
| D36P | ************************* | ******************** | | |
| C18S | CTGGGCGGGACTGGGGAGTGGCGAGCCC, | TCAGATGCTGCATATAAGCAG | | |
| C18M | CTGGGCGGGACTGGGGAGTGGCGAGCCC, | TCAGATGCTGCATATAAGCAG | | |
| C98H | CTGGGCGGGA-CTGGGGAGTGC-GAGCC-, | TCAGATGCTGCATATAGGCAG | | |
| C54P | CTGGGCGGGACTGGGGAGGGGCGAGCCC, | TCAGATGCTGCATATAAGCAG | | |
|  | Sp1 | | | |

|  | U3 | R | TAR | 9560 |
|---|---|---|---|---|
| NL43 | CTGCTTTTTGCCTGTACTGGGTCTCTCTGGTTAGACCAGATCTGAGCCTG | | | |
| D36P | CTGCTTTCTGCCTGTACTGGGTCTCTCTGGTTAGACCAGATCTGAGCCTG | | | |
| C18S | CTGCTTTCTGCCTGTACTGGGTCTCTCTGGTTAGACCAGATCTGAGCCTG | | | |
| C18M | CTGCTTTCTGCCTGTACTGGGTCTCTCTGGTTAGACCAGATCTGAGCCTG | | | |
| C98H | CTGCTTTCTGCCTGTACTGGGTCTCTCTGGTTAGACCAGATCTGAGCCTG | | | |
| C54P | CTGCTTTCTGCCTGTACTGGGTCTCTCTGGTTAGACCAGATCTGAGCCTG | | | |

FIGURE 1 (xvii)

```
                                                                    Polyadenylation
NL43    GGAGCTCTCTGGCTAACTAGGGAACCCACTGCTTAAGCCTCAATAAAGCT    9610
        ****************************************************
D36P    GGAGCTCTCTGGCTAACTAGGGAACCCACTGCTTAAGCCTCAATAAAGCT
        ****************************************************
C18S    GGAGCTCTCTGGCTAACTAGGGAACCCACTGCTTAAGCCTCAATAAAGCT
        **************
C18M    GGAGCTCTCTGGCTAGCTAGGGGACCTAGGGGACCCACTCCTTAAGCCTCAATAAAGCT
        ****************************************************
C98H    GGAGCTCTCTGGCTAACTAGGGAACCCACTGCTTAAGCCTCAATAAAGCT
        **********
C54P    G      incomplete R    ][    U5
NL43    TGCCTTGAGTGCTTCAAGTAGTGTGTGCCCGTCTGTTGTGTGACTCTGGT    9660
        ****************************************************
D36P    TGCCTTGAGTGCTTCAAGTAGTGTGTGCCCGTCTGTTGTGTGACTCTGGT
        ****************************************************
C18S    TGCCTTGAGTGCTTCAAGTAGTGTGTGCCCGTCTGTTGTGTGACTCTGGT
        ****************************************************
C18M    TGCCTTGAGTGCTTCAAGTAGTGTGTGCCCGTCTGTTGTGTGACTCTGGT
        ****************************************************
C98H    TGCCTTGAGTGCTTCAAGTAGTGTGTGCCCGTCTGTTGTGTGACTCTGGT
```

FIGURE 1 (xviii)

```
NL43   AACTAGAGATCCCTCAGACCCTTTTAGTCAGTGTGTGGAAAATCTCTAGCA    9709
       * *****
D36P   ATCTAGA                                              1305
       * *****
C18S   ATCTAGA                                              1209
       *  ******************* *************************
C18M   ATCTAGAGATCCCTCAGACCATTTTAGTCCGTGTGTGGAAAATCTCTAGCA   END
       * *****
C98H   ATCTAGA                                              1399
```

FIGURE 2A

```
NL43      73  PTSQSRGDPTGPKE#                                         86
D36PBMC       PSSQPRGDPTGPKESKKKVERETETDPLD#
C18 HIV_StV   PTSQPRRDPTGQKESKKKVERETEAAPLD#
C18 HIV_MBC   PTSQPRRDPTGQKESKKKVERETEAAPLD#
C98 HIV       PTSQPRRDPTGQKESKKKVERETETDPVD#
```

FIGURE 2B (i)

```
NL43      26  DPPPNPEGTRQARRNRRRRWRERQRQIHSISERILSTYLG              65
D36PBMC       DPPPNPEGTRQARRNRRRRWRERQRQIHSISTRILSTFLG
C18 HIV_StV   DPPPNPEGTRQARRNRRRRWRERQRQLHSISARILSTFLG
C18 HIV_MBC   DPPPNPEGTRQARRNRRRRWRERQRQLHSISARILSTFLG
C98 HIV       DPPPNPEGTRQARRNRRRRWRERQRQIQSISARILSTFLG
```

FIGURE 2B (ii)

```
NL43        RSAEPVPLQLPPLERLTLDCNEDCGTSGTQGVGSPQILVE  105
D36 PBMC    RPEEPVPLPLPPLERLTLDCNKDCGTSGTQGMGSPQILVE
C18 HIV_stv RPEESVPLQLPPLERLTLDCNEDCGTSGTQGMGSPQILVE
C18 HIV_MBC RPEESVPLQLPPLERLTLDCNEDCGTSGTQGMGSPQILVE
C98 HIV     RPEEPVPLQLPPLERLTLDCNEDCGTSGTQGVGSPQILVE NL43        SPTVLESGTKE#                              116
D36PBMC     PPKVLEPGTAEECCYLAQCHRHSSS#
C18 HIV_stv SPAVLEAGTTEECC#
C18 HIV_MBC SPAVLEAGTTEECC#
C98 HIV     SPTILESGTQEECY#
```

FIGURE 3(i)

```
                                                                              639
NL43         EQIWNNMTWMEWDREINNYTSLIHSLIEESQNQQEKNEQELLELDKWASL
D36 PBMC     EEIWENMTWMQWEKEIHNHTKYIYSLLEKSQNQQEKNEQELLELDQWASL
C18 HIV_stv  ETIWDNMTWMQWEREIDNYTNIIYTLIEESQNQQEKNELELELDKWANL
C18 HIV_MBC
C98 HIV      EINNYTRTIYNLIEESQNQQEKNEQDLLELDKWASL 689
NL43         WNWFNITNWLWYIKLFIMIVGGLVGLRIVFAVLSIVNRVRQGYSPLSFQT
D36 PBMC     WNWFDITKWLWYIKIFIMVVGGLIGLRIVFAVLSIVNRVRQGYSPLSFQT
C18 HIV_stv  WNWFSISNWLWYIKLFIMVVGGLVGLRIVFTVLSIVNRVRQGYSPLSFQT
C18 HIV_MBC
C98 HIV      WNWFDITSGLWYIKLFIMIVGGLVGLRIVLAVLSIVNRVRQGYSPLSFQT
```

Figure 3:
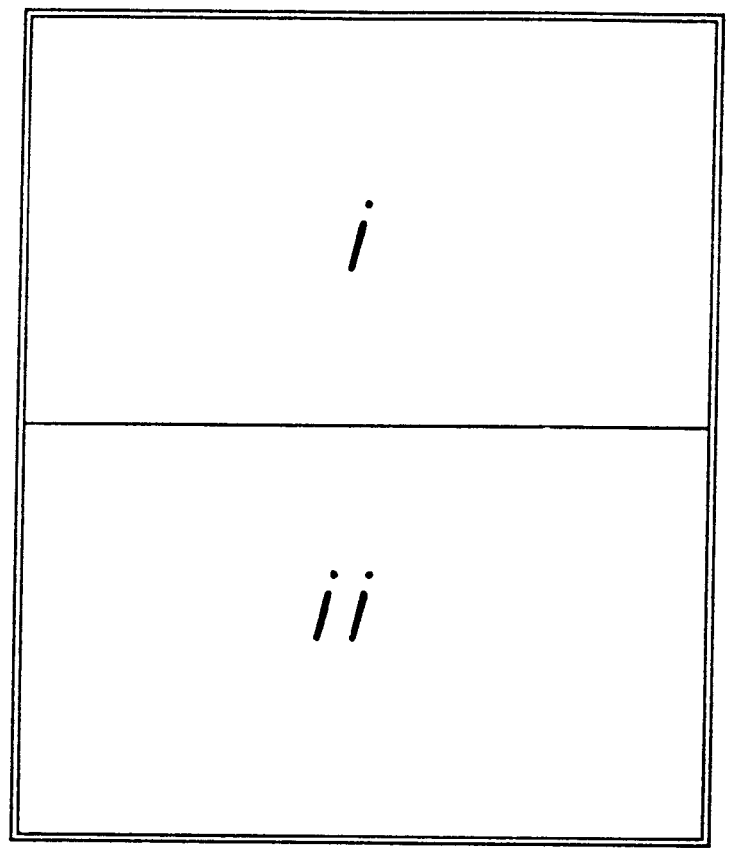

FIGURE 3 (ii)

```
NL43           HLPIPRGPDRPEGIEEEGGERDRDRSIRLVNGSLALIWDDLRSLCLFSYH    739
D36 PBMC       LLPTPRGPDRPEGIEEEGGERDRDRSTRLVHGFLALFWDDLRSLCLFLYH
C18 HIVStV     HLPTPKGPDRPEGIEEEGGERDRGSSTRLVHGFLALFWDDLRSLCLFSYH
C18 HIVMBC
C98 HIV        HLPTPRGPDRPEGIEEEGGERDRSSRLVHGFLALFWDDLRSLCLFSYH

NL43           RLRDLLLIVTRIVELLGRRGWEALKYWWNLLQYWSQELKNSAVNLLNATA    789
D36 PBMC       HLRDLLLIVTRIVELLGRRGWEALKYWWNLLKYWSQELQKSAVILLNATA
C18 HIVStV     HLRDLLLIVTRIVELLGRRGWEALKYWWNLLQYWRQELQKSAVSLFNGTA
C18 HIVMBC
C98 HIV        RLRDLLLIVTRIVELLGRRGWEALKYWWNLLQYWSQELKKSAISLFNATA

NL43           IAVAEGTDRVIEVLQAAYRAIRHIPRRIRQGLERILL#               839
D36 PBMC       IAVAEGTDRVLEVLQRAYRAILHIPRRIRQGLEMALL#
C18 HIVStV     IAVAEGTDRVIEALRRAYRAILHIPRRIRQGLERALL#
C18 HIVMBC
C98 HIV        IAVAEGTDRVIEVLQRACRAVLHIPRRIRQGFERAML#
```

FIGURE 4

```
NL43      MGGKWSKSSSVIGWPAVRERMRRAEPAADGVGAVSRDLEKHGAITSSNTAA    50
          ****
D36 PBMC  MGGK#                                                  4
          ******  ***
C18.HIVStV MGGKWSESSVVRRHVPLRQGSYRS#                            24
          *
C18 HIVMBC MRILATF#                                              7
          ******  *   ******  *    ****   *****  ****
C98 HIV   MGGKWLKSSMVRWPAVREKMKQAEPAAEGVGAISRDLGKHGAIPSSNTTT    50

NL43      NNAACAWLEAQEEEEVGFPVTPQVPLRPMTYKAAVDLSHFLKEKGGLEGL   100
          ***  ***********************  ************
C98 HIV   NNANCAWLEAQEEEEVGFPVKPQVPLRPMTYKATF#                  85

NL43      IHSQRRQDILDLWIYHTQGYFPDWQNYTPGPGVRYPLTFGWCYKLVPVEP   150

NL43      DKVEEANKGENTSLLHPVSLHGMDDPEREVLEWRFDSRLAFHHVARELHP   200

NL43      EYFKNC*                                              206
```

FIGURE 5

```
                NFkB              NFkkB
9419
NL43            CGAGCTTGCTACAAGGGACTTTCC,,,,GCTGGGGACTTTCCAGGA
                  **       **********     *  ******************
D36 PBMC        ΔCTGTTGGGGACTTTCCATCCGTTGGGACTTTCCAAGGC
                    *  **                *  ****************** ***
C18 HIVstv              ΔCCGTTGTTCCGTTGGGACTTTCCA-GGA
                             *                  **  ************* * *
C18 HIVMBC              ΔCTGCTTGCTCAGCTGGGACTTTCCA-GAA
                             *       *          *  ************* ***
C98 HIV         ΔACAGAGTGTGGGACTCTCCACAACAGAGTGTGGGACTTTCCAAGGA
                      *                   *         ***************
C54 PBMC                     ΔCCGTTGGGGACTTTCCAAGGA NFkB              NFkB
                Sp1   Sp1  Sp1                              9492
NL43            GGCGTGGCCTGGGCGGGACTGGGGAGTGGCG-AGCCCTCA
                ************ *                ****  *       **
DC36 PBMC       GGCGTGGCCTGGGTGACTAGTTCCGGTGGGG-ACTTTCCA
                **************  *     *        ***   *       *
C18 HIVstv      GACGTGGCCTGAGTGACTAAG-CCGCTGGGG-ACTTTCCG
                 * ***********  *     **         * **       *
C18 HIVMBC      GGCGCGGCCTGAGTGACTAAGCCCCGTTGGG-ACTTTCCG
                *** * ********  *     **         * **       *
C98 HIV         GGCGTGGCCTGAGTGACTAAGTTCCGTTGGGGACTTTCCA
                ***************  *     **        ****       *
C54 PBMC        GGCGTGGCCTGAGTGACTAAGTTCCGTTGGGACTTTCCAA
                Sp1              3' half NFkB       NFkB
```

Figure 9:
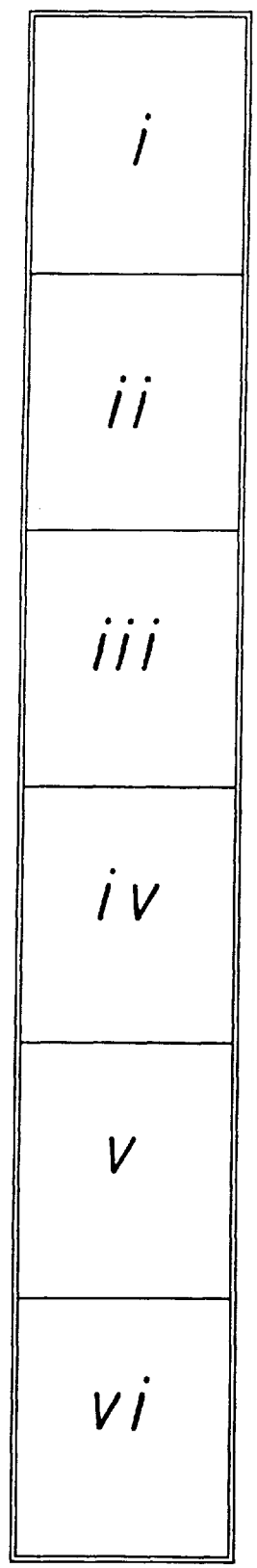

FIGURE 9 (i)

```
TGGAAGGGCTAATTCACTCACGGAAAAGACCAGTTGAACCAG
AAGAAGATAGAAGAGGCCATGAAGAAGAAAACAACAGATTGT
TCTGCTTGCTCAGCTGGGGACTTTCCAGAAGGCGCGGCCTGA
GTGACTAAGCCCCGTTGGGGACTTTCCGAAGAGGCATGAAGG
GACTTTCCAAGGCAGGCGTGGCCTGGGCGGGACTGGGGAGTG
GCGAGCCCTCAGATGCTGCATATAAGCAGCTGCTTTCTGCCT
GTACTGGGTCTCTGGTTAGACCAGATCTGAGCCTGGGAGC
TCTCTGGCTAGCTAGGGAACCCACTGCTTAAGCCTCAATAAA
GCTTGCCTTGAGTGCTTCAAGTAGTGTGTGCCCGTCTGTTGT
GTGACTCTGGTATCTAGAGATCCCTCAGACCATTTTAGTCCG
TGTGGAAATCTCTAGCAGTGGCGCCCGAACAGGGACTTGAA
AGCGAAAGGAAAACCAGAGGAGCTCTCTCGACGCAGGACTCG
GCTTGCTGAAGCGCGCACGGCAAGAGGCGAGGGGCGGCGACT
GGTGAGTACGCCGAAAATTTTGACTAGCGGAGGCTAGAAGGA
GAGAGATGGGTGCGAGAGCGTCAATATTAAGCGGGGAAAAT
TAGATAGATGGGAGAAATTCGGTTAAGGCCAGGAGGAAAGA
AAAAGTATAAATTAAAACATATAGTATGGGCAAGCAGGGAGC
TAGAACGATTCGCAGTCAATCCTGGCCTGTTGGAAACATCAG
AAGGCTGTAGACAAATACTGGACAGTTACACCCGTCCCTTC
AGACAGGATCAGAAGAACTTAAATCAGTATATAATGCAGTAG
CAGTCCTCTATTGTGTGCATCAAAACATAGACATAAAGGACA
CCAAGGAAGCTTTAGAAAGATAGAGGAAGAGCAAAACAAAT
GTAAGAAAAAGCACAGCAAGCAGCAGCACAGCAAGCAGCAG
CTGGCACAGGAAACAGCAACCCGGTCAGCCAAAATTACCCTA
TAGTACAGAACATGCAGGGGCAAATGGTACATCAGGCCATAT
CACCTAGAACTTTAAATGCATGGGTAAAAGTAATAGAAGAGA
AGGCTTTCAGCCCAGAGGTAATACCCATGTTTTCAGCATTAT
CAGAAGGAGCCACCCCACAAGATTTAAACACCATGCTAAACA
CAGTGGGGGGACATCAAGCAGCTATGCAAATGTTAAAAGAGA
CCATCAATGAGGAAGCTGCAGAATGGGATAGATTACATCCAG
CGCAGGCAGGGCCTGTTGCACCAGGCCAGATGAGAGACCCAA
GGGGAAGTGACATAGCAGGAACTACTAGTACCCTTCAGGAAC
AAATAGGATGGATGACAGGTAATCCAGCTATCCCAGTAGGAG
AAATCTATAAAGATGGATAATCCTGGGATTAAATAAAATAG
TAAGGATGTATAGCCCTATCAGCATTCTGGACATAAAACAAG
GACCAAAGGAACCCTTTAGAGACTATGTAGACCGGTTCTATA
AAACTCTAAGAGCCGAGCAAGCTACACAGGAGGTAAAAATT
GGATGACAGAAACCTTGTTGGTCCAAAATGCAAACCCAGATT
GTAAGACTATTTTAAAAGCATTGGGACCAGCAGCTACACTAG
```

FIGURE 9(ii)

```
AAGAAATGATGACAGCATGTCAGGGAGTGGGAGGACCCAGCC
ATAAAGCAAGAGTTTTGGCAGAAGCAATGAGCCAAGCAACAA
ATGCAGCTACTGTAATGATGCAGAGAAGCAATTTTAGAAACC
AAAGAAGAATGTTAAGTGTTTCAATTGTGGCAAAGAAGGGC
ACATAGCCAGAAATTGCAGGGCTCCTAGGAAAAGGGGCTGTT
GGAAATGTGGAAAGGAAGGACACCAAATGAAAGATTGTACTG
AGAGACAGGCTAATTTTTTAGGGAAAATCTGGCCTTCCCACA
AGGGGAGGCCAGGGAACTTTCTTCAGAGCAGGCCAGAACCAA
CAGCCCCTCTCCAGGGCAGGCCGGAGCCATCAGCCCCGCCAG
AAGAGAGCTTCAGGTTTGGGGAGGAGACAACAACTCCCTCTC
AGAAGCAGGAGCCGATAGACAGGGACAGGGATCTGTATCCTT
TAGCTTCCCTCAGATCACTCTTTGGCAACGACCCCTCGTCAC
AATAAAGATAGGGGGGCAGCTGAAGGAAGCTCTATTAGATAC
AGGAGCAGATGATACAGTATTAGAAGACATGCATTTGCCAGG
AAAATGGAAACCAAAATGATAGGGGAATTGGAGGTTTTAT
CAAAGTAAAACAATATGATGAAATTCTTGTAGAAATCTGTGG
ACATAAAGCTATAGGTACAGTATTAGTAGGACCTACACCTGT
CAACATAATTGGAAGAAATCTGTTGACTCAGATTGGTTGCAC
TTTAAATTTTCCCATTAGTCCTATTGAAACTGTACCAGTACA
ATTAAAGCCAGGAATGGATGGCCCAAAGGTTAAACAATGGCC
ATTGACAGAAGAGAAAATAAAAGCATTAGTAGAAATTTGTAC
AGAAATGGAAAAGGAAGGAAAGATTTCAAAAATTGGGCCTGA
AAATCCATACAATACTCCAGTATTTGCCATAAAGAAAAAGA
TGGTACTAAATGGAGAAAATTAGTAGATTTCAGAGACCTTAA
TAAGAGAACTCAAGACTTCTGGGAAGTTCAATTAGGAATACC
ACATCCCTCAGGATTAAAAAGAAAAAATCAGTAACAGTACT
GGATGTGGGTGATGCATACTTTTCAGTTCCCTTAGATGAAAA
CTTCAGGAAGTATACTGCATTTACCATACCTAGTATAAATAA
TGAGACACCAGGGATTAGATATCAGTACAATGTGCTTCCACA
GGGATGGAAAGGATCACCAGCAATATTCCAAAGTAGCATGAC
AAGAATCTTAGAGCCTTTTAGAAGACAAAATCCAGACATAGT
TATCTATCAATACATGGATGACTTGTATGTAGGATCTGATTT
AGAAATAGGACAGCATAGAATAAAATAGAGGAACTGAGACA
ACATCTGTTGAAGTGGGGATTTACCACACCAGACAAAAAGCA
TCAGAAAGAACCCCATTCCTTTGGATGGGTTATGAACTCCA
TCCTGATAAATGGACAGTGCAACCTATAGTACTGCCAGAAAA
AGACAGCTGGACTGTCAATGACATACAGAAGTTAGTGGGTAA
ATTAAATTGGGCAAGTCAGATTTACCCAGGAATTAAAGTAAG
GCAATTATGTAAACTCCTTAGGGGAACCAAAGCACTAACAGA
```

FIGURE 9 (iii)

```
AGTAATACCACTAACAGAAGAAGCAGAGCTAGAACTGGCAGA
AAACAGGGAAATTCTAAGAGAACCAGTACATGGAGTGTATTA
TGACCCATCAAAGACTTAATAGCAGAAATACAGAAGCAGGA
GCAAGGCCAATGGACATATCAAATTTATCAAGATCAATTTAA
AAATCTAAAAACAGGAAAGTATGCAAGATTGAGGGGTGCCCA
CACTAATGATGTAAACAATTTCCAGAGGCAGTGCAAAAAAT
AGCCACAGAAGCATAGTAATATGGGGAAAGACTCCTAAATT
TAGACTACCCATACAAAAGAAACATGGGACGCATGGTGGAC
AGAGTATTGGCAAGCCACCTGGATTCCTGAGTGGGAGTTTGT
CAATACCCCTCCCCTAGTAAAATTATGGTACCAGTTAGAAAA
AGAACCCATAATAGGAGCAGAAACTTTCTATGTAGATGGGGC
AGCTAACAGAGAGACTAAATTAGGAAAGCAGGATATGTTAC
TGACAGAGGAAGACAAAAGTTGTCTCCCTAACTGACACAAC
AAATCAGAAGACTGAGTTACAAGCAATTCATCTAGCTTTGCA
GGATTCAGGATTAGAAGTAAACATAGTAACAGACTCACAGTA
TGCATTAGGAATCATTCAAGCACAACCAGATAAAAGTGAATC
AGAAATAGTCAATCAAATAATAGAGCAATTAATAAAAAGGA
AAAGGTCTACCTGGCATGGGTACCAGCACACAAAGGAATTGG
AGGGAATGAACAAGTAGATAAATTAGTCAGTGCTGGAATCAG
GAAAATACTATTTTAGATGGAATAGATAAGGCACAAGAAGG
CCATGAGAAATATCACAGTAATTGGAGAGCAATGGCTAGTGG
TTTTAACCTGCCACCTATAGTAGCAAAAGAAATAGTAGCCAG
CTGTGATAAATGTCAGCTAAAGGAGAAGCCATGCATGGACA
AGTAGACTGTAGTCCAGGAATATGGCAACTAGATTGTACACA
TCTAGAAGGAAAAATTATCCTGGTAGCAGTTCATGTAGCCAG
TGGATATATAGAAGCAGAAGTTATTCCAGCAGAGACAGGGCA
GGAAACAGCATACTTTATCTTAAAATTAGCAGGAAGGTGGCC
AGTAAACACAATACATACAGACAATGGCGGCAATTTCATCAG
TACCACGGTTAAGGCCGCCTGTTGGTGGGCAGGGATCAAGCA
GGAATTTGGCATTCCTACAATCCCCAAAGCCAAGGAGTAGT
GGAATCTATGAATAGAATTAAGAAAATTATAGGACAGGT
AAGAGATCAGGCTGAACATCTTAAGACAGCAGTACAAATGGC
AGTATTCATCCACAATTTTAAAAGAAAGGGGGGATTGGGGG
ATACAGTGCAGGGGAAGAATAGTAGACATAATAGCAACAGA
CATACAAACTAAAGAATTACAAAGCAAATTACAAAAATTCA
AAATTTTCGGGTTTATTACAGGGACAGCAGAGATCCACTTTG
GAAAGGACCAGCAAAACTTCTCTGGAAAGGCGAAGGGCAGT
AGTAATACAAGATAATAGTGACATAAAAGTAGTGCCAAGAAG
AAAAGTAAAGATCATTAGGGATTATGGAAAACAGATGGCAGG
```

FIGURE 9 (iv)

```
TGATGATTGTGTGGCAAGTAGACAGGATGAGGATTAGAACAT
GGAACAGTTTAGTGAAACACCATATGTATGTTTCAAAGAAAG
CTAAGGGATGGATTTATAGACATCACTATGAAAACACTCATC
CAAAAATAAGCTCAGAAGTACACATCCCACTAGGGGAAGCTA
GATTGGTAATAACAACATATTGGGGTCTACATACAGGAGAAA
GAGACTGGCATTTGGGTCAGGGAGTCTCCATAGAATGGAGGG
AAAGGACATATAGAACACAAGTAGACCCCGAACTAGCAGACC
AACTAATTCATATACATTACTTTGATTGTTTTTCAGAATCTG
CCATAAGAAGTGCCATATTAGGATATAGAGTTAGGCATAGGT
GTGAATATCAAGCAGGACATAACAAGGTAGGATCTCTACAGT
ACTTGGCACTAACAGCATTAATAACACCAAAGAAGATAAAGC
CACCTTTGCCTAGTGTTGCGAAACTGACAGAGGATAGATGGA
ACAAGCCCCAGAAGACCAAGGGCCACAGAGGCAGCCATACAA
TGAATGGACACTAGAACTTTTAGAGGAGCTTAAGAATGAAGC
TGTTAGGCATTTTCCTAGGGTATGGCTCCATGGCTTAGGGCA
ACATATCTATGAAACTTATGGGGATACTTGGGAAGGAGTGGA
GGCCATAACAAGAACTCTGCAACAACTGCTGTTTATTCATTT
CAGAATTGGGTGTCAACATAGCAGAATAGGCATTATTCGACA
GAGGAGAGCAAGAAATGGAGCCAGTAGATCCTAGACTAGAGC
CCTGGAAGCATCCAGGAAGTCAGCCTAAGACTGCGTGTACCA
CTTGCTATTGTAAAAGTGCTGCTTTCATTGCCAAGTTTGTT
TTATGACAAAAGGCTTAGGCATCTCCTATGGCAGGAAGAAGC
GGAGACAGCGACGAAGAGCTCCTCAAGACAGTCAGACTCATC
AAGCTTATCTATCAAAGCAGTAAGTAATATATGTAATGCAAC
CTTTACAAATAGTAGCAATAGTAGCATTAGTAGTAGCAGGAA
TAATAGCAATAGTTGTGTGGACCATAGTATTCATAGAATATA
AGAAAATATTAAGACAAAGAAAATAGACAGGTTGATTGATA
GAATAAGAGAAAGAGCAGAAGACAGTGGCAATGACAGTGAAG
GGGATCAGGAAGAATTATCGGCACTTGTGGACATGGGGCACC
ATGATCCTTGGGATATTAATGATCTGTAGAGCTGCAAACAAT
TTGTGGGTCACAGTCTATTATGGGGTACCTGTGTGGAGAGAA
GCAACCACCACTCTATTTTGTGCATCAGATGCCAAGGCATAT
GATGCAGAGGTACATAATGTTTGGGCCACACATGCCTGTGTA
CCCACAGACCCTAACCCACAAGAAGTAGAATTGAAAATGTG
ACAGAAAATTTTAACATGTGGAAAATAACATGGTAGAACAG
ATGCATGAGGATATAATCAGTTTATGGGATCAAAGCCTGAAG
CCATGTGTAAAATTAACCCCACTCTGTGTTTCTTTAAATTGC
ACTGATGCTACTAATACCACTAATAGTAATACCACTAGCAGC
AGCGAGAAACCGAAGGGGACAGGGGAAATAAAAAACTGCTCT
```

FIGURE 9 (v)

```
TTCAATATCACCACAAGCATAAGAGATAAGGTGCAGAAACAA
TATGCACTTTTTTATAGCCTTGATGTAGTACCAATGGATGAT
AATGATAATAGTACAAGCTATAGGTTAATAAGTTGTAACACC
TCAATCATTACACAGGCCTGTCCAAAGATATCCTTTGAGCCA
ATTCCCATACATTATTGTGCCCGGCTGGTTTTGCGATTCTA
AAGTGTAAAGATAAAAGGTTCAATGGAAAGGACCATGTACA
AGTGTCAGCACAGTACAGTGTACATGGAATTAGGCCAGTA
GTATCAACTCAACTGTTGTTAAATGGCAGTCTAGCAGAAGAA
GAGGTAGTAATTAGATCTGACAATTTTACGAACAATGCTAAA
ACCATAATAGTACAGCTGAGCAAATCTGTAGAATTACTTGT
GTAAGACCCAACAACAATACAAGAAAAGTATAAGTATGGGA
CCAGGGAGAGCATTTTATACAACAGAAATAATAGGAGATATA
AGACAAGCATATTGTAACATTAGTAAAGCAAACTGGACTGAC
ACTTTAGAACAGATAGCTAGAAAATTAAGAGAACAATTTGAG
AATAAAACAATAGTCTTTAAGCCATCCTCAGGAGGGGACCCA
GAATTGTAACACAGTTTTACAGTTTTAATTGTGGAGGGGAA
TTTTCTACTGTAATTCAACACAACTGTTTAATGGTACTTGG
AATGGTACTTGGGTTAATGGTACTTGGAGTAGTAATAATACG
ACTGATACTGCAAATATCACACTCCCATGCAGAATAAAACAA
TTTATAAACATGTGGCAGGAAGTAGGAAAAGCAATGTATGCC
CCTCCCATCAAAGGACAAATTAAATGTACATCAAATATTACA
GGGCTGATATTAACAAGAGATGGTGGTAACAATAACACCACG
AACGACAACGAGACCGAGACCTTCAGACCTGGAGGAGGAGAT
ATGAGGGACAATTGGAGAAGTGAATTATATAAATATAAAGTA
GTACAAGTTGAACCATTAGGAGTAGCACCCACCAAGGCAAAG
AGAAGAGTGGTGCAAAGAGAAAAAGAGCAGTGGGAATAGGA
GCTATGTTCCTTGGGTTCTTAGGAGCAGCAGGAAGCACTATG
GGCGCAGCGTCAGTGACGCTGACGGTACAAGCCAGACAATTA
TTGTCTGGTATAGTGCAGCAGCAGAACAATCTGCTGAGGGCT
ATTGAGGCGCAACAGCATCTGTTGCAACTCACAGTCTGGGGC
ATCAAACAGCTCCAGGCAAGAGTCCTGGCTGTGGAAAGATAC
CTAAGGGATCAACAGCTCCTGGGACTTTGGGGTTGCTCTGGA
AAACTCATTTGCACCACTACTGTGCCTTGGAACAATAGCTGG
AGTAATAAATCTCTGGAACAATTTGGGATAACATGACCTGG
ATGCAGTGGGAAAGAGAATTGACAATTACACAAACATAATA
TACACCTTAATTGAAGAATCGCAGAACCAACAAGAAAAAAT
GAACTAGAATTATTGGAATTGGATAAATGGGCAAATTTGTGG
AATTGGTTTAGTATATCAAACTGGCTATGGTATATAAAATTA
TTCATAATGGTAGTAGGAGGCTTGGTAGGTTTAAGAATAGTT
```

FIGURE 9 (vi)

TTTACTGTACTTTCTATAGTTAATAGAGTTAGGCAGGGATAC
TCACCATTATCGTTTCAGACCCACCTCCCAACCCCGAAGGGA
CCCGACAGGCCAGAAGGAATCGAAGAAGAAGGTGGAGAGAGA
GACAGAGGCAGCTCCACTCGATTAGTGCACGGATTCTTAGCA
CTTTTCTGGGACGACCTGAGGAGTCTGTGCCTCTTCAGCTAC
CACCACTTGAGAGACTTACTCTTGATTGTAACGAGGATTGTG
GAACTTCTGGGACGCAGGGGATGGGAAGCCCTCAAATACTGG
TGGAATCTCCTGCAGTATTGGAGGCAGGAACTACAGAAGAGT
GCTGTTAGCTTGTTCAATGGCACGGCCATAGCAGTAGCTGAG
GGGACAGATAGAGTTATAGAAGCTTTACGAAGGGCTTATAGA
GCTATTCCACATACCTAGAAGAATAAGACAGGGCTTAGAA
AGGGCTTTGCTATAAATGGGTGGCAAGTGGTCAGAAAGTAG
TGTGGTTAGAAGGCATGTACCTTTAAGACAAGGCAGCTATAG
ATCTTAGCCGCTTTTTAAAAGAAAAGGGGGACTGGAAGGGC
TAATTCACTCACGGAAAGACCAGTTGAACCAGAAGAAGATA
GAAGAGGCCATGAAGAAGAAACAACAGATTGTTCTGCTTGC
TCAGCTGGGGACTTTCCAGAAGGCGCGGCCTGAGTGACTAAG
CCCCGTTGGGGACTTTCCGAAGAGGCATGAAGGGACTTTCCA
AGGCAGGCGTGGCCTGGGCGGGACTGGGGAGTGGCGAGCCCT
CAGATGCTGCATATAAGCAGCTGCTTTCTGCCTGTACTGGGT
CTCTCTGGTTAGACCAGATCTGAGCCTGGGAGCTCTCTGGCT
AGCTAGGGAACCCACTGCTTAAGCCTCAATAAAGCTTGCCTT
GAGTGCTTCAAGTAGTGTGTGCCCGTCTGTTGTGTGACTCTG
GTATCTAGAGATCCCTCAGACCATTTTAGTCCGTGTGGAAAA
TCTCTAGCA

Figure 10A:
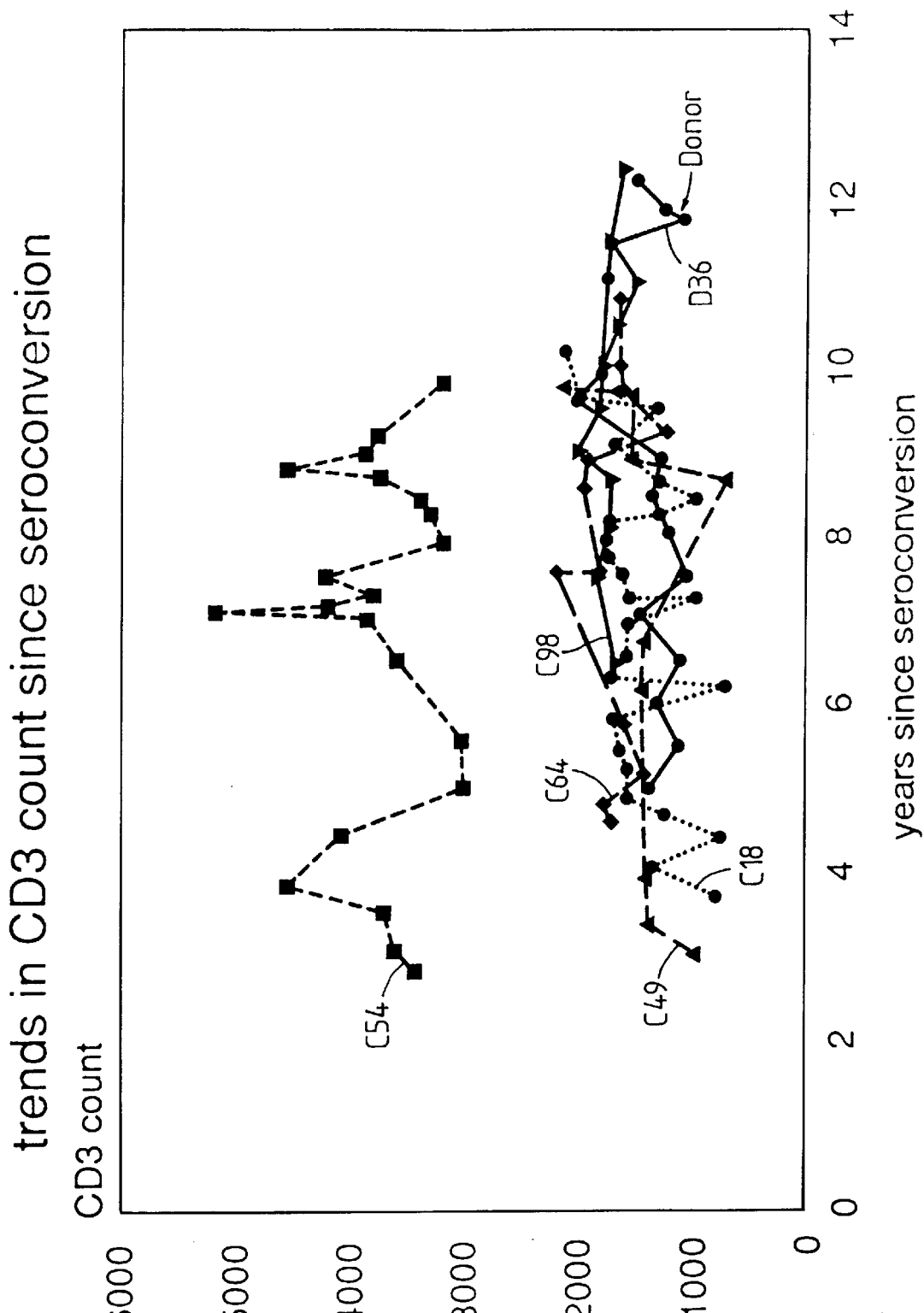
Figure 10B:
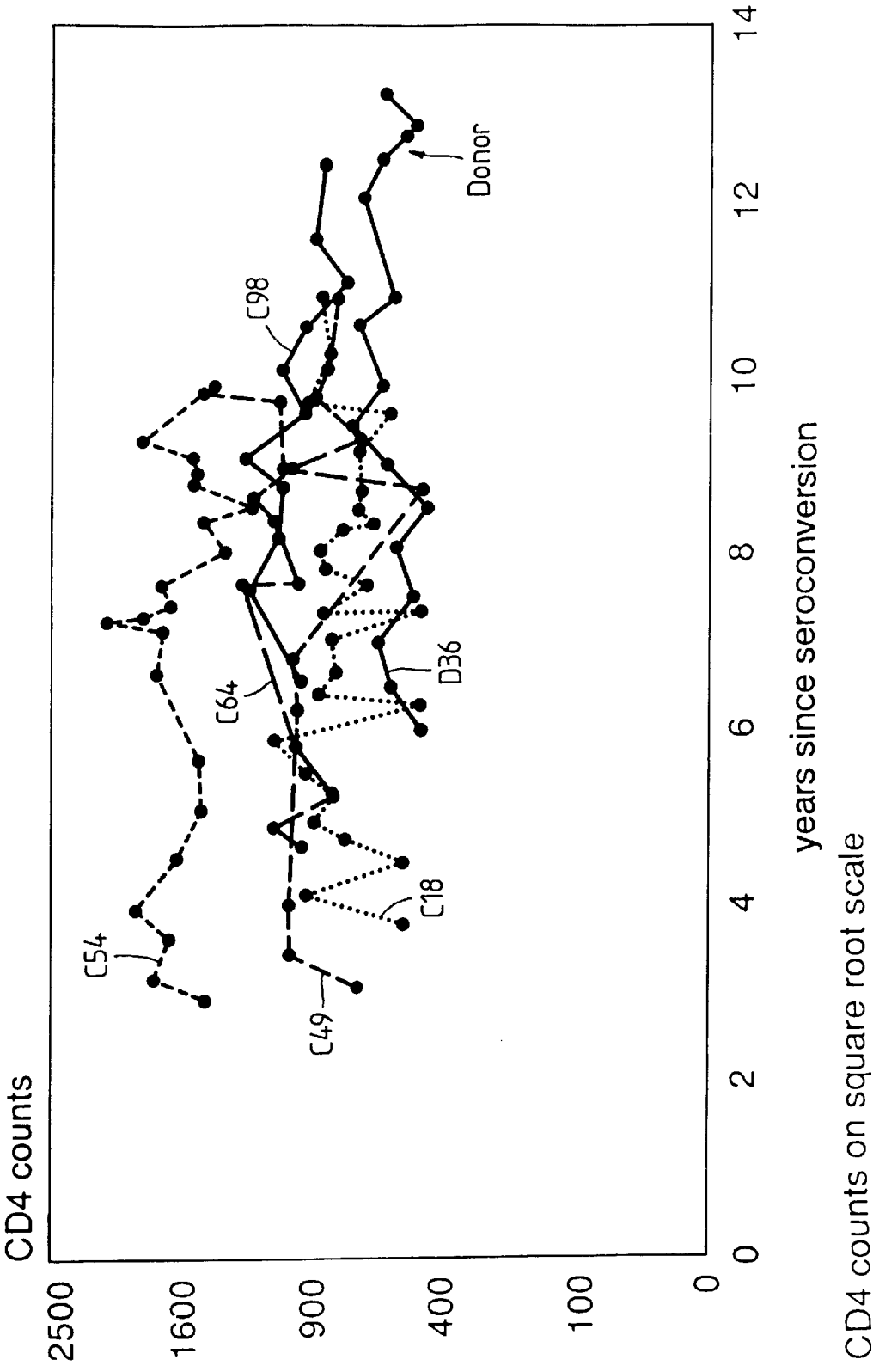
Figure 10C:
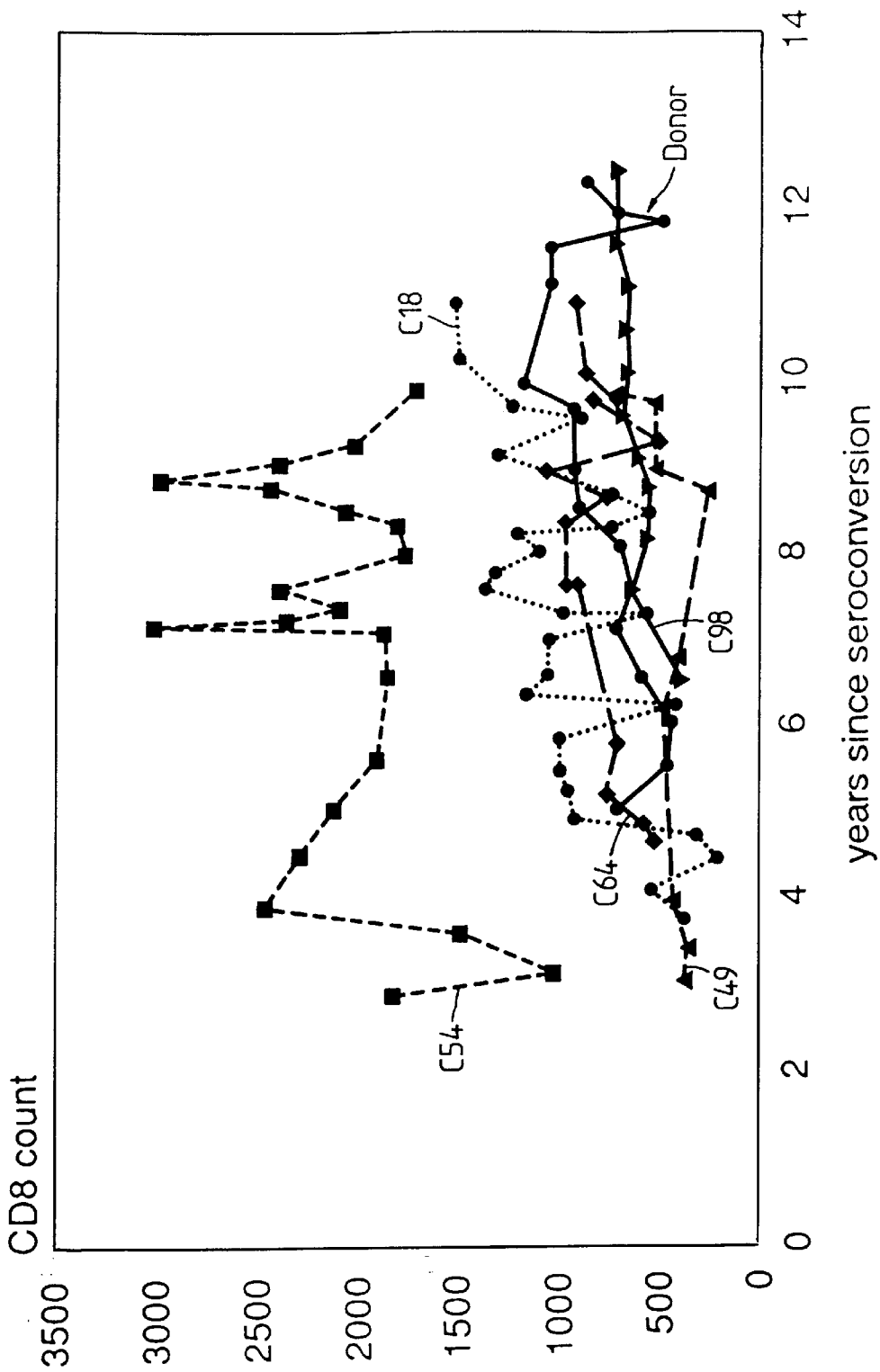

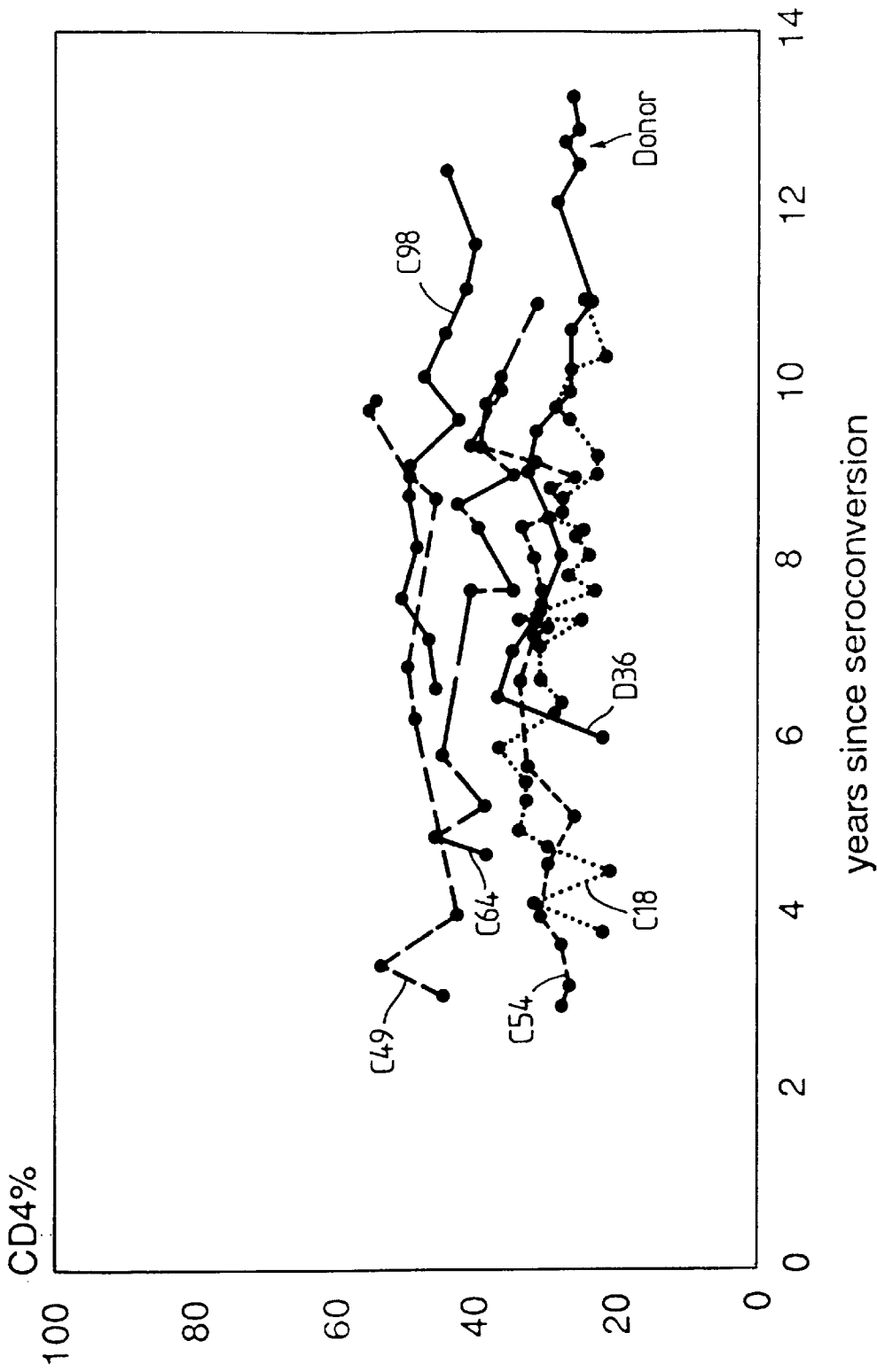
FIG 10(b)(ii)

Figure 10:
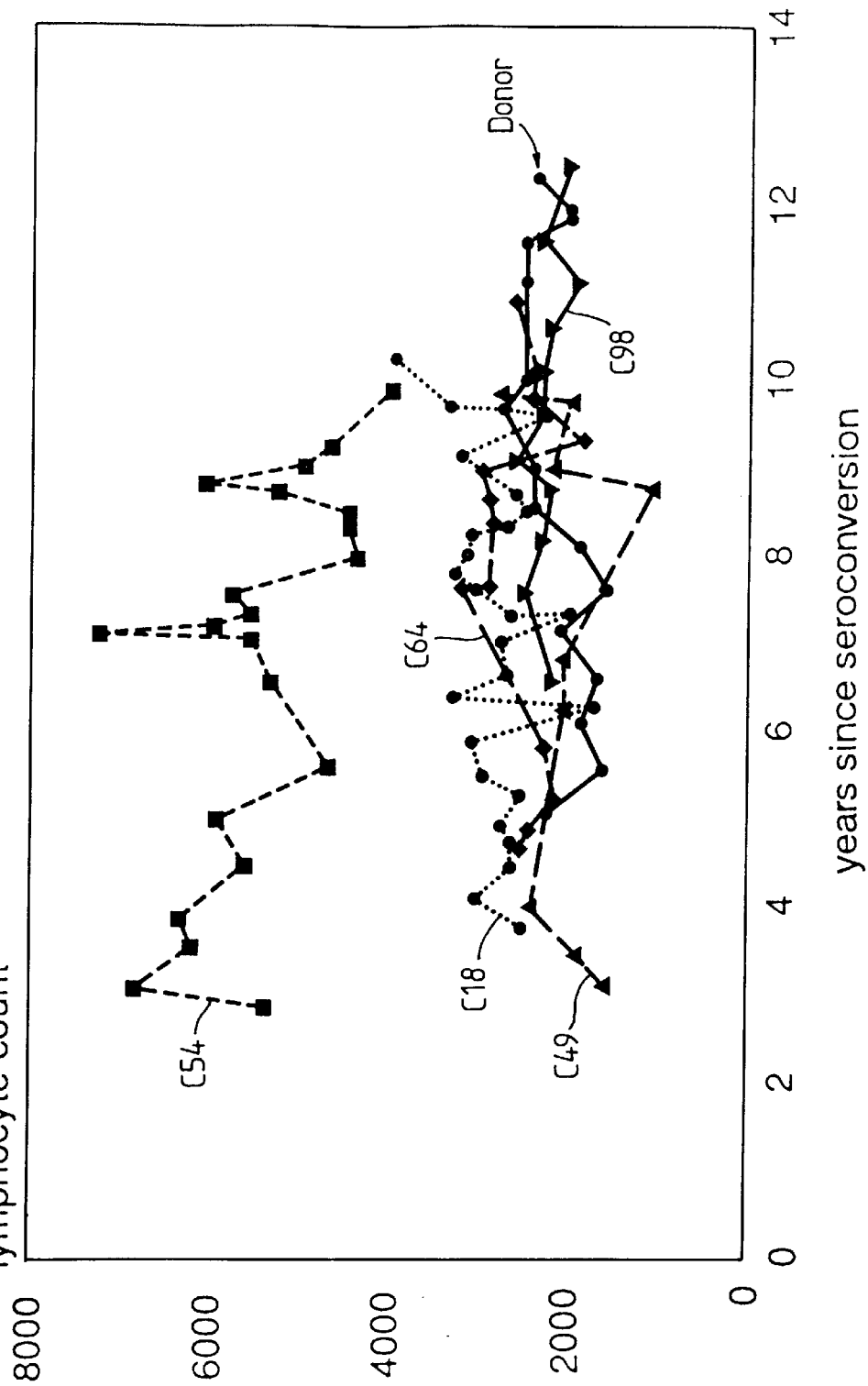
Figure 10G:
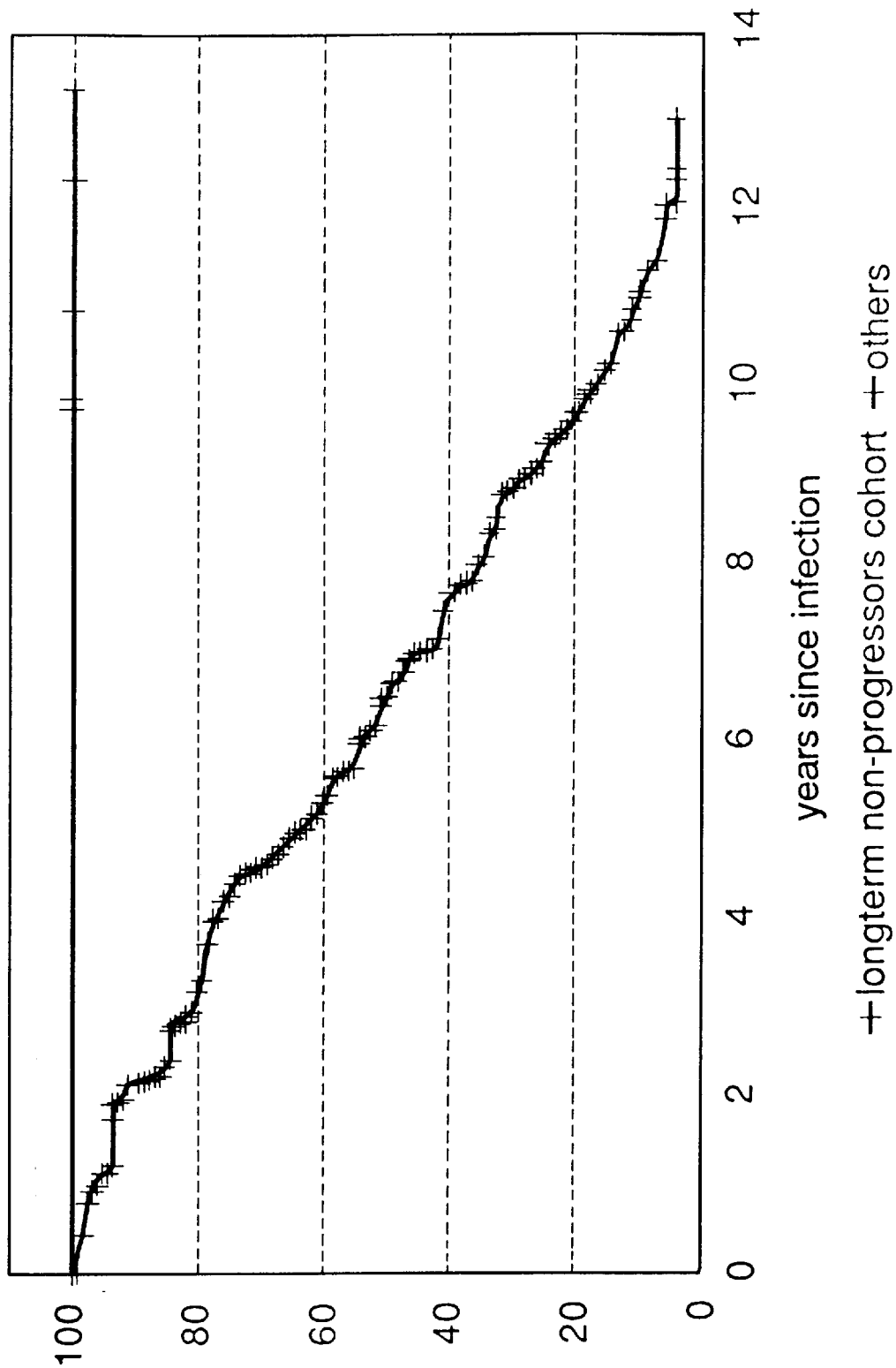

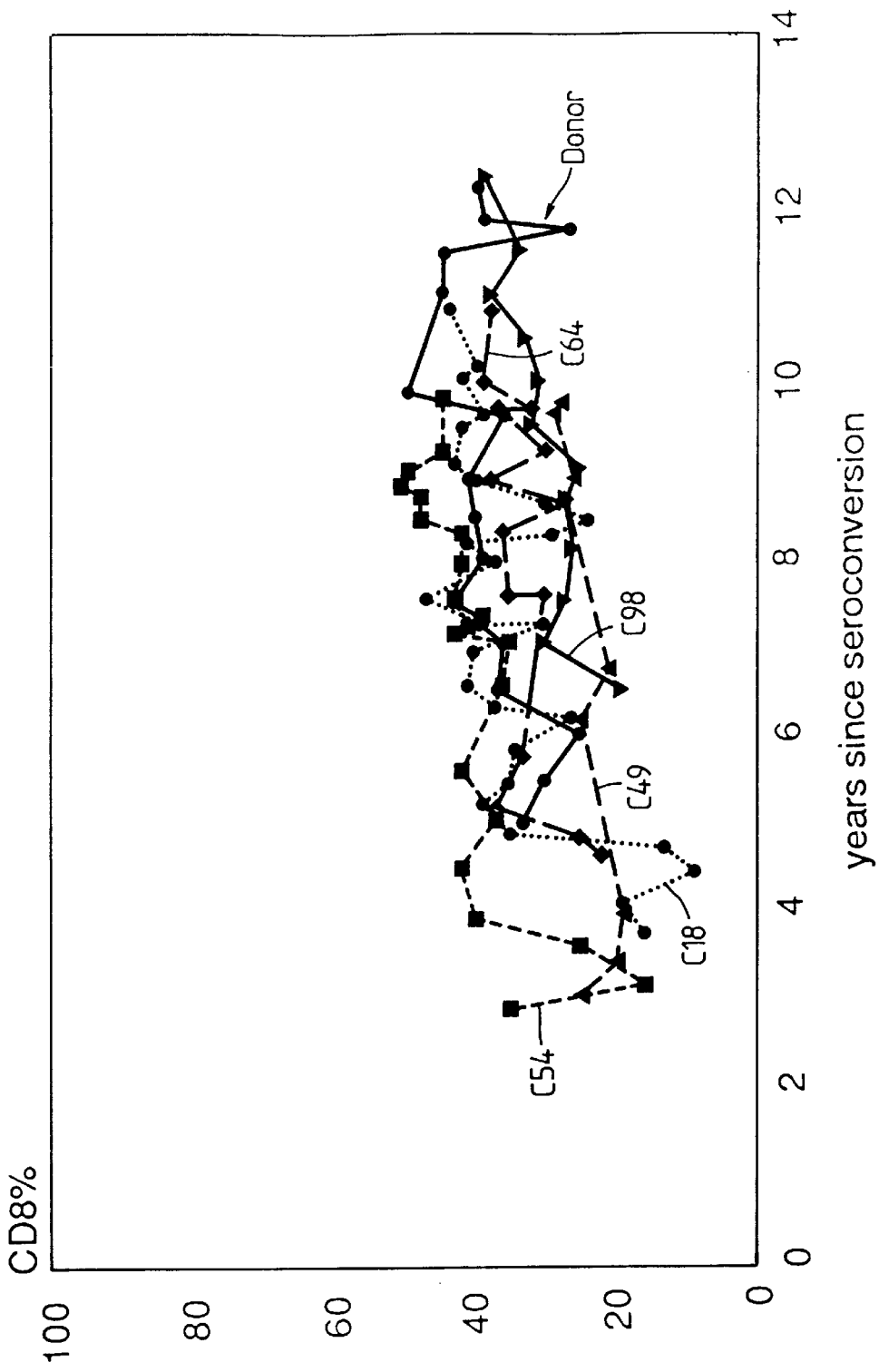
FIG 10 (c)(ii)

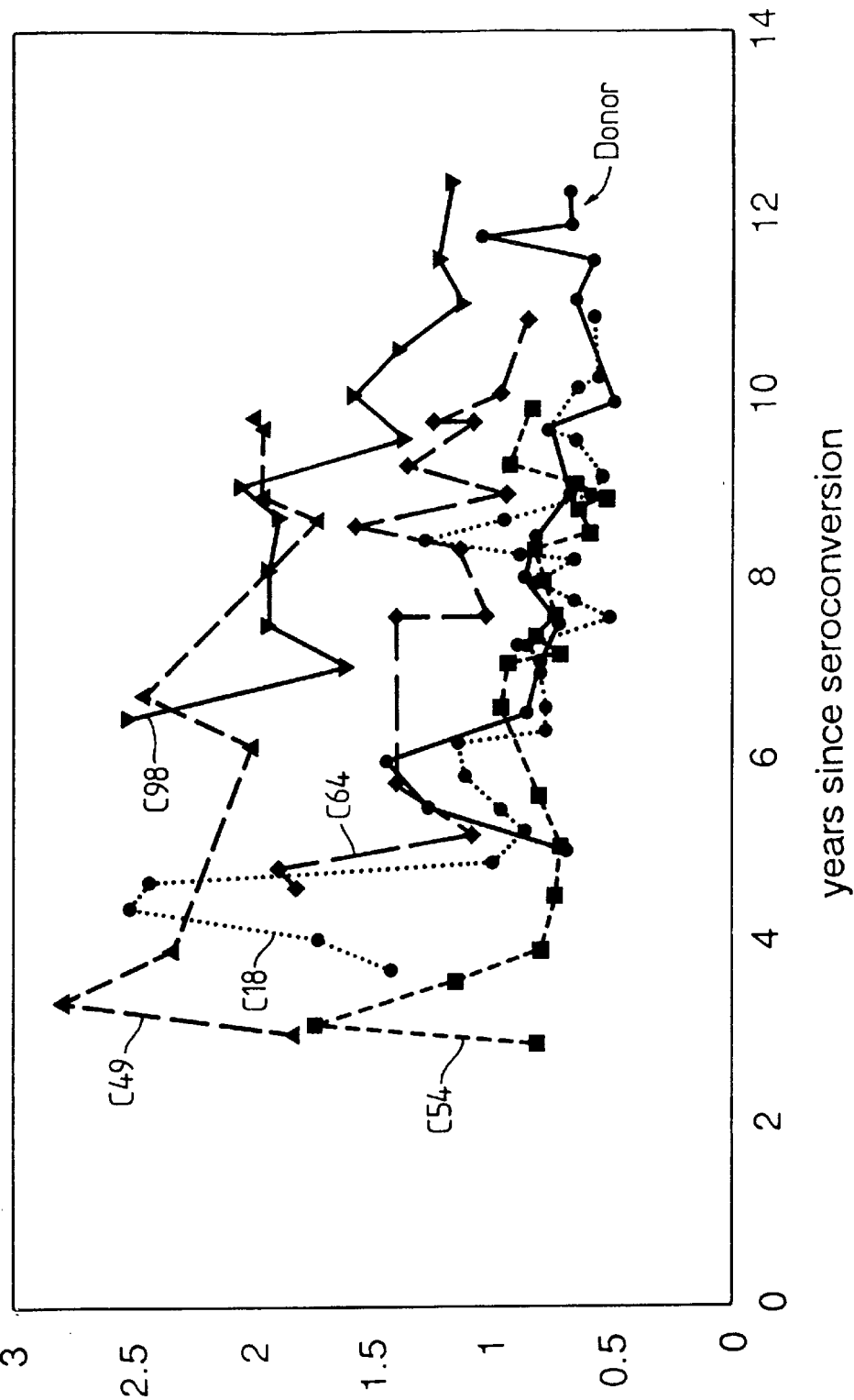

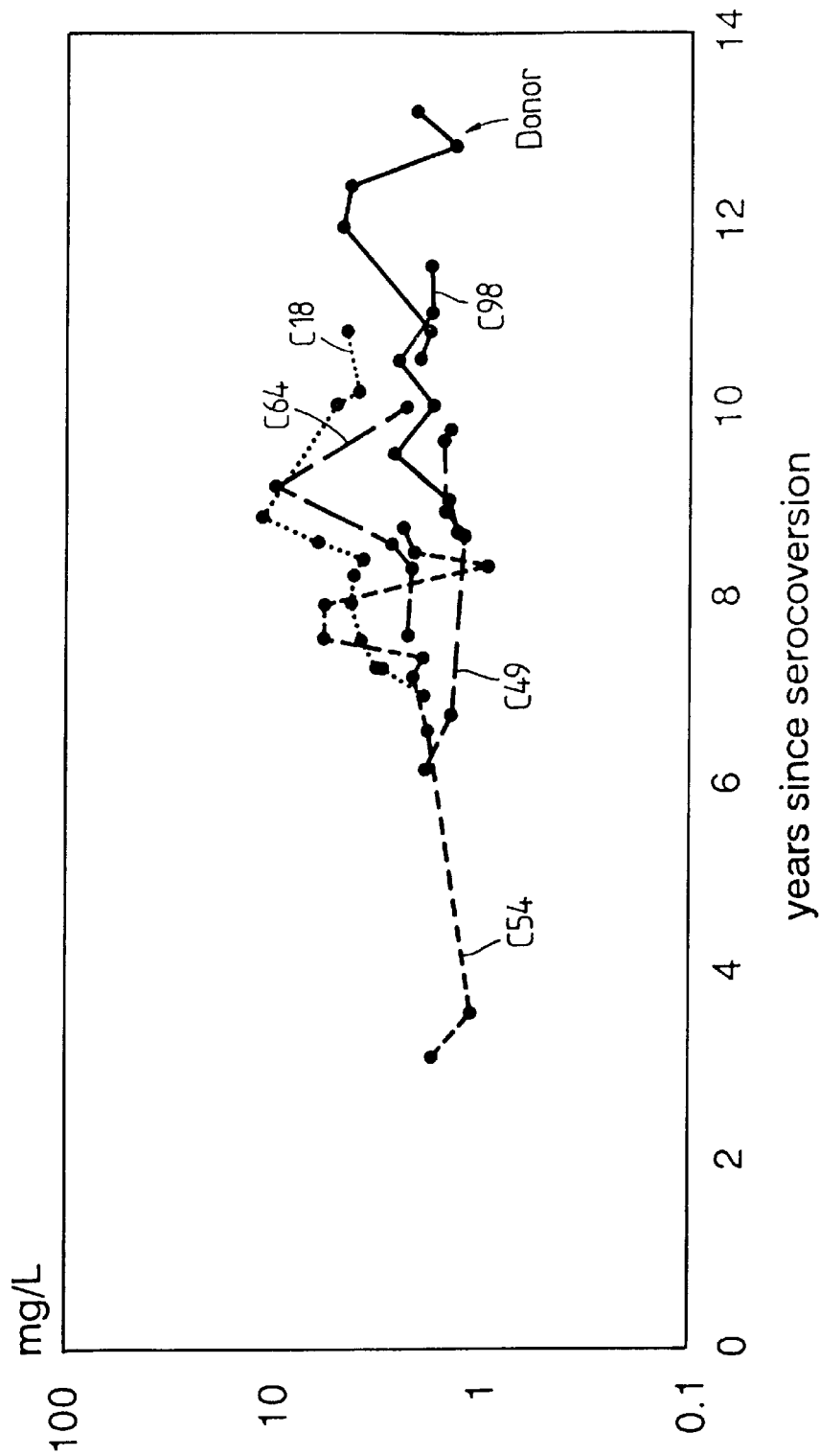

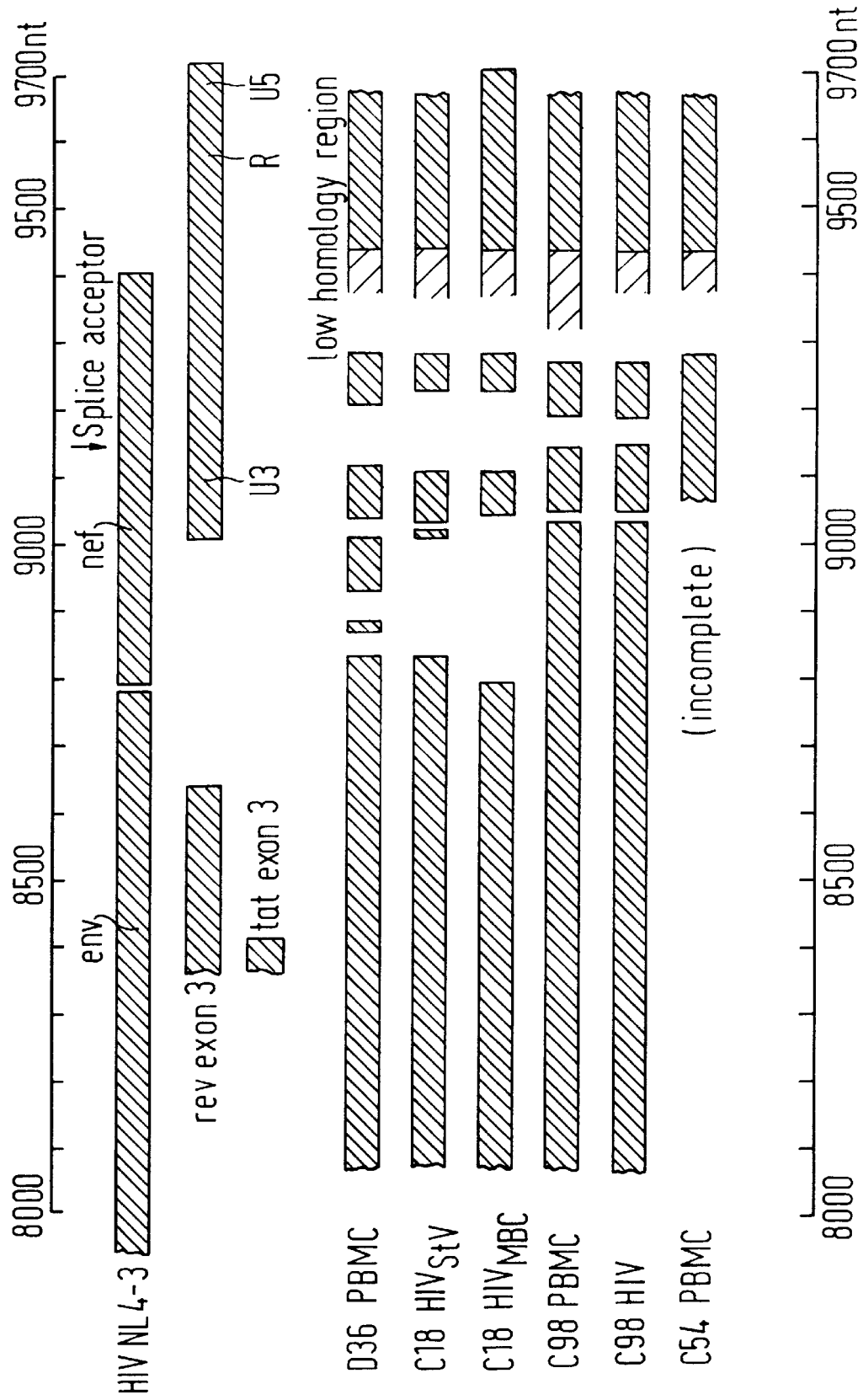

NON-PATHOGENIC STRAINS OF HIV-1 CONTAINING MUTATIONS IN THE NEF GENE OR THE U3 REGION OF THE LONG TERMINAL REPEAT

The present invention relates to non-pathogenic strains of HIV-1 and to components, parts, fragments and derivatives thereof and to genetic sequences derived therefrom and their use in the development of diagnostic and therapeutic compositions for the treatment and prophylaxis of AIDS and AIDS-related disorders. The present invention also relates to a method for attenuating pathogenic stains of HIV-1 by mutagenizing particular regions of the HIV-1 genome.

Bibliographic details of the publications referred to in this specification are collected at the end of the description. Sequence Identity Numbers (SEQ ID NOs.) for the nucleotide and amino acid sequences referred to in the specification are defined following the bibliography.

Throughout this specification, unless the context requires other wise, the word “comprise”, or variations such as “comprises” or “comprising”, will be understood to imply the inclusion of a stated element or integer or group of elements or integers but not the exclusion of any other element or integer or group of elements or integers.

Genomic nucleotide sequences of HIV-1 strains referred to herein are represented by their corresponding DNA sequence.

Exemplary viral isolates referred to herein as “C18” and “C98” were deposited at the PHLS Centre for Applied Microbiology and Research, European Collection of Animal Cell Cultures (ECACC), Division of Biologies, Porton Down, Salisibury, Wiltshire SP4 OJG. C18 was deposited on Oct. 17, 1994 under Provisional Accession Number V94101706 and C98 was deposited on Oct. 31, 1994 under Provisional Accession Number V941031169. Viral isolate “C54” was deposited at ECACC on Mar. 10, 1995 under Provisional Accession Number V95031022.

A summary of particular deletion mutants of HIV-1 of the present invention referred to herein is given in FIG. 11.

Acquired Immune Deficiency Syndrome (AIDS) and AIDS related disorders are the clinical result of infection by Human Immunodeficiency Virus type I (HIV-1) (Barre-Sinoussi et al, 1983). Infection by HIV-1 is generally characterised by progressive immune system damage (Teeuwsen et al, 1990; Clerici et al, 1989) leading to opportunistic infections, malignancies or wasting syndrome that constitute clinically-defined AIDS (Busch et al, 1991 ; Klaslow et al, 1990).

The high mortality rate of individuals Infected with HIV-1 together with the social and economic consequences of the continuing HIV-1 epidemic has created an urgent need for a safe and effective treatment and/or prophylaxis against the devastating effects of AIDS. However, despite over a decade of high level scientific research into the pathogenesis of HIV-1 and the clinical manifestations of the disease, together with a detailed molecular analysis of the virus, there has been little success in the development of an effective vaccine. To date, the most effective therapy is treatment with zidovudine (AZT) which delays the onset of full blown AIDS and alleviates to some extent the symptoms of HIV-1 infection. However, AZT is not an innocuous compound and AZT, metabolic products thereof or impurities therein can cause a number of side effects which limit long term treatment with the drug. Furthermore, AZT resistant isolates have been reported during treatment. Clearly, therefore, a need exists to develop alternative strategies in preventing and treating HIV-1 infection.

The initial phases of HIV-1 infection are summarised by Levy (1993) as involving attachment, fission and nucleocapsid entry. These phases have been the traditional foci in research into development of antiviral strategies. The molecular events at the virus genomic level have also been the subject of intense scientific research with an aim being the development of a live attenuated vaccine as a possible approach for the treatment or prophylaxis of HIV-1 infection.

There is a high variable rate of progression from initial HIV-1 infection to AIDS which reflects a rapidly changing pathogen and variable immune response of the host to infection (Sheppard et al, 1993). With regards to the latter, HIV-1 can be considered as a heterogenous group of viruses differing at the genetic level with concomitant variable pathogenicity. For example, HIV-1 strains can differ in their capacity to kill cells. Furthermore, it appears that HIV-1 strains evolve in a host after infection and that the evolution varies depending on the tissues infected by the virus. The major sites in the genome apparently responsible for biological and pathological variation are the highly variable envelope region (Cheng-Mayer et al, 1991; Shioda et al, 1992; Hwang, et al 1991; Sullivan et al, 1993; Groenink et al, 1993) and the viral regulatory regions such as tat (Leguern et al, 1993). The genetic complexity of the HIV-1 group of viruses together with their variable pathogenicity, are major difficulties in the development of live vaccines, genetic vaccines or component vaccines.

Notwithstanding the highly pathogenic nature of HIV-1, there are some reports of long term survival of subjects infected with the virus (Learmont et al, 1992; Levy, 1993; Sheppard et al, 1993; Lifson et al 1991). It is not always clear, however, whether a benign course following HIV-1 infection is due to host factors, viral factors or other unknown factors. There are reports that most infected people have at least laboratory evidence of progressive immune system damage in the form of CD4+cell loss (Lang et al, 1989) and defective immune responses (Clerici et al, 1989).

Although simian monkeys have been used as an in vivo model for HIV and Simian Immunodeficiency Virus (SIV) infection, a major handicap in AIDS research has been the absence of suitable in vivo models to study the pathogencsis of the disease and, in particular, to study the viruses involved in benign infection. The need for a suitable in vivo model is heightened by the fact that results obtained in vitro cannot necessarily be extrapolated to what occurs in vivo. This was clearly observed by Mosier et al (1993) where conflicting results were obtained in animals compared to cell cultures.

Despite the absence of suitable in vivo models, considerable scientific research has been directed to attenuating HIV-1 strains by mutagenesis of the virus genome. Deletions in the nef gene have been implicated in attenuated strains of SIV and their use in providing protective effects in monkeys (Daniel et al, 1992). However, there are conflicting reports on the possible negative influence the nef gene product has on the rate or extent of virus replication (Terwilliger et al, 1986,Luciw et al, 1987; Niederman et al, 1989; Kim et al, 1989; Hammes et al, 1989). In fact, Kim et al (1989) found that nef did not affect HIV-1 replication or HIV-1 long terminal repeat (LTR)-driven CAT expression. Kestler III et al (1991) found that nef gene is required for fill pathogenic potential in SIV. However, such is the complexity of the HIV-1 group of viruses and the variability of immune responses between individuals let alone different species, that it is far from clear whether nef deleted strains of HIV-1 would behave similarly to nef deleted strains of SIV-1. There is a need, therefore, in order to investigate the possibility of nef deleted HIV-1 strain as a vaccine candidate, to identify individuals infected with such modified viruses.

Learmont et al (1992) reported that a cohort of five persons infected with blood products from a single HIV-1 infected donor have remained asymptomatic from up to about 10–14 years after infection. Subsequently, a sixth person has been identified as being part of the cohort. Both the donor and recipients were HIV-1 seropositive but with no indications of clinical symptoms of HIV-1 related disease and CD4+cell number and $\beta_2$-microglobulin levels have remained in the normal range. The identification of this cohort of benignly infected individuals provides a unique In vivo model in which the pathogenesis of HIV-1 infection can be studied at the clinical and molecular biological levels.

However, it has not always possible using conventional isolation procedures to routinely and reproducibly isolate viral strains from the above mentioned donor or recipients which has frustrated efforts to investigate the cause of the asymptomatic individuals. In accordance with the present invention, methods have now been established to isolate viruses from the above individuals. It has been determined, in accordance with the present invention, that the six individuals of the cohort are infected by non-pathogenic strains of HIV-1. Furthermore, the non-pathogenic strains of HIV-1 carry one or more nucleotide mutations. The non-pathogenic strains of the present invention enable the generation of a range of therapeutic, diagnostic and targeting agents against HIV-1 infection. The present invention also enables the attenuation of previously pathogenic strains of HIV-1.

Accordingly, one aspect of the present invention contemplates a non-pathog enic isolate of HIV-1 or a component, part, fragment or derivative thereof.

In a related embodiment, there is provided a novel isolate of HIV-1 or a component, part, fragment or derivative thereof wherein said HIV-1 isolate is capable of stimulating in a human or primate subject an immune response such as a humoral immune response to at least one HIV-1 glycoprotein such as but not limited to gp41-45, gp120 and/or gp160 while not substantially reducing in said human or primate subject proliferative responses and cytokine production to a mitogen, alloantigen and/or recall antigen compared to a healthy, non-infected human or primate subject. Preferably, the cytokine is IL-2. Preferably, the mitogen is ConA or PHA and the recall antigen is influenza or tetanus toxoid. Preferably, the HIV-1 isolate is non-pathogenic.

More particularly, the present invention relates to an isolated HIV-1 strain which:

(i) is substantially non-pathogenic in human subjects; and (ii) carries one or more mutations in its genome resulting in the inability to direct synthesis of at least one pathogenic HIV-1 derived polypeptide or protein.

Even more particularly, the present invention provides an isolated HIV-1 strain which:

(i) is substantially non-pathogenic in human subjects; and (ii) carries a mutation in the nef gene and/or a long terminal repeat (LTR) region or in a functionally equivalent location in the HIV-1 genome.

Still even more particularly, the present invention is directed to an isolated virus which:

(i) has a genome which is capable of hybridising under medium stringency conditions to complementary nucleic acid from a pathogenic strain of HIV-1;

(ii) is substantially non-pathogenic in human subjects;

(iii) carries one or more deletion mutations in a region of its genome corresponding to a nef gene in said pathogenic strain of HIV-1 ; and (iv) optionally carries a mutation in one or both LTR regions.

In a related embodiment, there is provided an isolated virus which:

(i) has a genome which is capable of hybridising under medium stringency conditions to complementary nucleic acid from a pathogenic strain of HIV-1;

(ii) is substantially non-pathogenic in human subjects;

(iii) carries one or more deletion mutations in an LTR region of its genome; and (iv) optionally carries a mutation in a region corresponding to a nef gene in said pathogenic strain of HIV-1.

In a further related embodiment, there is provided an isolated virus which:

(i) has a genome which is capable of hybridising under medium stringency conditions to complementary nucleic acid from a pathogenic strain of HIV-1;

(ii) is substantially non-pathogenic in human subjects; and (iii) carries one or more deletion mutations in a region of its genome corresponding to a region which contains nef coding sequences and LTR nucleotide sequences.

In a particularly preferred embodiment, the present invention provides non-pathogenic HIV-1 isolate C18 deposited at the ECACC on Oct. 17, 1994 under Provisional Accession Number V94101706.

In a related embodiment, the present invention provides non-pathogenic HIV-1 isolate C98 deposited at the ECACC on Oct. 31, 1994 under Provisional Accession Number V941031169.

In another embodiment, the present invention provides non-pathogenic HIV-1 isolate C54 deposited at ECACC on Mar. 10, 1995 under Provisional Accession No. V95031022

Although pathogenicity is a relative term, it is used herein in relation to the capacity of a strain of HIV-1 to induce AIDS or AIDS-related disorders in an individual over time. Accordingly, a "non-pathogenic" strain of HIV-1 is a strain which, at the clinical level, does not lead to the development of AIDS, at least within the median time of 6–10 years following infection with HIV1. At the laboratory level, a non-pathogenic strain of HIV-1 is considered not to alter CD4+ cell counts or $\beta_2$-microglobulin concentrations. In addition, a non-pathogenic strain of HIV-1 may not alter CD8+and CD3+cell counts and would not alter lymphocyte counts. CD4+: CD8+ratios also remain unchanged relative to normal non-infected individuals. Furthermore, generally, a non-pathogenic strain of HIV-1 does not induce p24 antigenaemia A non-pathogenic HIV-1 of the present invention is generally still infectious but individuals infected with the virus remain free of symptoms for at least 6–10 years after infection.

A laboratory classified non-pathogenic strain of HIV-1 may be determined at any time after infection, The term "non-pathogenic" is not to be considered as a strain that is never pathogenic under any conditions as this might depend on the host individual, the level of immune responsiveness in that individual and the extent or otherwise of other, for example, immune comprising disorders. Accordingly, a "non-pathogenic"HIV-1 isolate of the present invention may also be considered a "low virulent" strain of the virus. A non-pathogenic strain of HIV-1 as contemplated herein may be isolated from an asymptomatic individual or may be derived from a pathogenic strain by mutation. Although the present invention is not to be limited to any particular pathogenic strain of HIV-1, for reference purposes, an example of a pathogenic strain is HIV-1 NL4-3 strain as described by Myers et al (1992).

The non-pathogenic nature of the HIV-1 of the present invention is conveniently evidenced by the cohort of seven individuals comprising one donor and six recipients which have remained free of symptoms or signs of HIV-1 Infection for greater than the median time of 6–10 years. However, the individuals of the cohort are seropositive for HIV-1 following infection with the virus as determined by Western blot analysis and genetic analysis (e.g. using PCR techniques). A seropositive individual is one showing reactivity to at least one HIV-1 glycoprotein (such as but not limited to gp 41-45, gp120, gp 160) and at least three other virus-specific bands.

In accordance with the present invention, a non-pathogenic HIV-1 isolate is also a strain of HIV-1 which:

(i) induces an immune response in a human or primate subject; and (ii) does not substantially reduce proliferative responses or cytokine production to a mitogen, alloantigen and/or recall antigen relative to a healthy, non-infected subject.

Preferably, the immune response such as to a glycoprotein, for example gp41-45, gp120 and/or gp1160. Preferably, the cytokine monitored is an interleukin, such as IL-2. Preferably, the recall antigen is influenza or tetanus toxoid. A non-pathogenic HIV-1 isolate is also one which:

(iii) does not substantially alter proliferative responses or cytokine production to allorgeneic mononuclear cells.

The genomes or complementary DNA therefrom of the non-pathogenic HIV-1 isolates of the present invention are capable of hybridising under medium stringency conditions to the corresponding genome or complementary DNA of a pathogenic strain of HIV-1 (e.g. HIV-1 strain NL4-3). The ability to hybridise to a pathogenic rain of HIV-1 only applies to a comparison of the entire genome/complementary DNA of a non-pathogenic strain or a fragment which includes genetic material corresponding to a region in the genome 3' of the nef gene in a pathogenic strain of HIV-1.

For the purposes of reference only, a suitable genomic nucleotide sequence from a pathogenic HIV-1 strain is set forth in SEQ ID NO: 1 from HIV-1 strain NL4-3 (Myers et al, 1992):

```
   1 TGGAAGGGCTAATTTGGTCCCAAAAAAGACAAGAGATCCTTGATCTGTGG
  51 ATCTACCACACACAAGGCTACTTCCCTGATTGGCAGAACTACACACCAGG
 101 GCCAGGGATCAGATATCCACTGACCTTTGGATGGTGCTTCAAGTTAGTAC
 151 CAGTTGAACCAGAGCAAGTAGAAGAGGCCAAATAAGGAGAGAAGAACAGC
 201 TTGTTACACCCTATGAGCCAGCATGGGATGGAGGACCCGGAGGGAGAAGT
 251 ATTAGTGTGGAAGTTTGACAGCCTCCTAGCATTTCGTCACATGGCCCGAG
 301 AGCTGCATCCGGAGTACTACAAAGACTGCTGACATCGAGCTTTCTACAAG
 351 GGACTTTCCGCTGGGGACTTTCCAGGGAGGTGTGGCCTGGGCGGGACTGG
 401 GGAGTGGCGAGCCCTCAGATGCTACATATAAGCAGCTGCTTTTTGCCTGT
 451 ACTGGGTCTCTCTGGTTAGACCAGATCTGAGCCTGGGAGCTCTCTGGCTA
 501 ACTAGGGAACCCACTGCTTAAGCCTCAATAAAGCTTGCCTTGAGTGCTCA
 551 AAGTAGTGTGTGCCCGTCTGTTGTGTGACTCTGGTAACTAGAGATCCCTC
 601 AGACCCTTTTAGTCAGTGTGGAAAATCTCTAGCAGTGGCGCCCGAACAGG
 651 GACTTGAAAGCGAAAGTAAAGCCAGAGGAGATCTCTCGACGCAGGACTCG
 701 GCTTGCTGAAGCGCGCACGGCAAGAGGCGAGGGGCGGCGACTGGTGAGTA
 751 CGCCAAAAATTTTGACTAGCGGAGGCTAGAAGGAGAGAGATGGGTGCGAG
 801 AGCGTCGGTATTAAGCGGGGGAGAATTAGATAAATGGGAAAAAATTCGGT
 851 TAAGGCCAGGGGGAAAGAAACAATATAAACTAAAACATATAGTATGGGCA
 901 AGCAGGGAGCTAGAACGATTCGCAGTTAATCCTGGCCTTTTAGAGACATC
 951 AGAAGGCTGTAGACAAATACTGGGACAGCTACAACCATCCCTTCAGACAG
1001 GATCAGAAGAACTTAGATCATTATATAATACAATAGCAGTCCTCTATTGT
1051 GTGCATCAAAGGATAGATGTAAAAGACACCAAGGAAGCCTTAGATAAGAT
1101 AGAGGAAGAGCAAAACAAAAGTAAGAAAAAGGCACAGCAAGCAGCAGCTG
1151 ACACAGGAAACAACAGCCAGGTCAGCCAAAATTACCCTATAGTGCAGAAC
1201 CTCCAGGGGCAAATGGTACATCAGGCCATATCACCTAGAACTTTAAATGC
1251 ATGGGTAAAAGTAGTAGAAGAGAAGGCTTTCAGCCCAGAAGTAATACCCA
1301 TGTTTTCAGCATTATCAGAAGGAGCCACCCCACAAGATTTAAATACCATG
```

-continued

```
1351 CTAAACACAGTGGGGGACATCAAGCAGCCATGCAAATGTTAAAAGAGAC
1401 CATCAATGAGGAAGCTGCAGAATGGGATAGATTGCATCCAGTGCATGCAG
1451 GGCCTATTGCACCAGGCCAGATGAGAGAACCAAGGGGAAGTGACATAGCA
1501 GGAACTACTAGTACCCTTCAGGAACAAATAGGATGGATGACACATAATCC
1551 ACCTATCCCAGTAGGAGAAATCTATAAAAGATGGATAATCCTGGGATTAA
1601 ATAAAATAGTAAGAATGTATAGCCCTACCAGCATTCTGGACATAAGACAA
1651 GGACCAAAGGAACCCTTTAGAGACTATGTAGACCGATTCTATAAAACTCT
1701 AAGAGCCGAGCAAGCTTCACAAGAGGTAAAAAATTGGATGACAGAAACCT
1751 TGTTGGTCCAAAATGCGAACCCAGATTGTAAGACTATTTTAAAAGCATTG
1801 GGACCAGGAGCGACACTAGAAGAAATGATGACAGCATGTCAGGGAGTGGG
1851 GGGACCCGGCCATAAAGCAAGAGTTTTGGCTGAAGCAATGAGCCAAGTAA
1901 CAAATCCAGCTACCATAATGATACAGAAAGGCAATTTTAGGAACCAAAGA
1951 AAGACTGTTAAGTGTTTCAATTGTGGCAAAGAAGGGCACATAGCCAAAAA
2001 TTGCAGGGCCCCTAGGAAAAAGGGCTGTTGGAAATGTGGAAAGGAAGGAC
2051 ACCAAATGAAAGATTGTACTGAGAGACAGGCTAATTTTTTAGGGAAGATC
2101 TGGCCTTCCCACAAGGGAAGGCCAGGGAATTTTCTTCAGAGCAGACCAGA
2151 GCCAACAGCCCCACCAGAAGAGAGCTTCAGGTTTGGGGAAGAGACAACAA
2201 CTCCCTCTCAGAAGCAGGAGCCGATAGACAAGGAACTGTATCCTTTAGCT
2251 TCCCTCAGATCACTCTTTGGCAGCGACCCCTCGTCACAATAAAGATAGGG
2301 GGGCAATTAAAGGAAGCTCTATTAGATACAGGAGCAGATGATACAGTATT
2351 AGAAGAAATGAATTTGCCAGGAAGATGGAAACCAAAAATGATAGGGGAA
2401 TTGGAGGTTTTATCAAAGTAGGACAGTATGATCAGATACTCATAGAAATC
2451 TGCGGACATAAAGCTATAGGTACAGTATTAGTAGGACCTACACCTGTCAA
2501 CATAATTGGAAGAAATCTGTTGACTCAGATTGGCTGCACTTTAAATTTTC
2551 CCATTAGTCCTATTGAGACTGTACCAGTAAAATTAAAGCCAGGAATGGAT
2601 GGCCCAAAAGTTAAACAATGGCCATTGACAGAAGAAAAAATAAAAGCATT
2651 AGTAGAAATTTGTACAGAAATGGAAAAGGAAGGAAAAATTTCAAAAATTG
2701 GGCCTGAAAATCCATACAATACTCCAGTATTTGCCATAAAGAAAAAAGAC
2751 AGTACTAAATGGAGAAAATTAGTAGATTTCAGAGAACTTAATAAGAGAAC
2801 TCAAGATTTCTGGGAAGTTCAATTAGGAATACCACATCCTGCAGGGTTAA
2851 AACAGAAAAAATCAGTAACAGTACTGGATGTGGGCGATGCATATTTTTCA
2901 GTTCCCTTAGATAAAGACTTCAGGAAGTATACTGCATTTACCATACCTAG
2951 TATAAACAATGAGACACCAGGGATTAGATATCAGTACAATGTGCTTCCAC
3001 AGGGATGGAAAGGATCACCAGCAATATTCCAGTGTAGCATGACAAAAATC
3051 TTAGAGCCTTTTAGAAAACAAAATCCAGACATAGTCATCTATCAATACAT
3101 GGATGATTTGTATGTAGGATCTGACTTAGAAATAGGGCAGCATAGAACAA
3151 AAATAGAGGAACTGAGACAACATCTGTTGAGGTGGGGATTTACCACACCA
3201 GACAAAAAACATCAGAAAGAACCTCCATTCCTTTGGATGGGTTATGAACT
3251 CCATCCTGATAAATGGACAGTACAGCCTATAGTGCTGCCAGAAAAGGACA
3301 GCTGGACTGTCAATGACATACAGAAATTAGTGGGAAAATTGAATTGGGCA
```

-continued

```
3351 AGTCAGATTTATGCAGGGATTAAAGTAAGGCAATTATGTAAACTTCTTAG
3401 GGGAACCAAAGCACTAACAGAAGTAGTACCACTAACAGAAGAAGCAGAGC
3451 TAGAACTGGCAGAAAACAGGGAGATTCTAAAAGAACCGGTACATGGAGTG
3501 TATTATGACCCATCAAAAGACTTAATAGCAGAAATACAGAAGCAGGGGCA
3551 AGGCCAATGGACATATCAAATTTATCAAGAGCCATTTAAAAATCTGAAAA
3601 CAGGAAAATATGCAAGAATGAAGGGTGCCCACACTAATGATGTGAAACAA
3651 TTAACAGAGGCAGTACAAAAAATAGCCACAGAAAGCATAGTAATATGGGG
3701 AAAGACTCCTAAATTTAAATTACCCATACAAAAGGAAACATGGGAAGCAT
3751 GGTGGACAGAGTATTGGCAAGCCACCTGGATTCCTGAGTGGGAGTTTGTC
3801 AATACCCCTCCCTTAGTGAAGTTATGGTACCAGTTAGAGAAAGAACCCAT
3851 AATAGGAGCAGAAACTTTCTATGTAGATGGGGCAGCCAATAGGGAAACTA
3901 AATTAGGAAAAGCAGGATATGTAACTGACAGAGGAAGACAAAAAGTTGTC
3951 CCCCTAACGGACACAACAAATCAGAAGACTGAGTTACAAGCAATTCATCT
4001 AGCTTTGCAGGATTCGGGATTAGAAGTAAACATAGTGACAGACTCACAAT
4051 ATGCATTGGGAATCATTCAAGCACAACCAGATAAGAGTGAATCAGAGTTA
4101 GTCAGTCAAATAATAGAGCAGTTAATAAAAAAGGAAAAAGTCTACCTGGC
4151 ATGGGTACCAGCACACAAAGGAATTGGAGGAAATGAACAAGTAGATGGGT
4201 TGGTCAGTGCTGGAATCAGGAAAGTACTATTTTTAGATGGAATAGATAAG
4251 GCCCAAGAAGAACATGAGAAATATCACAGTAATTGGAGAGCAATGGCTAG
4301 TGATTTTAACCTACCACCTGTAGTAGCAAAAGAAATAGTAGCCAGCTGTG
4351 ATAAATGTCAGCTAAAAGGGGAAGCCATGCATGGACAAGTAGACTGTAGC
4401 CCAGGAATATGGCAGCTAGATTGTACACATTTAGAAGGAAAAGTTATCTT
4451 GGTAGCAGTTCATGTAGCCAGTGGATATATAGAAGCAGAAGTAATTCCAG
4501 CAGAGACAGGGCAAGAAACAGCATACTTCCTCTTAAAATTAGCAGGAAGA
4551 TGGCCAGTAAAAACAGTACATACAGACAATGGCAGCAATTTCACCAGTAC
4601 TACAGTTAAGGCCGCCTGTTGGTGGGCGGGGATCAAGCAGGAATTTGGCA
4651 TTCCCTACAATCCCCAAAGTCAAGGAGTAATAGAATCTATGAATAAAGAA
4701 TTAAAGAAAATTATAGGACAGGTAAGAGATCAGGCTGAACATCTTAAGAC
4751 AGCAGTACAAATGGCAGTATTCATCCACAATTTTAAAAGAAAAGGGGGGA
4801 TTGGGGGGTACAGTGCAGGGGAAAGAATAGTAGACATAATAGCAACAGAC
4851 ATACAAACTAAAGAATTACAAAAACAAATTACAAAAATTCAAAATTTTCG
4901 GGTTTATTACAGGGACAGCAGAGATCCAGTTTGGAAAGGACCAGCAAAGC
4951 TCCTCTGGAAAGGTGAAGGGGCAGTAGTAATACAAGATAATAGTGACATA
5001 AAAGTAGTGCCAAGAAGAAAAGCAAAGATCATCAGGGATTATGGAAAACA
5051 GATGGCAGGTGATGATTGTGTGGCAAGTAGACAGGATGAGGATTAACACA
5101 TGGAAAAGATTAGTAAAACACCATATGTATATTTCAAGGAAAGCTAAGGA
5151 CTGGTTTTATAGACATCACTATGAAAGTACTAATCCAAAAATAAGTTCAG
5201 AAGTACACATCCCACTAGGGGATGCTAAATTAGTAATAACAACATATTGG
5251 GGTCTGCATACAGGAGAAAGAGACTGGCATTTGGGTCAGGGAGTCTCCAT
5301 AGAATGGAGGAAAAAGAGATATAGCACACAAGTAGACCCTGACCTAGCAG
5351 ACCAACTAATTCATCTGCACTATTTTGATTGTTTTTCAGAATCTGCTATA
```

-continued

```
5401 AGAAATACCATATTAGGACGTATAGTTAGTCCTAGGTGTGAATATCAAGC

5451 AGGACATAACAAGGTAGGATCTCTACAGTACTTGGCACTAGCAGCATTAA

5501 TAAAACCAAAACAGATAAAGCCACCTTTGCCTAGTGTTAGGAAACTGACA

5551 GAGGACAGATGGAACAAGCCCCAGAAGACCAAGGGCCACAGAGGGAGCCA

5601 TACAATGAATGGACACTAGAGCTTTTAGAGGAACTTAAGAGTGAAGCTGT

5651 TAGACATTTTCCTAGGATATGGCTCCATAACTTAGGACAACATATCTATG

5701 AAACTTACGGGGATACTTGGGCAGGAGTGGAAGCCATAATAAGAATTCTG

5751 CAACAACTGCTGTTTATCCATTTCAGAATTGGGTGTCGACATAGCAGAAT

5801 AGGCGTTACTCGACAGAGGAGAGCAAGAAATGGAGCCAGTAGATCCTAGA

5851 CTAGAGCCCTGGAAGCATCCAGGAAGTCAGCCTAAAACTGCTTGTACCAA

5901 TTGCTATTGTAAAAAGTGTTGCTTTCATTGCCAAGTTTGTTTCATGACAA

5951 AAGCCTTAGGCATCTCCTATGGCAGGAAGAAGCGGAGACAGCGACGAAGA

6001 GCTCATCAGAACAGTCAGACTCATCAAGCTTCTCTATCAAAGCAGTAAGT

6051 AGTACATGTAATGCAACCTATAATAGTAGCAATAGTAGCATTAGTAGTAG

6101 CAATAATAATAGCAATAGTTGTGTGGTCCATAGTAATCATAGAATATAGG

6151 AAAATATTAAGACAAAGAAAAATAGACAGGTTAATTGATAGACTAATAGA

6201 AAGAGCAGAAGACAGTGGCAATGAGAGTGAAGGAGAAGTATCAGCACTTG

6251 TGGAGATGGGGGTGGAAATGGGGCACCATGCTCCTTGGGATATTGATGAT

6301 CTGTAGTGCTACAGAAAAATTGTGGGTCACAGTCTATTATGGGGTACCTG

6351 TGTGGAAGGAAGCAACCACCACTCTATTTTGTGCATCAGATGCTAAAGCA

6401 TATGATACAGAGGTACATAATGTTTGGGCCACACATGCCTGTGTACCCAC

6451 AGACCCCAACCCACAAGAAGTAGTATTGGTAAATGTGACAGAAAATTTTA

6501 ACATGTGGAAAAATGACATGGTAGAACAGATGCATGAGGATATAATCAGT

6551 TTATGGGATCAAAGCCTAAAGCCATGTGTAAAATTAACCCCACTCTGTGT

6601 TAGTTTAAAGTGCACTGATTTGAAGAATGATACTAATACCAATAGTAGTA

6651 GCGGGAGAATGATAATGGAGAAAGGAGAGATAAAAAACTGCTCTTTCAAT

6701 ATCAGCACAAGCATAAGAGATAAGGTGCAGAAAGAATATGCATTCTTTTA

6751 TAAACTTGATATAGTACCAATAGATAATACCAGCTATAGGTTGATAAGTT

6801 GTAACACCTCAGTCATTACACAGGCCTGTCCAAAGGTATCCTTTGAGCCA

6851 ATTCCCATACATTATTGTGCCCCGGCTGGTTTTGCGATTCTAAAATGTAA

6901 TAATAAGACGTTCAATGGAACAGGACCATGTACAAATGTCAGCACAGTAC

6951 AATGTACACATGGAATCAGGCCAGTAGTATCAACTCAACTGCTGTTAAAT

7001 GGCAGTCTAGCAGAAGAAGATGTAGTAATTAGATCTGCCAATTTCACAGA

7051 CAATGCTAAAACCATAATAGTACAGCTGAACACATCTGTAGAAATTAATT

7101 GTACAAGACCCAACAACAATACAAGAAAAAGTATCCGTATCCAGAGGGGA

7151 CCAGGGAGAGCATTTGTTACAATAGGAAAAATAGGAAATATGAGACAAGC

7201 ACATTGTAACATTAGTAGAGCAAAATGGAATGCCACTTTAAAACAGATAG

7251 CTAGCAAATTAAGAGAACAATTTGGAAATAATAAAACAATAATCTTTAAG

7301 CAATCCTCAGGAGGGGACCCAGAAATTGTAACGCACAGTTTTAATTGTGG

7351 AGGGGAATTTTTCTACTGTAATTCAACACAACTGTTTAATAGTACTTGGT
```

-continued

```
7401 TTAATAGTACTTGGAGTACTGAAGGGTCAAATAACACTGAAGGAAGTGAC

7451 ACAATCACACTCCCATGCAGAATAAAACAATTTATAAACATGTGGCAGGA

7501 AGTAGGAAAAGCAATGTATGCCCCTCCCATCAGTGGACAAATTAGATGTT

7551 CATCAAATATTACTGGGCTGCTATTAACAAGAGATGGTGGTAATAACAAC

7601 AATGGGTCCGAGATCTTCAGACCTGGAGGAGGCGATATGAGGGACAATTG

7651 GAGAAGTGAATTATATAAATATAAAGTAGTAAAAATTGAACCATTAGGAG

7701 TAGCACCCACCAAGGCAAAGAGAAGAGTGGTGCAGAGAGAAAAAGAGCA

7751 GTGGGAATAGGAGCTTTGTTCCTTGGGTTCTTGGGAGCAGCAGGAAGCAC

7801 TATGGGCTGCACGTCAATGACGCTGACGGTACAGGCCAGACAATTATTGT

7851 CTGATATAGTGCAGCAGCAGAACAATTTGCTGAGGGCTATTGAGGCGCAA

7901 CAGCATCTGTTGCAACTCACAGTCTGGGGCATCAAACAGCTCCAGGCAAG

7951 AATCCTGGCTGTGGAAAGATACCTAAAGGATCAACAGCTCCTGGGGATTT

8001 GGGGTTGCTCTGGAAAACTCATTTGCACCACTGCTGTGCCTTGGAATGCT

8051 AGTTGGAGTAATAAATCTCTGGAACAGATTTGGAATAACATGACCTGGAT

8101 GGAGTGGGACAGAGAAATTAACAATTACACAAGCTTAATACACTCCTTAA

8151 TTGAAGAATCGCAAAACCAGCAAGAAAAGAATGAACAAGAATTATTGGAA

8201 TTAGATAAATGGGCAAGTTTGTGGAATTGGTTTAACATAACAAATTGGCT

8251 GTGGTATATAAAATTATTCATAATGATAGTAGGAGGCTTGGTAGGTTTAA

8301 GAATAGTTTTTGCTGTACTTTCTATAGTGAATAGAGTTAGGCAGGGATAT

8351 TCACCATTATCGTTTCAGACCCACCTCCCAATCCCGAGGGGACCCGACAG

8401 GCCCGAAGGAATAGAAGAAGAAGGTGGAGAGAGAGACAGAGACAGATCCA

8451 TTCGATTAGTGAACGGATCCTTAGCACTTATCTGGGACGATCTGCGGAGC

8501 CTGTGCCTCTTCAGCTACCACCGCTTGAGAGACTTACTCTTGATTGTAAC

8551 GAGGATTGTGGAACTTCTGGGACGCAGGGGGTGGGAAGCCCTCAAATATT

8601 GGTGGAATCTCCTACAGTATTGGAGTCAGGAACTAAAGAATAGTGCTGTT

8651 AACTTGCTCAATGCCACAGCCATAGCAGTAGCTGAGGGGACAGATAGGGT

8701 TATAGAAGTATTACAAGCAGCTTATAGAGCTATTCGCCACATACCTAGAA

8751 GAATAAGACAGGGCTTGGAAAGGATTTTGCTATAAGATGGGTGGCAAGTG

8801 GTCAAAAAGTAGTGTGATTGGATGGCCTGCTGTAAGGGAAAGAATGAGAC

8851 GAGCTGAGCCAGCAGCAGATGGGTGGGAGCAGTATCTCGAGACCTAGAA

8901 AAACATGGAGCAATCACAAGTAGCAATACAGCAGCTAACAATGCTGCTTG

8951 TGCCTGGCTAGAAGCACAAGAGGAGGAAGAGGTGGGTTTTCCAGTCACAC

9001 CTCAGGTACCTTTAAGACCAATGACTTACAAGGCAGCTGTAGATCTTAGC

9051 CACTTTTTAAAAGAAAAGGGGGGACTGGAAGGGCTAATTCACTCCCAAAG

9101 AAGACAAGATATCCTTGATCTGTGGATCTACCACACACAAGGCTACTTCC

9151 CTGATTGGCAGAACTACACACCAGGGCCAGGGGTCAGATATCCACTGACC

9201 TTTGGATGGTGCTACAAGCTAGTACCAGTTGAGCCAGATAAGGTAGAAGA

9251 GGCCAATAAAGGAGAGAACACCAGCTTGTTACACCCTGTGAGCCTGCATG

9301 GAATGGATGACCCTGAGAGAGAAGTGTTAGAGTGGAGGTTTGACAGCCGC

9351 CTAGCATTTCATCACGTGGCCCGAGAGCTGCATCCGGAGTACTTCAAGAA

9401 CTGCTGACATCGAGCTTGCTACAAGGGACTTTCCGCTGGGGACTTTCCAG
```

```
9451 GGAGGCGTGGCCTGGGCGGGACTGGGGAGTGGCGAGCCCTCAGATGCTGC

9501 ATATAAGCAGCTGCTTTTTGCCTGTACTGGGTCTCTCTGGTTAGACCAGA

9551 TCTGAGCCTGGGAGCTCTCTGGCTAACTAGGGAACCCACTGCTTAAGCCT

9601 CAATAAAGCTTGCCTTGAGTGCTTCAAGTAGTGTGTGCCCGTCTGTTGTG

9651 TGACTCTGGTAACTAGAGATCCCTCAGACCCTTTTAGTCAGTGTGGAAAA

9701 TCTCTAGCA
```

However, for the purposes of comparing the nucleotide sequences of non-pathogenic HIV-1 strains including the ability to hybridise to a reference strain, the present invention extends to a genomic nucleotide sequence from any pathogenic strain of HIV-1.

Accordingly, in a particularly preferred embodiment, there is provided a viral isolate which;

(i) caries a genome which is capable of hybridising under medium stringency conditions to SEQ ID NO: 1 or a complementary form thereof or an analogous sequence from another pathogenic strain of HIV-1; and (ii) carries a deletion mutation in a region corresponding to the nef gene and/or in an LTR region. Generally, such an HIV-1 isolate is non-pathogenic as hereinbefore defined.

In a related embodiment, there is provided an isolated virus which:

(i) has a genome which is capable of hybridising under medium stringency conditions to complementary nucleic acid from a pathogenic strain of HIV-1; and (ii) carries one or more deletion mutations in a region of its genome corresponding to a region which contains nef coding sequences and LTR nucleotide sequences.

For the purposes of defining the level of stringency, reference can conveniently be made to Maniatis et al (1982) at pages 387–389 which is herein incorporated by reference where the washing steps disclosed are considered high stringency. A low stringency is defined herein as being in 1–3×SSC/0.1–0.5% w/v SDS at 37–50° C. for 2–3 hours. Depending on the source and concentration of nucleic acid involved in the hybridisation, alternative conditions of stringency may be employed such as medium stringent conditions which are considered herein to be 0.1–1×SSC/0.25–0.5% w/v SDS at≧45° C. for 2–3 hours or high stringent conditions considered herein to be 0.1–1×SSC/0.1% w/v SDS at 60° C. for 1–3 hours.

In a particularly preferred embodiment of the present invention, the non-pathogenic strain of HIV-1 carries a mutation in the nef gene and/or LTR region of the genome.

A "mutation" is considered herein to include a single or multiple nucleotide substitution, deletion and/or addition. Most preferred mutations are single or multiple deletions of at least one, most preferably at least ten and even more preferably at least twenty contiguous nucleotides from a region corresponding to the nef gene and/or the LTR region. When the non-pathogenic virus carries a mutation in the LTR region, this generally occurs 5' of the Sp1 sites.

According to a preferred aspect of the present invention, there is provided a viral isolate which:

(i) is reactive to antibodies to a glycoprotein from HIV-1 such as at least one of gp41-45, gp120 and/or gp160;

(ii) is substantially non-pathogenic in human subjects; and (iii) carries a deletion mutation of at least ten nucleotides in a region corresponding to the nef gene and/or LTR region of a pathogenic strain of HIV-1.

In another embodiment, there is provided a viral isolate which:

(i) is capable of inducing an immune response to at least one of gag, pot and/or env;

(ii) is substantially non-pathogenic in human subjects; and (iii) carries a deletion mutation of at least ten nucleotides in a region corresponding to the nef gene and/or LTR region of a pathogenic strain of HIV-1.

Preferably, in respect of the latter embodiment, the immune response is an antibody or a cell mediated response. In a most preferred embodiment, the immune response is a humoral immune response.

The nucleotide sequence of the nef gene in HIV-1 NL4-3 is defined in SEQ ID NO: 650:

```
ATGGGTGGCAAGTGGTCAAAAAGTAGTGTGATTGGATGGCCTGCTGTAAGGGAAAGAAT

GAGACGAGCTGAGCCAGCAGCAGATGGGGTGGGAGCAGTATCTCGAGACCTAGAAAAAC

ATGGAGCAATCACAAGTAGCAATACAGCAGCTAACAATGCTGCTTGTGCCTGGCTAGAA

GCACAAGAGGAGGAAGAGGTGGGTTTTCCAGTCACACCTCAGGTACCTTTAAGACCAAT

GACTTACAAGGCAGCTGTAGATCTTAGCCACTTTTTAAAAGAAAAGGGGGGACTGGAAG

GGCTAATTCACTCCCAAAGAAGACAAGATATCCTTGATCTGTGGATCTACCACACACAA

GGCTACTTCCCTGATTGGCAGAACTACACACCAGGGCCAGGGGTCAGATATCCACTGAC

CTTTGGATGGTGCTACAAGCTAGTACCAGTTGAGCCAGATAAGGTAGAAGAGGCCAATA

AAGGAGAGAACACCAGCTTGTTACACCCTGTGAGCCTGCATGGAATGGATGACCCTGAG

AGAGAAGTGTTAGAGTGGAGGTTTGACAGCCGCCTAGCATTTCATCACGTGGCCCGAGA
```

-continued

GCTGCATCCGGAGTACTTCAAGAACTGCTGA

The present invention extends to any or all single or multiple nucleotide deletions to a contiguous series of at least ten nucleotides from the nef gene which render the strain avirulent. The deletions may encompass the entire gene or parts thereof and may represent a single deletion or two or more deletions. Put in alternative terms, the non-pathogenic HIV-1 isolates of the present invention comprise a nucleotide sequence at the corresponding nef gene region non-identifiable to SEQ ID NO: 650, said non-identity comprising at least 5%, more preferably at least 10% and even more preferably at least 20% variation thereon.

In a preferred embodiment, therefore, the present invention contemplates a viral isolate which:

(i) is reactive to antibodies to a glycoprotein from HIV-1 such as at least one of gp41-45, gp120 and/or gp160;
(ii) carries a genome or a part or fragment thereof capable of hybridising under medium stringency conditions to a nucleotide sequence as set forth in SEQ ID NO: 1 or a complementary form thereof or an analogous sequence from another pathogenic strain of HIV-1;
(iii) carries a deletion of at least ten nucleotides in a region corresponding to the nef gene in HIV-1 NL4-3; and wherein said deletion encompasses one or more of the following decanucleotides from the nef gene of HIV-1 NL4-3 or corresponding sequences from another pathogenic strain of HIV-1:

| | | | |
|---|---|---|---|
| ATGGGTGGCA | (SEQ ID NO: 2); | TGGGTGGCAA | (SEQ ID NO: 3); |
| GGGTGGCAAG | (SEQ ID NO: 4); | GGTGGCAAGT | (SEQ ID NO: 5); |
| GTGGCAAGTG | (SEQ ID NO: 6); | TGGCAAGTGG | (SEQ ID NO: 7); |
| GGCAAGTGGT | (SEQ ID NO: 8); | GCAAGTGGTC | (SEQ ID NO: 9); |
| CAAGTGGTCA | (SEQ ID NO: 10); | AAGTGGTCAA | (SEQ ID NO: 11); |
| AGTGGTCAAA | (SEQ ID NO: 12); | GTGGTCAAAA | (SEQ ID NO: 13); |
| TGGTCAAAAA | (SEQ ID NO: 14); | GGTCAAAAAG | (SEQ ID NO: 15); |
| GTCAAAAAGT | (SEQ ID NO: 16); | TCAAAAAGTA | (SEQ ID NO: 17); |
| CAAAAAGTAG | (SEQ ID NO: 18); | AAAAAGTAGT | (SEQ ID NO: 19); |
| AAAAGTAGTG | (SEQ ID NO: 20); | AAAGTAGTGT | (SEQ ID NO: 21); |
| AAGTAGTGTG | (SEQ ID NO: 22); | AGTAGTGTGA | (SEQ ID NO: 23); |
| GTAGTGTGAT | (SEQ ID NO: 24); | TAGTGTGATT | (SEQ ID NO: 25); |
| AGTGTGATTG | (SEQ ID NO: 26); | GTGTGATTGG | (SEQ ID NO: 27); |
| TGTGATTGGA | (SEQ ID NO: 28); | GTGATTGGAT | (SEQ ID NO: 29); |
| TGATTGGATG | (SEQ ID NO: 30); | GATTGGATGG | (SEQ ID NO: 31); |
| ATTGGATGGC | (SEQ ID NO: 32); | TTGGATGGCC | (SEQ ID NO: 33); |
| TGGATGGCCT | (SEQ ID NO: 34); | GGATGGCCTG | (SEQ ID NO: 35); |
| GATGGCCTGC | (SEQ ID NO: 36); | ATGGCCTGCT | (SEQ ID NO: 37); |
| TGGCCTGCTG | (SEQ ID NO: 38); | GGCCTGCTGT | (SEQ ID NO: 39); |
| GCCTGCTGTA | (SEQ ID NO: 40); | CCTGCTGTAA | (SEQ ID NO: 41); |
| CTGCTGTAAG | (SEQ ID NO: 42); | TGCTGTAAGG | (SEQ ID NO: 43); |
| GCTGTAAGGG | (SEQ ID NO: 44); | CTGTAAGGGA | (SEQ ID NO: 45); |
| TGTAAGGGAA | (SEQ ID NO: 46); | GTAAGGGAAA | (SEQ ID NO: 47); |
| TAAGGGAAAG | (SEQ ID NO: 48); | AAGGGAAAGA | (SEQ ID NO: 49); |
| AGGGAAAGAA | (SEQ ID NO: 50); | GGGAAAGAAT | (SEQ ID NO: 51); |
| GGAAAGAATG | (SEQ ID NO: 52); | GAAAGAATGA | (SEQ ID NO: 53); |
| AAAGAATGAG | (SEQ ID NO: 54); | AAGAATGAGA | (SEQ ID NO: 55); |
| AGAATGAGAC | (SEQ ID NO: 56); | GAATGAGACG | (SEQ ID NO: 57); |
| AATGAGACGA | (SEQ ID NO: 58); | ATGAGACGAG | (SEQ ID NO: 59); |
| TGAGACGAGC | (SEQ ID NO: 60); | GAGACGAGCT | (SEQ ID NO: 61); |

-continued

| | | | |
|---|---|---|---|
| AGACGAGCTG (SEQ ID NO: 62); | GACGAGCTGA (SEQ ID NO: 63); |
| ACGAGCTGAG (SEQ ID NO: 64); | CGAGCTGAGC (SEQ ID NO: 65); |
| GAGCTGAGCC (SEQ ID NO: 66); | AGCTGAGCCA (SEQ ID NO: 67); |
| GCTGAGCCAG (SEQ ID NO: 68); | CTGAGCCAGC (SEQ ID NO: 69); |
| TGAGCCAGCA (SEQ ID NO: 70); | GAGCCAGCAG (SEQ ID NO: 71); |
| AGCCAGCAGC (SEQ ID NO: 72); | GCCAGCAGCA (SEQ ID NO: 73); |
| CCAGCAGCAG (SEQ ID NO: 74); | CAGCAGCAGA (SEQ ID NO: 75); |
| AGCAGCAGAT (SEQ ID NO: 76); | GCAGCAGATG (SEQ ID NO: 77); |
| CAGCAGATGG (SEQ ID NO: 78); | AGCAGATGGG (SEQ ID NO: 79); |
| GCAGATGGGG (SEQ ID NO: 80); | CAGATGGGGT (SEQ ID NO: 81); |
| AGATGGGGTG (SEQ ID NO: 82); | GATGGGGTGG (SEQ ID NO: 83); |
| ATGGGGTGGG (SEQ ID NO: 84); | TGGGGTGGGA (SEQ ID NO: 85); |
| GGGGTGGGAG (SEQ ID NO: 86); | GGGTGGGAGC (SEQ ID NO: 87); |
| GGTGGGAGCA (SEQ ID NO: 88); | GTGGGAGCAG (SEQ ID NO: 89); |
| TGGGAGCAGT (SEQ ID NO: 90); | GGGAGCAGTA (SEQ ID NO: 91); |
| GGAGCAGTAT (SEQ ID NO: 92); | GAGCAGTATC (SEQ ID NO: 93); |
| AGCAGTATCT (SEQ ID NO: 94); | GCAGTATCTC (SEQ ID NO: 95); |
| CAGTATCTCG (SEQ ID NO: 96); | AGTATCTCGA (SEQ ID NO: 97); |
| GTATCTCGAG (SEQ ID NO: 98); | TATCTCGAGA (SEQ ID NO: 99); |
| ATCTCGAGAC (SEQ ID NO: 100); | TCTCGAGACC (SEQ ID NO: 101); |
| CTCGAGACCT (SEQ ID NO: 102); | TCGAGACCTA (SEQ ID NO: 103); |
| CGAGACCTAG (SEQ ID NO: 104); | GAGACCTAGA (SEQ ID NO: 105); |
| AGACCTAGAA (SEQ ID NO: 106); | GACCTAGAAA (SEQ ID NO: 107); |
| ACCTAGAAAA (SEQ ID NO: 108); | CCTAGAAAAA (SEQ ID NO: 109); |
| CTAGAAAAAC (SEQ ID NO: 110); | TAGAAAACA (SEQ ID NO: 111); |
| AGAAAACAT (SEQ ID NO: 112); | GAAAACATG (SEQ ID NO: 113); |
| AAAAACATGG (SEQ ID NO: 114); | AAAACATGGA (SEQ ID NO: 115); |
| AAACATGGAG (SEQ ID NO: 116); | AACATGGAGC (SEQ ID NO: 117); |
| ACATGGAGCA (SEQ ID NO: 118); | CATGGAGCAA (SEQ ID NO: 119); |
| ATGGAGCAAT (SEQ ID NO: 120); | TGGAGCAATC (SEQ ID NO: 121); |
| GGAGCAATCA (SEQ ID NO: 122); | GAGCAATCAC (SEQ ID NO: 123); |
| AGCAATCACA (SEQ ID NO: 124); | GCAATCACAA (SEQ ID NO: 125); |
| CAATCACAAG (SEQ ID NO: 126); | AATCACAAGT (SEQ ID NO: 127); |
| ATCACAAGTA (SEQ ID NO: 128); | TCACAAGTAG (SEQ ID NO: 129); |
| CACAAGTAGC (SEQ ID NO: 130); | ACAAGTAGCA (SEQ ID NO: 131); |
| CAAGTAGCAA (SEQ ID NO: 132); | AAGTAGCAAT (SEQ ID NO: 133); |
| AGTAGCAATA (SEQ ID NO: 134); | GTAGCAATAC (SEQ ID NO: 135); |
| TAGCAATACA (SEQ ID NO: 136); | AGCAATACAG (SEQ ID NO: 137); |
| GCAATACAGC (SEQ ID NO: 138); | CAATACAGCA (SEQ ID NO: 139); |
| AATACAGCAG (SEQ ID NO: 140); | ATACAGCAGC (SEQ ID NO: 141); |

-continued

TACAGCAGCT (SEQ ID NO: 142); ACAGCAGCTA (SEQ ID NO: 143);

CAGCAGCTAA (SEQ ID NO: 144); AGCAGCTAAC (SEQ ID NO: 145);

GCAGCTAACA (SEQ ID NO: 146); CAGCTAACAA (SEQ ID NO: 147);

AGCTAACAAT (SEQ ID NO: 148); GCTAACAATG (SEQ ID NO: 149);

CTAACAATGC (SEQ ID NO: 150); TAACAATGCT (SEQ ID NO: 151);

AACAATGCTG (SEQ ID NO: 152); ACAATGCTGC (SEQ ID NO: 153);

CAATGCTGCT (SEQ ID NO: 154); AATGCTGCTT (SEQ ID NO: 155);

ATGCTGCTTG (SEQ ID NO: 156); TGCTGCTTGT (SEQ ID NO: 157);

GCTGCTTGTG (SEQ ID NO: 158); CTGCTTGTGC (SEQ ID NO: 159);

TGCTTGTGCC (SEQ ID NO: 160); GCTTGTGCCT (SEQ ID NO: 161);

CTTGTGCCTG (SEQ ID NO: 162); TTGTGCCTGG (SEQ ID NO: 163);

TGTGCCTGGC (SEQ ID NO: 164); GTGCCTGGCT (SEQ ID NO: 165);

TGCCTGGCTA (SEQ ID NO: 166); GCCTGGCTAG (SEQ ID NO: 167);

CCTGGCTAGA (SEQ ID NO: 168); CTGGCTAGAA (SEQ ID NO: 169);

TGGCTAGAAG (SEQ ID NO: 170); GGCTAGAAGC (SEQ ID NO: 171);

GCTAGAAGCA (SEQ ID NO: 172); CTAGAAGCAC (SEQ ID NO: 173);

TAGAAGCACA (SEQ ID NO: 174); AGAAGCACAA (SEQ ID NO: 175);

GAAGCACAAG (SEQ ID NO: 176); AAGCACAAGA (SEQ ID NO: 177);

AGCACAAGAG (SEQ ID NO: 178); GCACAAGAGG (SEQ ID NO: 179);

CACAAGAGGA (SEQ ID NO: 180); ACAAGAGGAG (SEQ ID NO: 181);

CAAGAGGAGG (SEQ ID NO: 182); AAGAGGAGGA (SEQ ID NO: 183);

AGAGGAGGAA (SEQ ID NO: 184); GAGGAGGAAG (SEQ ID NO: 185);

AGGAGGAAGA (SEQ ID NO: 186); GGAGGAAGAG (SEQ ID NO: 187);

GAGGAAGAGG (SEQ ID NO: 188); AGGAAGAGGT (SEQ ID NO: 189);

GGAAGAGGTG (SEQ ID NO: 190); GAAGAGGTGG (SEQ ID NO: 191);

AAGAGGTGGG (SEQ ID NO: 192); AGAGGTGGGT (SEQ ID NO: 193);

GAGGTGGGTT (SEQ ID NO: 194); AGGTGGGTTT (SEQ ID NO: 195);

GGTGGGTTTT (SEQ ID NO: 196); GTGGGTTTTC (SEQ ID NO: 197);

TGGGTTTTCC (SEQ ID NO: 198); GGGTTTTCCA (SEQ ID NO: 199);

GGTTTTCCAG (SEQ ID NO: 200); GTTTTCCAGT (SEQ ID NO: 201);

TTTTCCAGTC (SEQ ID NO: 202); TTTCCAGTCA (SEQ ID NO: 203);

TTCCAGTCAC (SEQ ID NO: 204); TCCAGTCACA (SEQ ID NO: 205);

CCAGTCACAC (SEQ ID NO: 206); CAGTCACACC (SEQ ID NO: 207);

AGTCACACCT (SEQ ID NO: 208); GTCACACCTC (SEQ ID NO: 209);

TCACACCTCA (SEQ ID NO: 210); CACACCTCAG (SEQ ID NO: 211);

ACACCTCAGG (SEQ ID NO: 212); CACCTCAGGT (SEQ ID NO: 213);

ACCTCAGGTA (SEQ ID NO: 214); CCTCAGGTAC (SEQ ID NO: 215);

CTCAGGTACC (SEQ ID NO: 216); TCAGGTACCT (SEQ ID NO: 217);

CAGGTACCTT (SEQ ID NO: 218); AGGTACCTTT (SEQ ID NO: 219);

GGTACCTTTA (SEQ ID NO: 220); GTACCTTTAA (SEQ ID NO: 221);

TACCTTTAAG (SEQ ID NO: 222); ACCTTTAAGA (SEQ ID NO: 223);

-continued

CCTTTAAGAC (SEQ ID NO: 224); CTTTAAGACC (SEQ ID NO: 225);

TTTAAGACCA (SEQ ID NO: 226); TTAAGACCAA (SEQ ID NO: 227);

TAAGACCAAT (SEQ ID NO: 228); AAGACCAATG (SEQ ID NO: 229);

AGACCAATGA (SEQ ID NO: 230); GACCAATGAC (SEQ ID NO: 231);

ACCAATGACT (SEQ ID NO: 232); CCAATGACTT (SEQ ID NO: 233);

CAATGACTTA (SEQ ID NO: 234); AATGACTTAC (SEQ ID NO: 235);

ATGACTTACA (SEQ ID NO: 236); TGACTTACAA (SEQ ID NO: 237);

GACTTACAAG (SEQ ID NO: 238); ACTTACAAGG (SEQ ID NO: 239);

CTTACAAGGC (SEQ ID NO: 240); TTACAAGGCA (SEQ ID NO: 241);

TACAAGGCAG (SEQ ID NO: 242); ACAAGGCAGC (SEQ ID NO: 243);

CAAGGCAGCT (SEQ ID NO: 244); AAGGCAGCTG (SEQ ID NO: 245);

AGGCAGCTGT (SEQ ID NO: 246); GGCAGCTGTA (SEQ ID NO: 247);

GCAGCTGTAG (SEQ ID NO: 248); CAGCTGTAGA (SEQ ID NO: 249);

AGCTGTAGAT (SEQ ID NO: 250); GCTGTAGATC (SEQ ID NO: 251);

CTGTAGATCT (SEQ ID NO: 252); TGTAGATCTT (SEQ ID NO: 253);

GTAGATCTTA (SEQ ID NO: 254); TAGATCTTAG (SEQ ID NO: 255);

AGATCTTAGC (SEQ ID NO: 256); GATCTTAGCC (SEQ ID NO: 257);

ATCTTAGCCA (SEQ ID NO: 258); TCTTAGCCAC (SEQ ID NO: 259);

CTTAGCCACT (SEQ ID NO: 260); TTAGCCACTT (SEQ ID NO: 261);

TAGCCACTTT (SEQ ID NO: 262); AGCCACTTTT (SEQ ID NO: 263);

GCCACTTTTT (SEQ ID NO: 264); CCACTTTTTA (SEQ ID NO: 265);

CACTTTTTAA (SEQ ID NO: 266); ACTTTTTAAA (SEQ ID NO: 267);

CTTTTTAAAA (SEQ ID NO: 268); TTTTTAAAAG (SEQ ID NO: 269);

TTTTAAAAGA (SEQ ID NO: 270); TTTAAAAGAA (SEQ ID NO: 271);

TTAAAAGAAA (SEQ ID NO: 272); TAAAAGAAAA (SEQ ID NO: 273);

AAAAGAAAAG (SEQ ID NO: 274); AAAGAAAAGG (SEQ ID NO: 275);

AAGAAAAGGG (SEQ ID NO: 276); AGAAAAGGGG (SEQ ID NO: 277);

GAAAAGGGGG (SEQ ID NO: 278); AAAAGGGGGG (SEQ ID NO: 279);

AAAGGGGGGA (SEQ ID NO: 280); AAGGGGGGAC (SEQ ID NO: 281);

AGGGGGGACT (SEQ ID NO: 282); GGGGGGACTG (SEQ ID NO: 283);

GGGGGACTGG (SEQ ID NO: 284); GGGGACTGGA (SEQ ID NO: 285);

GGGACTGGAA (SEQ ID NO: 286); GGACTGGAAG (SEQ ID NO: 287);

GACTGGAAGG (SEQ ID NO: 288); ACTGGAAGGG (SEQ ID NO: 289);

CTGGAAGGGC (SEQ ID NO: 290); TGGAAGGGCT (SEQ ID NO: 291);

GGAAGGGCTA (SEQ ID NO: 292); GAAGGGCTAA (SEQ ID NO: 293);

AAGGGCTAAT (SEQ ID NO: 294); AGGGCTAATT (SEQ ID NO: 295);

GGGCTAATTC (SEQ ID NO: 296); GGCTAATTCA (SEQ ID NO: 297);

GCTAATTCAC (SEQ ID NO: 298); CTAATTCACT (SEQ ID NO: 299);

TAATTCACTC (SEQ ID NO: 300); AATTCACTCC (SEQ ID NO: 301);

ATTCACTCCC (SEQ ID NO: 302); TTCACTCCCA (SEQ ID NO: 303);

-continued

TCACTCCCAA (SEQ ID NO: 304); CACTCCCAAA (SEQ ID NO: 305);

ACTCCCAAAG (SEQ ID NO: 306); CTCCCAAAGA (SEQ ID NO: 307);

TCCCAAAGAA (SEQ ID NO: 308); CCCAAAGAAG (SEQ ID NO: 309);

CCAAAGAAGA (SEQ ID NO: 310); CAAAGAAGAC (SEQ ID NO: 311);

AAAGAAGACA (SEQ ID NO: 312); AAGAAGACAA (SEQ ID NO: 313);

AGAAGACAAG (SEQ ID NO: 314); GAAGACAAGA (SEQ ID NO: 315);

AAGACAAGAT (SEQ ID NO: 316); AGACAAGATA (SEQ ID NO: 317);

GACAAGATAT (SEQ ID NO: 318); ACAAGATATC (SEQ ID NO: 319);

CAAGATATCC (SEQ ID NO: 320); AAGATATCCT (SEQ ID NO: 321);

AGATATCCTT (SEQ ID NO: 322); GATATCCTTG (SEQ ID NO: 323);

ATATCCTTGA (SEQ ID NO: 324); TATCCTTGAT (SEQ ID NO: 325);

ATCCTTGATC (SEQ ID NO: 326); TCCTTGATCT (SEQ ID NO: 327);

CCTTGATCTG (SEQ ID NO: 328); CTTGATCTGT (SEQ ID NO: 329);

TTGATCTGTG (SEQ ID NO: 330); TGATCTGTGG (SEQ ID NO: 331);

GATCTGTGGA (SEQ ID NO: 332); ATCTGTGGAT (SEQ ID NO: 333);

TCTGTGGATC (SEQ ID NO: 334); CTGTGGATCT (SEQ ID NO: 335);

TGTGGATCTA (SEQ ID NO: 336); GTGGATCTAC (SEQ ID NO: 337);

TGGATCTACC (SEQ ID NO: 338); GGATCTACCA (SEQ ID NO: 339);

GATCTACCAC (SEQ ID NO: 340); ATCTACCACA (SEQ ID NO: 341);

TCTACCACAC (SEQ ID NO: 342); CTACCACACA (SEQ ID NO: 343);

TACCACACAC (SEQ ID NO: 344); ACCACACACA (SEQ ID NO: 345);

CCACACACAA (SEQ ID NO: 346); CACACACAAG (SEQ ID NO: 347);

ACACACAAGG (SEQ ID NO: 348); CACACAAGGC (SEQ ID NO: 349);

ACACAAGGCT (SEQ ID NO: 350); CACAAGGCTA (SEQ ID NO: 351);

ACAAGGCTAC (SEQ ID NO: 352); CAAGGCTACT (SEQ ID NO: 353);

AAGGCTACTT (SEQ ID NO: 354); AGGCTACTTC (SEQ ID NO: 355);

GGCTACTTCC (SEQ ID NO: 356); GCTACTTCCC (SEQ ID NO: 357);

CTACTTCCCT (SEQ ID NO: 358); TACTTCCCTG (SEQ ID NO: 359);

ACTTCCCTGA (SEQ ID NO: 360); CTTCCCTGAT (SEQ ID NO: 361);

TTCCCTGATT (SEQ ID NO: 362); TCCCTGATTG (SEQ ID NO: 363);

CCCTGATTGG (SEQ ID NO: 364); CCTGATTGGC (SEQ ID NO: 365);

CTGATTGGCA (SEQ ID NO: 366); TGATTGGCAG (SEQ ID NO: 367);

GATTGGCAGA (SEQ ID NO: 368); ATTGGCAGAA (SEQ ID NO: 369);

TTGGCAGAAC (SEQ ID NO: 370); TGGCAGAACT (SEQ ID NO: 371);

GGCAGAACTA (SEQ ID NO: 372); GCAGAACTAC (SEQ ID NO: 373);

CAGAACTACA (SEQ ID NO: 374); AGAACTACAC (SEQ ID NO: 375);

GAACTACACA (SEQ ID NO: 376); AACTACACAC (SEQ ID NO: 377);

ACTACACACC (SEQ ID NO: 378); CTACACACCA (SEQ ID NO: 379);

TACACACCAG (SEQ ID NO: 380); ACACACCAGG (SEQ ID NO: 381);

CACACCAGGG (SEQ ID NO: 382); ACACCAGGGC (SEQ ID NO: 383);

CACCAGGGCC (SEQ ID NO: 384); ACCAGGGCCA (SEQ ID NO: 385);

-continued

CCAGGGCCAG (SEQ ID NO: 386); CAGGGCCAGG (SEQ ID NO: 387);

AGGGCCAGGG (SEQ ID NO: 388); GGGCCAGGGG (SEQ ID NO: 389);

GGCCAGGGGT (SEQ ID NO: 390); GCCAGGGGTC (SEQ ID NO: 391);

CCAGGGGTCA (SEQ ID NO: 392); CAGGGGTCAG (SEQ ID NO: 393);

AGGGGTCAGA (SEQ ID NO: 394); GGGGTCAGAT (SEQ ID NO: 395);

GGGTCAGATA (SEQ ID NO: 396); GGTCAGATAT (SEQ ID NO: 397);

GTCAGATATC (SEQ ID NO: 398); TCAGATATCC (SEQ ID NO: 399);

CAGATATCCA (SEQ ID NO: 400); AGATATCCAC (SEQ ID NO: 401);

GATATCCACT (SEQ ID NO: 402); ATATCCACTG (SEQ ID NO: 403);

TATCCACTGA (SEQ ID NO: 404); ATCCACTGAC (SEQ ID NO: 405);

TCCACTGACC (SEQ ID NO: 406); CCACTGACCT (SEQ ID NO: 407);

CACTGACCTT (SEQ ID NO: 408); ACTGACCTTT (SEQ ID NO: 409);

CTGACCTTTG (SEQ ID NO: 410); TGACCTTTGG (SEQ ID NO: 411);

GACCTTTGGA (SEQ ID NO: 412); ACCTTTGGAT (SEQ ID NO: 413);

CCTTTGGATG (SEQ ID NO: 414); CTTTGGATGG (SEQ ID NO: 415);

TTTGGATGGT (SEQ ID NO: 416); TTGGATGGTG (SEQ ID NO: 417);

TGGATGGTGC (SEQ ID NO: 418); GGATGGTGCT (SEQ ID NO: 419);

GATGGTGCTA (SEQ ID NO: 420); ATGGTGCTAC (SEQ ID NO: 421);

TGGTGCTACA (SEQ ID NO: 422); GGTGCTACAA (SEQ ID NO: 423);

GTGCTACAAG (SEQ ID NO: 424); TGCTACAAGC (SEQ ID NO: 425);

GCTACAAGCT (SEQ ID NO: 426); CTACAAGCTA (SEQ ID NO: 427);

TACAAGCTAG (SEQ ID NO: 428); ACAAGCTAGT (SEQ ID NO: 429);

CAAGCTAGTA (SEQ ID NO: 430); AAGCTAGTAC (SEQ ID NO: 431);

AGCTAGTACC (SEQ ID NO: 432); GCTAGTACCA (SEQ ID NO: 433);

CTAGTACCAG (SEQ ID NO: 434); TAGTACCAGT (SEQ ID NO: 435);

AGTACCAGTT (SEQ ID NO: 436); GTACCAGTTG (SEQ ID NO: 437);

TACCAGTTGA (SEQ ID NO: 438); ACCAGTTGAG (SEQ ID NO; 439);

CCAGTTGAGC (SEQ ID NO: 440); CAGTTGAGCC (SEQ ID NO: 441);

AGTTGAGCCA (SEQ ID NO: 442); GTTGAGCCAG (SEQ ID NO: 443);

TTGAGCCAGA (SEQ ID NO: 444); TGAGCCAGAT (SEQ ID NO: 445);

GAGCCAGATA (SEQ ID NO: 446); AGCCAGATAA (SEQ ID NO: 447);

GCCAGATAAG (SEQ ID NO: 448); CCAGATAAGG (SEQ ID NO: 449);

CAGATAAGGT (SEQ ID NO: 450); AGATAAGGTA (SEQ ID NO: 451);

GATAAGGTAG (SEQ ID NO: 452); ATAAGGTAGA (SEQ ID NO: 453);

TAAGGTAGAA (SEQ ID NO: 454); AAGGTAGAAG (SEQ ID NO: 455);

AGGTAGAAGA (SEQ ID NO: 456); GGTAGAAGAG (SEQ ID NO: 457);

GTAGAAGAGG (SEQ ID NO: 458); TAGAAGAGGC (SEQ ID NO: 459);

AGAAGAGGCC (SEQ ID NO: 460); GAAGAGGCCA (SEQ ID NO: 461);

AAGAGGCCAA (SEQ ID NO: 462); AGAGGCCAAT (SEQ ID NO: 463);

GAGGCCAATA (SEQ ID NO: 464); AGGCCAATAA (SEQ ID NO: 465);

-continued

GGCCAATAAA (SEQ ID NO: 466); GCCAATAAAG (SEQ ID NO: 467);

CCAATAAAGG (SEQ ID NO: 468); CAATAAAGGA (SEQ ID NO: 469);

AATAAAGGAG (SEQ ID NO: 470); ATAAAGGAGA (SEQ ID NO: 471);

TAAAGGAGAG (SEQ ID NO: 472); AAAGGAGAGA (SEQ ID NO: 473);

AAGGAGAGAA (SEQ ID NO: 474); AGGAGAGAAC (SEQ ID NO: 475);

GGAGAGAACA (SEQ ID NO: 476); GAGAGAACAC (SEQ ID NO: 477);

AGAGAACACC (SEQ ID NO: 478); GAGAACACCA (SEQ ID NO: 479);

AGAACACCAG (SEQ ID NO: 480); GAACACCAGC (SEQ ID NO: 481);

AACACCAGCT (SEQ ID NO: 482); ACACCAGCTT (SEQ ID NO: 483);

CACCAGCTTG (SEQ ID NO: 484); ACCAGCTTGT (SEQ ID NO: 485);

CCAGCTTGTT (SEQ ID NO: 486); CAGCTTGTTA (SEQ ID NO: 487);

AGCTTGTTAC (SEQ ID NO: 488); GCTTGTTACA (SEQ ID NO: 489);

CTTGTTACAC (SEQ ID NO: 490); TTGTTACACC (SEQ ID NO: 491);

TGTTACACCC (SEQ ID NO: 492); GTTACACCCT (SEQ ID NO: 493);

TTACACCCTG (SEQ ID NO: 494); TACACCCTGT (SEQ ID NO: 495);

ACACCCTGTG (SEQ ID NO: 496); CACCCTGTGA (SEQ ID NO: 497);

ACCCTGTGAG (SEQ ID NO: 498); CCCTGTGAGC (SEQ ID NO: 499);

CCTGTGAGCC (SEQ ID NO: 500); CTGTGAGCCT (SEQ ID NO: 501);

TGTGAGCCTG (SEQ ID NO: 502); GTGAGCCTGC (SEQ ID NO: 503);

TGAGCCTGCA (SEQ ID NO: 504); GAGCCTGCAT (SEQ ID NO: 505);

AGCCTGCATG (SEQ ID NO: 506); GCCTGCATGG (SEQ ID NO: 507);

CCTGCATGGA (SEQ ID NO: 508); CTGCATGGAA (SEQ ID NO: 509);

TGCATGGAAT (SEQ ID NO: 510); GCATGGAATG (SEQ ID NO: 511);

CATGGAATGG (SEQ ID NO: 512); ATGGAATGGA (SEQ ID NO: 513);

TGGAATGGAT (SEQ ID NO: 514); GGAATGGATG (SEQ ID NO: 515);

GAATGGATGA (SEQ ID NO: 516); AATGGATGAC (SEQ ID NO: 517);

ATGGATGACC (SEQ ID NO: 518); TGGATGACCC (SEQ ID NO: 519);

GGATGACCCT (SEQ ID NO: 520); GATGACCCTG (SEQ ID NO: 521);

ATGACCCTGA (SEQ ID NO: 522); TGACCCTGAG (SEQ ID NO: 523);

GACCCTGAGA (SEQ ID NO: 524); ACCCTGAGAG (SEQ ID NO: 525);

CCCTGAGAGA (SEQ ID NO: 526); CCTGAGAGAG (SEQ ID NO: 527);

CTGAGAGAGA (SEQ ID NO: 528); TGAGAGAGAA (SEQ ID NO: 529);

GAGAGAGAAG (SEQ ID NO: 530); AGAGAGAAGT (SEQ ID NO: 531);

GAGAGAAGTG (SEQ ID NO: 532); AGAGAAGTGT (SEQ ID NO: 533);

GAGAAGTGTT (SEQ ID NO: 534); AGAAGTGTTA (SEQ ID NO: 535);

GAAGTGTTAG (SEQ ID NO: 536); AAGTGTTAGA (SEQ ID NO: 537);

AGTGTTAGAG (SEQ ID NO: 538); GTGTTAGAGT (SEQ ID NO: 539);

TGTTAGAGTG (SEQ ID NO: 540); GTTAGAGTGG (SEQ ID NO: 541);

TTAGAGTGGA (SEQ ID NO: 542); TAGAGTGGAG (SEQ ID NO: 543);

AGAGTGGAGG (SEQ ID NO: 544); GAGTGGAGGT (SEQ ID NO: 545);

AGTGGAGGTT (SEQ ID NO: 546); GTGGAGGTTT (SEQ ID NO: 547);

-continued

| | | | | |
|---|---|---|---|---|
| TGGAGGTTTG | (SEQ ID NO: 548); | GGAGGTTTGA | (SEQ ID NO: 549); | |
| GAGGTTTGAC | (SEQ ID NO: 550); | AGGTTTGACA | (SEQ ID NO: 551); | |
| GGTTTGACAG | (SEQ ID NO: 552); | GTTTGACAGC | (SEQ ID NO: 553); | |
| TTTGACAGCC | (SEQ ID NO: 554); | TTGACAGCCG | (SEQ ID NO: 555); | |
| TGACAGCCGC | (SEQ ID NO: 556); | GACAGCCGCC | (SEQ ID NO: 557); | |
| ACAGCCGCCT | (SEQ ID NO: 558); | CAGCCGCCTA | (SEQ ID NO: 559); | |
| AGCCGCCTAG | (SEQ ID NO: 560); | GCCGCCTAGC | (SEQ ID NO: 561); | |
| CCGCCTAGCA | (SEQ ID NO: 562); | CGCCTAGCAT | (SEQ ID NO: 563); | |
| GCCTAGCATT | (SEQ ID NO: 564); | CCTAGCATTT | (SEQ ID NO: 565); | |
| CTAGCATTTC | (SEQ ID NO: 566); | TAGCATTTCA | (SEQ ID NO: 567); | |
| AGCATTTCAT | (SEQ ID NO: 568); | GCATTTCATC | (SEQ ID NO: 569); | |
| CATTTCATCA | (SEQ ID NO: 570); | ATTTCATCAC | (SEQ ID NO: 571); | |
| TTTCATCACG | (SEQ ID NO: 572); | TTCATCACGT | (SEQ ID NO: 573); | |
| TCATCACGTG | (SEQ ID NO: 574); | CATCACGTGG | (SEQ ID NO: 575); | |
| ATCACGTGGC | (SEQ ID NO: 576); | TCACGTGGCC | (SEQ ID NO: 577); | |
| CACGTGGCCC | (SEQ ID NO: 578); | ACGTGGCCCG | (SEQ ID NO: 579); | |
| CGTGGCCCGA | (SEQ ID NO: 580); | GTGGCCCGAG | (SEQ ID NO: 581); | |
| TGGCCCGAGA | (SEQ ID NO: 582); | GGCCCGAGAG | (SEQ ID NO: 583); | |
| GCCCGAGAGC | (SEQ ID NO: 584); | CCCGAGAGCT | (SEQ ID NO: 585); | |
| CCGAGAGCTG | (SEQ ID NO: 586); | CGAGAGCTGC | (SEQ ID NO: 587); | |
| GAGAGCTGCA | (SEQ ID NO: 588); | AGAGCTGCAT | (SEQ ID NO: 589); | |
| GAGCTGCATC | (SEQ ID NO: 590); | AGCTGCATCC | (SEQ ID NO: 591); | |
| GCTGCATCCG | (SEQ ID NO: 592); | CTGCATCCGG | (SEQ ID NO: 593); | |
| TGCATCCGGA | (SEQ ID NO: 594); | GCATCCGGAG | (SEQ ID NO: 595); | |
| CATCCGGAGT | (SEQ ID NO: 596); | ATCCGGAGTA | (SEQ ID NO: 597); | |
| TCCGGAGTAC | (SEQ ID NO: 598); | CCGGAGTACT | (SEQ ID NO: 599); | |
| CGGAGTACTT | (SEQ ID NO: 600); | GGAGTACTTC | (SEQ ID NO: 601); | |
| GAGTACTTCA | (SEQ ID NO: 602); | AGTACTTCAA | (SEQ ID NO: 603); | |
| GTACTTCAAG | (SEQ ID NO: 604); | TACTTCAAGA | (SEQ ID NO: 605); | |
| ACTTCAAGAA | (SEQ ID NO: 606); | CTTCAAGAAC | (SEQ ID NO: 607); | |
| TTCAAGAACT | (SEQ ID NO: 608); | TCAAGAACTG | (SEQ ID NO: 609); | |
| CAAGAACTGC | (SEQ ID NO: 610); | AAGAACTGCT | (SEQ ID NO: 611); | |
| AGAACTGCTG | (SEQ ID NO: 612); | GAACTGCTGA | (SEQ ID NO: 613). | |

Generally, the subject HIV-1 isolate is non-pathogenic as hereinbefore defined. Additionally, reference herein to "a deletion" includes reference to a contiguous or non-contiguous series of two or more deletions.

The non-pathogenic isolate may carry a single decanucleotide deletion or may carry more than one decanucleotide deletion. Where it carries multiple deletions these may all correspond to a contiguous sequence or be from different parts of the nef gene. Furthermore, the terminal end portions of a deletion may lie within a decanucleotide as defined above. It is emphasised that the present invention extends to analogous sequences from other pathogenic strains of HIV-1 which might carry nef genes with a slightly altered sequence relative to HIV-1 strain NL4-3.

In a most preferred embodiment of the present invention, there is provided a non-pathogenic strain of HIV-1 carrying a nucleotide sequence in its genome as set forth in SEQ ID No. 614:

GAAGAGATTTGGGAGAACATGACCTGGATGCAGTGGGAAAAAGAAATTCAC

AATCACACAAAATACATATACTCCTTACTTGAAAAATCGCAGAACCAACAA

-continued
GAAAAGAATGAACAAGAACTATTGGAATTGGATCAATGGGCAAGTTTGTGG

AATTGGTTTGACATAACAAAATGGCTGTGGTATATAAAAATATTCATAATG

GTAGTAGGAGGCTTGATAGGTTTAAGAATAGTTTTTGCTGTACTTTCTATA

GTGAATAGAGTTAGGCAGGGATACTCACCATTGTCGTTTCAGACCCTCCTC

CCAACCCCGAGGGGACCCGACAGGCCCGAAGGAATCGAAGAAGAAGGTGGA

GAGAGAGACAGAGACAGATCCACTCGATTAGTACACGGATTCTTAGCACTT

TTCTGGGACGACCTGAGGAGCCTGTGCCTCTTCCTCTACCACCACTTGAGA

GACTTACTCTTGATTGTAACAAGGATTGTGGAACTTCTGGGACGCAGGGGA

TGGGAAGCCCTCAAATATTGGTGGAACCTCCTAAAGTATTGGAGCCAGGAA

CTGCAGAAGAGTGCTGTTATCTTGCTCAATGCCACCGCCATAGCAGTAGCT

GAGGGGACAGATAGAGTTTTAGAAGTATTACAAAGAGCTTATAGAGCTATC

CTCCACATACCTAGAAGAATAAGACAGGGCCTCGAAATGGCTTTGCTATAA

AATGGGTGGCAAGTGAGCAAAAAGTAGTGTAGTCAGATAGCATGCATCATA

AGGGGTGGGGCCAACAACTAACAATGCTGATCGTGCCTGGCTAGAAGCAC

AAGAGAAGGAAGAAGCGGGTTTTCCAGTCAAACCTCAGGTAGCTGTAGATC

TTAGCCACTTTTTAAAAGAAAAGGGGGGACTGGAAGGGCTAATTCACTCCC

AAAGAAGACAAGATACACAGTGCTGCAAACTATTACCAGTGGAGTCAGCGA

AGATAGAAGAGGCCAATGGAGGAGAAAACCACAGATTGTTCTGTTGGGGAC

TTTCCATCCGTTGGGGACTTTCCAAGGCGGCGTGGCCTGGGTGACTAGTTC

CGGTGGGGACTTTCCAAGAAGGCGCGGCCTGGGCGGGACTGGGGAGTGGCG

AGCCCTCAGATGCTGCATATAAGCAGCTGCTTTCTGCTGTTACTGGGTCTC

TCGGGTTAGACCAGATCTGAGCCTGGGAGCTCTCTGGCTAACTAGGGAACC

CACTGCTTAAGCCTCAATAAAGCTTGCCTTGAGTGCTTCAAGTAGTGTGTG

CCCGTCTGTTGTGTGACTCTGGTATCTAG;

and/or SEQ ID NO: 615:

GAAACAATTTGGGATAACATGACCTGGATGCAGTGGGAAAGAGAAATTGAC

AATTACACAAACATAATATACACCTTAATTGAAGAATCGCAGAACCAACAA

GAAAAAAATGAACTAGAATTATTGGAATTGGATAAATGGGCAAATTTGTGG

AATTGGTTTAGTATATCAAACTGGCTATGGTATATAAAATTATTCATAATG

GTAGTAGGAGGCTTGGTAGGTTTAAGAATAGTTTTTACTGTACTTTCTATA

GTGAATAGAGTTAGGCAGGGATACTCACCATTGTCGTTTCAGACCCACCTC

-continued

CCAACCCCGAAGGGACCCGACAGGCCAGAAGGAATCGAAGAAGAAGGTGGA

GAGAGAGACAGAGGCAGCTCCACTCGATTAGTGCACGGATTCTTAGCACTT

TTCTGGGACGACCTGAGGAGTCTGTGCCTCTTCAGCTACCACCACTTGAGA

GACTTACTCTTGATTGTAACGAGGATTGTGGAACTTCTGGGACGCAGGGGA

TGGGAAGCCCTCAAATACTGGTGGAATCTCCTGCAGTATTGGAGGCAGGAA

CTACAGAAGAGTGCTGTTAGCTTGTTCAATGGCACGGCCATAGCAGTAGCT

GAGGGGACAGATAGAGTTATAGAAGCTTTACGAAGGGCTTATAGAGCTATT

CTCCACATACCTAGAAGAATAAGACAGGGCTTAGAAAGGGCTTTGCTATAA

AATGGGTGGCAAGTGGTCAGAAAGTAGTGTGGTTAGAAGGCATGTACCTTT

AAGACAAGGCAGCTATAGATCTTAGCCGCTTTTTAAAAGAAAAGGGGGGAC

TGGAAGGGCTAATTCACTCACAGAGAAGATCAGTTGAACCAGAAGAAGATA

GAAGAGGCCATGAAGAAGAAAACAACAGATTGTTCCGTTTGTTCCGTTGGG

GACTTTCCAGGAGACGTGGCCTGAGTGATAAGCCGCTGGGGACTTTCCGAA

GAGGCGTGACGGGACTTTCCAAGGCGACGTGGCCTGGGCGGGACTGGGGAG

TGGCGAGCCCTCAGATGCTGCATATAAGCAGCTGCTTTCTGCCTGTACTGG

GTCTCTCTGGTTAGACCAGATCTGAGCCTGGGAGCTCTCTGGCTAACTAGG

GAACCCACTGCTTAAGCCTCAATAAAGCTTGCCTTGAGTGCTTCAAGTAGT

GTGTGCCCGTCTGTTGTGTGACTCTGGTATCTAGA.

The present invention, however, extends to HIV-1 isolates which are non-pathogenic; carry genomes capable of hybridising under low stringency conditions to SEQ ID NO: 614 or SEQ ID NO: 615; and which do not direct the synthesis of a full length nef gene product.

In a further embodiment the present invention contemplates a viral isolate which:

(i) is reactive to antibodies to a glycoprotein from HIV-1 such as at least one of gp41-45, gp120 and/or gp160;

(ii) carries a genome or a part or fragment thereof capable of hybridising under medium stringency conditions to a nucleotide sequence as set forth in SEQ ID NO: 1 or a complementary form thereof or an analogous sequence from another pathogenic strain of HIV-1;

(iii) carries a deletion of at least ten nucleotides in a region corresponding to the LTR region in HIV-1 NL4-3; and wherein said deletion encompasses one or more of the following decanucleotides from the LTR region of HIV-1 NL4-3 or corresponding sequences from another pathogenic strain of HIV-1:

GCTTTTTGCC (SEQ ID NO: 652); CTTTTTGCCT (SEQ ID NO: 653);
TTTTTGCCTG (SEQ ID NO: 654); TTTTGCCTGT (SEQ ID NO: 655);
TTTGCCTGTA (SEQ ID NO: 656); TTGCCTGTAC (SEQ ID NO: 657);
TGCCTGTACT (SEQ ID NO: 658); GCCTGTACTG (SEQ ID NO: 659);
CCTGTACTGG (SEQ ID NO: 660); CTGTACTGGG (SEQ ID NO: 661);
TGTACTGGGT (SEQ ID NO: 662); GTACTGGGTC (SEQ ID NO: 663);
TACTGGGTCT (SEQ ID NO: 664); ACTGGGTCTC (SEQ ID NO: 665);
CTGGGTCTCT (SEQ ID NO: 666); TGGGTCTCTC (SEQ ID NO: 667);
GGGTCTCTCT (SEQ ID NO: 668); GGTCTCTCTG (SEQ ID NO: 669);
GTCTCTCTGG (SEQ ID NO: 670); TCTCTCTGGT (SEQ ID NO: 671);
CTCTCTGGTT (SEQ ID NO: 672); TCTCTGGTTA (SEQ ID NO: 673);
CTCTGGTTAG (SEQ ID NO: 674); TCTCTGGTTA (SEQ ID NO: 675);
CTGGTTAGAC (SEQ ID NO: 676); TGGTTAGACC (SEQ ID NO: 677);
GGTTAGACCA (SEQ ID NO: 678); GTTAGACCAG (SEQ ID NO: 679);
TTAGACCAGA (SEQ ID NO: 680); TAGACCAGAT (SEQ ID NO: 681);

-continued

| | | | | |
|---|---|---|---|---|
| AGACCAGATC | (SEQ ID NO: 682); | GACCAGATCT | (SEQ ID NO: 683); |
| ACCAGATCTG | (SEQ ID NO: 684); | CCAGATCTGA | (SEQ ID NO: 685); |
| CAGATCTGAG | (SEQ ID NO: 686); | AGATCTGAGC | (SEQ ID NO: 687); |
| GATCTGAGCC | (SEQ ID NO: 688); | ATCTGAGCCT | (SEQ ID NO: 689); |
| TCTGAGCCTG | (SEQ ID NO: 690); | CTGAGCCTGG | (SEQ ID NO: 691); |
| TGAGCCTGGG | (SEQ ID NO: 692); | GAGCCTGGGA | (SEQ ID NO: 693); |
| AGCCTGGGAG | (SEQ ID NO: 694); | GCCTGGGAGC | (SEQ ID NO: 695); |
| CCTGGGAGCT | (SEQ ID NO: 696); | CTGGGAGCTC | (SEQ ID NO: 697); |
| TGGGAGCTCT | (SEQ ID NO: 698); | GGGAGCTCTC | (SEQ ID NO: 699); |
| GGAGCTCTCT | (SEQ ID NO: 700); | GAGCTCTCTG | (SEQ ID NO: 701); |
| AGCTCTCTGG | (SEQ ID NO: 702); | GCTCTCTGGC | (SEQ ID NO: 703); |
| CTCTCTGGCT | (SEQ ID NO: 704); | TCTCTGGCTA | (SEQ ID NO: 705); |
| CTCTGGCTAA | (SEQ ID NO: 706); | TCTGGCTAAC | (SEQ ID NO: 707); |
| CTGGCTAACT | (SEQ ID NO: 708); | TGGCTAACTA | (SEQ ID NO: 709); |
| GGCTAACTAG | (SEQ ID NO: 710); | GCTAACTAGG | (SEQ ID NO: 711); |
| CTAACTAGGG | (SEQ ID NO: 712); | TAACTAGGGA | (SEQ ID NO: 713); |
| AACTAGGGAA | (SEQ ID NO: 714); | ACTAGGGAAC | (SEQ ID NO: 715); |
| CTAGGGAACC | (SEQ ID NO: 716); | TAGGGAACCC | (SEQ ID NO: 717); |
| AGGGAACCCA | (SEQ ID NO: 718); | GGGAACCCAC | (SEQ ID NO: 719); |
| GGAACCCACT | (SEQ ID NO: 720); | GAACCCACTG | (SEQ ID NO: 721); |
| AACCCACTGC | (SEQ ID NO: 722); | ACCCACTGCT | (SEQ ID NO: 723); |
| CCCACTGCTT | (SEQ ID NO: 724); | CCACTGCTTA | (SEQ ID NO: 725); |
| CACTGCTTAA | (SEQ ID NO: 726); | ACTGCTTAAG | (SEQ ID NO: 727); |
| CTGCTTAAGC | (SEQ ID NO: 728); | TGCTTAAGCC | (SEQ ID NO: 729); |
| GCTTAAGCCT | (SEQ ID NO: 730); | CTTAAGCCTC | (SEQ ID NO: 731); |
| TTAAGCCTCA | (SEQ ID NO: 732); | TAAGCCTCAA | (SEQ ID NO: 733); |
| AAGCCTCAAT | (SEQ ID NO: 734); | AGCCTCAATA | (SEQ ID NO: 735); |
| GCCTCAATAA | (SEQ ID NO: 736); | CCTCAATAAA | (SEQ ID NO: 737); |
| CTCAATAAAG | (SEQ ID NO: 738); | TCAATAAAGC | (SEQ ID NO: 739); |
| CAATAAAGCT | (SEQ ID NO: 740); | AATAAAGCTT | (SEQ ID NO: 741); |
| ATAAAGCTTG | (SEQ ID NO: 742); | TAAAGCTTGC | (SEQ ID NO: 743); |
| AAAGCTTGCC | (SEQ ID NO: 744); | AAGCTTGCCT | (SEQ ID NO: 745); |
| AGCTTGCCTT | (SEQ ID NO: 746); | GCTTGCCTTG | (SEQ ID NO: 747); |
| CTTGCCTTGA | (SEQ ID NO: 748); | TTGCCTTGAG | (SEQ ID NO: 749); |
| TGCCTTGAGT | (SEQ ID NO: 750); | GCCTTGAGTG | (SEQ ID NO: 751); |
| CCTTGAGTGC | (SEQ ID NO: 752); | CTTGAGTGCT | (SEQ ID NO: 753); |
| TTGAGTGCTT | (SEQ ID NO: 754); | TGAGTGCTTC | (SEQ ID NO: 755); |
| GAGTGCTTCA | (SEQ ID NO: 756); | AGTGCTTCAA | (SEQ ID NO: 757); |
| GTGCTTCAAG | (SEQ ID NO: 758); | TGCTTCAAGT | (SEQ ID NO: 759); |
| GCTTCAAGTA | (SEQ ID NO: 760); | CTTCAAGTAG | (SEQ ID NO: 761); |
| TTCAAGTAGT | (SEQ ID NO: 762); | TCAAGTAGTG | (SEQ ID NO: 763); |
| CAAGTAGTGT | (SEQ ID NO: 764); | AAGTAGTGTG | (SEQ ID NO: 765); |
| AGTAGTGTGT | (SEQ ID NO: 766); | GTAGTGTGTG | (SEQ ID NO: 767); |
| TAGTGTGTGC | (SEQ ID NO: 768); | AGTGTGTGCC | (SEQ ID NO: 769); |
| GTGTGTGCCC | (SEQ ID NO: 770); | TGTGTGCCCG | (SEQ ID NO: 771); |
| GTGTGCCCGT | (SEQ ID NO: 772); | TGTGCCCGTC | (SEQ ID NO: 773); |
| GTGCCCGTCT | (SEQ ID NO: 774); | TGCCCGTCTG | (SEQ ID NO: 775); |
| GCCCGTCTGT | (SEQ ID NO: 776); | CCCGTCTGTT | (SEQ ID NO: 777); |
| CCGTCTGTTG | (SEQ ID NO: 778); | CGTCTGTTGT | (SEQ ID NO: 779); |
| GTCTGTTGTG | (SEQ ID NO: 780); | TCTGTTGTGT | (SEQ ID NO: 781); |
| CTGTTGTGTG | (SEQ ID NO: 782); | TGTTGTGTGA | (SEQ ID NO: 783); |
| GTTGTGTGAC | (SEQ ID NO: 784); | TTGTGTGACT | (SEQ ID NO: 785); |
| TGTGTGACTC | (SEQ ID NO: 786); | GTGTGACTCT | (SEQ ID NO: 787); |
| TGTGTGACTC | (SEQ ID NO: 788); | GTGTGACTCT | (SEQ ID NO: 789); |
| TGTGACTCTG | (SEQ ID NO: 790); | GTGACTCTGG | (SEQ ID NO: 791); |
| TGACTCTGGT | (SEQ ID NO: 792); | GACTCTGGTA | (SEQ ID NO: 793); |
| ACTCTGGTAA | (SEQ ID NO: 794); | CTCTGGTAAC | (SEQ ID NO: 795); |
| TCTGGTAACT | (SEQ ID NO: 796); | CTGGTAACTA | (SEQ ID NO: 797); |
| TGGTAACTAG | (SEQ ID NO: 798); | GGTAACTAGA | (SEQ ID NO: 799). |

The non-pathogenic isolate may carry a single decanucleotide deletion in the LTR region or may carry multiple deletions in the same region or in the LTR region and another region such as the nef gene. In particular, the mutation may be in the LTR /nef overlap region. Where it carries multiple deletions, these may correspond to a contiguous sequence or be from different parts of the LTR region and/or nef gene. Furthermore, the terminal end portions of a deletion may lie within a decanucleotide as defined above.

Yet another aspect of the present invention provides an infectious molecular clone comprising genetic sequences derived from the non-pathogenic HIV-1 isolates as hereinbefore described and includes genetic sequences encoding major structural proteins such as gag, env and pol. Infectious molecular clones are particularly useful as genetic compositions capable of "infecting" host cells without need of viral coat. The infectious molecular clones of the present invention may also be derived from pathogenic HIV-1 strains rendered non-pathogenic as hereindescribed.

According to this latter embodiment, there is contemplated a method of attenuating a pathogenic strain of HIV-1, said method comprising inducing a mutation in the nef gene and/or an LTR region to generate a non-pathogenic HIV-1 strain as hereinbefore described. Preferred mutations are deletions of at least ten nucleotides such as one or more of the decanucleotides as hereinbefore described. The mutations may also constitute substitutions and/or insertions of heterologous nucleic acid molecules in the nef and/or LTR regions such as the incorporation of a sense (i.e. co-suppression) antisense or ribozyme molecule (see below).

In still yet another embodiment of the present invention, there is provided an isolated, non-pathogenic strain of HIV-1 comprising a deletion in its genome of at least 10 nucleotide within the region of nucleotide 8787 and 9709 and more particularly within the region 8800 and 9700 and even more preferably within the region 8800 and 9410, using the nucleotide numbering of HIV-1 NL4-3.

In one embodiment, the deletion of at least 10 nucleotides is from within a region selected from the list consisting of (using the nucleotide numbers of HIV-1 NL4-3):

| | | |
|---|---|---|
| nucleotide | (i) | 8830–8862; |
| | (ii) | 9009–9035; |
| | (iii) | 9019–9029; and |
| | (iv) | 9033–9049. |

In another embodiment, the deletion of at least 10 nucleotides is from within a region selected from the list consisting of (using the nucleotide numbers of HIV-1 NL4-3):

| | | |
|---|---|---|
| nucleotide | (v) | 9281–9371; |
| | (vi) | 9281–9362; |
| | (vii) | 9105–9224; and |
| | (viii) | 9271–9370. |

In yet another embodiment, the deletion of at least 10 nucleotides is from within a region selected from the list consisting of (using the nucleotide numbers of HIV-1 NL4-3):

| | | |
|---|---|---|
| nucleotide | (ix) | 8882–8928; |
| | (x) | 8850–9006; |
| | (xi) | 8792–9041; and |
| | (xii) | 9112–9204. |

In still yet another embodiment, the deletion of at least 10 nucleotides is from within a region selected from the list consisting of (using the nucleotide numbers of HIV-1 NL4-3):

| | | |
|---|---|---|
| nucleotide | (xiii) | 9105–9224; |
| | (xiv) | 9389–9395; and |
| | (xv) | 9281–9366. |

The above embodiments including any combinations thereof or functional equivalents thereof. Most preferred variants of HIV-1 are defined in Table 3.

Reference herein to the non-pathogenic HIV-1 strains of the present invention includes reference to components, parts, fragments and derivatives thereof including both genetic and non-genetic material. Furthermore, the non-pathogenic HIV-1 strains may be in isolated form or resident in peripheral blood mononuclear cells (PBMCs) or other like cells where the genome of the HIV-1 strains is integrated as DNA from said HIV-1 strains such as proviral DNA. In addition, the present invention extends to recombinant virus such as from (or resident in) prokaryotes or eukaryotes as well as in the form of infectious molecular clones.

Accordingly, the present invention provides for the non-pathogenic HIV-1 isolate, genomic material therefrom, complementary proviral DNA, molecular infectious clones, recombinant viral particles or genetic sequences therefrom or cells expressing same or blood cells carrying proviral DNA or to any mutants, derivatives, components, fragments, parts, homologues or analogues of the foregoing.

The non-pathogenic HIV-1 strains of the present invention are particularly useful in the development of therapeutic compositions, therapeutic molecules and/or diagnostic reagents. With regards to the former, the non-pathogenic HIV-1 strain may be considered as a live attenuated vaccine where individuals carrying DNA derived from said non-pathogenic HIV-1 strain such as proviral DNA in target cells are protected from infection by a corresponding pathogenic strain. The term "vaccine" is used in its broadest sense as a therapeutic composition or molecule which prevents or reduces HIV-1 infection or risk of infection or which ameliorates the symptoms of infection. It may involve the stimulation of an immune response or may involve blocking HIV-1 cells receptors and/or the use of genetic compositions, for example, to introduce riboymes or antisense molecules to HIV-1 directed genetic sequences or to prepare infectious molecular clones. For convenience, all such compositions are referred hereinafter to "therapeutic compositions".

Accordingly, the present invention contemplates a method for inhibiting or reducing the risk of infection by a pathogenic strain of HIV-1, said method comprising administering to a subject a non-pathogenic HIV-1 as hereinbefore defined in an amount effective to infect target cells and to generate target cells carrying proviral DNA from said non-pathogenic HIV-1. More particularly, the present invention contemplates a method for inhibiting or reducing productive infection of an individual by a pathogenic strain of HIV-1, said method comprising administering to a subject a non-pathogenic isolate of HIV-1 in an amount effective to infect target cells and to generate target cells carrying proviral DNA from said non-pathogenic HIV-1. By "productive infection" as used in the specification and claims herein is meant the infection of a cell or cells by a pathogenic strain of HIV-1 which leads ultimately to the symptomology of AIDS or AIDS related diseases. A cell infected productively produces pathogenic virions. By definition, infection of an individual by a non-pathogenic strain of HIV-1 would not lead to productive in infection. Non pathogenic HIV-1 strains generally replicate to a sufficient extent to protect cells against challenge by virulent or pathogenic strains. The methods of the present invention are applicable prophylactically (i.e. to prevent de novo infection) or therapeutically (i.e. to reduce or slow disease progression).

The present invention further provides a method for vaccinating an individual against the development of AIDS or AIDS related diseases, said method comprising administering to said individual a non-pathogenic isolate of HIV-1 in an amount effective to infect target cells and to generate target cells carrying proviral DNA from said non-pathogenic HIV-1. The term "vaccinating" should not be taken as limiting the invention to t he prevention of HIV-1 infection by solely immunological means. The term "vaccinating" includes any means of preventing productive infection of an individual by pathogenic HIV-1.

As an alternative to the above methods, a therapeutic composition as hereinbefore defined is administered. The non-pathogenic isolate may be administered inter alia as an isolated viral preparation or via infected blood cells. Another aspect of the invention provides a therapeutic composition for inhibiting or reducing the risk of infection by a pathogenic strain of HIV-1 said therapeutic composition comprising a non-pathogenic strain of HIV-1 or genetic sequences derived therefrom as hereinbefore described and optionally one or more pharmaceutically acceptable carriers and/or diluents. The therapeutic composition of the present invention is generally suitable for intravenous, intraperitoneal, intramuscular, intramucosal (e.g. nasal spray, respiratory spray) or other forms of parenteral administration. The therapeutic composition might also be administered via an implant or rectally or orally. In addition to the mutations contemplated above, the non-pathogenic HIV-1 strain may also contain one or more other mutations to further reduce the risk of reversion to virulence and/or to insert a genetic sequence capable of providing directly or indirectly an identifiable signal, having further anti-HIV-1 properties and /or immunostimulatory or cell regulatory properties, For example, the non-pathogenic HIV-1 isolate in the therapeutic composition may comprise additional genetic material capable of directing expression of antisense nucleotide sequences to inhibit expression of one or more proteins encoded by a pathogenic strain of HIV-1. Alternatively, sense co-suppression may be employed. Preferred sense or antisense molecules would reduce expression of the nef gene or affect normal functioning of the LTR region.

According to this embodiment, the non-pathogenic HIV-1 strain may be considered as a targeting agent to introduce genetic constructs capable of reducing expression of one or more HIV-1 proteins or polypeptides. In this embodiment there is provided a viral isolate which:

(i) is genetically or immunologically related to a pathogenic strain of HIV-1;

(ii) is substantially non-pathogenic in human subjects;

(iii) comprises a first nucleotide sequence constituting its genome which is capable of hybridising under medium stringency conditions to SEQ ID NO: 1 or a complementary form thereof; and (iv) comprises a second nucleotide sequence within said first nucleotide sequence and which second nucleotide sequence directs expression of a mRNA molecule capable of inhibiting, reducing or otherwise down-regulating translation of a protein or polypeptide encoded by a pathogenic strain of HIV-1 or inhibit, reduce or otherwise down regulate operation of a non-protein encoding a region of a pathogenic strain of HIV-1.

Preferred proteins or polypeptides targeted for reduced expression are those encoded by one or more of the following: gag, pol, env, tat, rev, vpu, vpr, vif and/or nef genes. The most preferred protein or polypeptide targeted for reduced expression is the product of the nef gene. Alternatively, the target nucleotide sequence does not encode a polypeptide or protein but is required for other functions such as integration or excision from the human genome or expression of genes on the viral genome. An example of such a nucleotide sequence is the LTR region. Accordingly, the present invention extends to disruption to the function of such regions.

The above aspect relates to use of antisense technology. The present invention extends, however, to use of ribozymes and/or co-suppression to achieve the same results. In an alternative embodiment, or in addition to, the second (or optionally a third) nucleotide sequence encodes an antiviral agent (e.g. interferon) and/or an immune enhancing agent.

The identification of deletions Inter alia in the nef gene and/or LTR region in asymptomatic subjects provides a unique opportunity to study the in vivo effects of attenuated HIV-1 strains carrying one or more mutations in selected genetic regions. In particular, the present invention provides a means for designing therapeutic compositions directed to inhibiting expression of a nef gene and/or LTR region in a pathogenic HIV-1 strain (such as contemplated above) as well as developing a therapeutic regimem aimed at inhibiting the activity of the nef gene product for the function of the LTR region. According to this latter embodiment, the present invention provides a therapeutic composition comprising a molecule capable of inhibiting the intracellular activity of the nef gene product and/or LTR region, said composition further comprising one or more pharmaceutically acceptable carriers and/or diluents.

The molecule contemplated by the above aspect of the subject invention may be a protein, polypeptide, peptide, chemical compound, sugar moiety or derivative of the nef gene product. The molecule will need to be capable of entering an infected cell. Where the molecule is a protein, polypeptide or peptide, it may be encoded by the second nucleotide sequence on the targeting vector as contemplated above. Alternatively, the molecule may be a nucleic acid molecule capable of targeting the nef gene or LTR region.

The deletion mutants of the present invention may result in a modified nef gene product either having no readily discernable activity or having activity different to the naturally occurring nef protein. In any event, if a mutant nef gene product is produced, it will generally have a lower molecular weight than the naturally occurring nef protein and will have a different overall amino acid sequence. This provides, therefore, for a means for diagnosing individuals with benign HIV-1 infection by, for example, assaying for a modified nef protein or screening for a modified nef gene sequence. Alternatively, benign HIV-1 infection may be detected by assaying for a modified LTR region such as an altered nucleotide sequence.

According to one embodiment, there is provided a method for determining the pathogenicity of an HIV-1 strain after said HIV-1 strain infects cells of an individual, said method comprising contacting a biological sample from said individual with an effective amount of an antibody specific to a nef protein from a non-pathogenic strain of HIV-1 (as hereinbefore defined) for a time and under conditions sufficient to form an antibody-modified nef protein complex and then detecting said complex. The presence of said complex is indicative of a modified nef gene product and of the non-pathogenicity of the strain of HIV-1. The biological sample is a sample likely to contain the modified nef gene product such as tissue extract or cell extract of an infected cell. However, where the modified nef gene product is capable of permeation or transport out of the cell, suitable biological fluid would include serum, whole blood, lymph and mucosal secretion amongst other fluids. Many variations in the subject assay are possible and are contemplated herein. For example, an assay could be based on the inability for a nef specific antibody to bind to a modified nef protein. For the purposes of the present invention the term "contacting" including "mixing".

The presence of a modified nef molecule in biological fluid can be detected using a wide range of immunoassay techniques such as those described in U.S. Pat. Nos. 4,016,043, 4,424,279 and 4,018,653. These include both single-site and two-site, or "sandwich", assays of the non-competitive types, as well as in the traditional competitive binding assays and include ELISA and RIA techniques. Sandwich assays are among the most useful and commonly used assays and are favoured for use in the present invention. A number of variations of the sandwich assay technique exist, and all are intended to be encompassed by the present invention. Briefly, and by way of example only, in a typical forward assay, a modified nef product-specific antibody is immobilised onto a solid substrate to form a first complex and the sample to be tested for modified nef product brought into contact with the bound molecule. After a suitable period of incubation, for a period of time sufficient to allow formation of an antibody-modified nef product secondary complex, a second modified nef protein antibody, labelled with a reporter molecule capable of producing a detectable signal, is then added and incubated, allowing time sufficient for the formation of a tertiary complex of antibody-modified nef product-antibody. Any unreacteded material is washed away, and the presence of the tertiary complex is determined by observation of a signal produced by the reporter molecule. The results may either be qualitative, by simple observation of the visible signal or may be quantitated by comparison with a control sample containing known amounts of hapten. Variations of the forward assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent. The antibodies used above may be monoclonal or polyclonal.

The solid substrate is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay re either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with the specific enzymes are generally chosen for the production,upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining complex is then exposed to the light of the appropriate wavelength, the fluorescence observed indicates the presence of the hapten of interest. Immunofluorescence and EIA techniques arc both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose. It will also be apparent that the foregoing can be used to label a modified nef product and to use same directly in the detection of, for example, circulatory antibodies specific to said modified nef product.

Alternatively, genetic assays may be conducted to screen for abberations in the nef gene and/or LTR region. Such a genetic assay may be by Southern or Northern blot analysis, PCR analysis or the like using oligonucleotides specific to a deleted region of a nef gene and/or LTR region.

According to this embodiment there is provided a method for determining the pathogenicity of an HIV-1 strain after said HIV-1 strain infects cells of an individual, said method comprising determining directly or indirectly the presence of a deletion mutation in the genome of said HIV-1 wherein the presence of a such a mutation is indicative of the presence of a non-pathogenic strain of HIV-1. The deletion mutation may result in the genome being unable to synthesise a polypeptide or protein from a pathogenic strain of HIV-1 or may direct the synthesis of a truncated form of said polypeptide or protein. The mutation may also lead to altered expression of a polypeptide detectable by, for example, decreased synthesis of a particular protein, such as the nef gene product. Alternatively, the deletion mutation affects the LTR region or a regulatory region of the HIV-1 genome. In either case, affected viruses may also be detected by, for example, observing low viral copy numbers such as low viral loads.

Preferably, said non-pathogenic HIV-1 carries a deletion in its genome of at least 10 nucleotides within the region from nucleotide 8787 to nucleotide 9709 using the nucleotide numbering of HIV-1 strain NL4-3.

Preferably, said non-pathogenic HIV-1 carries a deletion in its genome of at least 10 nucleotides from within a region selected from the list consisting of:

| nucleotide | (i) | 8830–8862; |
|---|---|---|
| | (ii) | 9009–9035; |
| | (iii) | 9019–9029; and |
| | (iv) | 9033–9049. |

Preferably, said non-pathogenic HIV-1 carries a deletion in its genome of at least 10 nucleotides from within a region selected from the list consisting of:

| nucleotide | (v) | 9281–9371; |
|---|---|---|
| | (vi) | 9281–9362; |
| | (vii) | 9105–9224; and |
| | (viii) | 9271–9370. |

Preferably, said non-pathogenic HIV-1 carries a deletion in its genome of at least 10 nucleotides from within a region selected from the list consisting of:

| nucleotide | (ix) | 8882–8928; |
|---|---|---|
| | (x) | 8850–9006; |
| | (xi) | 8792–9041; and |
| | (xii) | 9112–9204. |

Preferably, said non-pathogenic HIV-1 carries a deletion in its genome of at least 10 nucleotides from within a region selected from the list consisting of:

| nucleotide | (xiii) | 9105–9224; |
|---|---|---|
| | (xiv) | 9389–9395; and |
| | (xv) | 9281–9366. |

The above nucleotide numbers are based on the nucleotide numbering in the NL4-3 genome.

Particularly preferred oligonucleotides are based on the deleted regions of the nef gene and/or LTR region such as but not limited to one or more oligonucleotides based on SEQ ID NO: 2 to SEQ ID NO: 613 and/or SEQ ID NO: 652 to SEQ ID NO: 799.

The present invention further extends to kits for the diagnosis of infection by pathogenic strains of HIV-1 or for determining the pathogenicity of infecting virus. The kits would be in compartmental form each comprising one or more suitable reagents for conducting the assay.

The present invention is further described by the following non-limiting Figures and Examples.

IN THE FIGURES:

FIG. 1 is a representation showing the alignment of the nucleotide sequences from donor D36 peripheral blood mononuclear cell (PBMC) [D36P] and non-pathogenic HIV-1 from recipient C18 $HIV_{SrV}$ [C18S], C18 $HIV_{MBC}$ [C18M] and C98 HIV [C98H] and C54 PBMC [C54P] with the equivalent region of HIV-1 NL4-3. Sequences labelled PBMC are from patient PBMC, those labelled HIV are from virus isolated from patient PBMC and grown in culture. Numbering for HIV-1 NL4-3 is as per Myer et al (1992) where nucleotide 1 is the first nucleotide of the complete proviral DNA sequence. D36P, C18S, C18M, C98H and C54P are numbered from the start of the region sequenced. Identity with NL4-3 sequence is shown by (*). Deleted nucleotides are shown by (-). Spaces introduced to maximise alignment are shown by (,). Features in NL4-3 are marked by overlining the sequence, features in D36 and C18 are marked by underlining the sequence.

FIG. 2 shows the alignment of encoded amino acid sequences of (a) tat exon 3 and (b) rev exon 3 from HIV-1 NL4-3, D36 PBMC, C18 $HIV_{SrV}$ and C98 HIV. In-phase termination codons (*) and NL4-3 encoded amino acid numbers are shown.

FIG. 3 is a representation showing the alignment of C-terminal envelope glycoprotein gp41 amino acid sequences encoded by D36 PMBC, C18 $HIV_{SrV}$, C18 $HIV_{MBC}$ and C98 HIV. Numbering is that of the amino acid sequence of the mature envelope glycoprotein of HIV NL4-3. Termination in shown by (#).

FIG. 4 is a representation showing alignment of amino acid sequences encoded by the nef genes of HIV-1 NL4-3, D36 PBMC, C18 $HIV_{SrV}$, C18 $HIV_{MBC}$ and C98 HIV. In phase termination codons are shown by (#). Identical amino acids are shown by (*). Residues underlined are those immediately before a deletion.

FIG. 5 shows a duplication of NFKB and Sp1 sequences in D36 PBMC, C18 $HIV_{SrV}$, C18 $HIV_{MBC}$ and C98 HIV demonstrated by alignment of their low homology region sequences with the NFKB-Sp1 region of HIV-1 NL4-3. Nucleotide numbering according to FIG. 1. Identity with NL4-3 sequence shown by (*) and NFKB and Sp1 sites in NL4-3 ovetlined. Position of nef/LTR region sequence deletion shown by (Δ).

Figure 6:
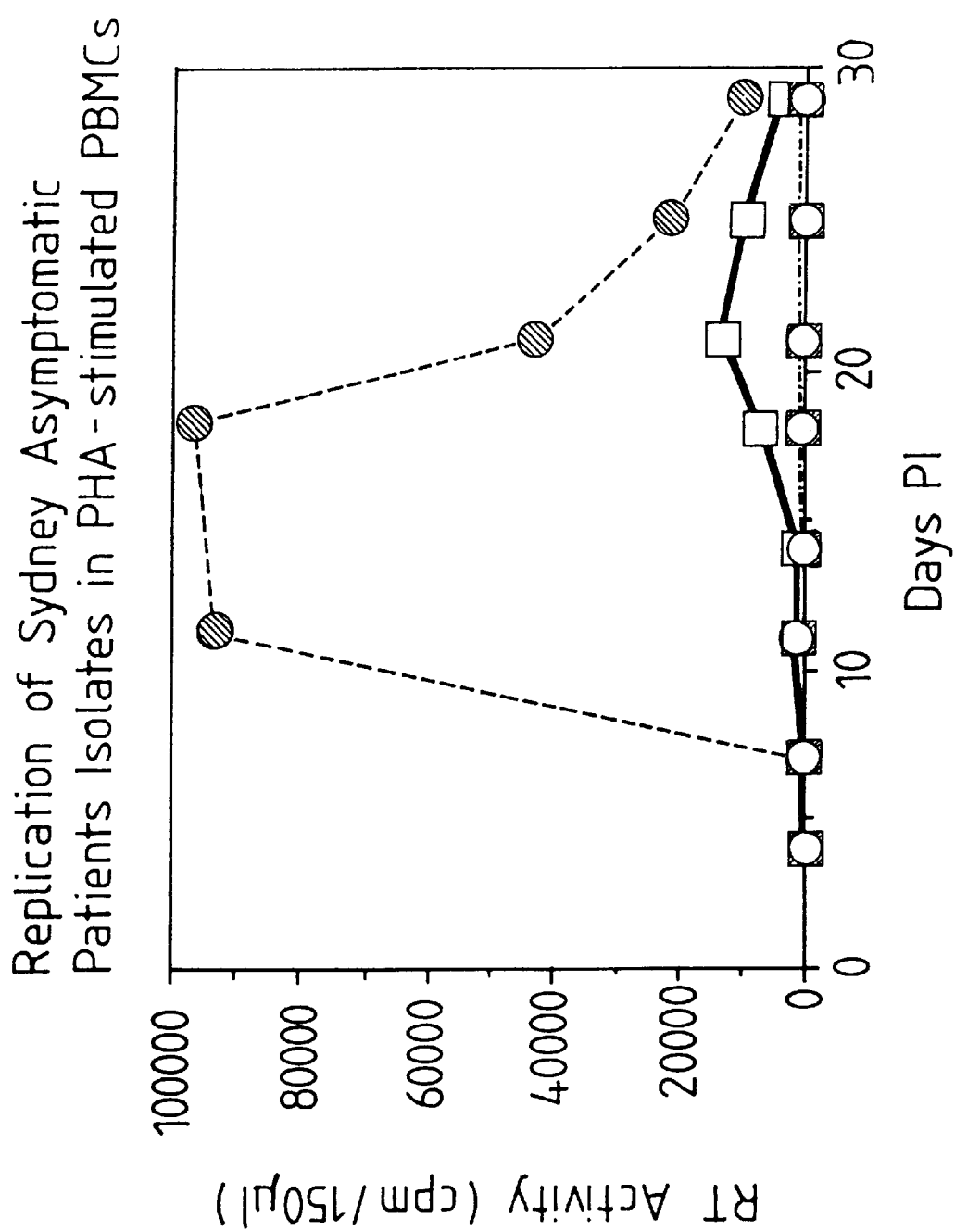

FIG. 6 is a graphical representation showing replication of C18 and C98 viral isolates and D36 PBMCs from asymptomatic patients in PHA-stimulated PBMCs.

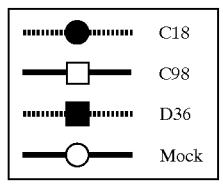

Figure 7:
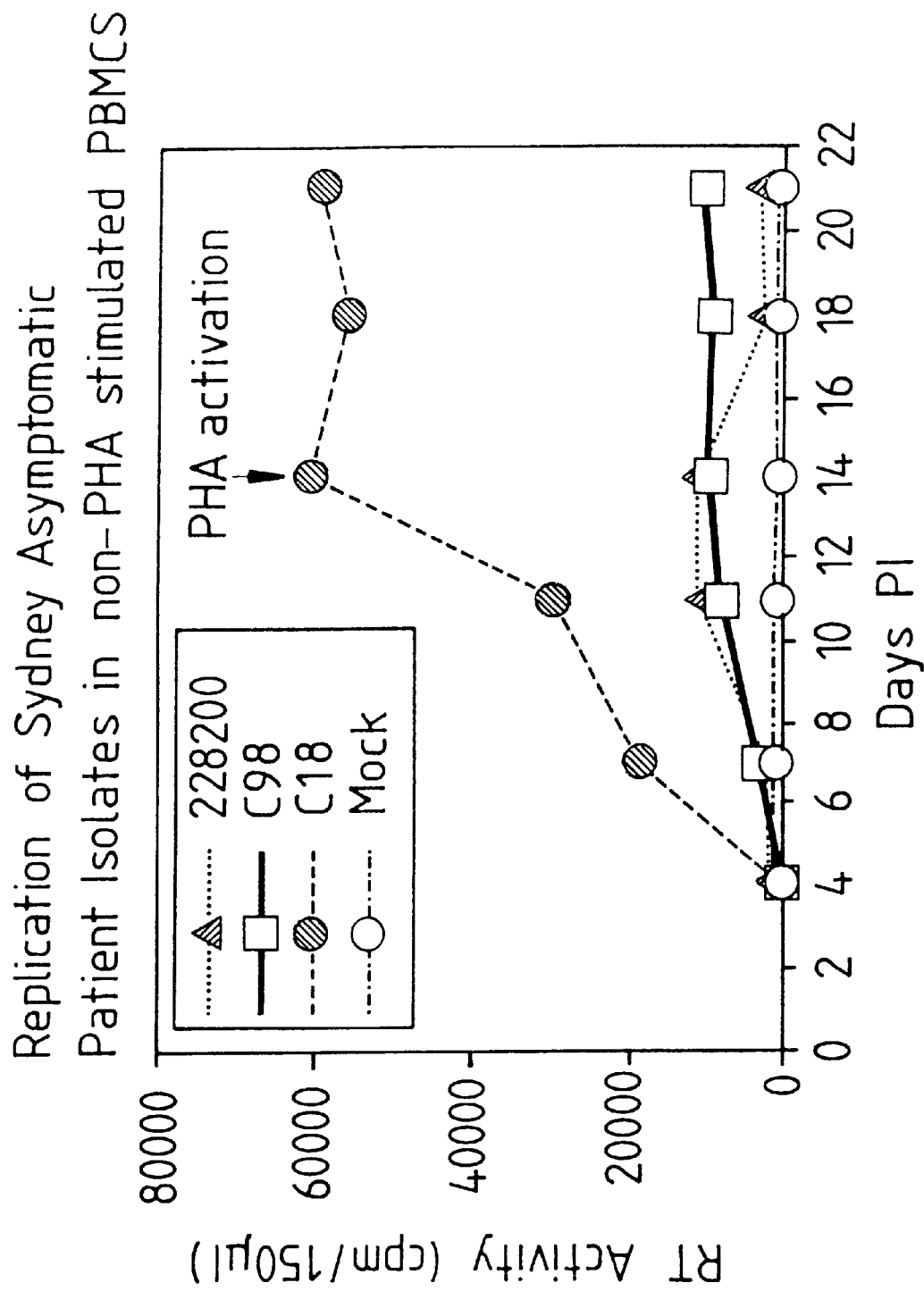

FIG. 7 is a graphical representation showing replication of viral isolates from asymptomatic patients in non-PHA stimulated PBMCs.

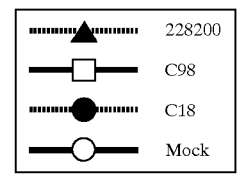

228200 is an Australian isolate of HIV-1 described by Kiernan, R. et al (1990). Its characteristics include being, T cell trophic, with fast kinetics, high producer of HIV-1 and /or SI phenotype.

Figure 8:
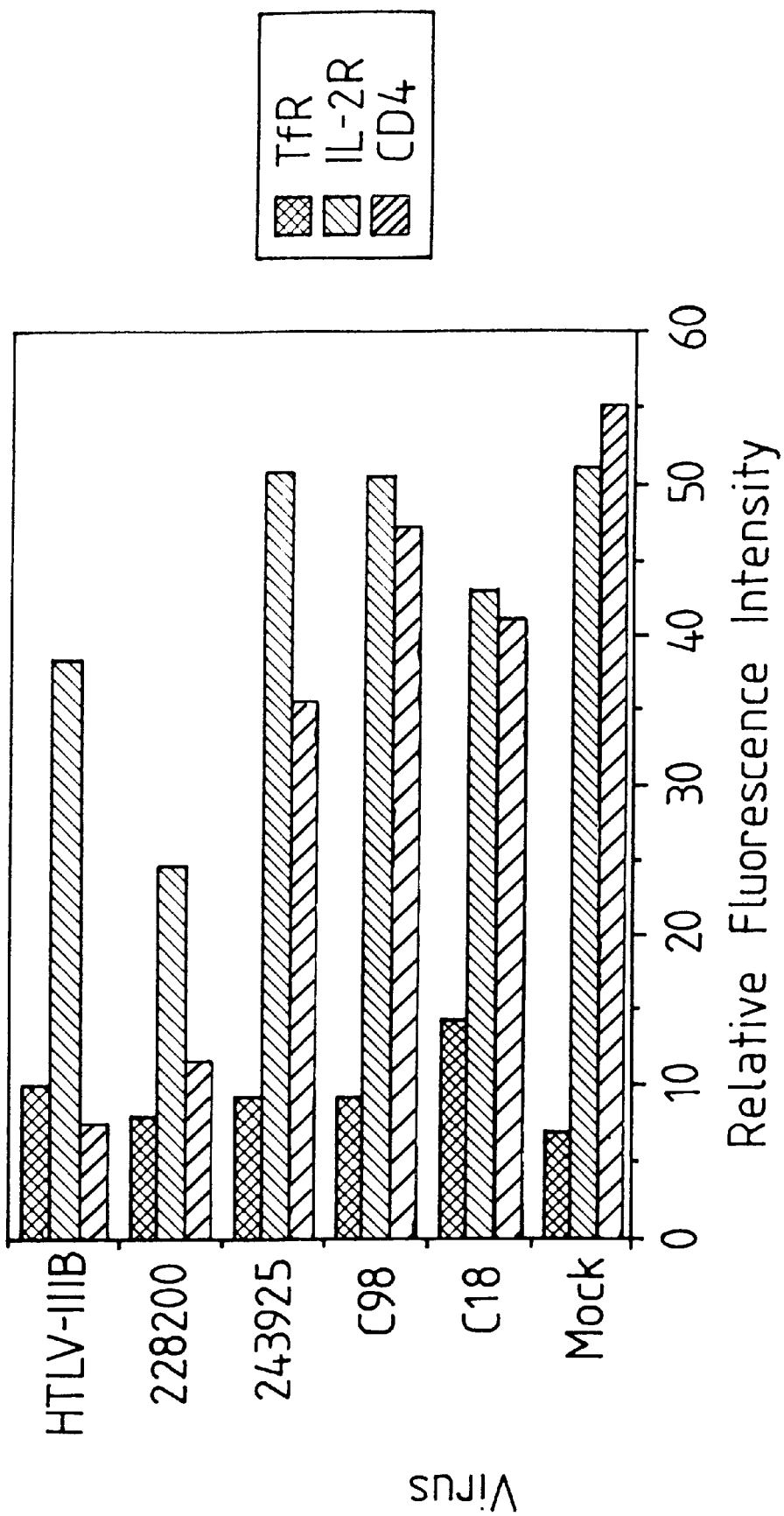

FIG. 8 is a graphical representation of cell surface receptor expression for syncytia-inducing inducing (SI)/ non-syncytia-inducing (NSI)/asymptomatic patient isolates.

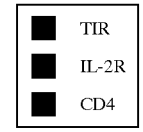

228200 is defined in the legend to FIG. 7. 243925 is a viral isolate of HIV-1 which is monocyte/macrophage trophic and exhibits NSI phenotype (Dr Karen Coats-Fryer, PhD thesis entitled "Viral determinants of HIV-1 syncytium formation", the University of Melbourne, Parkville, Victoria, Australia.

FIG. 9 is a representation of the nucleotide sequence of C18 $HIV-1_{MBC}$ (SEQ ID NO: 800).

FIG. 10(a)–(g) are graphical representations showing clinical immunology of cohort; (a) CD3; (b)(i) CD4 (ii) CD4%; (c)(i) CD8; (ii) CD8%; (d) lymphocyte count; (e) CD4/CD8 ratio; (f) β2-microglobulin; and (g) Kaplan-Meier estimates of time to disease progression (Cox & Oakes, 1989).

FIG. 11 is a schematic representation of the deletion mutants of the present invention.

A summary of the SEQ ID Nos. used in the subject specification is shown below:

| SEQ ID NO: | DESCRIPTION |
| --- | --- |
| 1 | Nucleotide sequence of HIV-1 strain NL4-3 genome |
| 2–613 | Decanucleotides of nef gene from HIV-1 strain NL4-3 |
| 614 | Partial nucleotide sequence of D36 HIV-1 isolate |
| 615 | Partial nucleotide sequence of C18 $HIV-1_{MBC}$ isolate |
| 616–625 | PCR primers shown in Table 1 |
| 626–633 | Sequence primers shown in Table 2 |
| 634 | Amino acid residues 15–27 of HIV-1 NL4-3 nef protein |
| 635 | HIV-1 NL4-3 tat exons (FIG. 2) |
| 636 | HIV-1 D36 tat exons (FIG. 2) |
| 637 | HIV-1 C18 tat exons (FIG. 2) |
| 638 | HIV-1 NL4-3 rev exons (FIG. 2) |
| 639 | HIV-1 D36 rev exons (FIG. 2) |
| 640 | HIV-1 C18 rev exons (FIG. 2) |
| 641 | HIV-1 NL4-3 C-terminal of gp41 (FIG. 3) |
| 642 | HIV-1 D36 C-terminal of gp41 (FIG. 3) |
| 643 | HIV-1 C18 C-terminal of gp41 (FIG. 3) |
| 644 | HIV-1 NL4-3 nef gene (FIG. 4) |
| 645 | HIV-1 D36 nef gene (FIG. 4) |
| 646 | HIV-1 C18 nef gene (FIG. 4) |
| 647 | HIV-1 NL4-3 NFKB/SP1 sequence (FIG. 5) |
| 648 | HIV-1 D36 NFKB/SP1 sequence (FIG. 5) |
| 649 | HIV-1 C18 NFKB/SP1 sequence (FIG. 5) |
| 650 | Nucleotide sequence of nef gene from HIV-1 strain NL4-3 |
| 651 | Nucleotide sequence of env and nef regions of NL4-3 |
| 652–799 | Decanucleotides of LTR region from HIV-1 strain NL4-3 |
| 800 | Nucleotide sequence of C18 $HIV-1_{MBC}$ |

EXAMPLE 1

Source Material

For the purposes of the following examples, a non-pathogenic HIV-1 strain was isolated from a recipient of HIV-1 infected blood. The recipient is designated "C18". Other recipients are defied as "C54" and "C98". The donor is identified herein as "D36". Viral isolate D36 was deposited on Aug. 23, 1996 as Accession No. V96082324. The place of isolation may be indicated after the abbreviation of "HIV". For example, St Vincents Hospital, Sydney ($HIV_{StV}$) or Macfarlane Burnet Centre of Medical Research, Melbourne ($HIV_{MBC}$).

Exemplary viral isolates referred to herein as "C18" and "C98" were deposited at the PHLS Centre for Applied Microbiology and Research, European Collection of Animal Cell Cultures (ECACC), Division of Biologies, Porton Down, Salisbury, Wiltshire SP4 OJG. C18 was deposited on Oct. 17, 1994 under Provisional Accession Number V94101706 and C98 was deposited on Oct. 31, 1994 under Provisional Accession Number V941031169.

FIG. 11 is a summary of the deletion mutants of the present invention.

Viruses were isolated by the following procedures:
1. Infected peripheral blood mononuclear cells (PBMCs) were co cultured with HIV-1 seronegative donor PBMCs. A convenient source of seronegaitve donor PBMCs is a blood bank. The supernatants and cells are harvested every 7 days and fresh medium added with CD8 depleted PBMCs. CD8 depletion promotes the ability to isolate HIV-1. The culture and procedure is continued for up to approximately 5 weeks;
2. The infected PBMCs are purified from whole blood and these cells are cultured alone for up to 5 weeks, PMBCs alone are used because the virus is more likely to be monocytotropic. Fresh medium is added weekly and supernatant fluid is harvested at this time;
3. Supernatant fluids are harvested every approximately 7 days, fresh medium and fresh HIV-1 seronegative CD8 depleted PBMCs are added at this time;
4. HIV-1 seronegative PBMCs are pretreated with with M-CSF for approximately 72 hours prior to the addition of infected PBMCs. M-CSF has been shown to enhance HIV-1 replication in monocytes (Gendelman et al, 1988); or
5. The supernatant fluid is harvested from the cultures of step 4 every approximately 7 days, fresh medium added together with HIV-1 s seronegative stimulated CD8 depleted PBMCs. The virus is isolated from the infected PBMCs.

EXAMPLE 2

DNA Preparation and PCR Amplification

Non-pathogenic HIV-1 (e.g. strain C18) infected peripheral blood mononuclear cells (PBMC) were harvested 4 days after infection of phytohaemagglutinin (PHA) stimulated HIV-1 negative donor PBMC cultured by the method of Neate et al (1987) and washed in phosphate buffered saline (PBS). PBMC from Donor D36 and Recipients C18, C54 and C98 were prepared by Ficoll isopaque centrifugation of buffy coat cells and washed with PBS.

Approximately $10^7$ cells were lysed in 1 ml lysis solution (0.45% v/v NP40, 0.45% v/v Tween 20, 10 mM Tris-HCl pH 8.3, 40 mM KCl 2.5 mM $MgCl_2$) and digested with 60 µg/ml proteinase K (Boehringer Mannheim) at 55° C. for 1 hour followed by 100° C. for 10 minutes. Lysates were stored at −20° C.

All polymerase chain reaction (PCR) primers (Table 1) and sequencing primers (Table 2) were synthesised using an Applied Biosystems model 391 DNA synthesiser using phosphoramidite chemistry.

Strict physical separation was maintained for sample, PCR reagent mix and PCR reaction preparations as well as amplification and analysis. Final reaction mixes (50 µl) contained 2 µl neat or diluted cell lysate, 0.2 µM each primer, 200 mM dNTPs and 1.25,units Taq polymerase (Boehringer Mannheim) in PCR buffer, (10 mM Tris-HCl pH.3, 50 mM KCl, 100 µg/ml gelatine) adjusted to the optimum $MgCl_2$ concentration for the primer pair (1.5–3.0 mM). Aliquoted reagent mix was overlaid with 50 µl mineral oil prior to addition of DNA template lysate. After template denaturation at 94° C. for 3 min amplification was achieved with 30 cycles of 94° C., 1 min; 55° C., 1 min; 72° C., 2 mins. A final elongation reaction was conducted at 72° C. for 7 minutes. For double PCR amplification 2 µl of first round product was added to the second reagent mix and amplified as before.

PCR amplified DNA was checked for quality, quantity and fragment size by agarose gel electrophoresis in Tris-Acetate-EDTA buffer (Sambrook et al, 1989) stained in ethidium bromide and viewed by UV transillumination.

EXAMPLE 3

DNA Sequence Analysis

The DNA sequence of PCR amplified HIV-1 regions was determined by the dideoxynucleotide method (Sanger et al, 1997) using Sequenase T7 polymerase (United States Biochemicals).

PCR amplified DNA was purified by PCR Magic prep resin chromatography (Promega). Approximately 2 to 7 µg purified DNA plus long specific primer (Table 2) were denatured by boiling for 3 mins and snap frozen to −20° C. The initial labelling reaction was for 3 minutes at 22° C. (room temperature) with $^{35}$SdNTP (500 Ci/mmol; Dupont) followed by dideoxynucleotide termination reactions at 37° C. for 5 minutes. NP40, to 0.45% a v/v, was included in denaturation and reaction mixes (Bachman et al, 1990). Sequencing reaction products were denatured in formamide and resolved on a 6% w/v polyacrylamide gel containing 8M urea, fixed in 10% v/v acetic acid, 10% v/v methanol and dried. Following autoradiography on XKI film (Kodak) the gel sequences were read assembled, translated to protein and aligned using the PC/GENE suite of programs (IntelliGenetics, USA).

TABLE 1

PCR PRIMERS

| PRIMER | SEQUENCE[1,3] | POSITION[2] |
|---|---|---|
| Cl-1 | TGGAAGGGCTAATTTGGT (616) | 1–18 |
| Cl-2 | ATCTTCCCTAAAAAATTAGCCTGTC (617) | 2099–2075 |
| LTR-3' | AGGCTCAGATCTGGTCTAAC (618) | 9559–9540 |
| SK68 | AGCAGCAGGAAGCACTATGG (619) | 7786–7805 |

TABLE 1-continued

PCR PRIMERS

| PRIMER | SEQUENCE[1,3] | POSITION[2] |
|---|---|---|
| Cl-6 | TGCTAGAGATTTTCCACAC (620) | 9709–9691 |
| KS-2 | AGTGAATAGAGTTAGGCAGG (621) | 8326–8345 |
| RT5'-v3 | GTAAGACAGTATGATCAGATA (622) | 2418–2438 |
| RT3'-v2 | TTGTAGGGAATTCCAAATTCC (623) | 4660–4640 |
| RT5'-v2 | CAGGATCCTACACCTGTCAACATAAT (624) | 2487–2506 |
| RT3'-v1 | GGGAATTCCTTATTCCTGCTTG (625) | 4655–4634 |

[1]. Sequence is presented from 5' to 3' of the primer.
[2]. Position is according to the numbering of HIV NL4-3 in Myers et al (1992).
[3]. SEQ ID NOs are given in parentheses.

TABLE 2

SEQUENCING PRIMERS

| PRIMER | SEQUENCE[1,3] | POSITION[2] |
|---|---|---|
| KS3 | CCAGAAGTTCCACAATCC (626) | 8570–8553 |
| KS4 | TTCTTCTAGGTATGTGGAG (627) | 8753–8735 |
| KS5 | AGTGAATTAGCCCTTCCAG (628) | 9093–9075 |
| KS6 | TGCTAGAGATTTTCCACAC (629) | 9709–9691 |
| SP2 | TGCTCTGGAAAACTCAT (630) | 8006–8022 |
| SP3 | CTTTCTATAGTGAATAGAG (631) | 8318–8336 |
| SP4 | TATTGGAGTCAGGAACT (632) | 8618–8634 |
| SPR | GGTCTAACCAGAGAGAC (633) | 9547–9531 |

[1]. Sequence is presented from 5' to 3' of the primer.
[2]. Position is according to the numbering of HIV NL4-3 in Myers et al (1992).
[3]. SEQ ID NOs are given in parentheses.

EXAMPLE 4

Cells and Cell Culture

Peripheral blood was obtained from HIV-1 sero-negative volunteers and mononuclear cells prepared by centrifugation on a Ficoll/Hypaque density gradient (Peper et al, 1968). PBMC were activated with phytohemagglutinin (PHA; 10 $\mu$l/$10^6$ cells) for 48 h at 37° C. washed and then cultured in RPMI 1640 medium containing 10% v/v heat inactivated foetal calf serum, 15 mM HEPES, 0.1% v/v sodium bicarbonate, 25 $\mu$g/ml polybrene (Sigma), 10% v/v interleukin 2 (Bochringer Mannheim) and 1:1000 anti-interferon (Miles) (IL-2 medium). Non-PHA stimulated cells were prepared in a similar manner except they were cultured in medium lacking PHA and IL-2.

EXAMPLE 5

Antipeptide-antisera

Antibodies specific for HIV-1 Nef were raised against a peptide corresponding to the predicted amino acid residues 15–27 (AVRERMRRAEPAA SEQ ID NO: 634) of Nef encoded by the HIV-1 clone pNL4.3 (Kemp et al, 1988). The peptide was conjugated to keyhole limpet hemocyanin (KLH; Calbiochem, Behring Diagnostics, CA) via glutaraldehyde and this complex used to immunise sheep (0.5 mg peptide conjugate/sheep). Antibodies to the peptide were purified by affinity chromatography. Reactivity of the antibodies with recombinant HIV-1 Nef 25 and 27 was demonstrated by immunoblotting.

EXAMPLE 6

Reactivity of anti-Nef ($_{15-27}$) with HIV C18-infected Cells in Immunoblotting Seven days post-infection HIV-1 C18-infected PBMCs and mock—infected cells were washed in PBS then lysed (0.5% w/v NP-40, 0.5% w/v sodium deoxycholate, 50 mM NaCl, 25 mM Tris-HCl, 10 mM EDTA, 0.01% w/v sodium azide and 10 mM phenylmethylsulphonylfluoride). After nuclei were spun out lysates were electrophoresed in a 13% w/v SDS-polyacrylamide gel (SDS-PAGE) and subsequently transferred to Hybond-C nitrocellulose (Amersham, Buckinghamshire, England) for 1 h at 100 V using a Bio-Rad protein transfer cell (Bio-Rad, Richmond, Calif.). Membranes were pre-incubated with 1% w/v BSA/PBS for 2 h at room temperature and then reacted with affinity purified sheep anti-Nef($_{15-27}$), diluted 1:100, overnight at room temperature. After three washes in 1% w/v BSA/PBS, the blots were incubated with donkey anti-sheep Ig conjugated to biotin (Amersham, diluted 1:500) for 1 h at room temperature. After extensive washing as described above the membranes were incubated with streptavidin-conjugated horse radish peroxidase (Amersham; diluted 1;500 for 1 h at room temperature. All dilutions were made with 1% w/v BSA in PBS. After further washing the membrane was developed with phenylenediamine substrate (Dako, Dapopatts, Denmark). The antibody preparation used in the immunoblotting experiments was free of detectable antibodies to the immunogenic carrier protein and coupling reagent.

EXAMPLE 7

Analysis by Polymerase Chain Reaction Amplification

A 5' fragment defined by primers Cl-1 and Cl-2 containing the 5' LTR and part of the gag gene was amplified. DNA from HIV-1 C18 infected PBMC gave an amplified fragment (amplimer) of about 1.9 kb compared with 2.1 kb for pHXB2 control template, implying a deletion of about 200 bp from HIV C18. Further amplification of this fragment with primers defining the U3 region of the LTR (Cl-1 and LTR-3') gave amplimers of about 300 bp for HIV-1 C18 infected PBMC DNA compared with 340 bp for C18 and D36 PBMC DNA and 484 bp for pHXB2 control. This implies the loss of approximately 140 to 180 bp from the U3 region of these proviral DNAs.

To analyse the nef-gene-3'LTR region, the nested primer pairs SK68-Cl-6 and KS-2-LTR-3' were used in a double PCR. Amplimers of approximately 830bp were obtained for HIV-1 C18 infected PBMC DNA as well as for PBMC DNA from Donor D36 and Recipients C18, C54 and C98 compared with approximately 1230 bp for pHXB2 DNA. These results suggest that about 400 bp of DNA have been deleted from the Donor and Recipient proviral DNAs.

In comparison, amplification of the polymerase gene region by double PCR with the nested primer pairs RT5'-v3-RT3'-v2 and RT5'-v2-RT3'-v1 gave a fragment (approximately 2.1 kb) the same size as the molecular clone pHXB2 fragment for HIV-1 C18 infected PBMC DNA, suggesting that deletions from this region were unlikely.

EXAMPLE 8

Nucleotide Sequence of the nef-3 ' LTR Region

PCR amplification experiments indicated an approximately 200 bp nucleotide deletion from both the nef gene and LTR regions of Donor D36 PBMC and Recipient C18 HIV-1 proviral DNA. To further analyse these regions, the DNA sequence was determined for the PCR amplified nef-3'-LTR region of D36 PBMC, C18 isolates $HIV_{MBC}$ and $HIV_{StV}$ as well as isolate C98 HIV infected PBMC proviral DNA. The 3' region was amplified with outer primers (SK68-C16) and inner primers (SK68-LTR 3' or KS2-C16) and sequenced directly using a number of internal sequencing primers based on the HIV-1 NL4-3 nucleotide sequence (Table 2).

Alignment of the nucleotide sequences of the amplified 3' region of donor D36 PBMC and recipient C18 isolates $HIV_{MBC}$ and $HIV_{StV}$ and C98 HIV (FIG. 1) showed a number of nucleotide sequences changes, including deletions, relative to the nucleotide sequence of wild-type infectious HIV-1 (HIV-1 NL4-3). In the region of alignment, D36 PBMC lacked 291 nucleotides, C18 $HIV_{StV}$ differed in size by 388 nucleotides (comprising deletions of 397 nucleotides and an insertion of 9 nucleotides), C18 $HIV_{MBC}$ differed by 456 nucleotides and C98 HIV lacked 158 nucleotides compared with HIV-1 NL4-3. The overall identity with HIV-1 NL4-3 nucleotide sequence of D36 PBMC, C18 $HIV_{StV}$, $HIV_{MBC}$ and C98 HIV nucleotide sequences, including deletions, was 73% (1157/1596), 67% (1459/1592), 62% (982/1592) and 79% (1105/1399), respectively.

The D36 PBMC sequence differed from HIV-1 NL4-3 in a number of features. A change in the wild type tat termination codon from TAG to TCG (Ser) extended the third tat exon (which starts at splice acceptor 10) by a further 15 amino acids to terminate at a conserved TAG (FIG. 1). The resulting C-terminal peptide is rich in charged amino acids (8/15) (FIG. 2a). The wild type rev termination codon has also changed (TAG to GAG, Glu) and the third rev exon is extended for 14 codons to terminate at a conserved TAG (FIG. 2b). The encoded extra amino acids are mainly polar (11/14) and charged in nature (FIG. 2b). The sequence also encodes the C-terminal 237 amino acids of Env gp41 (FIG. 3) terminating at the normal termination codon. The D36 PBMC Env amino acid sequence has 85% identity with the HIV NL4-3 sequence, increasing to 89% if similarities are included.

There are significant differences from HIV-1 NL4-3 downstream of the env (gp41) gene. A change in the fifth nef codon, from TGG (Trp) to TGA (FIG. 1), introduces an early termination in the D36 PBMC nef gene. The encoded Nef protein is identical to the N-terminal 4 amino acids of NL4-3 Nef (FIG. 4). Following the early termination there are deletions of 33, 47, 93 and 91 nucleotides and a region of low sequence homology, compared with HIV NL4-3, prior to the wild type nef termination codon site (HIV NL4-3nts 9405–9407) As well as removing a significant part of the nef gene, these deletions also bring into phase a further 6 termination codons. While the polypurine tract (plus strand primer binding site) and the first 38 nucleotides of the LTR U3 region are perfectly conserved, downstream U3 region sequences are disrupted by the 93 and 91 nucleotide deletions and the low homology region. The resulting U3 region lacks recognition sequences for the transcription factors c-myb, USF and TCF1α as well as one of the suggested NF-AT sites (Gaynor et al, 1992). Downstream from the 91 nucleotide deletion, a 59 nucleotide region of low homology contains two extra NFKB enhancer sites 19 nucleotides upstream of the usual site of a pair of NFKB sites, the upstream one of which is altered in its 5'-half in D36. Sequences further downstream are highly conserved with respect to HIV-1 NL4-3, including the position and number of Sp1 basal promoter sites, TATA box, TAR and polyadenylation signal sequences.

Similar to D36 PBMC, the C18 $HIV_{StV}$ and $HIV_{MBC}$ sequences show the tat third exon to be extended by 15 codons. All but two codons (altered by point mutations) are identical to those of D36 PBMC (FIG. 2a). The rev third exon of both C18 isolates is also extended (FIG. 2b) but by only three codons, identical to the first three codons of the D36 PBMC rev extension. The same 237 amino acid coding region of Env gp41 is found in both the C18 HIV DNA sequences (FIG. 3) and shows 85% identify, increasing to 88% if similarities are included, with the same region of the NL4-3 Env gp41is It is in the nef gene and LTR regions that the major differences from wild-type HIV-1 arise, just as in D36 PBMC. The nef gene of C18 $HIV_{StV}$ encodes 24 amino acids with 9 of the 10 N-terminal being identical to the NL4-3 Nef protein (FIG. 4). Thereafter, deletions of 177 and 11 nucleotides cause a frameshift and termination at the 25th codon (FIG. 1). Downstream deletions of 120, 82 and 7 nucleotides cause further loss of wild type nef gene sequence and bring into phase a further three termination codons.

The nef gene of C18 $HIV_{MBC}$ encodes only 7 amino acids with only the initiator methionine identical to the NL4-3 Nef protein. This loss of identity and early termination is brought about by a 250 nucleotide deletion after the fifth nucleotide of the nef gene. Downstream deletions of 120 and 86 nucleotides cause further loss of wild-type nef gene sequences. In both C18 isolates there is perfect conservation of the polypurine tract and 29/31 nucleotides at the 5' end of the U3 region immediately before the 120 nucleotide deletion (FIG. 1). This deletion together with the downstream 82 and 7 nucleotide deletions in $HIV_{StV}$ and 86 nucleotide deletion in $HIV_{MBC}$ and the low homology region cause the loss of the 5' half of the NRT-1 site (Yamamoto et al 1992) and the downstream NFAT site. A third NFKB site is present 31 ($HIV_{StV}$) and 33 ($HIV_{MBC}$) nucleotides upstream of the expected pair of NFKB sites which are themselves separated by 13 nucleotides instead of the 4 nucleotides in HIV-1 NL4-3. The 5'-most Sp1 site sequence is slightly altered but sequences downstream including the other 2 Sp1 sites, the TATA box, TAR and polyadenylation signal sequences are identical to HIV-1 NL4-3 sequence.

The three sequences, D36 PBMC, C18 $HIV_{StV}$ and C18 $HIV_{MBC}$ show a number of similarities consistent with the transmission of virus from person D36 to person C18 as well as a number of differences indicating post-transmission divergence of sequence. All three have tat open reading frames (ORFs) extended by 15 codons. All three have extended rev ORFs. The new rev termination codon in both C18 HIV-1 isolates, three codons downstream of the NL4-3 rev termination codon, has a point mutation in D36 PBMC to make a Glu codon so that it continues for a further 11 codons (FIG. 2b) to terminate at a conserved TGA. The partial Env gp41 amino acid sequences are more closely related to each other (86% identity or 90% including similarities) than to HIV NL4-3 (85% and 89%, respectively).

The nucleotide sequence of the nef and LTR region of the HIV-1 isolate from recipient C98 (C98 HIV) is 90.3% identical (1264/1399) to the HIV NL4-3 sequence, ignoring deletions. Similar to the D36 PBMC and C18 $HIV_{StV}$ and $HIV_{MBC}$ isolates the C98 HIV sequence shows the third exon of tat to be extended by 15 codons with all but one being identical to the D36 PBMC tat extension. Also, the rev gene is extended by 3 codons, 2 of which are identical to the first 2 codons of the D36 PBMC rev extension. The sequence also encodes the C-terminal 223 amino acids of Env gp41 terminating at the normal termination codon. The C98 HIV Env amino acid sequence has 89% identity with HIV NL4-3 Env sequence, increasing to 92% of similarities are included.

As with the D36 PBMC and the C98 HIV isolate sequences it is the nef gene and LTR regions that major differences from the HIV NL4-3 sequence arise. The nef gene open reading frame of C98 HIV is much longer than in D36 PBMC, C18 HIV$_{StV}$ and HIV$_{MBC}$, encoding 85 amino acids compared with 206 amino acids for NL4-3. Sixty eight of those 85 amino acids are identical to the N-terminal sequence of NL4-3 Nef. The single, small deletion (16 nucleotides) in the C98 HIV nef-alone regions (Table 3) occurs after nef codon 82 causing a frameshift and termination after a further 3 condons at the start of the highly conserved polypurine tract sequence immediately before the 3'-LTR. The nef/LTR region has two deletions totalling 142 nucleotides. The 5'-most deletion of 42 nucleotides includes the splice acceptor 12 sequence. The NRT-1, dyad symmetry and myb response element sequences are all intact. However, the downstream 100 nucleotide deletion includes sequences from the 3' end of the 5'-NF-AT and all of the 3' NF-AT sequences as well as the USF transcription factor recognition sequence. The downstream low homology region of 77 nucleotides lacks the TCP-1α sequence but has two additional NFKB sites 13 nucleotides apart and 26 nucleotides upstream of the 3'-half-remmant of the normal 5'-NFKB site. Sequence downstream, including the 3'-NFKB site, the 3 Sp1 sites, TATA box TAR and polyadenylation signal sequences are all highly conserved.

The main feature of the sequences is the series of deletions, with respect to HIV NL4-3, in the nef gene-3'-LTR region. These can be grouped into two regions namely the nef-alone region, that part of the nef gene upstream of the LTR, and the nef/LTR region, where the nef gene and LTR U3 regions overlap. The deletions in these regions of each of the sequences start and end at the same or similar positions (Table 3). The deletions are larger in C18 HIV$_{StV}$ and C18 HIV$_{MBC}$ sequences where totals of 397 and 456 nucleotides have been deleted (relative to NL4-3) compared to 291 nucleotides, from D36 and 158 nucleotides from C98 HIV. In the nef-alone region the two deletions in C18 HIV$_{StV}$ and the single deletion in C18 HIV$_{MBC}$ occupy the same region as the three deletions in D36 PBMC. Similarly, the nef/LTR region in the three deletions in the C18 HIV$_{StV}$, the two deletions in the C18 HIV$_{MBC}$ and the D36 PBMC sequences occupy the same region. These findings indicate that mutant virus was transmitted from D36 to C18 after which further deletions and rearrangements occurred. Similarly, the sequence of C98 HIV in the nef/LTR region indicates two deletions occupying the same region as the nef/LTR deletions in D36 and the C18 sequences. However, the size (only 16 nucleotides) and the position of the deletion in the nef-alone region of C98 HIV are distinct from those of the D36 PBMC and C18 sequences.

The timing of transmission of virus by transfusion was that recipient C18 was transfused approximately 19 months after C98. Consistent with the relative timing of transmission and the sequence similarities and differences is the suggestion that at the time of transmission to C98, the D36 sequence had deletions in the nef/LTR region but not in nef-alone region, After transmission to C98, the C98 virus developed further deletions and rearrangements, including the deletion in the nef-alone region. The D36 virus evolved so that at the time of transmission to C18, further deletions and rearrangements had occurred including deletion of sequence from the nef-alone region distinct from the C98 HIV nef-alone region deletion. After transmission to C18, further deletions and rearrangements occurred in the C18 virus giving rise to at least two sequences (HIV$_{StV}$ and HIV$_{MBC}$).

The nef-alone deletion region may be a mutation or recombination "hotspot" as it includes sequences that were found to be variably duplicated in 28 out of 54 Nef protein sequences derived from 8 of 12 patients analysed in a study (Shugars et al 1993). The sequence between the nef-alone and the nef/LTR region deletions is highly conserved and is important in provirus integration into the infected cell genome and interacts with a number of cellular proteins. It is interesting that the sequence equivalent to NL4-3 nucleotides 9209 to 9225 is retained in D36 and C98 HIV but lost in the C18 HIV sequences. This includes part of a sequence of dyad symmetry (9210 to 9231) and is a significant part of the binding site for NRT-1 (Yamamoto et al 1991) which has been shown to have a negative regulatory effect on HIV-1 expression. The presence of this sequence in D36 and C98 HIV and its absence from the C18 isolates may correlate with the inability to isolate virus from D36 PBMC and the poor replication of C98 HIV but the ability to isolate HIV-1 from C18 PBMC, The deletion of sequence equivalent to nucleotides 9281 to 9395 of NL4-3 causes the loss of some transcription factor binding sites including NFAT and USF from the D36, C18 HIV and C98 HIV sequences.

A further similarity between the D36, C18 HIV$_{StV}$, C18 HIV$_{MBC}$ and C98 HIV sequences is a region of low homology to HIV-1 NL4-3 extending downstream of the nef/LTR deleted region to the NFKB enhancer/Sp1 promoter site region. This low homology region in fact consists of incomplete duplications of part of the NFKB/Sp1 region (FIG. 5) resulting in D36 and C98 HIV having 2 extra NFKB sites upstream of an altered 5' NFKB site while the C18 sequences have one extra NFKB site and altered spacing between the 5' and 3' wild type NFKB sites due to an insertion of 9 nucleotides.

For the C18 and C98 HIV-1 isolates virus replication was assessed in PHA-stimulated and non-stimulated PBMCs (FIGS. 6 and 7). In PHA-stimulated PBMCs we also studied cell surface CD4 and IL-2R expression (FIG. 8). In comparison with HIV-1 wild type SI and NSI isolates clearly both C18 HIV$_{MBC}$ and C98 viruses are replication competent, though C98 HIV replicates more poorly than C18 HIV$_{MBC}$ and are of the NSI phenotype when syncytium formation and CD4 and IL-2R surface expression are taken into account. Additionally, and more surprisingly, these two viruses replicated almost as efficiently in non-PHA stimulated PBMCs when compared to a typical local wild type SI isolate (HIV-1 228200, FIG. 7).

When protein expression was assessed for C18 $HIV_{MBC}$ and C98 $HIV_{MBC}$ although structural proteins were identified, no typical Nef protein was seen in infected cells. However, analysis of cell lysates prepared front PBMC infected with C18 $HIV_{MBC}$ or PBMC infected with C98 $HIV_{MBC}$ (which were subsequently stimulated by UV irradiation, see Valerie et al, 1988) by Western immunoblotting using two antibodies specific for the N-terminal region of Nef showed the presence of smaller proteins of 19 kDa and 21 kDa, respectively. These proteins were not observed in mock-injected control PBMC lysates and were not observed when the infected-cell lysates were probed were probed with antibodies reactive with the C-terminus of Nef.

Thus, although the C18 and C98 HIV isolates are replication competent in vitro they clearly replicate differently using different conditions for cell activation and from the known functions of HIV-1 Nef protein and the LTR show that the major deletion in the nef gene and/or the LTR is at least in part responsible for the outcome of infection implicating the importance of Nef and/or the LTR in the clinical outcome of infection in vivo.

EXAMPLE 9

Determination of Degree of Relatedness Between Viruses

To determine the degree of relatedness between viruses such as between mutants or between mutants and a wild-type virus and to ascertain putative infected patients, the method of Delwart et al was employed.

EXAMPLE 10

Immune Responsiveness of Subjects Infected by Non-pathogenic HIV-1 Isolate

In this example, the donor and recipients of the cohort were tissue typed and assessed for basic cellular immune responses. Proliferative responses and IL-2 production to the mitogens ConA and PHA, to allogeneic mononuclear cells (irradiated pooled mononuclear cells from 20 random donors) and to recall antigens (e.g. influenza and tetanus toxoid) were within normal ranges. While at the immunogenetic level, HLA typing failed to identify a consistently common allele or haplotype within the group.

The conservation of CD4+ counts observed in the cohort, the relative integrity of their immune system and the varied HLA types of the donor and recipients further supports the fact that the symptomless condition of the cohort members is due to a non-pathogenic strain of HIV-1 or a stain of low virulence.

Accordingly, this provides a screening procedure for subjects putatively infected by a non-pathogenic HIV-1 isolate where such subjects are seropositive for HIV-1 (e.g. have antibodies to an HIV-1 glycoprotein) yet have normal proliferative responses and cytokine production to mitogens, allogeneic mononuclear cells and to recall antigens.

EXAMPLE 11

Clinical Immunology of Cohort

To establish that the donor and the recipients belonging to the cohort exhibit normal immunological profiles, members of the cohort were assayed for CD3, CD4, CD8, lymphocyte count, CD4/CD8 ratio and β-2-microglobulin over time since seroconversion.

Parameters considered normal in non-infected individuals range as follows:

| Parameter | | |
|---|---|---|
| CD3 | 55–82% | 620–2200 (× $10^6$/L) |
| CD4 | 29–58% | 420–1410 (× $10^6$/L) |
| CD8 | 12–43% | 200–980 (× $10^6$/L) |
| Lymphocyte count | 1000–3500 (× $10^6$/L) | |
| CD4/CD8 | 0.7–3.7 | |
| β-2-microglobulin | 0.00–2.20 mg/L | |

The results are shown in FIGS. 10(*a*)–(*g*) and clearly show that the immunological profiles of cohort members are substantially normal further highlighting the non-pathogenicity of the HIV-1 isolates of the present invention. FIG. 10(*g*) shows a graph of the Kaplan-Meier (Ox and Oates, 1989) estimates of time to dime a progression (AIDS or CD4>250). The results demonstrate that the difference is large in spite of the conservative bias, with a median time to progression of 6.2 years in the main database. An exact logrank test (Cytel Software Corporation, 1989, StatXact: Statistical Software for Exact Nonparametric Inference. Cambridge, Mass.) was performed, demonstrating that the difference between the groups was highly statistically significant (logrank statistic 11.8, p<0.0001).

TABLE 3

Deletions and their sizes in the nef-alone and the nef/LTR regions of the Long-Term Asymptomatic HIV-1 Sequences

| Sequence | nef-alone Region | Region Deletion (nt) | nef/LTR Region | Region Deletion (nt) | Total Deletion (nt) |
|---|---|---|---|---|---|
| D36 PBMC | 8830–8862 (33)<br>8882–8928 (47)<br>9009–9035 (27) | 107 | 9112–9204 (93)<br>9281–9371 (91) | 184 | 291 |
| C18 $HIV_{StV}$ | 8830–9006 (177)<br>9019–9029 (11) | 188 | 9105–9224 (120)<br>9281–9362 (82) | 202 | 390 |
| C18 $HIV_{MBC}$ | 8792–9041 (250) | 250 | 9105–9224 (120)<br>9281–9366 (86) | 206 | 456 |
| C98 HIV | 9033–9048 (16) | 16 | 9148–9189 (42)<br>9271–9370 (100) | 142 | 158 |
| C54 PBMC | incomplete | ? | 9281–9375 (95) | 95 | 95+ |

Sequence numbering relates to the equivalent position in HIV-1 NL4-3. Numbers in brackets are the deletion sizes in nucleotides (nt). The nef ORF starts at nt 8787 and the 3'-LTR starts at nt 9074 in HIV-1 NL4-3.

EXAMPLE 12

Sequencing of Isolate HIV-1 $C18_{MBC}$

The genome of variant HIV-1 designated C18 $HIV\text{-}1_{MBC}$ was amplified by the polymerase chain reaction (PCR) as 7 overlapping fragments using the sets of inner and outer oligonucleotide primers, designed using the programme PCRPLAN (IntelliGenetics), listed in Table 5 and either UlTma (Applied Biosystems) or a mixture of KlenTaq and Pfu (KlenTaq LA, Ab Peptides Inc) polymerases (for faithful amplification of long fragments). The resulting fragments were cloned into the SmaI site of the plasmid vector pGEM7Zf+. Insert-containing clones representing each region of the full length variant HIV-1 were sequenced by a nested deletion strategy (Gou & Wu, 1982) and cycle sequencing with Taq polymerase and dye labelled primers complimentary to the T7 or SP6 sites within the cloning vector. Nucleotide sequences were entered and collated by ASSEMGEL and SEQIN (IntelliGenetics) and SEQED (Applied Biosystems) and translated to the encoded amino acid sequences using TRANSL (IntelliGenetics) programmes. Sequence alignments used NALIGN, CLUSTAL (IntelliGenetics) and SEQED programmes.

The full length sequence (FIG. 9; SEQ ID NO:800) of isolate HIV-1 C18$_{MBC}$ is 9207 nucleotides long which is 506 nucleotides shorter than the HIV NL4-3 sequence. This size difference is comprised of 126 nucleotides of insertions and 632 nucleotides of deletions, see Table 6. The most extensive differences between the HIV-1 C18$_{MBC}$ sequence and HIV-1 NL4-3 are in the U3 region of the LTR and in the nef gene, as hereinafter described.

The 5' LTR has deletions of 120 and 87 nucleotides and a region of low sequence homology, which is the result of an imperfect duplication of the downstream NFκB and Sp1 response sequences. These result in the loss of sequence from a number sites important in the regulation of transcription of HIV-1 genes, including the negative response element (NRE) and the response elements for a number of transcription factors including NF-AT, NRT-1, USF and TCF-1α. Furthermore, the low homology region contains an extra NFκB and Sp1 sites as well as an insertion of 9 nucleotides between the usual NFκB sites. Downstream of the NFκB sites the sequence of the LTR has a high level of homology (96.2%) with the same region of HIV NL4-3.

The gag gene contains 3 insertions, which represent direct repetitions of adjacent sequences. The first is a perfect repeat of 15 nucleotides after the equivalent of nucleotide 1134 of HIV- NL4-3 and adds 5 amino acids to the C-terminus region of p17$^{gag}$. The remaining 2 insertions are imperfect and perfect repeats of 30 and 6 nucleotides, respectively, after the equivalent of HIV NL4-3 nucleotides 2163 and 2232, respectively. These encode an extra 12 amino acids in the C-terminus region of p15$^{gag}$ just downstream of the gag to pol frameshift sequences. The variation in sequence length of the gag gene at these two positions is unusual. The homology of the encoded amino acid sequence of HIV-1 C18$_{MBC}$ and HIV NL4-3 for the gag p17, p24, and p15 proteins is 87.1%, 93.5% and 94.3%, respectively.

In the pol ORF, the encoded proteins have high homology with the NL4-3 sequences being 95.5% overall comprising p10 protease 92.9%, p66 reverse transcriptase 95.4% and p34 integrase 95.8%. The amino acid sequence of the p61 RT lacks the mutations associated with resistance to the nucleoside (AZT, ddI, ddC) and non-nucleoside (Nevirapine) analogue drugs used in the treatment of HIV-1-infected persons.

The vif gene encodes a 192 amino acid protein with 88.0% homology with that of HIV-1 NL4-3. The vpr gene encodes a 96 amino acid protein with 89.6% homology with that of HIV-1 NL4-3.

There are 2 insertions and 1 deletion of sequences in the vpu gene. The insertions of 3 and 9 nucleotides are after the equivalent of nucleotide 6071 and 6234, respectively, of HIV-1 NL4-3. These add 1 amino acid after amino acid 3, and 3 amino acids after amino acid 59 of the encoded Vpu protein. The deletion of 12 nucleotides after the equivalent of HIV-1 NL4-3 nucleotide 6261 deletes 4 amino acids from the C-terminal region of Vpu as well as from the signal peptide of the env polyprotein, which is encoded by an overlapping reading frame. Amino acid sequence homology of HIV-1 C18$_{MBC}$ Vpu with NL4-3 is 85.2%.

The sequence encoding the env gp120 has 9 insertions totalling 45 nucleotides (encoding 15 amino acids) and the deletion of a total of 18 nucleotides (encoding 6 amino acids). These are listed in Table 6. All of these events (insertions and deletions) are at positions in the env gene. This is within the env V3 coding region, immediately upstream of the sequence encoding the so called V3 tip (or loop) amino acid sequence, Gly Pro Gly Arg. The V3 region sequence is that of a typical clade B subtype (North America, Europe and Australia) being identical to the clad B consensus sequence (based on 186 env sequences) at 29/35 positions. The type of amino acid at positions 11 and 28 of the V3 loop region (where position 1 is the Cys at amino acid 266 of the env gpl120) is predictive of the viral non-syncytium/syncytium forming phenotype (Fouchier et al. 1992). The HIV-1 C18$_{MBC}$ env gene encoded amino acid sequence has Ser at position 11 and Ile at position 28 of the V3 loop region. The lack of a positively charged amino acid at both positions is strongly indicative of a non-syncytium viral phenotype. The overall amino acid sequence homology with HIV-1 NL4-3 (ignoring deletions and insertions) is 86.1%, comprising 85.5% for the gp120 region and 87.6% for the gp41 region.

Both the tat and rev second exon open reading frames (ORF) are longer than in HIV-1 NL4-3. A change of the tat termination codon from TAG to TCG extends the tat ORF to a downstream in phase termination codon extending the encoded tat amino acid sequence by 15 residues, compared with the 86 amino acid long NL4-3 tat protein, to a total length of 101 amino acids. However, this is the usual length of the HIV-1 tat protein.

Similarly, the normal rev termination codon is changed from TAG to GAG. This extends the rev ORF to an in-phase termination codon 3 codons downstream so that the encoded Rev protein is 119 amino acids long instead of the usual 116.

As mentioned above the most extensive differences between the sequences of the isolate HIV-1 C18$_{MBC}$ and HIV-1 NL4-3 are in the nef gene and the LTR region. While the nef gene overlaps the 3' LTR, these differences are found in both the nef alone and the nef/LTR overlap regions. The HIV C18$_{MBC}$-encoded nef protein is only 24 amino acids long compared with the normal length of 206 amino acids. This severe shortening of the nef protein is due to the deletion of 18 nucleotides (the 177 and 11 nucleotide deletions) from the nef-alone region which also brings into phase a termination codon, TAG, at the resulting 25th codon. Downstream there is further loss of potential nef gene sequences by the 120 and 87 nucleotide deletions situated in the nef/LTR overlap region. The resulting 24 amino acid nef protein is identical to the N-terminus of the HIV-1 NL4-3 nef at 9 of the first 10 positions. Thereafter, homology is lost completely.

Some sequences used in the generation of mature mRNAs are altered or lost in C18$_{MBC}$. The dinucleotide immediately after the splice donor site 2 (SD2) at nts 4818–4819 NL4-3 equivalent nts 4963–4964)is changed from the conserved GT to GC. It is expected that this change would lead to loss of function of this site as a splice donor. Splice donor 2 is used in the processing of HIV-1 transcripts to some of the mRNAs that encode Tat, Rev and nef proteins. Similarly the splice acceptor site 7 (SA7) sequence at nts 6477–6478 (NL4-3 equivalent nts 6602–6603) is changed from the conserved AG dinucleotide to TC. This change is expected to lead to loss of function of this site as a splice acceptor. While this SA site is used in HIV-1 mRNA processing it is not a major site and is not used in the production of the regulatory proteins (Tat, Rev or nef) mRNAs. The splice donor 12 site is absent from the C18$_{MBC}$ sequence (NL43 equivalent nts 9161–9162) as it is within the first deletion region in the nef/LTR overlap region which occurs at nt 8797 and results in the loss of NL43 nucleotides 9105 to 9224. It is significant that the SA12 site is absent from the sequence of all of the cohort virus isolates so far obtained as well as from the sequence of D36 PBMC, however, the C$_{54}$ PBMC sequence does contain the SA12 site. SA12 is not used in the processing of mRNAs that encode the viral regulatory proteins. Normally SA12 is used in splicing in conjunction with SD1, 2, 3 and 4 and the resulting spliced RNA is probably not a mRNA but may have a regulatory role involving binding to cellular proteins (Smith et al, 1992).

An interesting feature of the sequence of the HIV-1 C18$_{MBC}$ isolate is the deletion and rearrangement of sequence from the 5'-LTR U3 region and the deletion of sequence from the nef gene (both nef alone and nef/3' LTR regions). These being the only features of the sequence distinct from disease-causing HIV-1. The lack of AIDS or AIDS-like symptoms in the patient C18 is attributed to the effects of the loss of LTR sequence and/or the loss of nef coding sequences and their role in the pathogenesis of AIDS.

TABLE 5

Sequence Deletions and Insertions in HIV-1 C18$_{MBC}$. Compared with HIV-1 NL43

| Gene or Region | Position (nt) C18$_{MBC}$ | Position (nt) NL43 | Deletions (nt) | Insertions (nt) |
|---|---|---|---|---|
| 5'-LTR U3 | 29 | 29 | 120 | — |
| 5'-LTR U3 | 85 | 205 | 87 | — |
| 5'-LTR U3 | 154 | 360 | — | 9 |
| gag p17 | 939 | 1134 | — | 15 |
| gag p15 | 1982 | 2163 | — | 30 |
| gag p15 | 2081 | 2232 | — | 6 |
| vpu | 5927 | 6062 | — | 3 |
| vpu/env | 6092 | 6234 | — | 9 |
| vpu/env | 6128 | 6261 | 12 | — |
| env | 6483 | 6628 | — | 6 |
| env | 6514 | 6653 | 2 | — |
| env | 6524 | 6665 | 1 | — |
| env | 6630 | 6772 | — | 9 |
| env | 6646 | 6778 | — | 3 |
| env | 7011 | 7141 | 6 | — |

TABLE 5-continued

Sequence Deletions and Insertions in HIV-1 C18$_{MBC}$. Compared with HIV-1 NL43

| Gene or Region | Position (nt) C18$_{MBC}$ | Position (nt) NL43 | Deletions (nt) | Insertions (nt) |
|---|---|---|---|---|
| env | 7140 | 7276 | 3 | — |
| env | 7195 | 7334 | — | 6 |
| env | 7266 | 7399 | 3 | — |
| env | 7278 | 7414 | — | 6 |
| env | 7290 | 7420 | — | 2 |
| env | 7300 | 7429 | — | 1 |
| env | 7314 | 7441 | 3 | — |
| env | 7463 | 7593 | — | 3 |
| env | 7471 | 7598 | — | 9 |
| nef | 8711 | 8829 | 177 | — |
| nef | 8723 | 9018 | 11 | — |
| nef/LTR | 8798 | 9104 | 120 | — |
| nef/LTR | 8854 | 9280 | 87 | — |
| LTR U3 | 8923 | 9435 | — | 9 |
| | | | 632 | 126 |

TABLE 4

Primers used to Amplify Overlapping regions of HIV-1 C18$_{MBC}$

| Primer | 5'- Coordinate | Direction (+/−) | Primer Length | Sequence (nt) |
|---|---|---|---|---|
| CL 1A | 1 | + | 30 | TGGAAGGGCTAATTTACTCCCAAAAAAGAC |
| CL 14 | 896 | − | 25 | AATCGTTCTAGCTCCCTGCTTGCCC |
| CL 1B | 1 | + | 30 | <u>AATCCCGGG</u>TGGAAGGGCTAATTTACTCCC |
| CL 13 | 796 | − | 31 | <u>CCTCTAGA</u>CCGCTTAATACTGACGCTCTCGC |
| CL 11 | 682 | + | 23 | TCTCTCGACGCAGGACTCGGCTT |
| CL 18 | 3440 | − | 30 | CTGTTTTCTGCCAGTTCTAGCTCTGCTTCT |
| CL 12A | 732 | + | 26 | <u>TTTCCC</u>GGGCGGCGACTGGTGAGTAC |
| CL 17 | 3330 | − | 32 | <u>CCCTCTAGA</u>CTTGCCCAATTCAATTTTCCCAC |
| CL 26 | 3193 | + | 39 | CCACACCAGACAAAAAGCATCAGAAAGAACCCCCATTCC |
| CL 6B | 9671 | − | 39 | TGCTAGAGATTTTCCACACGGACTAAAATGGTCTGAGGG |
| CL 27 | 3251 | + | 39 | CCATCCTGATAAATGGACAGTACAACCCATAGTACTGCC |
| CL 28 | 639 | − | 37 | TGGCCCAAACATTATGTACCTCTGCATCATATGC |
| CL 19 | 5449 | + | 30 | AGCAGGACATAACAAGGTAGGATCTCTACA |
| CL 24 | 8422 | − | 28 | GGATCTGTCTCTGTCTCTCTCTCCACCT |

Underlined sequences depict added restriction enzyme site
+ and − orientations refer to sense and antisense strands of the double stranded DNA sequence

EXAMPLE 13

Macrophage Isolates of HIV-1 C18 and HIV-1 C98

HIV-1 has been isolated from the macrophages of patients C18 and C98

Patient monocytes were prepared as follows. Whole blood was spun at 2000 rpm for 10 minutes. Plasma was removed into a separate tube and the remaining cells were diluted 1:2 in PBS$^-$ (magnesium and calcium free phosphate buffered saline). This was underlaid with 10 ml of Ficoll Isopaque and spun at 2000 rpm for 20 minutes. Cells were collected from the interphase and washed three times with PBS$^-$. These cells were then seeded into a 6 well Costar tray at a concentration of $1.0 \times 10^7$/ml and allowed to adhere for 1 hour, Any non-adherent cells were removed by aspiration.

Donor HIV-1 negative macrophages for use in co-cultivation were prepared as follows. Peripheral blood mononuclear cells were purified from whole blood using Ficoll/sopaque density gradient. These cells were seeded at a concentration of $2.0 \times 10^6$/ml in teflon. PBMC wore cultured in the presence of 3 $\mu$g/ml of PHA and 1000 U/ml of M-CSF 3 days prior to co-culture.

On day of co-culture, donor PBMC were CD8 depleted. Dyna beads coated with anti-CD8 were used for this purpose. Dyna beads were washed once in PBS⁻ and then applied to a magnet for 3 minutes. Supernatant was removed and the beads were then resuspended in 250 μl of RF-10. Aliquots of $2.0 \times 10^8$ patient cells were then added to 250 μl (3 beads: 1 CD8 T-cell) of Dyne beads and allowed to incubate for 30 minutes on ice with occasional mixing. After 30 minutes the cell suspension was placed onto a magnet for 3 minutes. The supernatant was then removed placed into a second tube containing 142 μl (1 bead: 1 CD8 T-cell) of Dyna beads. This suspension was placed on ice for an additional 30 minutes with occasional mixing. After 30 minutes cell suspension was placed onto a magnet for 3 minutes. Supernatant was removed and washed once in RF-10.

For co-culture, CD8 depleted PBMC were then added to patient monocytes. Half media changes were done every 7 days for a period of 21 days. Aliquots of 2.5 ml of medium was removed from these cultures and replaced with CD9 depleted donor PBMC in Iscoves containing 10% HuS (Human serum), 5% v/v FCS and 5% w/v IL-2 and 1000 μ/ml of M-CSF. Harvested supernatants were spun at 1400 rpm for 10 minutes and stored as 1 ml aliquots. Cell pellets were lysed in 200 μl of lysis buffer for PCR analysis. Infection was quantitated using a p24 EIA Kit.

Cells were harvested from the co-cultures and used to prepare DNA as described above. The nef/3'-LTR region of both virus isolates was amplified by PCR using the above described primer sets and conditions (Example 12). The resulting amplimers were cloned into the plasmid vector pT7T3U19 and the nucleotide sequence determined by the Taq cycle sequencing method with dye-labelled primers.

The C18 macrophage sequence has 3 deletions starting and finishing at positions within 3 nucleotides of the same deletions in $C18_{MBC}$. The encoded nef protein is 3 amino acids long compared with 7 amino acids for $C18_{MBC}$. The low homology region of the LTR U 3 region of C18 macrophage is very similar in sequence to $C18_{MBC}$ and similarly it has one extra upstream NFκB site.

On the other hand, the sequence of C98 macrophage has a number of differences from the C98 isolate. While it has exactly the same first deletion of 16 nucleotides just upstream of the polypurine tract (PPT), in the nef-alone region, and exactly the same second deletion (position and size) it has an extra deletion of 18 nucleotides at NL4-3 equivalent nucleotides 9206 to 9223. The final deletion is in approximately the same position as in the C98 isolate but is 5 nucleotides longer. The encoded nef protein is 34 amino acids long compared with 86 amino acids for the C98 isolate. The low homology region is very similar to the C98 isolate, having the same 2 extra upstream NF-κB sites and completely lacking the normal 5'-NFκB site.

EXAMPLE 14

Construction and Use of an Infectious A Molecular Clone

Molecular biological techniques can be used to construct a molecular clone of, for example, HIV-1 $C18_{MBC}$. Two schemes may be used. In the first scheme genomic DNA, extracted from either the CD4 positive PBMC of the patient C18 or donor PBMC that have been infected with the isolate HIV-1 $C18_{MBC}$, is used as the template for polymerase chain reaction amplification, using thermostable polymerase of high transcriptional fidelity (eg UlTma polymerase or KlenTaq/Pfu polymerase mixture), of long (6 to 7 kb) overlapping fragments representing the 5'- and 3'-parts of the HIV-1 $C18_{MBC}$ proviral genome of total length 9207 nts. The amplified fragments may then be ligated together after digestion with a restriction enzyme that cleaves at a unique site common to the overlapping region of the amplified fragments, for example the unique Bgl I or Nco I sites. Ligation of this full length proviral DNA into a plasmid vector will allow its propagation in E coli and the subsequent preparation of large (mg) quantities of this molecularly cloned proviral DNA.

In the second scheme donor PBMC that have been infected with the isolate HIV-1 $C18_{MBC}$ are used as a source of non-integrated proviral DNA which can be extracted from the infected cells by the Hirt extraction method (Hirt, 1967). Circular proviral DNA molecules may be linearised by digestion with a restriction enzyme that cleaves at a unique position in the genome (eg the Bgl I or Nco I sites). The resilting linearised molecules can be ligated into a plasmid or, more usually, a bacteriophage lambda (λ) based vector (eg Charon 4a, λWES) after modification of the end to provide blunt or cohesive ends compatible with the vector. Transformation or transduction of E coli with the recombinant plasmid or bacteriophage material, respectively allows the propagation of the proviral DNA. Clones of E coli containing proviral DNA may be selected and DNA prepared. Molecular clones of retroviral genomes prepared in this way are often permuted. Rearrangement to the functional arrangement of sequences is achieved by restriction enzyme cleavage and religation of fragments to reconstruct the correctly permuted proviral genome.

The molecularly cloned DNA products of both schemes can be used to prepare variant proviral genomes that may be used as the basis of a biologically attenuated HIV-1 vaccine strain. Similarly, they may be modified to contain extra DNA sequences in the nef-alone deletion region that may deliver sequences that may be of therapeutic advantage (eg antisense or ribozyme sequences).

Infectious virus particles of HIV-1 $C18_{MBC}$, or modified virus, can be produced by transfection of human cells (eg HeLa cells) which will produce, and release to the culture medium, virus particles of HIV-1 $C18_{MBC}$, or modified virus. These virus particles can be used to infect a variety of CD4 positive cells for further propagation or experimentation.

EXAMPLE 15

In vivo Primate Model

Following construction of infectious molecular clones of the mutant HIV-1 strains, studies are then undertaken in primates to establish attenuation, immunogenicity and vaccine prophylactic efficacy. All studies compare mutant clones of HIV-1 with isogenic wild-type (WT) virus. Initial studies are performed using the macaque (M. nemistrina) model of HIV-1 infection. Macaque infectious WT HIV-1 and mutant clones are compared with respect to duration of viremia, anatomic sites of replication, and cellular and humoral immune responses. Where the mutant HIV-1 clones induce an immune response in the macques infected, challenge studies with WT virus are also performed. Studies are performed in a limited number of chimpanzees, generally in parallel with the macaque studies. Relevant mutations are engineered into WT HIV-1 clones previously shown to produce chronic infection in chimps, and the course of chimp infection with mutant clones compared with historical controls. If infection is established, WT challenge studies is also performed.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bibliography

BACHMANN B, LÜKE W AND HUNSMANN G (1990). *Nucl Acids Res* 18: 1309.

BARRE-SINOUSSI F, CHERMANN J C, REY F, et al (1983) *Science* 220: 868–871.

BUSCH M P, E L AMAD Z, SHEPPARD H W, ASCHER M S, LANG W (1991) *N Engl J Med* 325: 733–735.

CHENG-MAYER C, SHIODA T, LEVY J A (1991) *J Virol* 65: 6931–6941.

CLERICI M, STOCKS N I, ZAJAC R A, et al (1989) *J Clin Invest* 84: 1892–1899.

COX and OAKES (1989) *Survival Analysis*, Chapman & Hall.

DANIEL M D, KIRCHHOFF F, CZAJAK S C, SEHGAL P AND DESROSIERS R C (1992). *Science* 258: 1938–1941.

DELWART E L, et al (1993) *Science* 262: 1257–1261.

FOUCHER RAM, et al (1992) *J. Virol.* 66: 3183–3187.

GAYNOR R (1992). *AIDS* 6m 347–363.

GOU L-H and WU R. (1982) *Nucleic Acids Research* 10: 2065–2084.

GREENWAY et al (1994) *Virology* 198: 245–256.

GROENINK M, FOUCHIER RAM, BROERSEN S, et al (1993) *Science* 260: 1513–1515.

HAMMES S R, DIXON E P, MALIM M H, CULLEN B R and GREENE W C, (1989) *Proc Natl Acad Sci USA* 86: 9549–9553.

HIRT B. (1967) *J Mol Biol* 26: 365–369.

HWANG S S, BOYLE T J, LYERLY H K, CULLEN B R (1991) *Science* 253: 71–74.

KASLOW R A, DUQUESNOY R, VAN RADEN M, KINGSLEY L, MARRARI M. (1990) *Lancet* 335: 927–930.

KEMP B E, RYLATT D B, BUNDESEN P G, DOHERTY R R, MCPHEE D A, STAPLETON D, COTTIS L E, WILSON K, JOHN M A, KHAN J M, DINH D P, MILES S & HILLYARD C J (1988). *Science* 241: 1352–1354.

KESTLER H W, RINGLER D J, MORI K, PANICALI D L, SEHGAL P K, DANIEL M D & DESROSIERS R C (1991). *Cell* 65: 651–662.

KIERNAN R. et al (1990) *AIDS Res. Hum. Retroviruses* 6: 743–752.

KIM S, IKEUCHI K, BYRN R, GROOPMAN J and BALTIMORE D (1989) *Proc Natl Acad Sci USA* 86: 9544–9548.

LANG W. PERKINS H, ANDERSON R E, ROYCE R. JEWELL N. WILKELSTEIN W. (1989) *J Acquir Immune Defic Syndr* 2: 63–69.

LEARMONT J, TINDALL B, EVANS L, CUNNINGHAM A, CUNNINGHAM P, WELLS J, PENNY R, KALDOR J AND COOPER D A. (1992). *Lancet* 340: 863–867.

LEGUERN M, SHIODA T, LEVY J A, CHENG-MAYER C. (1993) *Virology* 195: 441–447.

LEVY J A, (1993) *AIDS* 7: 1401–1410.

LIFSON A R, BUCHBINDER S P, SHEPPARD H W, et al (1991) *J infect Dis* 163: 959–965.

LUCIW P A, CHENG-MAYER C and LEVY J A (1987) *Proc Natl Acad Sci USA* 84: 1434–1438.

MANIATIS T et al (1982). Molecular cloning. A Laboratory Manual, 1st edition Pub. Cold Spring Harbor Laboratory Press.

MOSIER D E, GULIZIA R J, MACISAAC P D, TORBETT B E, LEVY J A (1993) *Science* 260: 689–692.

MYERS A, KORBAR B, BERZOFSKY J A, SMITH R F & PAVLAKIS S A eds (1992; 1993). Human retroviruses and AIDS. A compilation and analysis of nucleic acid and amino acid sequences. Pub Theoretical Biology and Biophysics Group. Los Alamos National Laboratory, Los Alamos, N. Mex. USA.

NEATE E V, HEALY D S, PRINGLE R C, GUST I D, AND JOWLETT J M B (1987). *Aus NZ J Med* 17: 461–466.

NIEDERMAN T M J, THIELAN B J, and RATNER L. (1989) *Proc Natl Acad Sci USA* 86: 1128–1132.

PEPER R J, TINA W Z, & MICHELSON M M (1968). *J Lab Clin Med* 72: 842–846.

SANGER F, NICKLEN S AND COULSON A R (1977). *Proc Natl Acad Sci USA* 4: 5463–67.

SHEPPARD H W, LANG W, ASCHER M S, VITTINGHOF E and WINKELSTEIN W. (1993) *AIDS* 7: 1159–1166.

SHIODA T, LEVY J A, CHENG-MAYER C (1992) *Proc Natl Acad Sci USA* 89: 9434–9438.

SHUGARS D C, SMITH M S, GLUECK D H, NANTERMET P V, SEILLIER-MOISEIWITSCH F AND SWANSTROM R (1993). *J Virol* 67: 4639–4650.

SMITH J, AZAD A A, and DEACON N J (1992) *J Gen Virol* 73: 1825–1828.

SULLIVAN N, THALI M, FURMAN C, HO D D, SODROSKI J (1993) *J Virol* 67: 3674–3679.

TEEUWSEN V J P, SIEBELINK K H J, DE WOLF F, GOUDSMIT J, UYTDEHAAG F G C M, OSTERHAUS A D M E (1990) *AIDS* 4: 77–81.

TERSMETTE M, DE GOEDE R E Y, BERT J M, et al (1988) *J Virol* 62: 2026–2032.

TERWILLIGER E, SODROSKI J G, ROSEN C A, and HASELTINE W A, (1986) *J Virol* 60: 754–760.

YAMANOTO K MORI S, OKAMOTO T, SHINOTOHNO K, AND KYOGOKU Y (1991). *Nucl, Acids Res* 22: 6107–6112.

YANISCH-PERRON C, VIEIRA J, and MESSING J *Gene* 13: 103–119.

We claim:

1. An isolated non-pathogenic HIV-1 strain comprising a genomic deletion in the region corresponding to nucleotides 9281–9438 of the nef gene and U3 long terminal repeat, wherein said nucleotide numbering is based upon HIV-1 strain NL4-3 and said deletion corresponds to amino acids 166–206 of the nef protein.

2. The HIV-1 strain of claim 1 wherein said deletion results in reduced expression of the nef gene product.

3. The HIV-1 strain of claim 1 wherein said deletion results in the expression of a truncated nef gene product.

4. The HIV-1 strain of claim 1 wherein said strain is recognized by HIV-1, gp41-45-, gp120-and/or gp160-specific antibodies and is capable of stimulating an immune response in humans to at least one of the gag, pol, or env gene products without reducing proliferative responses and cytokine production to a mitogen.

5. An isolated non-pathogenic HIV-1 strain comprising a genomic deletion of at least 10 nucleotides in the region corresponding to nucleotides 9281–9438 of the nef gene and U3 long terminal repeat, wherein said nucleotide numbering is based upon HIV-1 strain NL4-3.

6. An HIV-1 strain selected from the group of viruses having the ECACC designations V94101706, V941031169, and V95031022.

7. An immunogenic composition comprising the HIV-1 strain of claim 1.

* * * * *

UNITED STATES PATENT AND TRADEMARK OFFICE
CERTIFICATE OF CORRECTION

PATENT NO. : 6,010,895
DATED : January 4, 2000
INVENTOR(S) : Nicholas J. Deacon, et al.

It is certified that error appears in the above-identified patent and that said Letters Patent are hereby corrected as shown below:

On the Title Page, Section [73]: "Macfarlane Burnet Centre for Medical Research Limited, Victoria; Australian Red Cross Society, Sidney, both of Australia" should read --The Macfarlane Burnet Centre for Medical Research Limited, Victoria; Australian Red Cross Society (NSW Division) of Sidney, Sidney, both of Australia--

On the Title Page, after Section [22], insert the following:

-- [30]  Foreign/PCT Application Priority Data

Feb. 14, 1994 [AU]   Australia..........PM3864/94

Feb. 21, 1994 [AU]   Australia..........PM4002/94

Dec. 23, 1994 [AU]   Australia..........PN0284/94 --

Signed and Sealed this

Third Day of April, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 800

(2) INFORMATION FOR SEQ ID NO:1:

(i) SEQUENCE CHARACTERISTICS:
       (A) LENGTH: 9709 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:1:

| | | | | | |
|---|---|---|---|---|---|
| TGGAAGGGCT | AATTTGGTCC | CAAAAAAGAC | AAGAGATCCT | TGATCTGTGG | ATCTACCACA | 60 |
| CACAAGGCTA | CTTCCCTGAT | TGGCAGAACT | ACACACCAGG | GCCAGGGATC | AGATATCCAC | 120 |
| TGACCTTTGG | ATGGTGCTTC | AAGTTAGTAC | CAGTTGAACC | AGAGCAAGTA | GAAGAGGCCA | 180 |
| AATAAGGAGA | GAAGAACAGC | TTGTTACACC | CTATGAGCCA | GCATGGGATG | GAGGACCCGG | 240 |
| AGGGAGAAGT | ATTAGTGTGG | AAGTTTGACA | GCCTCCTAGC | ATTTCGTCAC | ATGGCCCGAG | 300 |
| AGCTGCATCC | GGAGTACTAC | AAAGACTGCT | GACATCGAGC | TTTCTACAAG | GGACTTTCCG | 360 |
| CTGGGGACTT | TCCAGGGAGG | TGTGGCCTGG | GCGGGACTGG | GGAGTGGCGA | GCCCTCAGAT | 420 |
| GCTACATATA | AGCAGCTGCT | TTTTGCCTGT | ACTGGGTCTC | TCTGGTTAGA | CCAGATCTGA | 480 |
| GCCTGGGAGC | TCTCTGGCTA | ACTAGGGAAC | CCACTGCTTA | AGCCTCAATA | AAGCTTGCCT | 540 |
| TGAGTGCTCA | AAGTAGTGTG | TGCCCGTCTG | TTGTGTGACT | CTGGTAACTA | GAGATCCCTC | 600 |
| AGACCCTTTT | AGTCAGTGTG | GAAAATCTCT | AGCAGTGGCG | CCCGAACAGG | GACTTGAAAG | 660 |
| CGAAAGTAAA | GCCAGAGGAG | ATCTCTCGAC | GCAGGACTCG | GCTTGCTGAA | GCGCGCACGG | 720 |
| CAAGAGGCGA | GGGGCGGCGA | CTGGTGAGTA | CGCCAAAAAT | TTTGACTAGC | GGAGGCTAGA | 780 |
| AGGAGAGAGA | TGGGTGCGAG | AGCGTCGGTA | TTAAGCGGGG | GAGAATTAGA | TAAATGGGAA | 840 |
| AAAATTCGGT | TAAGGCCAGG | GGGAAAGAAA | CAATATAAAC | TAAAACATAT | AGTATGGGCA | 900 |
| AGCAGGGAGC | TAGAACGATT | CGCAGTTAAT | CCTGGCCTTT | TAGAGACATC | AGAAGGCTGT | 960 |
| AGACAAATAC | TGGGACAGCT | ACAACCATCC | CTTCAGACAG | GATCAGAAGA | ACTTAGATCA | 1020 |
| TTATATAATA | CAATAGCAGT | CCTCTATTGT | GTGCATCAAA | GGATAGATGT | AAAAGACACC | 1080 |
| AAGGAAGCCT | TAGATAAGAT | AGAGGAAGAG | CAAAACAAAA | GTAAGAAAAA | GGCACAGCAA | 1140 |
| GCAGCAGCTG | ACACAGGAAA | CAACAGCCAG | GTCAGCCAAA | ATTACCCTAT | AGTGCAGAAC | 1200 |
| CTCCAGGGGC | AAATGGTACA | TCAGGCCATA | TCACCTAGAA | CTTTAAATGC | ATGGGTAAAA | 1260 |
| GTAGTAGAAG | AGAAGGCTTT | CAGCCCAGAA | GTAATACCCA | TGTTTTCAGC | ATTATCAGAA | 1320 |
| GGAGCCACCC | CACAAGATTT | AAATACCATG | CTAAACACAG | TGGGGGGACA | TCAAGCAGCC | 1380 |
| ATGCAAATGT | TAAAAGAGAC | CATCAATGAG | GAAGCTGCAG | AATGGGATAG | ATTGCATCCA | 1440 |
| GTGCATGCAG | GGCCTATTGC | ACCAGGCCAG | ATGAGAGAAC | CAAGGGGAAG | TGACATAGCA | 1500 |
| GGAACTACTA | GTACCCTTCA | GGAACAAATA | GGATGGATGA | CACATAATCC | ACCTATCCCA | 1560 |
| GTAGGAGAAA | TCTATAAAAG | ATGGATAATC | CTGGGATTAA | ATAAAATAGT | AAGAATGTAT | 1620 |
| AGCCCTACCA | GCATTCTGGA | CATAAGACAA | GGACCAAAGG | AACCCTTTAG | AGACTATGTA | 1680 |
| GACCGATTCT | ATAAAACTCT | AAGAGCCGAG | CAAGCTTCAC | AAGAGGTAAA | AAATTGGATG | 1740 |
| ACAGAAACCT | TGTTGGTCCA | AAATGCGAAC | CCAGATTGTA | AGACTATTTT | AAAAGCATTG | 1800 |

```
GGACCAGGAG CGACACTAGA AGAAATGATG ACAGCATGTC AGGGAGTGGG GGGACCCGGC    1860

CATAAAGCAA GAGTTTTGGC TGAAGCAATG AGCCAAGTAA CAAATCCAGC TACCATAATG    1920

ATACAGAAAG GCAATTTTAG GAACCAAAGA AAGACTGTTA AGTGTTTCAA TTGTGGCAAA    1980

GAAGGGCACA TAGCCAAAAA TTGCAGGGCC CCTAGGAAAA AGGGCTGTTG GAAATGTGGA    2040

AAGGAAGGAC ACCAAATGAA AGATTGTACT GAGAGACAGG CTAATTTTTT AGGGAAGATC    2100

TGGCCTTCCC ACAAGGGAAG GCCAGGGAAT TTTCTTCAGA GCAGACCAGA GCCAACAGCC    2160

CCACCGAAAG AGAGCTTCAG GTTTGGGGAA GAGACAACAA CTCCCTCTCA GAAGCAGGAG    2220

CCGATAGACA AGGAACTGTA TCCTTTAGCT TCCCTCAGAT CACTCTTTGG CAGCGACCCC    2280

TCGTCACAAT AAAGATAGGG GGGCAATTAA AGGAAGCTCT ATTAGATACA GGAGCAGATG    2340

ATACAGTATT AGAAGAAATG AATTTGCCAG GAAGATGGAA ACCAAAAATG ATAGGGGGAA    2400

TTGGAGGTTT TATCAAAGTA GGACAGTATG ATCAGATACT CATAGAAATC TGCGGACATA    2460

AAGCTATAGG TACAGTATTA GTAGGACCTA CACCTGTCAA CATAATTGGA AGAAATCTGT    2520

TGACTCAGAT TGGCTGCACT TTAAATTTTC CCATTAGTCC TATTGAGACT GTACCAGTAA    2580

AATTAAAGCC AGGAATGGAT GGCCCAAAAG TTAAACAATG GCCATTGACA GAAGAAAAAA    2640

TAAAAGCATT AGTAGAAATT TGTACAGAAA TGGAAAAGGA AGGAAAAATT TCAAAAATTG    2700

GGCCTGAAAA TCCATACAAT ACTCCAGTAT TTGCCATAAA GAAAAAGAC AGTACTAAAT    2760

GGAGAAAATT AGTAGATTTC AGAGAACTTA ATAAGAGAAC TCAAGATTTC TGGGAAGTTC    2820

AATTAGGAAT ACCACATCCT GCAGGGTTAA AACAGAAAAA ATCAGTAACA GTACTGGATG    2880

TGGGCGATGC ATATTTTTCA GTTCCCTTAG ATAAAGACTT CAGGAAGTAT ACTGCATTTA    2940

CCATACCTAG TATAAACAAT GAGACACCAG GGATTAGATA TCAGTACAAT GTGCTTCCAC    3000

AGGGATGGAA AGGATCACCA GCAATATTCC AGTGTAGCAT GACAAAAATC TTAGAGCCTT    3060

TTAGAAAACA AAATCCAGAC ATAGTCATCT ATCAATACAT GGATGATTTG TATGTAGGAT    3120

CTGACTTAGA AATAGGGCAG CATAGAACAA AAATAGAGGA ACTGAGACAA CATCTGTTGA    3180

GGTGGGGATT TACCACACCA GACAAAAAAC ATCAGAAAGA ACCTCCATTC CTTTGGATGG    3240

GTTATGAACT CCATCCTGAT AAATGGACAG TACAGCCTAT AGTGCTGCCA GAAAAGGACA    3300

GCTGGACTGT CAATGACATA CAGAAATTAG TGGGAAAATT GAATTGGGCA AGTCAGATTT    3360

ATGCAGGGAT TAAAGTAAGG CAATTATGTA AACTTCTTAG GGGAACCAAA GCACTAACAG    3420

AAGTAGTACC ACTAACAGAA GAAGCAGAGC TAGAACTGGC AGAAAACAGG GAGATTCTAA    3480

AAGAACCGGT ACATGGAGTG TATTATGACC CATCAAAAGA CTTAATAGCA GAAATACAGA    3540

AGCAGGGGCA AGGCCAATGG ACATATCAAA TTTATCAAGA GCCATTTAAA AATCTGAAAA    3600

CAGGAAAATA TGCAAGAATG AAGGGTGCCC ACACTAATGA TGTGAAACAA TTAACAGAGG    3660

CAGTACAAAA AATAGCCACA GAAAGCATAG TAATATGGGG AAAGACTCCT AAATTTAAAT    3720

TACCCATACA AAAGGAAACA TGGGAAGCAT GGTGGACAGA GTATTGGCAA GCCACCTGGA    3780

TTCCTGAGTG GGAGTTTGTC AATACCCCTC CCTTAGTGAA GTTATGGTAC CAGTTAGAGA    3840

AAGAACCCAT AATAGGAGCA GAAACTTTCT ATGTAGATGG GGCAGCCAAT AGGGAAACTA    3900

AATTAGGAAA AGCAGGATAT GTAACTGACA GAGGAAGACA AAAAGTTGTC CCCCTAACGG    3960

ACACAACAAA TCAGAAGACT GAGTTACAAG CAATTCATCT AGCTTTGCAG GATTCGGGAT    4020

TAGAAGTAAA CATAGTGACA GACTCACAAT ATGCATTGGG AATCATTCAA GCACAACCAG    4080

ATAAGAGTGA ATCAGAGTTA GTCAGTCAAA TAATAGAGCA GTTAATAAAA AAGGAAAAAG    4140

TCTACCTGGC ATGGGTACCA GCACACAAAG GAATTGGAGG AAATGAACAA GTAGATGGGT    4200
```

```
TGGTCAGTGC TGGAATCAGG AAAGTACTAT TTTTAGATGG AATAGATAAG GCCCAAGAAG    4260

AACATGAGAA ATATCACAGT AATTGGAGAG CAATGGCTAG TGATTTTAAC CTACCACCTG    4320

TAGTAGCAAA AGAAATAGTA GCCAGCTGTG ATAAATGTCA GCTAAAAGGG AAGCCATGC     4380

ATGGACAAGT AGACTGTAGC CCAGGAATAT GGCAGCTAGA TTGTACACAT TTAGAAGGAA    4440

AAGTTATCTT GGTAGCAGTT CATGTAGCCA GTGGATATAT AGAAGCAGAA GTAATTCCAG    4500

CAGAGACAGG GCAAGAAACA GCATACTTCC TCTTAAAATT AGCAGGAAGA TGGCCAGTAA    4560

AAACAGTACA TACAGACAAT GGCAGCAATT TCACCAGTAC TACAGTTAAG GCCGCCTGTT    4620

GGTGGGCGGG GATCAAGCAG GAATTTGGCA TTCCCTACAA TCCCCAAAGT CAAGGAGTAA    4680

TAGAATCTAT GAATAAAGAA TTAAAGAAAA TTATAGGACA GGTAAGAGAT CAGGCTGAAC    4740

ATCTTAAGAC AGCAGTACAA ATGGCAGTAT TCATCCACAA TTTTAAAAGA AAAGGGGGGA    4800

TTGGGGGGTA CAGTGCAGGG GAAAGAATAG TAGACATAAT AGCAACAGAC ATACAAACTA    4860

AAGAATTACA AAAACAAATT ACAAAAATTC AAAATTTTCG GGTTTATTAC AGGGACAGCA    4920

GAGATCCAGT TTGGAAAGGA CCAGCAAAGC TCCTCTGGAA AGGTGAAGGG GCAGTAGTAA    4980

TACAAGATAA TAGTGACATA AAAGTAGTGC CAAGAAGAAA AGCAAAGATC ATCAGGGATT    5040

ATGGAAAACA GATGGCAGGT GATGATTGTG TGGCAAGTAG ACAGGATGAG GATTAACACA    5100

TGGAAAAGAT TAGTAAAACA CCATATGTAT ATTTCAAGGA AAGCTAAGGA CTGGTTTTAT    5160

AGACATCACT ATGAAAGTAC TAATCCAAAA ATAAGTTCAG AAGTACACAT CCCACTAGGG    5220

GATGCTAAAT TAGTAATAAC AACATATTGG GGTCTGCATA CAGGAGAAAG AGACTGGCAT    5280

TTGGGTCAGG GAGTCTCCAT AGAATGGAGG AAAAAGAGAT ATAGCACACA AGTAGACCCT    5340

GACCTAGCAG ACCAACTAAT TCATCTGCAC TATTTTGATT GTTTTTCAGA ATCTGCTATA    5400

AGAAATACCA TATTAGGACG TATAGTTAGT CCTAGGTGTG AATATCAAGC AGGACATAAC    5460

AAGGTAGGAT CTCTACAGTA CTTGGCACTA GCAGCATTAA TAAAACCAAA ACAGATAAAG    5520

CCACCTTTGC CTAGTGTTAG GAAACTGACA GAGGACAGAT GGAACAAGCC CCAGAAGACC    5580

AAGGGCCACA GAGGGAGCCA TACAATGAAT GGACACTAGA GCTTTTAGAG GAACTTAAGA    5640

GTGAAGCTGT TAGACATTTT CCTAGGATAT GGCTCCATAA CTTAGGACAA CATATCTATG    5700

AAACTTACGG GGATACTTGG GCAGGAGTGG AAGCCATAAT AAGAATTCTG CAACAACTGC    5760

TGTTTATCCA TTTCAGAATT GGGTGTCGAC ATAGCAGAAT AGGCGTTACT CGACAGAGGA    5820

GAGCAAGAAA TGGAGCCAGT AGATCCTAGA CTAGAGCCCT GGAAGCATCC AGGAAGTCAG    5880

CCTAAAACTG CTTGTACCAA TTGCTATTGT AAAAAGTGTT GCTTTCATTG CCAAGTTTGT    5940

TTCATGACAA AAGCCTTAGG CATCTCCTAT GGCAGGAAGA AGCGGAGACA GCGACGAAGA    6000

GCTCATCAGA ACAGTCAGAC TCATCAAGCT TCTCTATCAA AGCAGTAAGT AGTACATGTA    6060

ATGCAACCTA TAATAGTAGC AATAGTAGCA TTAGTAGTAG CAATAATAAT AGCAATAGTT    6120

GTGTGGTCCA TAGTAATCAT AGAATATAGG AAAATATTAA GACAAAGAAA AATAGACAGG    6180

TTAATTGATA GACTAATAGA AAGAGCAGAA GACAGTGGCA ATGAGAGTGA AGGAGAAGTA    6240

TCAGCACTTG TGGAGATGGG GGTGGAAATG GGGCACCATG CTCCTTGGGA TATTGATGAT    6300

CTGTAGTGCT ACAGAAAAAT TGTGGGTCAC AGTCTATTAT GGGGTACCTG TGTGGAAGGA    6360

AGCAACCACC ACTCTATTTT GTGCATCAGA TGCTAAAGCA TATGATACAG AGGTACATAA    6420

TGTTTGGGCC ACACATGCCT GTGTACCCAC AGACCCCAAC CCACAAGAAG TAGTATTGGT    6480

AAATGTGACA GAAAATTTTA ACATGTGGAA AAATGACATG GTAGAACAGA TGCATGAGGA    6540

TATAATCAGT TTATGGGATC AAAGCCTAAA GCCATGTGTA AAATTAACCC CACTCTGTGT    6600
```

```
TAGTTTAAAG TGCACTGATT TGAAGAATGA TACTAATACC AATAGTAGTA GCGGGAGAAT    6660

GATAATGGAG AAAGGAGAGA TAAAAAACTG CTCTTTCAAT ATCAGCACAA GCATAAGAGA    6720

TAAGGTGCAG AAAGAATATG CATTCTTTTA TAAACTTGAT ATAGTACCAA TAGATAATAC    6780

CAGCTATAGG TTGATAAGTT GTAACACCTC AGTCATTACA CAGGCCTGTC CAAAGGTATC    6840

CTTTGAGCCA ATTCCCATAC ATTATTGTGC CCCGGCTGGT TTTGCGATTC TAAAATGTAA    6900

TAATAAGACG TTCAATGGAA CAGGACCATG TACAAATGTC AGCACAGTAC AATGTACACA    6960

TGGAATCAGG CCAGTAGTAT CAACTCAACT GCTGTTAAAT GGCAGTCTAG CAGAAGAAGA    7020

TGTAGTAATT AGATCTGCCA ATTTCACAGA CAATGCTAAA ACCATAATAG TACAGCTGAA    7080

CACATCTGTA GAATTAATT GTACAAGACC CAACAACAAT ACAAGAAAAA GTATCCGTAT     7140

CCAGAGGGGA CCAGGGAGAG CATTTGTTAC AATAGGAAAA ATAGGAAATA TGAGACAAGC    7200

ACATTGTAAC ATTAGTAGAG CAAAATGGAA TGCCACTTTA AAACAGATAG CTAGCAAATT    7260

AAGAGAACAA TTTGGAAATA ATAAAACAAT AATCTTTAAG CAATCCTCAG GAGGGGACCC    7320

AGAAATTGTA ACGCACAGTT TTAATTGTGG AGGGGAATTT TTCTACTGTA ATTCAACACA    7380

ACTGTTTAAT AGTACTTGGT TTAATAGTAC TTGGAGTACT GAAGGGTCAA ATAACACTGA    7440

AGGAAGTGAC ACAATCACAC TCCCATGCAG AATAAAACAA TTTATAAACA TGTGGCAGGA    7500

AGTAGGAAAA GCAATGTATG CCCCTCCCAT CAGTGGACAA ATTAGATGTT CATCAAATAT    7560

TACTGGGCTG CTATTAACAA GAGATGGTGG TAATAACAAC AATGGGTCCG AGATCTTCAG    7620

ACCTGGAGGA GGCGATATGA GGGACAATTG GAGAAGTGAA TTATATAAAT ATAAAGTAGT    7680

AAAAATTGAA CCATTAGGAG TAGCACCCAC CAAGGCAAAG AGAAGAGTGG TGCAGAGAGA    7740

AAAAAGAGCA GTGGGAATAG GAGCTTTGTT CCTTGGGTTC TTGGGAGCAG CAGGAAGCAC    7800

TATGGGCTGC ACGTCAATGA CGCTGACGGT ACAGGCCAGA CAATTATTGT CTGATATAGT    7860

GCAGCAGCAG AACAATTTGC TGAGGGCTAT TGAGGCGCAA CAGCATCTGT TGCAACTCAC    7920

AGTCTGGGGC ATCAAACAGC TCCAGGCAAG AATCCTGGCT GTGGAAAGAT ACCTAAAGGA    7980

TCAACAGCTC CTGGGGATTT GGGGTTGCTC TGGAAAACTC ATTTGCACCA CTGCTGTGCC    8040

TTGGAATGCT AGTTGGAGTA ATAAATCTCT GGAACAGATT TGGAATAACA TGACCTGGAT    8100

GGAGTGGGAC AGAGAAATTA ACAATTACAC AAGCTTAATA CACTCCTTAA TTGAAGAATC    8160

GCAAAACCAG CAAGAAAAGA ATGAACAAGA ATTATTGGAA TTAGATAAAT GGGCAAGTTT    8220

GTGGAATTGG TTTAACATAA CAAATTGGCT GTGGTATATA AAATTATTCA TAATGATAGT    8280

AGGAGGCTTG GTAGGTTTAA GAATAGTTTT TGCTGTACTT TCTATAGTGA ATAGAGTTAG    8340

GCAGGGATAT TCACCATTAT CGTTTCAGAC CCACCTCCCA ATCCCGAGGG GACCCGACAG    8400

GCCCGAAGGA ATAGAAGAAG AAGGTGGAGA GAGAGACAGA GACAGATCCA TTCGATTAGT    8460

GAACGGATCC TTAGCACTTA TCTGGGACGA TCTGCGGAGC CTGTGCCTCT TCAGCTACCA    8520

CCGCTTGAGA GACTTACTCT TGATTGTAAC GAGGATTGTG GAACTTCTGG GACGCAGGGG    8580

GTGGGAAGCC CTCAAATATT GGTGGAATCT CCTACAGTAT GGAGTCAGG AACTAAAGAA     8640

TAGTGCTGTT AACTTGCTCA ATGCCACAGC CATAGCAGTA GCTGAGGGGA CAGATAGGGT    8700

TATAGAAGTA TTACAAGCAG CTTATAGAGC TATTCGCCAC ATACCTAGAA GAATAAGACA    8760

GGGCTTGGAA AGGATTTTGC TATAAGATGG GTGGCAAGTG GTCAAAAAGT AGTGTGATTG    8820

GATGGCCTGC TGTAAGGGAA AGAATGAGAC GAGCTGAGCC AGCAGCAGAT GGGGTGGGAG    8880

CAGTATCTCG AGACCTAGAA AAACATGGAG CAATCACAAG TAGCAATACA GCAGCTAACA    8940

ATGCTGCTTG TGCCTGGCTA GAAGCACAAG AGGAGGAAGA GGTGGGTTTT CCAGTCACAC    9000
```

```
CTCAGGTACC TTTAAGACCA ATGACTTACA AGGCAGCTGT AGATCTTAGC CACTTTTTAA    9060

AAGAAAAGGG GGGACTGGAA GGGCTAATTC ACTCCCAAAG AAGACAAGAT ATCCTTGATC    9120

TGTGGATCTA CCACACACAA GGCTACTTCC CTGATTGGCA GAACTACACA CCAGGGCCAG    9180

GGGTCAGATA TCCACTGACC TTTGGATGGT GCTACAAGCT AGTACCAGTT GAGCCAGATA    9240

AGGTAGAAGA GGCCAATAAA GGAGAGAACA CCAGCTTGTT ACACCCTGTG AGCCTGCATG    9300

GAATGGATGA CCCTGAGAGA GAAGTGTTAG AGTGGAGGTT TGACAGCCGC CTAGCATTTC    9360

ATCACGTGGC CCGAGAGCTG CATCCGGAGT ACTTCAAGAA CTGCTGACAT CGAGCTTGCT    9420

ACAAGGGACT TTCCGCTGGG GACTTTCCAG GGAGGCGTGG CCTGGGCGGG ACTGGGGAGT    9480

GGCGAGCCCT CAGATGCTGC ATATAAGCAG CTGCTTTTTG CCTGTACTGG GTCTCTCTGG    9540

TTAGACCAGA TCTGAGCCTG GGAGCTCTCT GGCTAACTAG GGAACCCACT GCTTAAGCCT    9600

CAATAAAGCT TGCCTTGAGT GCTTCAAGTA GTGTGTGCCC GTCTGTTGTG TGACTCTGGT    9660

AACTAGAGAT CCCTCAGACC CTTTTAGTCA GTGTGGAAAA TCTCTAGCA              9709
```

(2) INFORMATION FOR SEQ ID NO:2:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
ATGGGTGGCA                                                            10
```

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
TGGGTGGCAA                                                            10
```

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GGGTGGCAAG                                                            10
```

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GGTGGCAAGT                                                                  10

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTGGCAAGTG                                                                  10

(2) INFORMATION FOR SEQ ID NO:7:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TGGCAAGTGG                                                                  10

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGCAAGTGGT                                                                  10

(2) INFORMATION FOR SEQ ID NO:9:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCAAGTGGTC                                                                  10

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CAAGTGGTCA                                                                  10

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AAGTGGTCAA    10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGTGGTCAAA    10

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GTGGTCAAAA    10

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TGGTCAAAAA    10

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

GGTCAAAAAG    10

(2) INFORMATION FOR SEQ ID NO:16:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:16:

GTCAAAAAGT                                                              10

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TCAAAAAGTA                                                              10

(2) INFORMATION FOR SEQ ID NO:18:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CAAAAAGTAG                                                              10

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

AAAAAGTAGT                                                              10

(2) INFORMATION FOR SEQ ID NO:20:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AAAAGTAGTG                                                              10

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:21:

AAAGTAGTGT                                                                       10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

AAGTAGTGTG                                                                       10

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

AGTAGTGTGA                                                                       10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GTAGTGTGAT                                                                       10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TAGTGTGATT                                                                       10

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

AGTGTGATTG                                                                       10

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GTGTGATTGG                                                        10

(2) INFORMATION FOR SEQ ID NO:28:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TGTGATTGGA                                                        10

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GTGATTGGAT                                                        10

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

TGATTGGATG                                                        10

(2) INFORMATION FOR SEQ ID NO:31:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GATTGGATGG                                                        10

(2) INFORMATION FOR SEQ ID NO:32:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:32:

ATTGGATGGC                                                          10

(2) INFORMATION FOR SEQ ID NO:33:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

TTGGATGGCC                                                          10

(2) INFORMATION FOR SEQ ID NO:34:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

TGGATGGCCT                                                          10

(2) INFORMATION FOR SEQ ID NO:35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GGATGGCCTG                                                          10

(2) INFORMATION FOR SEQ ID NO:36:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

GATGGCCTGC                                                          10

(2) INFORMATION FOR SEQ ID NO:37:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

```
    (xi) SEQUENCE DESCRIPTION: SEQ ID NO:37:

ATGGCCTGCT                                                              10

(2) INFORMATION FOR SEQ ID NO:38:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

TGGCCTGCTG                                                              10

(2) INFORMATION FOR SEQ ID NO:39:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

GGCCTGCTGT                                                              10

(2) INFORMATION FOR SEQ ID NO:40:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

GCCTGCTGTA                                                              10

(2) INFORMATION FOR SEQ ID NO:41:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

CCTGCTGTAA                                                              10

(2) INFORMATION FOR SEQ ID NO:42:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

CTGCTGTAAG                                                              10
```

(2) INFORMATION FOR SEQ ID NO:43:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

TGCTGTAAGG    10

(2) INFORMATION FOR SEQ ID NO:44:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

GCTGTAAGGG    10

(2) INFORMATION FOR SEQ ID NO:45:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

CTGTAAGGGA    10

(2) INFORMATION FOR SEQ ID NO:46:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

TGTAAGGGAA    10

(2) INFORMATION FOR SEQ ID NO:47:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

GTAAGGGAAA    10

(2) INFORMATION FOR SEQ ID NO:48:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:48:

TAAGGGAAAG                                                              10

(2) INFORMATION FOR SEQ ID NO:49:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

AAGGGAAAGA                                                              10

(2) INFORMATION FOR SEQ ID NO:50:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

AGGGAAAGAA                                                              10

(2) INFORMATION FOR SEQ ID NO:51:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

GGGAAAGAAT                                                              10

(2) INFORMATION FOR SEQ ID NO:52:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

GGAAAGAATG                                                              10

(2) INFORMATION FOR SEQ ID NO:53:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:53:

GAAAGAATGA                                                                10

(2) INFORMATION FOR SEQ ID NO:54:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

AAAGAATGAG                                                                10

(2) INFORMATION FOR SEQ ID NO:55:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

AAGAATGAGA                                                                10

(2) INFORMATION FOR SEQ ID NO:56:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

AGAATGAGAC                                                                10

(2) INFORMATION FOR SEQ ID NO:57:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

GAATGAGACG                                                                10

(2) INFORMATION FOR SEQ ID NO:58:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

AATGAGACGA                                                                10

(2) INFORMATION FOR SEQ ID NO:59:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

ATGAGACGAG          10

(2) INFORMATION FOR SEQ ID NO:60:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

TGAGACGAGC          10

(2) INFORMATION FOR SEQ ID NO:61:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

GAGACGAGCT          10

(2) INFORMATION FOR SEQ ID NO:62:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

AGACGAGCTG          10

(2) INFORMATION FOR SEQ ID NO:63:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

GACGAGCTGA          10

(2) INFORMATION FOR SEQ ID NO:64:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:64:

ACGAGCTGAG                                                                10

(2) INFORMATION FOR SEQ ID NO:65:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

CGAGCTGAGC                                                                10

(2) INFORMATION FOR SEQ ID NO:66:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

GAGCTGAGCC                                                                10

(2) INFORMATION FOR SEQ ID NO:67:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

AGCTGAGCCA                                                                10

(2) INFORMATION FOR SEQ ID NO:68:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:68:

GCTGAGCCAG                                                                10

(2) INFORMATION FOR SEQ ID NO:69:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

CTGAGCCAGC                                                                    10

(2) INFORMATION FOR SEQ ID NO:70:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:70:

TGAGCCAGCA                                                                    10

(2) INFORMATION FOR SEQ ID NO:71:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:71:

GAGCCAGCAG                                                                    10

(2) INFORMATION FOR SEQ ID NO:72:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:72:

AGCCAGCAGC                                                                    10

(2) INFORMATION FOR SEQ ID NO:73:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:73:

GCCAGCAGCA                                                                    10

(2) INFORMATION FOR SEQ ID NO:74:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:74:

CCAGCAGCAG                                                                    10

(2) INFORMATION FOR SEQ ID NO:75:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

CAGCAGCAGA                                      10

(2) INFORMATION FOR SEQ ID NO:76:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

AGCAGCAGAT                                      10

(2) INFORMATION FOR SEQ ID NO:77:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

GCAGCAGATG                                      10

(2) INFORMATION FOR SEQ ID NO:78:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

CAGCAGATGG                                      10

(2) INFORMATION FOR SEQ ID NO:79:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:79:

AGCAGATGGG                                      10

(2) INFORMATION FOR SEQ ID NO:80:

(i) SEQUENCE CHARACTERISTICS:
        (A) LENGTH: 10 base pairs
        (B) TYPE: nucleic acid -continued

```
            (C) STRANDEDNESS: single
            (D) TOPOLOGY: linear (ii) MOLECULE TYPE: DNA (genomic)

(xi) SEQUENCE DESCRIPTION: SEQ ID NO:80:

GCAGATGGGG                                                              10

(2) INFORMATION FOR SEQ ID NO:81:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:81:

CAGATGGGGT                                                              10

(2) INFORMATION FOR SEQ ID NO:82:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:82:

AGATGGGGTG                                                              10

(2) INFORMATION FOR SEQ ID NO:83:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:83:

GATGGGGTGG                                                              10

(2) INFORMATION FOR SEQ ID NO:84:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:84:

ATGGGGTGGG                                                              10

(2) INFORMATION FOR SEQ ID NO:85:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)
```

```
    (xi) SEQUENCE DESCRIPTION: SEQ ID NO:85:

TGGGGTGGGA                                                          10

(2) INFORMATION FOR SEQ ID NO:86:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

GGGGTGGGAG                                                          10

(2) INFORMATION FOR SEQ ID NO:87:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:87:

GGGTGGGAGC                                                          10

(2) INFORMATION FOR SEQ ID NO:88:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:88:

GGTGGGAGCA                                                          10

(2) INFORMATION FOR SEQ ID NO:89:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:89:

GTGGGAGCAG                                                          10

(2) INFORMATION FOR SEQ ID NO:90:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:90:

TGGGAGCAGT                                                          10
```

(2) INFORMATION FOR SEQ ID NO:91:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:91:

GGGAGCAGTA                                              10

(2) INFORMATION FOR SEQ ID NO:92:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:92:

GGAGCAGTAT                                              10

(2) INFORMATION FOR SEQ ID NO:93:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:93:

GAGCAGTATC                                              10

(2) INFORMATION FOR SEQ ID NO:94:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:94:

AGCAGTATCT                                              10

(2) INFORMATION FOR SEQ ID NO:95:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:95:

GCAGTATCTC                                              10

(2) INFORMATION FOR SEQ ID NO:96:

(i) SEQUENCE CHARACTERISTICS:
        (A) LENGTH: 10 base pairs
        (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO:96:

CAGTATCTCG                                                              10

(2) INFORMATION FOR SEQ ID NO:97:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:97:

AGTATCTCGA                                                              10

(2) INFORMATION FOR SEQ ID NO:98:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:98:

GTATCTCGAG                                                              10

(2) INFORMATION FOR SEQ ID NO:99:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:99:

TATCTCGAGA                                                              10

(2) INFORMATION FOR SEQ ID NO:100:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:100:

ATCTCGAGAC                                                              10

(2) INFORMATION FOR SEQ ID NO:101:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)
```

```
    (xi) SEQUENCE DESCRIPTION: SEQ ID NO:101:

TCTCGAGACC                                                              10

(2) INFORMATION FOR SEQ ID NO:102:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:102:

CTCGAGACCT                                                              10

(2) INFORMATION FOR SEQ ID NO:103:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:103:

TCGAGACCTA                                                              10

(2) INFORMATION FOR SEQ ID NO:104:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:104:

CGAGACCTAG                                                              10

(2) INFORMATION FOR SEQ ID NO:105:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:105:

GAGACCTAGA                                                              10

(2) INFORMATION FOR SEQ ID NO:106:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:106:

AGACCTAGAA                                                              10
```

(2) INFORMATION FOR SEQ ID NO:107:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:107:

GACCTAGAAA          10

(2) INFORMATION FOR SEQ ID NO:108:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:108:

ACCTAGAAAA          10

(2) INFORMATION FOR SEQ ID NO:109:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:109:

CCTAGAAAAA          10

(2) INFORMATION FOR SEQ ID NO:110:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:110:

CTAGAAAAAC          10

(2) INFORMATION FOR SEQ ID NO:111:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:111:

TAGAAAAACA          10

(2) INFORMATION FOR SEQ ID NO:112:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:112:

AGAAAAACAT                                                              10

(2) INFORMATION FOR SEQ ID NO:113:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:113:

GAAAAACATG                                                              10

(2) INFORMATION FOR SEQ ID NO:114:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:114:

AAAAACATGG                                                              10

(2) INFORMATION FOR SEQ ID NO:115:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:115:

AAAACATGGA                                                              10

(2) INFORMATION FOR SEQ ID NO:116:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:116:

AAACATGGAG                                                              10

(2) INFORMATION FOR SEQ ID NO:117:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:117:

AACATGGAGC                                                                  10

(2) INFORMATION FOR SEQ ID NO:118:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:118:

ACATGGAGCA                                                                  10

(2) INFORMATION FOR SEQ ID NO:119:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:119:

CATGGAGCAA                                                                  10

(2) INFORMATION FOR SEQ ID NO:120:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:120:

ATGGAGCAAT                                                                  10

(2) INFORMATION FOR SEQ ID NO:121:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:121:

TGGAGCAATC                                                                  10

(2) INFORMATION FOR SEQ ID NO:122:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:122:

GGAGCAATCA                                                                  10

(2) INFORMATION FOR SEQ ID NO:123:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:123:

GAGCAATCAC    10

(2) INFORMATION FOR SEQ ID NO:124:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:124:

AGCAATCACA    10

(2) INFORMATION FOR SEQ ID NO:125:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:125:

GCAATCACAA    10

(2) INFORMATION FOR SEQ ID NO:126:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:126:

CAATCACAAG    10

(2) INFORMATION FOR SEQ ID NO:127:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:127:

AATCACAAGT    10

(2) INFORMATION FOR SEQ ID NO:128:

(i) SEQUENCE CHARACTERISTICS:
        (A) LENGTH: 10 base pairs
        (B) TYPE: nucleic acid (C) STRANDEDNESS: single
          (D) TOPOLOGY: linear (ii) MOLECULE TYPE: DNA (genomic)

(xi) SEQUENCE DESCRIPTION: SEQ ID NO:128:

ATCACAAGTA                                                                10

(2) INFORMATION FOR SEQ ID NO:129:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:129:

TCACAAGTAG                                                                10

(2) INFORMATION FOR SEQ ID NO:130:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:130:

CACAAGTAGC                                                                10

(2) INFORMATION FOR SEQ ID NO:131:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:131:

ACAAGTAGCA                                                                10

(2) INFORMATION FOR SEQ ID NO:132:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:132:

CAAGTAGCAA                                                                10

(2) INFORMATION FOR SEQ ID NO:133:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

```
    (xi) SEQUENCE DESCRIPTION: SEQ ID NO:133:

AAGTAGCAAT                                                                    10

(2) INFORMATION FOR SEQ ID NO:134:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:134:

AGTAGCAATA                                                                    10

(2) INFORMATION FOR SEQ ID NO:135:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:135:

GTAGCAATAC                                                                    10

(2) INFORMATION FOR SEQ ID NO:136:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:136:

TAGCAATACA                                                                    10

(2) INFORMATION FOR SEQ ID NO:137:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:137:

AGCAATACAG                                                                    10

(2) INFORMATION FOR SEQ ID NO:138:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:138:

GCAATACAGC                                                                    10
```

(2) INFORMATION FOR SEQ ID NO:139:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:139:

CAATACAGCA    10

(2) INFORMATION FOR SEQ ID NO:140:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:140:

AATACAGCAG    10

(2) INFORMATION FOR SEQ ID NO:141:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:141:

ATACAGCAGC    10

(2) INFORMATION FOR SEQ ID NO:142:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:142:

TACAGCAGCT    10

(2) INFORMATION FOR SEQ ID NO:143:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:143:

ACAGCAGCTA    10

(2) INFORMATION FOR SEQ ID NO:144:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:144:

CAGCAGCTAA                                                              10

(2) INFORMATION FOR SEQ ID NO:145:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:145:

AGCAGCTAAC                                                              10

(2) INFORMATION FOR SEQ ID NO:146:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:146:

GCAGCTAACA                                                              10

(2) INFORMATION FOR SEQ ID NO:147:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:147:

CAGCTAACAA                                                              10

(2) INFORMATION FOR SEQ ID NO:148:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:148:

AGCTAACAAT                                                              10

(2) INFORMATION FOR SEQ ID NO:149:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

-continued (xi) SEQUENCE DESCRIPTION: SEQ ID NO:149:

GCTAACAATG                                                                  10

(2) INFORMATION FOR SEQ ID NO:150:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:150:

CTAACAATGC                                                                  10

(2) INFORMATION FOR SEQ ID NO:151:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:151:

TAACAATGCT                                                                  10

(2) INFORMATION FOR SEQ ID NO:152:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:152:

AACAATGCTG                                                                  10

(2) INFORMATION FOR SEQ ID NO:153:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:153:

ACAATGCTGC                                                                  10

(2) INFORMATION FOR SEQ ID NO:154:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:154:

CAATGCTGCT                                                                  10

(2) INFORMATION FOR SEQ ID NO:155:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:155:

AATGCTGCTT                                                              10

(2) INFORMATION FOR SEQ ID NO:156:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:156:

ATGCTGCTTG                                                              10

(2) INFORMATION FOR SEQ ID NO:157:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:157:

TGCTGCTTGT                                                              10

(2) INFORMATION FOR SEQ ID NO:158:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:158:

GCTGCTTGTG                                                              10

(2) INFORMATION FOR SEQ ID NO:159:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:159:

CTGCTTGTGC                                                              10

(2) INFORMATION FOR SEQ ID NO:160:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:160:

TGCTTGTGCC                                                              10

(2) INFORMATION FOR SEQ ID NO:161:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:161:

GCTTGTGCCT                                                              10

(2) INFORMATION FOR SEQ ID NO:162:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:162:

CTTGTGCCTG                                                              10

(2) INFORMATION FOR SEQ ID NO:163:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:163:

TTGTGCCTGG                                                              10

(2) INFORMATION FOR SEQ ID NO:164:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:164:

TGTGCCTGGC                                                              10

(2) INFORMATION FOR SEQ ID NO:165:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:165:

GTGCCTGGCT                                                              10

(2) INFORMATION FOR SEQ ID NO:166:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:166:

TGCCTGGCTA                                                              10

(2) INFORMATION FOR SEQ ID NO:167:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:167:

GCCTGGCTAG                                                              10

(2) INFORMATION FOR SEQ ID NO:168:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:168:

CCTGGCTAGA                                                              10

(2) INFORMATION FOR SEQ ID NO:169:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:169:

CTGGCTAGAA                                                              10

(2) INFORMATION FOR SEQ ID NO:170:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:170:

TGGCTAGAAG                                                              10

(2) INFORMATION FOR SEQ ID NO:171:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:171:

GGCTAGAAGC                                                                      10

(2) INFORMATION FOR SEQ ID NO:172:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:172:

GCTAGAAGCA                                                                      10

(2) INFORMATION FOR SEQ ID NO:173:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:173:

CTAGAAGCAC                                                                      10

(2) INFORMATION FOR SEQ ID NO:174:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:174:

TAGAAGCACA                                                                      10

(2) INFORMATION FOR SEQ ID NO:175:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:175:

AGAAGCACAA                                                                      10

(2) INFORMATION FOR SEQ ID NO:176:

(i) SEQUENCE CHARACTERISTICS:
        (A) LENGTH: 10 base pairs
        (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO:176:

GAAGCACAAG                                                                      10

(2) INFORMATION FOR SEQ ID NO:177:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:177:

AAGCACAAGA                                                                      10

(2) INFORMATION FOR SEQ ID NO:178:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:178:

AGCACAAGAG                                                                      10

(2) INFORMATION FOR SEQ ID NO:179:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:179:

GCACAAGAGG                                                                      10

(2) INFORMATION FOR SEQ ID NO:180:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:180:

CACAAGAGGA                                                                      10

(2) INFORMATION FOR SEQ ID NO:181:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:181:

ACAAGAGGAG                                                                        10

(2) INFORMATION FOR SEQ ID NO:182:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:182:

CAAGAGGAGG                                                                        10

(2) INFORMATION FOR SEQ ID NO:183:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:183:

AAGAGGAGGA                                                                        10

(2) INFORMATION FOR SEQ ID NO:184:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:184:

AGAGGAGGAA                                                                        10

(2) INFORMATION FOR SEQ ID NO:185:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:185:

GAGGAGGAAG                                                                        10

(2) INFORMATION FOR SEQ ID NO:186:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:186:

AGGAGGAAGA                                                                        10

(2) INFORMATION FOR SEQ ID NO:187:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:187:

GGAGGAAGAG          10

(2) INFORMATION FOR SEQ ID NO:188:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:188:

GAGGAAGAGG          10

(2) INFORMATION FOR SEQ ID NO:189:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:189:

AGGAAGAGGT          10

(2) INFORMATION FOR SEQ ID NO:190:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:190:

GGAAGAGGTG          10

(2) INFORMATION FOR SEQ ID NO:191:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:191:

GAAGAGGTGG          10

(2) INFORMATION FOR SEQ ID NO:192:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:192:

AAGAGGTGGG                                                              10

(2) INFORMATION FOR SEQ ID NO:193:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:193:

AGAGGTGGGT                                                              10

(2) INFORMATION FOR SEQ ID NO:194:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:194:

GAGGTGGGTT                                                              10

(2) INFORMATION FOR SEQ ID NO:195:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:195:

AGGTGGGTTT                                                              10

(2) INFORMATION FOR SEQ ID NO:196:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:196:

GGTGGGTTTT                                                              10

(2) INFORMATION FOR SEQ ID NO:197:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:197:

GTGGGTTTTC                                                            10

(2) INFORMATION FOR SEQ ID NO:198:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:198:

TGGGTTTTCC                                                            10

(2) INFORMATION FOR SEQ ID NO:199:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:199:

GGGTTTTCCA                                                            10

(2) INFORMATION FOR SEQ ID NO:200:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:200:

GGTTTTCCAG                                                            10

(2) INFORMATION FOR SEQ ID NO:201:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:201:

GTTTTCCAGT                                                            10

(2) INFORMATION FOR SEQ ID NO:202:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:202:

TTTTCCAGTC                                                            10

(2) INFORMATION FOR SEQ ID NO:203:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:203:

TTTCCAGTCA                                                              10

(2) INFORMATION FOR SEQ ID NO:204:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:204:

TTCCAGTCAC                                                              10

(2) INFORMATION FOR SEQ ID NO:205:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:205:

TCCAGTCACA                                                              10

(2) INFORMATION FOR SEQ ID NO:206:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:206:

CCAGTCACAC                                                              10

(2) INFORMATION FOR SEQ ID NO:207:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:207:

CAGTCACACC                                                              10

(2) INFORMATION FOR SEQ ID NO:208:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:208:

AGTCACACCT                                                           10

(2) INFORMATION FOR SEQ ID NO:209:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:209:

GTCACACCTC                                                           10

(2) INFORMATION FOR SEQ ID NO:210:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:210:

TCACACCTCA                                                           10

(2) INFORMATION FOR SEQ ID NO:211:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:211:

CACACCTCAG                                                           10

(2) INFORMATION FOR SEQ ID NO:212:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:212:

ACACCTCAGG                                                           10

(2) INFORMATION FOR SEQ ID NO:213:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:213:

CACCTCAGGT                                                                                              10

(2) INFORMATION FOR SEQ ID NO:214:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:214:

ACCTCAGGTA                                                                                              10

(2) INFORMATION FOR SEQ ID NO:215:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:215:

CCTCAGGTAC                                                                                              10

(2) INFORMATION FOR SEQ ID NO:216:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:216:

CTCAGGTACC                                                                                              10

(2) INFORMATION FOR SEQ ID NO:217:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:217:

TCAGGTACCT                                                                                              10

(2) INFORMATION FOR SEQ ID NO:218:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:218:

CAGGTACCTT                                                                                              10

(2) INFORMATION FOR SEQ ID NO:219:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:219:

AGGTACCTTT                                                              10

(2) INFORMATION FOR SEQ ID NO:220:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:220:

GGTACCTTTA                                                              10

(2) INFORMATION FOR SEQ ID NO:221:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:221:

GTACCTTTAA                                                              10

(2) INFORMATION FOR SEQ ID NO:222:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:222:

TACCTTTAAG                                                              10

(2) INFORMATION FOR SEQ ID NO:223:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:223:

ACCTTTAAGA                                                              10

(2) INFORMATION FOR SEQ ID NO:224:

(i) SEQUENCE CHARACTERISTICS:
        (A) LENGTH: 10 base pairs
        (B) TYPE: nucleic acid

```
         (C) STRANDEDNESS: single
         (D) TOPOLOGY: linear (ii) MOLECULE TYPE: DNA (genomic)

(xi) SEQUENCE DESCRIPTION: SEQ ID NO:224:

CCTTTAAGAC                                                              10

(2) INFORMATION FOR SEQ ID NO:225:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:225:

CTTTAAGACC                                                              10

(2) INFORMATION FOR SEQ ID NO:226:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:226:

TTTAAGACCA                                                              10

(2) INFORMATION FOR SEQ ID NO:227:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:227:

TTAAGACCAA                                                              10

(2) INFORMATION FOR SEQ ID NO:228:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:228:

TAAGACCAAT                                                              10

(2) INFORMATION FOR SEQ ID NO:229:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)
```

(xi) SEQUENCE DESCRIPTION: SEQ ID NO:229:

AAGACCAATG                                                                10

(2) INFORMATION FOR SEQ ID NO:230:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:230:

AGACCAATGA                                                                10

(2) INFORMATION FOR SEQ ID NO:231:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:231:

GACCAATGAC                                                                10

(2) INFORMATION FOR SEQ ID NO:232:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:232:

ACCAATGACT                                                                10

(2) INFORMATION FOR SEQ ID NO:233:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:233:

CCAATGACTT                                                                10

(2) INFORMATION FOR SEQ ID NO:234:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:234:

CAATGACTTA                                                                10

(2) INFORMATION FOR SEQ ID NO:235:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:235:

AATGACTTAC          10

(2) INFORMATION FOR SEQ ID NO:236:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:236:

ATGACTTACA          10

(2) INFORMATION FOR SEQ ID NO:237:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:237:

TGACTTACAA          10

(2) INFORMATION FOR SEQ ID NO:238:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:238:

GACTTACAAG          10

(2) INFORMATION FOR SEQ ID NO:239:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:239:

ACTTACAAGG          10

(2) INFORMATION FOR SEQ ID NO:240:

(i) SEQUENCE CHARACTERISTICS:
        (A) LENGTH: 10 base pairs
        (B) TYPE: nucleic acid

```
          (C) STRANDEDNESS: single
          (D) TOPOLOGY: linear (ii) MOLECULE TYPE: DNA (genomic)

(xi) SEQUENCE DESCRIPTION: SEQ ID NO:240:

CTTACAAGGC                                                              10

(2) INFORMATION FOR SEQ ID NO:241:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:241:

TTACAAGGCA                                                              10

(2) INFORMATION FOR SEQ ID NO:242:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:242:

TACAAGGCAG                                                              10

(2) INFORMATION FOR SEQ ID NO:243:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:243:

ACAAGGCAGC                                                              10

(2) INFORMATION FOR SEQ ID NO:244:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:244:

CAAGGCAGCT                                                              10

(2) INFORMATION FOR SEQ ID NO:245:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)
```

(xi) SEQUENCE DESCRIPTION: SEQ ID NO:245:

AAGGCAGCTG                                                                              10

(2) INFORMATION FOR SEQ ID NO:246:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:246:

AGGCAGCTGT                                                                              10

(2) INFORMATION FOR SEQ ID NO:247:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:247:

GGCAGCTGTA                                                                              10

(2) INFORMATION FOR SEQ ID NO:248:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:248:

GCAGCTGTAG                                                                              10

(2) INFORMATION FOR SEQ ID NO:249:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:249:

CAGCTGTAGA                                                                              10

(2) INFORMATION FOR SEQ ID NO:250:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:250:

AGCTGTAGAT                                                                              10

(2) INFORMATION FOR SEQ ID NO:251:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:251:

GCTGTAGATC    10

(2) INFORMATION FOR SEQ ID NO:252:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:252:

CTGTAGATCT    10

(2) INFORMATION FOR SEQ ID NO:253:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:253:

TGTAGATCTT    10

(2) INFORMATION FOR SEQ ID NO:254:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:254:

GTAGATCTTA    10

(2) INFORMATION FOR SEQ ID NO:255:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:255:

TAGATCTTAG    10

(2) INFORMATION FOR SEQ ID NO:256:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:256:

AGATCTTAGC                                                           10

(2) INFORMATION FOR SEQ ID NO:257:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:257:

GATCTTAGCC                                                           10

(2) INFORMATION FOR SEQ ID NO:258:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:258:

ATCTTAGCCA                                                           10

(2) INFORMATION FOR SEQ ID NO:259:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:259:

TCTTAGCCAC                                                           10

(2) INFORMATION FOR SEQ ID NO:260:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:260:

CTTAGCCACT                                                           10

(2) INFORMATION FOR SEQ ID NO:261:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:261:

TTAGCCACTT                                                          10

(2) INFORMATION FOR SEQ ID NO:262:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:262:

TAGCCACTTT                                                          10

(2) INFORMATION FOR SEQ ID NO:263:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:263:

AGCCACTTTT                                                          10

(2) INFORMATION FOR SEQ ID NO:264:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:264:

GCCACTTTTT                                                          10

(2) INFORMATION FOR SEQ ID NO:265:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:265:

CCACTTTTTA                                                          10

(2) INFORMATION FOR SEQ ID NO:266:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:266:

CACTTTTTAA                                                          10

(2) INFORMATION FOR SEQ ID NO:267:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:267:

ACTTTTTAAA    10

(2) INFORMATION FOR SEQ ID NO:268:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:268:

CTTTTTAAAA    10

(2) INFORMATION FOR SEQ ID NO:269:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:269:

TTTTTAAAAG    10

(2) INFORMATION FOR SEQ ID NO:270:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:270:

TTTTAAAAGA    10

(2) INFORMATION FOR SEQ ID NO:271:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:271:

TTTAAAAGAA    10

(2) INFORMATION FOR SEQ ID NO:272:

(i) SEQUENCE CHARACTERISTICS:
        (A) LENGTH: 10 base pairs
        (B) TYPE: nucleic acid 173
174
-continued

```
        (C) STRANDEDNESS: single
        (D) TOPOLOGY: linear (ii) MOLECULE TYPE: DNA (genomic)

(xi) SEQUENCE DESCRIPTION: SEQ ID NO:272:

TTAAAAGAAA                                                          10

(2) INFORMATION FOR SEQ ID NO:273:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:273:

TAAAAGAAAA                                                          10

(2) INFORMATION FOR SEQ ID NO:274:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:274:

AAAAGAAAAG                                                          10

(2) INFORMATION FOR SEQ ID NO:275:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:275:

AAAGAAAAGG                                                          10

(2) INFORMATION FOR SEQ ID NO:276:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:276:

AAGAAAAGGG                                                          10

(2) INFORMATION FOR SEQ ID NO:277:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

```
    (xi) SEQUENCE DESCRIPTION: SEQ ID NO:277:

AGAAAAGGGG                                                                          10

(2) INFORMATION FOR SEQ ID NO:278:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:278:

GAAAAGGGGG                                                                          10

(2) INFORMATION FOR SEQ ID NO:279:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:279:

AAAAGGGGGG                                                                          10

(2) INFORMATION FOR SEQ ID NO:280:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:280:

AAAGGGGGGA                                                                          10

(2) INFORMATION FOR SEQ ID NO:281:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:281:

AAGGGGGGAC                                                                          10

(2) INFORMATION FOR SEQ ID NO:282:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:282:

AGGGGGGACT                                                                          10
```

(2) INFORMATION FOR SEQ ID NO:283:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:283:

GGGGGGACTG    10

(2) INFORMATION FOR SEQ ID NO:284:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:284:

GGGGGACTGG    10

(2) INFORMATION FOR SEQ ID NO:285:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:285:

GGGGACTGGA    10

(2) INFORMATION FOR SEQ ID NO:286:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:286:

GGGACTGGAA    10

(2) INFORMATION FOR SEQ ID NO:287:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:287:

GGACTGGAAG    10

(2) INFORMATION FOR SEQ ID NO:288:

(i) SEQUENCE CHARACTERISTICS:
        (A) LENGTH: 10 base pairs
        (B) TYPE: nucleic acid -continued

```
            (C) STRANDEDNESS: single
            (D) TOPOLOGY: linear (ii) MOLECULE TYPE: DNA (genomic)

(xi) SEQUENCE DESCRIPTION: SEQ ID NO:288:

GACTGGAAGG                                                            10

(2) INFORMATION FOR SEQ ID NO:289:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:289:

ACTGGAAGGG                                                            10

(2) INFORMATION FOR SEQ ID NO:290:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:290:

CTGGAAGGGC                                                            10

(2) INFORMATION FOR SEQ ID NO:291:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:291:

TGGAAGGGCT                                                            10

(2) INFORMATION FOR SEQ ID NO:292:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:292:

GGAAGGGCTA                                                            10

(2) INFORMATION FOR SEQ ID NO:293:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:293:

GAAGGGCTAA                                                                        10

(2) INFORMATION FOR SEQ ID NO:294:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:294:

AAGGGCTAAT                                                                        10

(2) INFORMATION FOR SEQ ID NO:295:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:295:

AGGGCTAATT                                                                        10

(2) INFORMATION FOR SEQ ID NO:296:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:296:

GGGCTAATTC                                                                        10

(2) INFORMATION FOR SEQ ID NO:297:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:297:

GGCTAATTCA                                                                        10

(2) INFORMATION FOR SEQ ID NO:298:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:298:

GCTAATTCAC                                                                        10

(2) INFORMATION FOR SEQ ID NO:299:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:299:

CTAATTCACT    10

(2) INFORMATION FOR SEQ ID NO:300:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:300:

TAATTCACTC    10

(2) INFORMATION FOR SEQ ID NO:301:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:301:

AATTCACTCC    10

(2) INFORMATION FOR SEQ ID NO:302:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:302:

ATTCACTCCC    10

(2) INFORMATION FOR SEQ ID NO:303:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:303:

TTCACTCCCA    10

(2) INFORMATION FOR SEQ ID NO:304:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:304:

TCACTCCCAA                                                                      10

(2) INFORMATION FOR SEQ ID NO:305:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:305:

CACTCCCAAA                                                                      10

(2) INFORMATION FOR SEQ ID NO:306:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:306:

ACTCCCAAAG                                                                      10

(2) INFORMATION FOR SEQ ID NO:307:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:307:

CTCCCAAAGA                                                                      10

(2) INFORMATION FOR SEQ ID NO:308:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:308:

TCCCAAAGAA                                                                      10

(2) INFORMATION FOR SEQ ID NO:309:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

```
        (xi) SEQUENCE DESCRIPTION: SEQ ID NO:309:

CCCAAAGAAG                                                              10

(2) INFORMATION FOR SEQ ID NO:310:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:310:

CCAAAGAAGA                                                              10

(2) INFORMATION FOR SEQ ID NO:311:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:311:

CAAAGAAGAC                                                              10

(2) INFORMATION FOR SEQ ID NO:312:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:312:

AAAGAAGACA                                                              10

(2) INFORMATION FOR SEQ ID NO:313:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:313:

AAGAAGACAA                                                              10

(2) INFORMATION FOR SEQ ID NO:314:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:314:

AGAAGACAAG                                                              10
```

(2) INFORMATION FOR SEQ ID NO:315:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:315:

GAAGACAAGA                                                                10

(2) INFORMATION FOR SEQ ID NO:316:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:316:

AAGACAAGAT                                                                10

(2) INFORMATION FOR SEQ ID NO:317:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:317:

AGACAAGATA                                                                10

(2) INFORMATION FOR SEQ ID NO:318:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:318:

GACAAGATAT                                                                10

(2) INFORMATION FOR SEQ ID NO:319:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:319:

ACAAGATATC                                                                10

(2) INFORMATION FOR SEQ ID NO:320:

(i) SEQUENCE CHARACTERISTICS:
(A) LENGTH: 10 base pairs
(B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO:320:

CAAGATATCC                                                          10

(2) INFORMATION FOR SEQ ID NO:321:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:321:

AAGATATCCT                                                          10

(2) INFORMATION FOR SEQ ID NO:322:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:322:

AGATATCCTT                                                          10

(2) INFORMATION FOR SEQ ID NO:323:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:323:

GATATCCTTG                                                          10

(2) INFORMATION FOR SEQ ID NO:324:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:324:

ATATCCTTGA                                                          10

(2) INFORMATION FOR SEQ ID NO:325:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:325:

TATCCTTGAT                                                                  10

(2) INFORMATION FOR SEQ ID NO:326:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:326:

ATCCTTGATC                                                                  10

(2) INFORMATION FOR SEQ ID NO:327:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:327:

TCCTTGATCT                                                                  10

(2) INFORMATION FOR SEQ ID NO:328:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:328:

CCTTGATCTG                                                                  10

(2) INFORMATION FOR SEQ ID NO:329:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:329:

CTTGATCTGT                                                                  10

(2) INFORMATION FOR SEQ ID NO:330:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:330:

TTGATCTGTG                                                                  10

(2) INFORMATION FOR SEQ ID NO:331:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:331:

TGATCTGTGG                                                              10

(2) INFORMATION FOR SEQ ID NO:332:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:332:

GATCTGTGGA                                                              10

(2) INFORMATION FOR SEQ ID NO:333:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:333:

ATCTGTGGAT                                                              10

(2) INFORMATION FOR SEQ ID NO:334:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:334:

TCTGTGGATC                                                              10

(2) INFORMATION FOR SEQ ID NO:335:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:335:

CTGTGGATCT                                                              10

(2) INFORMATION FOR SEQ ID NO:336:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:336:

TGTGGATCTA                                                              10

(2) INFORMATION FOR SEQ ID NO:337:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:337:

GTGGATCTAC                                                              10

(2) INFORMATION FOR SEQ ID NO:338:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:338:

TGGATCTACC                                                              10

(2) INFORMATION FOR SEQ ID NO:339:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:339:

GGATCTACCA                                                              10

(2) INFORMATION FOR SEQ ID NO:340:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:340:

GATCTACCAC                                                              10

(2) INFORMATION FOR SEQ ID NO:341:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:341:

ATCTACCACA                                                              10

(2) INFORMATION FOR SEQ ID NO:342:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:342:

TCTACCACAC                                                              10

(2) INFORMATION FOR SEQ ID NO:343:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:343:

CTACCACACA                                                              10

(2) INFORMATION FOR SEQ ID NO:344:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:344:

TACCACACAC                                                              10

(2) INFORMATION FOR SEQ ID NO:345:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:345:

ACCACACACA                                                              10

(2) INFORMATION FOR SEQ ID NO:346:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:346:

CCACACACAA                                                              10

(2) INFORMATION FOR SEQ ID NO:347:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:347:

CACACACAAG    10

(2) INFORMATION FOR SEQ ID NO:348:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:348:

ACACACAAGG    10

(2) INFORMATION FOR SEQ ID NO:349:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:349:

CACACAAGGC    10

(2) INFORMATION FOR SEQ ID NO:350:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:350:

ACACAAGGCT    10

(2) INFORMATION FOR SEQ ID NO:351:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:351:

CACAAGGCTA    10

(2) INFORMATION FOR SEQ ID NO:352:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:352:

ACAAGGCTAC                                                                  10

(2) INFORMATION FOR SEQ ID NO:353:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:353:

CAAGGCTACT                                                                  10

(2) INFORMATION FOR SEQ ID NO:354:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:354:

AAGGCTACTT                                                                  10

(2) INFORMATION FOR SEQ ID NO:355:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:355:

AGGCTACTTC                                                                  10

(2) INFORMATION FOR SEQ ID NO:356:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:356:

GGCTACTTCC                                                                  10

(2) INFORMATION FOR SEQ ID NO:357:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:357:

GCTACTTCCC                                                          10

(2) INFORMATION FOR SEQ ID NO:358:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:358:

CTACTTCCCT                                                          10

(2) INFORMATION FOR SEQ ID NO:359:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:359:

TACTTCCCTG                                                          10

(2) INFORMATION FOR SEQ ID NO:360:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:360:

ACTTCCCTGA                                                          10

(2) INFORMATION FOR SEQ ID NO:361:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:361:

CTTCCCTGAT                                                          10

(2) INFORMATION FOR SEQ ID NO:362:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:362:

TTCCCTGATT                                                          10

(2) INFORMATION FOR SEQ ID NO:363:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:363:

TCCCTGATTG                                                              10

(2) INFORMATION FOR SEQ ID NO:364:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:364:

CCCTGATTGG                                                              10

(2) INFORMATION FOR SEQ ID NO:365:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:365:

CCTGATTGGC                                                              10

(2) INFORMATION FOR SEQ ID NO:366:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:366:

CTGATTGGCA                                                              10

(2) INFORMATION FOR SEQ ID NO:367:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:367:

TGATTGGCAG                                                              10

(2) INFORMATION FOR SEQ ID NO:368:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:368:

GATTGGCAGA                                                          10

(2) INFORMATION FOR SEQ ID NO:369:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:369:

ATTGGCAGAA                                                          10

(2) INFORMATION FOR SEQ ID NO:370:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:370:

TTGGCAGAAC                                                          10

(2) INFORMATION FOR SEQ ID NO:371:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:371:

TGGCAGAACT                                                          10

(2) INFORMATION FOR SEQ ID NO:372:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:372:

GGCAGAACTA                                                          10

(2) INFORMATION FOR SEQ ID NO:373:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:373:

GCAGAACTAC                                                            10

(2) INFORMATION FOR SEQ ID NO:374:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:374:

CAGAACTACA                                                            10

(2) INFORMATION FOR SEQ ID NO:375:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:375:

AGAACTACAC                                                            10

(2) INFORMATION FOR SEQ ID NO:376:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:376:

GAACTACACA                                                            10

(2) INFORMATION FOR SEQ ID NO:377:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:377:

AACTACACAC                                                            10

(2) INFORMATION FOR SEQ ID NO:378:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:378:

ACTACACACC                                                            10

(2) INFORMATION FOR SEQ ID NO:379:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:379:

CTACACACCA    10

(2) INFORMATION FOR SEQ ID NO:380:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:380:

TACACACCAG    10

(2) INFORMATION FOR SEQ ID NO:381:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:381:

ACACACCAGG    10

(2) INFORMATION FOR SEQ ID NO:382:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:382:

CACACCAGGG    10

(2) INFORMATION FOR SEQ ID NO:383:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:383:

ACACCAGGGC    10

(2) INFORMATION FOR SEQ ID NO:384:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:384:

CACCAGGGCC                                                                              10

(2) INFORMATION FOR SEQ ID NO:385:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:385:

ACCAGGGCCA                                                                              10

(2) INFORMATION FOR SEQ ID NO:386:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:386:

CCAGGGCCAG                                                                              10

(2) INFORMATION FOR SEQ ID NO:387:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:387:

CAGGGCCAGG                                                                              10

(2) INFORMATION FOR SEQ ID NO:388:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:388:

AGGGCCAGGG                                                                              10

(2) INFORMATION FOR SEQ ID NO:389:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:389:

GGGCCAGGGG                                                                10

(2) INFORMATION FOR SEQ ID NO:390:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:390:

GGCCAGGGGT                                                                10

(2) INFORMATION FOR SEQ ID NO:391:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:391:

GCCAGGGGTC                                                                10

(2) INFORMATION FOR SEQ ID NO:392:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:392:

CCAGGGGTCA                                                                10

(2) INFORMATION FOR SEQ ID NO:393:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:393:

CAGGGGTCAG                                                                10

(2) INFORMATION FOR SEQ ID NO:394:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:394:

AGGGGTCAGA                                                                10

(2) INFORMATION FOR SEQ ID NO:395:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:395:

GGGGTCAGAT    10

(2) INFORMATION FOR SEQ ID NO:396:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:396:

GGGTCAGATA    10

(2) INFORMATION FOR SEQ ID NO:397:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:397:

GGTCAGATAT    10

(2) INFORMATION FOR SEQ ID NO:398:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:398:

GTCAGATATC    10

(2) INFORMATION FOR SEQ ID NO:399:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:399:

TCAGATATCC    10

(2) INFORMATION FOR SEQ ID NO:400:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:400:

CAGATATCCA                                                                          10

(2) INFORMATION FOR SEQ ID NO:401:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:401:

AGATATCCAC                                                                          10

(2) INFORMATION FOR SEQ ID NO:402:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:402:

GATATCCACT                                                                          10

(2) INFORMATION FOR SEQ ID NO:403:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:403:

ATATCCACTG                                                                          10

(2) INFORMATION FOR SEQ ID NO:404:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:404:

TATCCACTGA                                                                          10

(2) INFORMATION FOR SEQ ID NO:405:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

```
    (xi) SEQUENCE DESCRIPTION: SEQ ID NO:405:

ATCCACTGAC                                                              10

(2) INFORMATION FOR SEQ ID NO:406:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:406:

TCCACTGACC                                                              10

(2) INFORMATION FOR SEQ ID NO:407:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:407:

CCACTGACCT                                                              10

(2) INFORMATION FOR SEQ ID NO:408:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:408:

CACTGACCTT                                                              10

(2) INFORMATION FOR SEQ ID NO:409:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:409:

ACTGACCTTT                                                              10

(2) INFORMATION FOR SEQ ID NO:410:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:410:

CTGACCTTTG                                                              10
```

(2) INFORMATION FOR SEQ ID NO:411:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:411:

TGACCTTTGG        10

(2) INFORMATION FOR SEQ ID NO:412:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:412:

GACCTTTGGA        10

(2) INFORMATION FOR SEQ ID NO:413:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:413:

ACCTTTGGAT        10

(2) INFORMATION FOR SEQ ID NO:414:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:414:

CCTTTGGATG        10

(2) INFORMATION FOR SEQ ID NO:415:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:415:

CTTTGGATGG        10

(2) INFORMATION FOR SEQ ID NO:416:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:416:

TTTGGATGGT                                                              10

(2) INFORMATION FOR SEQ ID NO:417:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:417:

TTGGATGGTG                                                              10

(2) INFORMATION FOR SEQ ID NO:418:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:418:

TGGATGGTGC                                                              10

(2) INFORMATION FOR SEQ ID NO:419:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:419:

GGATGGTGCT                                                              10

(2) INFORMATION FOR SEQ ID NO:420:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:420:

GATGGTGCTA                                                              10

(2) INFORMATION FOR SEQ ID NO:421:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

```
      (xi) SEQUENCE DESCRIPTION: SEQ ID NO:421:

ATGGTGCTAC                                                              10

(2) INFORMATION FOR SEQ ID NO:422:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:422:

TGGTGCTACA                                                              10

(2) INFORMATION FOR SEQ ID NO:423:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:423:

GGTGCTACAA                                                              10

(2) INFORMATION FOR SEQ ID NO:424:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:424:

GTGCTACAAG                                                              10

(2) INFORMATION FOR SEQ ID NO:425:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:425:

TGCTACAAGC                                                              10

(2) INFORMATION FOR SEQ ID NO:426:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:426:

GCTACAAGCT                                                              10
```

(2) INFORMATION FOR SEQ ID NO:427:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:427:

CTACAAGCTA        10

(2) INFORMATION FOR SEQ ID NO:428:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:428:

TACAAGCTAG        10

(2) INFORMATION FOR SEQ ID NO:429:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:429:

ACAAGCTAGT        10

(2) INFORMATION FOR SEQ ID NO:430:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:430:

CAAGCTAGTA        10

(2) INFORMATION FOR SEQ ID NO:431:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:431:

AAGCTAGTAC        10

(2) INFORMATION FOR SEQ ID NO:432:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:432:

AGCTAGTACC                                                            10

(2) INFORMATION FOR SEQ ID NO:433:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:433:

GCTAGTACCA                                                            10

(2) INFORMATION FOR SEQ ID NO:434:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:434:

CTAGTACCAG                                                            10

(2) INFORMATION FOR SEQ ID NO:435:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:435:

TAGTACCAGT                                                            10

(2) INFORMATION FOR SEQ ID NO:436:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:436:

AGTACCAGTT                                                            10

(2) INFORMATION FOR SEQ ID NO:437:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:437:

GTACCAGTTG                                                          10

(2) INFORMATION FOR SEQ ID NO:438:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:438:

TACCAGTTGA                                                          10

(2) INFORMATION FOR SEQ ID NO:439:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:439:

ACCAGTTGAG                                                          10

(2) INFORMATION FOR SEQ ID NO:440:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:440:

CCAGTTGAGC                                                          10

(2) INFORMATION FOR SEQ ID NO:441:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:441:

CAGTTGAGCC                                                          10

(2) INFORMATION FOR SEQ ID NO:442:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:442:

AGTTGAGCCA                                                          10

(2) INFORMATION FOR SEQ ID NO:443:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:443:

GTTGAGCCAG    10

(2) INFORMATION FOR SEQ ID NO:444:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:444:

TTGAGCCAGA    10

(2) INFORMATION FOR SEQ ID NO:445:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:445:

TGAGCCAGAT    10

(2) INFORMATION FOR SEQ ID NO:446:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:446:

GAGCCAGATA    10

(2) INFORMATION FOR SEQ ID NO:447:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:447:

AGCCAGATAA    10

(2) INFORMATION FOR SEQ ID NO:448:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:448:

GCCAGATAAG                                                              10

(2) INFORMATION FOR SEQ ID NO:449:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:449:

CCAGATAAGG                                                              10

(2) INFORMATION FOR SEQ ID NO:450:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:450:

CAGATAAGGT                                                              10

(2) INFORMATION FOR SEQ ID NO:451:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:451:

AGATAAGGTA                                                              10

(2) INFORMATION FOR SEQ ID NO:452:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:452:

GATAAGGTAG                                                              10

(2) INFORMATION FOR SEQ ID NO:453:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:453:

ATAAGGTAGA					10

(2) INFORMATION FOR SEQ ID NO:454:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:454:

TAAGGTAGAA					10

(2) INFORMATION FOR SEQ ID NO:455:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:455:

AAGGTAGAAG					10

(2) INFORMATION FOR SEQ ID NO:456:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:456:

AGGTAGAAGA					10

(2) INFORMATION FOR SEQ ID NO:457:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:457:

GGTAGAAGAG					10

(2) INFORMATION FOR SEQ ID NO:458:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:458:

GTAGAAGAGG					10

(2) INFORMATION FOR SEQ ID NO:459:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:459:

TAGAAGAGGC                                                                10

(2) INFORMATION FOR SEQ ID NO:460:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:460:

AGAAGAGGCC                                                                10

(2) INFORMATION FOR SEQ ID NO:461:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:461:

GAAGAGGCCA                                                                10

(2) INFORMATION FOR SEQ ID NO:462:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:462:

AAGAGGCCAA                                                                10

(2) INFORMATION FOR SEQ ID NO:463:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:463:

AGAGGCCAAT                                                                10

(2) INFORMATION FOR SEQ ID NO:464:

(i) SEQUENCE CHARACTERISTICS:
        (A) LENGTH: 10 base pairs
        (B) TYPE: nucleic acid

```
          (C) STRANDEDNESS: single
          (D) TOPOLOGY: linear (ii) MOLECULE TYPE: DNA (genomic)

(xi) SEQUENCE DESCRIPTION: SEQ ID NO:464:

GAGGCCAATA                                                              10

(2) INFORMATION FOR SEQ ID NO:465:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:465:

AGGCCAATAA                                                              10

(2) INFORMATION FOR SEQ ID NO:466:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:466:

GGCCAATAAA                                                              10

(2) INFORMATION FOR SEQ ID NO:467:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:467:

GCCAATAAAG                                                              10

(2) INFORMATION FOR SEQ ID NO:468:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:468:

CCAATAAAGG                                                              10

(2) INFORMATION FOR SEQ ID NO:469:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)
```

```
    (xi) SEQUENCE DESCRIPTION: SEQ ID NO:469:

CAATAAAGGA                                                               10

(2) INFORMATION FOR SEQ ID NO:470:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:470:

AATAAAGGAG                                                               10

(2) INFORMATION FOR SEQ ID NO:471:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:471:

ATAAAGGAGA                                                               10

(2) INFORMATION FOR SEQ ID NO:472:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:472:

TAAAGGAGAG                                                               10

(2) INFORMATION FOR SEQ ID NO:473:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:473:

AAAGGAGAGA                                                               10

(2) INFORMATION FOR SEQ ID NO:474:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:474:

AAGGAGAGAA                                                               10
```

(2) INFORMATION FOR SEQ ID NO:475:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:475:

AGGAGAGAAC                                                          10

(2) INFORMATION FOR SEQ ID NO:476:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:476:

GGAGAGAACA                                                          10

(2) INFORMATION FOR SEQ ID NO:477:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:477:

GAGAGAACAC                                                          10

(2) INFORMATION FOR SEQ ID NO:478:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:478:

AGAGAACACC                                                          10

(2) INFORMATION FOR SEQ ID NO:479:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:479:

GAGAACACCA                                                          10

(2) INFORMATION FOR SEQ ID NO:480:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:480:

AGAACACCAG                                                                    10

(2) INFORMATION FOR SEQ ID NO:481:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:481:

GAACACCAGC                                                                    10

(2) INFORMATION FOR SEQ ID NO:482:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:482:

AACACCAGCT                                                                    10

(2) INFORMATION FOR SEQ ID NO:483:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:483:

ACACCAGCTT                                                                    10

(2) INFORMATION FOR SEQ ID NO:484:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:484:

CACCAGCTTG                                                                    10

(2) INFORMATION FOR SEQ ID NO:485:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:485:

ACCAGCTTGT                                                                    10

(2) INFORMATION FOR SEQ ID NO:486:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:486:

CCAGCTTGTT                                                                    10

(2) INFORMATION FOR SEQ ID NO:487:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:487:

CAGCTTGTTA                                                                    10

(2) INFORMATION FOR SEQ ID NO:488:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:488:

AGCTTGTTAC                                                                    10

(2) INFORMATION FOR SEQ ID NO:489:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:489:

GCTTGTTACA                                                                    10

(2) INFORMATION FOR SEQ ID NO:490:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:490:

CTTGTTACAC                                                                    10

(2) INFORMATION FOR SEQ ID NO:491:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:491:

TTGTTACACC                                                              10

(2) INFORMATION FOR SEQ ID NO:492:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:492:

TGTTACACCC                                                              10

(2) INFORMATION FOR SEQ ID NO:493:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:493:

GTTACACCCT                                                              10

(2) INFORMATION FOR SEQ ID NO:494:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:494:

TTACACCCTG                                                              10

(2) INFORMATION FOR SEQ ID NO:495:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:495:

TACACCCTGT                                                              10

(2) INFORMATION FOR SEQ ID NO:496:

(i) SEQUENCE CHARACTERISTICS:
        (A) LENGTH: 10 base pairs
        (B) TYPE: nucleic acid -continued (C) STRANDEDNESS: single
      (D) TOPOLOGY: linear (ii) MOLECULE TYPE: DNA (genomic)

(xi) SEQUENCE DESCRIPTION: SEQ ID NO:496:

ACACCCTGTG                            10

(2) INFORMATION FOR SEQ ID NO:497:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:497:

CACCCTGTGA                            10

(2) INFORMATION FOR SEQ ID NO:498:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:498:

ACCCTGTGAG                            10

(2) INFORMATION FOR SEQ ID NO:499:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:499:

CCCTGTGAGC                            10

(2) INFORMATION FOR SEQ ID NO:500:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:500:

CCTGTGAGCC                            10

(2) INFORMATION FOR SEQ ID NO:501:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:501:

CTGTGAGCCT 10

(2) INFORMATION FOR SEQ ID NO:502:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:502:

TGTGAGCCTG 10

(2) INFORMATION FOR SEQ ID NO:503:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:503:

GTGAGCCTGC 10

(2) INFORMATION FOR SEQ ID NO:504:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:504:

TGAGCCTGCA 10

(2) INFORMATION FOR SEQ ID NO:505:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:505:

GAGCCTGCAT 10

(2) INFORMATION FOR SEQ ID NO:506:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:506:

AGCCTGCATG 10

(2) INFORMATION FOR SEQ ID NO:507:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:507:

GCCTGCATGG                                                                10

(2) INFORMATION FOR SEQ ID NO:508:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:508:

CCTGCATGGA                                                                10

(2) INFORMATION FOR SEQ ID NO:509:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:509:

CTGCATGGAA                                                                10

(2) INFORMATION FOR SEQ ID NO:510:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:510:

TGCATGGAAT                                                                10

(2) INFORMATION FOR SEQ ID NO:511:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:511:

GCATGGAATG                                                                10

(2) INFORMATION FOR SEQ ID NO:512:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:512:

CATGGAATGG                                                                              10

(2) INFORMATION FOR SEQ ID NO:513:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:513:

ATGGAATGGA                                                                              10

(2) INFORMATION FOR SEQ ID NO:514:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:514:

TGGAATGGAT                                                                              10

(2) INFORMATION FOR SEQ ID NO:515:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:515:

GGAATGGATG                                                                              10

(2) INFORMATION FOR SEQ ID NO:516:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:516:

GAATGGATGA                                                                              10

(2) INFORMATION FOR SEQ ID NO:517:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:517:

AATGGATGAC                                                                  10

(2) INFORMATION FOR SEQ ID NO:518:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:518:

ATGGATGACC                                                                  10

(2) INFORMATION FOR SEQ ID NO:519:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:519:

TGGATGACCC                                                                  10

(2) INFORMATION FOR SEQ ID NO:520:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:520:

GGATGACCCT                                                                  10

(2) INFORMATION FOR SEQ ID NO:521:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:521:

GATGACCCTG                                                                  10

(2) INFORMATION FOR SEQ ID NO:522:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:522:

ATGACCCTGA                                                                  10

(2) INFORMATION FOR SEQ ID NO:523:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:523:

TGACCCTGAG                                                                10

(2) INFORMATION FOR SEQ ID NO:524:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:524:

GACCCTGAGA                                                                10

(2) INFORMATION FOR SEQ ID NO:525:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:525:

ACCCTGAGAG                                                                10

(2) INFORMATION FOR SEQ ID NO:526:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:526:

CCCTGAGAGA                                                                10

(2) INFORMATION FOR SEQ ID NO:527:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:527:

CCTGAGAGAG                                                                10

(2) INFORMATION FOR SEQ ID NO:528:

(i) SEQUENCE CHARACTERISTICS:
        (A) LENGTH: 10 base pairs
        (B) TYPE: nucleic acid

```
        (C) STRANDEDNESS: single
        (D) TOPOLOGY: linear (ii) MOLECULE TYPE: DNA (genomic)

(xi) SEQUENCE DESCRIPTION: SEQ ID NO:528:

CTGAGAGAGA                                                               10

(2) INFORMATION FOR SEQ ID NO:529:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:529:

TGAGAGAGAA                                                               10

(2) INFORMATION FOR SEQ ID NO:530:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:530:

GAGAGAGAAG                                                               10

(2) INFORMATION FOR SEQ ID NO:531:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:531:

AGAGAGAAGT                                                               10

(2) INFORMATION FOR SEQ ID NO:532:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:532:

GAGAGAAGTG                                                               10

(2) INFORMATION FOR SEQ ID NO:533:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:533:

AGAGAAGTGT                                                                            10

(2) INFORMATION FOR SEQ ID NO:534:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:534:

GAGAAGTGTT                                                                            10

(2) INFORMATION FOR SEQ ID NO:535:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:535:

AGAAGTGTTA                                                                            10

(2) INFORMATION FOR SEQ ID NO:536:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:536:

GAAGTGTTAG                                                                            10

(2) INFORMATION FOR SEQ ID NO:537:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:537:

AAGTGTTAGA                                                                            10

(2) INFORMATION FOR SEQ ID NO:538:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:538:

AGTGTTAGAG                                                                            10

(2) INFORMATION FOR SEQ ID NO:539:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:539:

GTGTTAGAGT                                                              10

(2) INFORMATION FOR SEQ ID NO:540:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:540:

TGTTAGAGTG                                                              10

(2) INFORMATION FOR SEQ ID NO:541:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:541:

GTTAGAGTGG                                                              10

(2) INFORMATION FOR SEQ ID NO:542:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:542:

TTAGAGTGGA                                                              10

(2) INFORMATION FOR SEQ ID NO:543:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:543:

TAGAGTGGAG                                                              10

(2) INFORMATION FOR SEQ ID NO:544:

(i) SEQUENCE CHARACTERISTICS:
        (A) LENGTH: 10 base pairs
        (B) TYPE: nucleic acid (C) STRANDEDNESS: single
          (D) TOPOLOGY: linear (ii) MOLECULE TYPE: DNA (genomic)

(xi) SEQUENCE DESCRIPTION: SEQ ID NO:544:

AGAGTGGAGG                                                              10

(2) INFORMATION FOR SEQ ID NO:545:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:545:

GAGTGGAGGT                                                              10

(2) INFORMATION FOR SEQ ID NO:546:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:546:

AGTGGAGGTT                                                              10

(2) INFORMATION FOR SEQ ID NO:547:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:547:

GTGGAGGTTT                                                              10

(2) INFORMATION FOR SEQ ID NO:548:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:548:

TGGAGGTTTG                                                              10

(2) INFORMATION FOR SEQ ID NO:549:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:549:

GGAGGTTTGA                                                              10

(2) INFORMATION FOR SEQ ID NO:550:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:550:

GAGGTTTGAC                                                              10

(2) INFORMATION FOR SEQ ID NO:551:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:551:

AGGTTTGACA                                                              10

(2) INFORMATION FOR SEQ ID NO:552:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:552:

GGTTTGACAG                                                              10

(2) INFORMATION FOR SEQ ID NO:553:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:553:

GTTTGACAGC                                                              10

(2) INFORMATION FOR SEQ ID NO:554:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:554:

TTTGACAGCC                                                              10

(2) INFORMATION FOR SEQ ID NO:555:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:555:

TTGACAGCCG    10

(2) INFORMATION FOR SEQ ID NO:556:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:556:

TGACAGCCGC    10

(2) INFORMATION FOR SEQ ID NO:557:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:557:

GACAGCCGCC    10

(2) INFORMATION FOR SEQ ID NO:558:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:558:

ACAGCCGCCT    10

(2) INFORMATION FOR SEQ ID NO:559:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:559:

CAGCCGCCTA    10

(2) INFORMATION FOR SEQ ID NO:560:

(i) SEQUENCE CHARACTERISTICS:
        (A) LENGTH: 10 base pairs
        (B) TYPE: nucleic acid

```
         (C) STRANDEDNESS: single
         (D) TOPOLOGY: linear (ii) MOLECULE TYPE: DNA (genomic)

(xi) SEQUENCE DESCRIPTION: SEQ ID NO:560:

AGCCGCCTAG                                                              10

(2) INFORMATION FOR SEQ ID NO:561:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:561:

GCCGCCTAGC                                                              10

(2) INFORMATION FOR SEQ ID NO:562:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:562:

CCGCCTAGCA                                                              10

(2) INFORMATION FOR SEQ ID NO:563:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:563:

CGCCTAGCAT                                                              10

(2) INFORMATION FOR SEQ ID NO:564:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:564:

GCCTAGCATT                                                              10

(2) INFORMATION FOR SEQ ID NO:565:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)
```

(xi) SEQUENCE DESCRIPTION: SEQ ID NO:565:

CCTAGCATTT                                                                  10

(2) INFORMATION FOR SEQ ID NO:566:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:566:

CTAGCATTTC                                                                  10

(2) INFORMATION FOR SEQ ID NO:567:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:567:

TAGCATTTCA                                                                  10

(2) INFORMATION FOR SEQ ID NO:568:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:568:

AGCATTTCAT                                                                  10

(2) INFORMATION FOR SEQ ID NO:569:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:569:

GCATTTCATC                                                                  10

(2) INFORMATION FOR SEQ ID NO:570:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:570:

CATTTCATCA                                                                  10

(2) INFORMATION FOR SEQ ID NO:571:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:571:

ATTTCATCAC                                      10

(2) INFORMATION FOR SEQ ID NO:572:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:572:

TTTCATCACG                                      10

(2) INFORMATION FOR SEQ ID NO:573:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:573:

TTCATCACGT                                      10

(2) INFORMATION FOR SEQ ID NO:574:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:574:

TCATCACGTG                                      10

(2) INFORMATION FOR SEQ ID NO:575:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:575:

CATCACGTGG                                      10

(2) INFORMATION FOR SEQ ID NO:576:

(i) SEQUENCE CHARACTERISTICS:
        (A) LENGTH: 10 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:576:

ATCACGTGGC                                                              10

(2) INFORMATION FOR SEQ ID NO:577:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:577:

TCACGTGGCC                                                              10

(2) INFORMATION FOR SEQ ID NO:578:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:578:

CACGTGGCCC                                                              10

(2) INFORMATION FOR SEQ ID NO:579:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:579:

ACGTGGCCCG                                                              10

(2) INFORMATION FOR SEQ ID NO:580:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:580:

CGTGGCCCGA                                                              10

(2) INFORMATION FOR SEQ ID NO:581:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

```
      (xi) SEQUENCE DESCRIPTION: SEQ ID NO:581:

GTGGCCCGAG                                                             10

(2) INFORMATION FOR SEQ ID NO:582:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:582:

TGGCCCGAGA                                                             10

(2) INFORMATION FOR SEQ ID NO:583:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:583:

GGCCCGAGAG                                                             10

(2) INFORMATION FOR SEQ ID NO:584:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:584:

GCCCGAGAGC                                                             10

(2) INFORMATION FOR SEQ ID NO:585:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:585:

CCCGAGAGCT                                                             10

(2) INFORMATION FOR SEQ ID NO:586:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:586:

CCGAGAGCTG                                                             10
```

-continued (2) INFORMATION FOR SEQ ID NO:587:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:587:

CGAGAGCTGC          10

(2) INFORMATION FOR SEQ ID NO:588:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:588:

GAGAGCTGCA          10

(2) INFORMATION FOR SEQ ID NO:589:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:589:

AGAGCTGCAT          10

(2) INFORMATION FOR SEQ ID NO:590:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:590:

GAGCTGCATC          10

(2) INFORMATION FOR SEQ ID NO:591:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:591:

AGCTGCATCC          10

(2) INFORMATION FOR SEQ ID NO:592:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:592:

GCTGCATCCG                                                              10

(2) INFORMATION FOR SEQ ID NO:593:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:593:

CTGCATCCGG                                                              10

(2) INFORMATION FOR SEQ ID NO:594:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:594:

TGCATCCGGA                                                              10

(2) INFORMATION FOR SEQ ID NO:595:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:595:

GCATCCGGAG                                                              10

(2) INFORMATION FOR SEQ ID NO:596:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:596:

CATCCGGAGT                                                              10

(2) INFORMATION FOR SEQ ID NO:597:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:597:

ATCCGGAGTA                                                                               10

(2) INFORMATION FOR SEQ ID NO:598:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:598:

TCCGGAGTAC                                                                               10

(2) INFORMATION FOR SEQ ID NO:599:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:599:

CCGGAGTACT                                                                               10

(2) INFORMATION FOR SEQ ID NO:600:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:600:

CGGAGTACTT                                                                               10

(2) INFORMATION FOR SEQ ID NO:601:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:601:

GGAGTACTTC                                                                               10

(2) INFORMATION FOR SEQ ID NO:602:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:602:

GAGTACTTCA                                                                               10

(2) INFORMATION FOR SEQ ID NO:603:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:603:

AGTACTTCAA                                                          10

(2) INFORMATION FOR SEQ ID NO:604:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:604:

GTACTTCAAG                                                          10

(2) INFORMATION FOR SEQ ID NO:605:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:605:

TACTTCAAGA                                                          10

(2) INFORMATION FOR SEQ ID NO:606:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:606:

ACTTCAAGAA                                                          10

(2) INFORMATION FOR SEQ ID NO:607:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:607:

CTTCAAGAAC                                                          10

(2) INFORMATION FOR SEQ ID NO:608:

(i) SEQUENCE CHARACTERISTICS:
        (A) LENGTH: 10 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:608:

TTCAAGAACT                                                          10

(2) INFORMATION FOR SEQ ID NO:609:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:609:

TCAAGAACTG                                                          10

(2) INFORMATION FOR SEQ ID NO:610:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:610:

CAAGAACTGC                                                          10

(2) INFORMATION FOR SEQ ID NO:611:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:611:

AAGAACTGCT                                                          10

(2) INFORMATION FOR SEQ ID NO:612:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:612:

AGAACTGCTG                                                          10

(2) INFORMATION FOR SEQ ID NO:613:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:613:

| GAACTGCTGA | 10 |

(2) INFORMATION FOR SEQ ID NO:614:

(i) SEQUENCE CHARACTERISTICS:
        (A) LENGTH: 1305 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:614:

| GAAGAGATTT GGGAGAACAT GACCTGGATG CAGTGGGAAA AAGAAATTCA CAATCACACA | 60 |
| AAATACATAT ACTCCTTACT TGAAAAATCG CAGAACCAAC AAGAAAAGAA TGAACAAGAA | 120 |
| CTATTGGAAT TGGATCAATG GGCAAGTTTG TGGAATTGGT TTGACATAAC AAAATGGCTG | 180 |
| TGGTATATAA AAATATTCAT AATGGTAGTA GGAGGCTTGA TAGGTTTAAG AATAGTTTTT | 240 |
| GCTGTACTTT CTATAGTGAA TAGAGTTAGG CAGGGATACT CACCATTGTC GTTTCAGACC | 300 |
| CTCCTCCCAA CCCCGAGGGG ACCCGACAGG CCCGAAGGAA TCGAAGAAGA AGGTGGAGAG | 360 |
| AGAGACAGAG ACAGATCCAC TCGATTAGTA CACGGATTCT TAGCACTTTT CTGGGACGAC | 420 |
| CTGAGGAGCC TGTGCCTCTT CCTCTACCAC CACTTGAGAG ACTTACTCTT GATTGTAACA | 480 |
| AGGATTGTGG AACTTCTGGG ACGCAGGGGA TGGGAAGCCC TCAAATATTG GTGGAACCTC | 540 |
| CTAAAGTATT GGAGCCAGGA ACTGCAGAAG AGTGCTGTTA TCTTGCTCAA TGCCACCGCC | 600 |
| ATAGCAGTAG CTGAGGGGAC AGATAGAGTT TTAGAAGTAT TACAAAGAGC TTATAGAGCT | 660 |
| ATCCTCCACA TACCTAGAAG AATAAGACAG GGCCTCGAAA TGGCTTTGCT ATAAAATGGG | 720 |
| TGGCAAGTGA GCAAAAAGTA GTGTAGTCAG ATAGCATGCA TCATAAGGGG TGGGGGCCAA | 780 |
| CAACTAACAA TGCTGATCGT GCCTGGCTAG AAGCACAAGA GAAGGAAGAA GCGGGTTTTC | 840 |
| CAGTCAAACC TCAGGTAGCT GTAGATCTTA GCCACTTTTT AAAAGAAAAG GGGGACTGG | 900 |
| AAGGGCTAAT TCACTCCCAA AGAAGACAAG ATACACAGTG CTGCAAACTA TTACCAGTGG | 960 |
| AGTCAGCGAA GATAGAAGAG GCCAATGGAG GAGAAAACCA CAGATTGTTC TGTTGGGGAC | 1020 |
| TTTCCATCCG TTGGGGACTT TCCAAGGCGG CGTGGCCTGG GTGACTAGTT CCGGTGGGGA | 1080 |
| CTTTCCAAGA AGGCGCGGCC TGGGCGGGAC TGGGGAGTGG CGAGCCCTCA GATGCTGCAT | 1140 |
| ATAAGCAGCT GCTTTCTGCT GTTACTGGGT CTCTCGGGTT AGACCAGATC TGAGCCTGGG | 1200 |
| AGCTCTCTGG CTAACTAGGG AACCCACTGC TTAAGCCTCA ATAAAGCTTG CCTTGAGTGC | 1260 |
| TTCAAGTAGT GTGTGCCCGT CTGTTGTGTG ACTCTGGTAT CTAGA | 1305 |

(2) INFORMATION FOR SEQ ID NO:615:

(i) SEQUENCE CHARACTERISTICS:
        (A) LENGTH: 1208 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:615:

| GAAACAATTT GGGATAACAT GACCTGGATG CAGTGGGAAA GAGAAATTGA CAATTACACA | 60 |
| AACATAATAT ACACCTTAAT TGAAGAATCG CAGAACCAAC AAGAAAAAAA TGAACTAGAA | 120 |
| TTATTGGAAT TGGATAAATG GGCAAATTTG TGGAATTGGT TTAGTATATC AAACTGGCTA | 180 |

```
TGGTATATAA AATTATTCAT AATGGTAGTA GGAGGCTTGG TAGGTTTAAG AATAGTTTTT      240

ACTGTACTTT CTATAGTGAA TAGAGTTAGG CAGGGATACT CACCATTGTC GTTTCAGACC      300

CACCTCCCAA CCCCGAAGGG ACCCGACAGG CCAGAAGGAA TCGAAGAAGA AGGTGGAGAG      360

AGAGACAGAG GCAGCTCCAC TCGATTAGTG CACGGATTCT TAGCACTTTT CTGGGACGAC      420

CTGAGGAGTC TGTGCCTCTT CAGCTACCAC CACTTGAGAG ACTTACTCTT GATTGTAACG      480

AGGATTGTGG AACTTCTGGG ACGCAGGGGA TGGGAAGCCC TCAAATACTG GTGGAATCTC      540

CTGCAGTATT GGAGGCAGGA ACTACAGAAG AGTGCTGTTA GCTTGTTCAA TGGCACGGCC      600

ATAGCAGTAG CTGAGGGGAC AGATAGAGTT ATAGAAGCTT TACGAAGGGC TTATAGAGCT      660

ATTCTCCACA TACCTAGAAG AATAAGCACAG GGCTTAGAAA GGGCTTTGCT ATAAAATGGG      720

TGGCAAGTGG TCAGAAAGTA GTGTGGTTAG AAGGCATGTA CCTTTAAGAC AAGGCAGCTA      780

TAGATCTTAG CCGCTTTTTA AAAGAAAAGG GGGGACTGGA AGGGCTAATT CACTCACAGA      840

GAAGATCAGT TGAACCAGAA GAAGATAGAA GAGGCCATGA AGAAGAAAAC AACAGATTGT      900

TCCGTTTGTT CCGTTGGGGA CTTTCCAGGA GACGTGGCCT GAGTGATAAG CCGCTGGGGA      960

CTTTCCGAAG AGGCGTGACG GGACTTTCCA AGGCGACGTG GCCTGGGCGG GACTGGGGAG     1020

TGGCGAGCCC TCAGATGCTG CATATAAGCA GCTGCTTTCT GCCTGTACTG GGTCTCTCTG     1080

GTTAGACCAG ATCTGAGCCT GGGAGCTCTC TGGCTAACTA GGGAACCCAC TGCTTAAGCC     1140

TCAATAAAGC TTGCCTTGAG TGCTTCAAGT AGTGTGTGCC CGTCTGTTGT GTGACTCTGG     1200

TATCTAGA                                                              1208

(2) INFORMATION FOR SEQ ID NO:616:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:616:

TGGAAGGGCT AATTTGGT                                                     18

(2) INFORMATION FOR SEQ ID NO:617:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:617:

ATCTTCCCTA AAAAATTAGC CTGTC                                             25

(2) INFORMATION FOR SEQ ID NO:618:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:618:

AGGCTCAGAT CTGGTCTAAC                                                   20
```

(2) INFORMATION FOR SEQ ID NO:619:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:619:

AGCAGCAGGA AGCACTATGG                                                    20

(2) INFORMATION FOR SEQ ID NO:620:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:620:

TGCTAGAGAT TTTCCACAC                                                     19

(2) INFORMATION FOR SEQ ID NO:621:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:621:

AGTGAATAGA GTTAGGCAGG                                                    20

(2) INFORMATION FOR SEQ ID NO:622:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:622:

GTAAGACAGT ATGATCAGAT A                                                  21

(2) INFORMATION FOR SEQ ID NO:623:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:623:

TTGTAGGGAA TTCCAAATTC C                                                  21

(2) INFORMATION FOR SEQ ID NO:624:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:624:

CAGGATCCTA CACCTGTCAA CATAAT                                            26

(2) INFORMATION FOR SEQ ID NO:625:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:625:

GGGAATTCCT TATTCCTGCT TG                                                22

(2) INFORMATION FOR SEQ ID NO:626:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:626:

CCAGAAGTTC CACAATCC                                                     18

(2) INFORMATION FOR SEQ ID NO:627:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:627:

TTCTTCTAGG TATGTGGAG                                                    19

(2) INFORMATION FOR SEQ ID NO:628:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:628:

AGTGAATTAG CCCTTCCAG                                                    19

(2) INFORMATION FOR SEQ ID NO:629:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:629:

TGCTAGAGAT TTTCCACAC                                                19

(2) INFORMATION FOR SEQ ID NO:630:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:630:

TGCTCTGGAA AACTCAT                                                  17

(2) INFORMATION FOR SEQ ID NO:631:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:631:

CTTTCTATAG TGAATAGAG                                                19

(2) INFORMATION FOR SEQ ID NO:632:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:632:

TATTGGAGTC AGGAACT                                                  17

(2) INFORMATION FOR SEQ ID NO:633:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:633:

GGTCTAACCA GAGAGAC                                                  17

(2) INFORMATION FOR SEQ ID NO:634:

(i) SEQUENCE CHARACTERISTICS:
          (A) LENGTH: 13 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:634:

Ala Val Arg Glu Arg Met Arg Arg Ala Glu Pro Ala Ala (2) INFORMATION FOR SEQ ID NO:635:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:635:

```
Pro Thr Ser Gln Ser Arg Gly Asp Pro Thr Gly Pro Lys Glu Lys
1               5                   10                  15
Lys Lys Val Glu Arg Glu Thr Glu Thr Asp Pro Phe Asp Thr Asp
                20                  25                  30
Pro His
    32
```

(2) INFORMATION FOR SEQ ID NO:636:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:636:

```
Pro Ser Ser Gln Pro Arg Gly Asp Pro Thr Gly Pro Lys Glu Ser
1               5                   10                  15
Lys Lys Lys Val Glu Arg Glu Thr Glu Thr Asp Pro Leu Asp Tyr
                20                  25                  30
Thr Asp Ser His
```

(2) INFORMATION FOR SEQ ID NO:637:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:637:

```
Pro Thr Ser Gln Pro Arg Arg Asp Pro Thr Gly Gln Lys Glu Ser
1               5                   10                  15
Thr Lys Lys Lys Val Glu Arg Glu Thr Glu Ala Ala Pro Leu Asp
                20                  25                  30
Cys Asp Ser His
```

(2) INFORMATION FOR SEQ ID NO:638:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:638:

```
Asp Pro Pro Pro Asn Pro Glu Gly Thr Arg Gln Ala Arg Arg Asn Arg
```

```
                1               5                    10                        15
Arg Arg Arg Trp Arg Glu Arg Gln Arg Gln Ile His Ser Ile Ser Glu
                20                        25                  30

Arg Ile Leu Ser Thr Tyr Leu Gly Arg Ser Ala Glu Pro Val Pro Leu
                35                        40                  45

Gln Leu Pro Pro Leu Glu Arg Leu Thr Leu Asp Cys Asn Glu Asp Cys
    50                        55                  60

Gly Thr Ser Gly Thr Gln Gly Val Gly Ser Pro Gln Ile Leu Val Glu
65                      70                  75                          80

Ser Pro Thr Val Leu Glu Ser Gly Thr Lys Glu Cys Cys Leu Ala Gln
                85                        90                  95

Cys His Ser His Ser Ser Ser Gly Asp Arg
                100                      105
```

(2) INFORMATION FOR SEQ ID NO:639:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:639:

```
Asp Pro Pro Pro Asn Pro Glu Gly Thr Arg Gln Ala Arg Arg Asn Arg
1               5                    10                        15

Arg Arg Arg Trp Arg Glu Arg Gln Arg Gln Ile His Ser Ile Ser Thr
                20                        25                  30

Arg Ile Leu Ser Thr Phe Leu Gly Arg Pro Glu Glu Pro Val Pro Leu
                35                        40                  45

Pro Leu Pro Pro Leu Glu Arg Leu Thr Leu Asp Cys Asn Lys Asp Cys
    50                        55                  60

Gly Thr Ser Gly Thr Gln Gly Met Gly Ser Pro Gln Ile Leu Val Glu
65                      70                  75                          80

Pro Pro Lys Val Leu Glu Pro Gly Thr Ala Glu Glu Cys Cys Tyr Leu
                85                        90                  95

Ala Gln Cys His Arg His Ser Ser Ser Gly Asp Arg
                100                      105
```

(2) INFORMATION FOR SEQ ID NO:640:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:640:

```
Asp Pro Pro Pro Asn Pro Glu Gly Thr Arg Gln Ala Arg Arg Asn Arg
1               5                    10                        15

Arg Arg Arg Trp Arg Glu Arg Gln Arg Gln Leu His Ser Ile Ser Ala
                20                        25                  30

Arg Ile Leu Ser Thr Phe Leu Gly Arg Pro Glu Glu Ser Val Pro Leu
                35                        40                  45

Gln Leu Pro Pro Leu Glu Arg Leu Thr Leu Asp Cys Asn Glu Asp Cys
    50                        55                  60

Gly Thr Ser Gly Thr Gln Gly Met Gly Ser Pro Gln Ile Leu Val Glu
```

```
                65                  70                  75                  80
Ser Pro Ala Val Leu Glu Ala Gly Thr Thr Glu Glu Cys Cys Leu Val
                        85                  90                  95

Gln Trp His Gly His Ser Ser Ser Gly Asp Arg
            100                 105
```

(2) INFORMATION FOR SEQ ID NO:641:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:641:

```
Glu Gln Ile Trp Asn Asn Met Thr Trp Met Glu Trp Asp Arg Glu Ile
1               5                   10                  15

Asn Asn Tyr Thr Ser Leu Ile His Ser Leu Ile Glu Glu Ser Gln Asn
            20                  25                  30

Gln Gln Glu Lys Asn Glu Gln Glu Leu Leu Glu Leu Asp Lys Trp Ala
        35                  40                  45

Ser Leu Trp Asn Trp Phe Asn Ile Thr Asn Trp Leu Trp Tyr Ile Lys
    50                  55                  60

Leu Phe Ile Met Ile Val Gly Leu Val Gly Leu Arg Ile Val Phe
65                  70                  75                  80

Ala Val Leu Ser Ile Val Asn Arg Val Arg Gln Gly Tyr Ser Pro Leu
                85                  90                  95

Ser Phe Gln Thr His Leu Pro Ile Pro Arg Gly Pro Asp Arg Pro Glu
            100                 105                 110

Gly Ile Glu Glu Glu Gly Gly Glu Arg Asp Arg Asp Arg Ser Ile Arg
        115                 120                 125

Leu Val Asn Gly Ser Leu Ala Leu Ile Trp Asp Asp Leu Arg Ser Leu
    130                 135                 140

Cys Leu Phe Ser Tyr His Arg Leu Arg Asp Leu Leu Leu Ile Val Thr
145                 150                 155                 160

Arg Ile Val Glu Leu Leu Gly Arg Arg Gly Trp Glu Ala Leu Lys Tyr
                165                 170                 175

Trp Trp Asn Leu Leu Gln Tyr Trp Ser Gln Glu Leu Lys Asn Ser Ala
            180                 185                 190

Val Asn Leu Leu Asn Ala Thr Ala Ile Ala Val Ala Glu Gly Thr Asp
        195                 200                 205

Arg Val Ile Glu Val Leu Gln Ala Ala Tyr Arg Ala Ile Arg His Ile
    210                 215                 220

Pro Arg Arg Ile Arg Gln Gly Leu Glu Arg Ile Leu Leu
225                 230                 235
```

(2) INFORMATION FOR SEQ ID NO:642:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:642:

Glu Glu Ile Trp Glu Asn Met Thr Trp Met Gln Trp Glu Lys Glu Ile

```
              1               5                  10                 15
           His Asn His Thr Lys Tyr Ile Tyr Ser Leu Leu Glu Lys Ser Gln Asn
                           20                  25                  30

Gln Gln Glu Lys Asn Glu Gln Glu Leu Leu Glu Leu Asp Gln Trp Ala
                           35                  40                  45

Ser Leu Trp Asn Trp Phe Asp Ile Thr Lys Trp Leu Trp Tyr Ile Lys
                   50                  55                  60

Ile Phe Ile Met Val Val Gly Gly Leu Ile Gly Leu Arg Ile Val Phe
           65                  70                  75                  80

Ala Val Leu Ser Ile Val Asn Arg Val Arg Gln Gly Tyr Ser Pro Leu
                           85                  90                  95

Ser Phe Gln Thr Leu Leu Pro Thr Pro Arg Gly Pro Asp Arg Pro Glu
                           100                 105                 110

Gly Ile Glu Glu Met Gly Gly Glu Arg Asp Arg Asp Arg Ser Thr Arg
                           115                 120                 125

Leu Val His Gly Phe Leu Ala Leu Phe Trp Asp Asp Leu Arg Ser Leu
                   130                 135                 140

Cys Leu Phe Leu Tyr His His Leu Arg Asp Leu Leu Leu Ile Val Thr
           145                 150                 155                 160

Arg Ile Val Glu Leu Leu Gly Arg Arg Gly Trp Glu Ala Leu Lys Tyr
                           165                 170                 175

Trp Trp Asn Leu Leu Lys Tyr Trp Ser Gln Glu Leu Gln Lys Ser Ala
                           180                 185                 190

Val Ile Leu Leu Asn Ala Thr Ala Ile Ala Val Ala Glu Gly Thr Asp
                           195                 200                 205

Arg Val Leu Glu Val Leu Gln Arg Ala Tyr Arg Ala Ile Leu His Ile
                           210                 215                 220

Pro Arg Arg Ile Arg Gln Gly Leu Glu Met Ala Leu Leu
           225                 230                 235

(2) INFORMATION FOR SEQ ID NO:643:

(i) SEQUENCE CHARACTERISTICS:
           (A) LENGTH: 237 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:643:

Glu Thr Ile Trp Asp Asn Met Thr Trp Met Gln Trp Glu Arg Glu Ile
           1               5                  10                  15

Asp Asn Tyr Thr Asn Ile Ile Tyr Thr Leu Ile Glu Glu Ser Gln Asn
                           20                  25                  30

Gln Gln Glu Lys Asn Glu Leu Glu Leu Leu Glu Leu Asp Lys Trp Ala
                           35                  40                  45

Asn Leu Trp Asn Trp Phe Ser Ile Ser Asn Trp Leu Trp Tyr Ile Lys
                   50                  55                  60

Leu Phe Ile Met Val Val Gly Gly Leu Val Gly Leu Arg Ile Val Phe
           65                  70                  75                  80

Thr Val Leu Ser Ile Val Asn Arg Val Arg Gln Gly Tyr Ser Pro Leu
                           85                  90                  95

Ser Phe Gln Thr His Leu Pro Thr Pro Lys Gly Pro Asp Arg Pro Glu
                           100                 105                 110

Gly Ile Glu Glu Glu Gly Gly Glu Arg Asp Arg Gly Ser Ser Thr Arg
                           115                 120                 125
```

Leu Val His Gly Phe Leu Ala Leu Phe Trp Asp Asp Leu Arg Ser Leu
    130                 135                 140

Cys Leu Phe Ser Tyr His His Leu Arg Asp Leu Leu Leu Ile Val Thr
145                 150                 155                 160

Arg Ile Val Glu Leu Leu Gly Arg Arg Gly Trp Glu Ala Leu Lys Tyr
                165                 170                 175

Trp Trp Asn Leu Leu Gln Tyr Trp Arg Gln Glu Leu Gln Lys Ser Ala
                180                 185                 190

Val Ser Leu Phe Asn Gly Thr Ala Ile Ala Val Ala Glu Gly Thr Asp
                195                 200                 205

Arg Val Ile Glu Ala Leu Arg Arg Ala Tyr Arg Ala Ile Leu His Ile
                210                 215                 220

Pro Arg Arg Ile Arg Gln Gly Leu Glu Arg Ala Leu Leu
225                 230                 235

(2) INFORMATION FOR SEQ ID NO:644:

(i) SEQUENCE CHARACTERISTICS:
        (A) LENGTH: 206 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:644:

Met Gly Gly Lys Trp Ser Lys Ser Ser Val Ile Gly Trp Pro Ala Val
1               5                   10                  15

Arg Glu Arg Met Arg Arg Ala Glu Pro Ala Ala Asp Gly Val Gly Ala
                20                  25                  30

Val Ser Arg Asp Leu Glu Lys His Gly Ala Ile Thr Ser Ser Asn Thr
            35                  40                  45

Ala Ala Asn Asn Ala Ala Cys Ala Trp Leu Glu Ala Gln Glu Glu Glu
        50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
                100                 105                 110

Trp Ile Tyr His Thr Gln Gly Tyr Phe Pro Asp Trp Gln Asn Tyr Thr
            115                 120                 125

Pro Gly Pro Gly Val Arg Tyr Pro Leu Thr Phe Gly Trp Cys Tyr Lys
        130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
                180                 185                 190

His Val Ala Arg Glu Leu His Pro Glu Tyr Phe Lys Asn Cys
            195                 200                 205

(2) INFORMATION FOR SEQ ID NO:645:

(i) SEQUENCE CHARACTERISTICS:
        (A) LENGTH: 22 amino acids
        (B) TYPE: amino acid (C) STRANDEDNESS: single
          (D) TOPOLOGY: linear (ii) MOLECULE TYPE: protein (xi) SEQUENCE DESCRIPTION: SEQ ID NO:645:

Met Gly Gly Lys Ala Lys Ser Ser Val Val Arg His Ala Ser Gly
1               5                   10                  15

Val Gly Ala Asn Asn Gln Cys
            20

(2) INFORMATION FOR SEQ ID NO:646:

(i) SEQUENCE CHARACTERISTICS:
          (A) LENGTH: 26 amino acids
          (B) TYPE: amino acid
          (C) STRANDEDNESS: single
          (D) TOPOLOGY: linear (ii) MOLECULE TYPE: protein (xi) SEQUENCE DESCRIPTION: SEQ ID NO:646:

Met Gly Gly Lys Trp Ser Glu Ser Ser Val Val Arg Arg His Val
1               5                   10                  15

Pro Leu Arg Gln Gly Ser Tyr Arg Ser Pro Leu
            20                  25

(2) INFORMATION FOR SEQ ID NO:647:

(i) SEQUENCE CHARACTERISTICS:
          (A) LENGTH: 74 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:647:

CTACAAGGGA CTTTCCGCTG GGGACTTTCC AGGGAGGCGT GGCCTGGGCG GACTGGGGA          60

GTGGCGAGCC CTCA                                                          74

(2) INFORMATION FOR SEQ ID NO:648:

(i) SEQUENCE CHARACTERISTICS:
          (A) LENGTH: 78 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:648:

CTGTTGGGGA CTTTCCATCC GTTGGGGACT TTCCAAGGCG GCGTGGCCTG GGTGACTAGT         60

TCCGGTGGGG ACTTTCCA                                                      78

(2) INFORMATION FOR SEQ ID NO:649:

(i) SEQUENCE CHARACTERISTICS:
          (A) LENGTH: 67 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:649:

CCGTTTGTTC CGTTGGGGAC TTTCCAGGAG ACGTGGCCTG AGTGACTAAG CCGCTGGGGA         60

CTTTCCG                                                                    67

(2) INFORMATION FOR SEQ ID NO:650:

(i) SEQUENCE CHARACTERISTICS:
        (A) LENGTH: 621 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:650:

ATGGGTGGCA AGTGGTCAAA AAGTAGTGTG ATTGGATGGC CTGCTGTAAG GGAAAGAATG          60

AGACGAGCTG AGCCAGCAGC AGATGGGGTG GGAGCAGTAT CTCGAGACCT AGAAAAACAT         120

GGAGCAATCA CAAGTAGCAA TACAGCAGCT AACAATGCTG CTTGTGCCTG GCTAGAAGCA         180

CAAGAGGAGG AAGAGGTGGG TTTTCCAGTC ACACCTCAGG TACCTTTAAG ACCAATGACT         240

TACAAGGCAG CTGTAGATCT TAGCCACTTT TTAAAAGAAA AGGGGGGACT GGAAGGGCTA         300

ATTCACTCCC AAAGAAGACA AGATATCCTT GATCTGTGGA TCTACCACAC ACAAGGCTAC         360

TTCCCTGATT GGCAGAACTA CACACCAGGG CCAGGGGTCA GATATCCACT GACCTTTGGA         420

TGGTGCTACA AGCTAGTACC AGTTGAGCCA GATAAGGTAG AAGAGGCCAA TAAAGGAGAG         480

AACACCAGCT TGTTACACCC TGTGAGCCTG CATGGAATGG ATGACCCTGA GAGAGAAGTG         540

TTAGAGTGGA GGTTTGACAG CCGCCTAGCA TTTCATCACG TGGCCCGAGA GCTGCATCCG         600

GAGTACTTCA AGAACTGCTG A                                                   621

(2) INFORMATION FOR SEQ ID NO:651:

(i) SEQUENCE CHARACTERISTICS:
        (A) LENGTH: 1596 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:651:

GAACAGATTT GGAATAACAT GACCTGGATG GAGTGGGACA GAGAAATTAA CAATTACACA          60

AGCTTAATAC ACTCCTTAAT TGAAGAATCG CAAAACCAGC AAGAAAAGAA TGAACAAGAA         120

TTATTGGAAT TAGATAAATG GGCAAGTTTG TGGAATTGGT TTAACATAAC AAATTGGCTG         180

TGGTATATAA AATTATTCAT AATGATAGTA GGAGGCTTGG TAGGTTTAAG AATAGTTTTT         240

GCTGTACTTT CTATAGTGAA TAGAGTTAGG CAGGGATATT CACCATTATC GTTTCAGACC         300

CACCTCCCAA TCCCGAGGGG ACCCGACAGG CCCGAAGGAA TAGAAGAAGA AGGTGGAGAG         360

AGAGACAGAG ACAGATCCAT TCGATTAGTG AACGGATCCT TAGCACTTAT CTGGGACGAT         420

CTGCGGAGCC TGTGCCTCTT CAGCTACCAC CGCTTGAGAG ACTTACTCTT GATTGTAACG         480

AGGATTGTGG AACTTCTGGG ACGCAGGGGG TGGGAAGCCC TCAAATATTG GTGGAATCTC         540

CTACAGTATT GGAGTCAGGA ACTAAAGAAT AGTGCTGTTA ACTTGCTCAA TGCCACAGCC         600

ATAGCAGTAG CTGAGGGGAC AGATAGGGTT ATAGAAGTAT TACAAGCAGC TTATAGAGCT         660

ATTCGCCACA TACCTAGAAG AATAAGACAG GGCTTGGAAA GGATTTTGCT ATAAGATGGG         720

TGGCAAGTGG TCAAAAAGTA GTGTGATTGG ATGGCCTGCT GTAAGGGAAA GAATGAGACG         780

AGCTGAGCCA GCAGCAGATG GGGTGGGAGC AGTATCTCGA GACCTAGAAA AACATGGAGC         840

AATCACAAGT AGCAATACAG CAGCTAACAA TGCTGCTTGT GCCTGGCTAG AAGCACAAGA         900

```
GGAGGAAGAG GTGGGTTTTC CAGTCACACC TCAGGTACCT TTAAGACCAA TGACTTACAA      960

GGCAGCTGTA GATCTTAGCC ACTTTTTAAA AGAAAAGGGG GGACTGGAAG GGCTAATTCA     1020

CTCCCAAAGA AGACAAGATA TCCTTGATCT GTGGATCTAC CACACACAAG GCTACTTCCC     1080

TGATTGGCAG AACTACACAC CAGGGCCAGG GGTCAGATAT CCACTGACCT TTGGATGGTG     1140

CTACAAGCTA GTACCAGTTG AGCCAGATAA GGTAGAAGAG GCCAATAAAG GAGAGAACAC     1200

CAGCTTGTTA CACCCTGTGA GCCTGCATGG AATGGATGAC CCTGAGAGAG AAGTGTTAGA     1260

GTGGAGGTTT GACAGCCGCC TAGCATTTCA TCACGTGGCC CGAGAGCTGC ATCCGGAGTA     1320

CTTCAAGAAC TGCTGACATC GAGCTTGCTA CAAGGGACTT TCCGCTGGGG ACTTTCCAGG     1380

GAGGCGTGGC CTGGGCGGGA CTGGGGAGTG GCGAGCCCTC AGATGCTGCA TATAAGCAGC     1440

TGCTTTTTGC CTGTACTGGG TCTCTCTGGT TAGACCAGAT CTGAGCCTGG GAGCTCTCTG     1500

GCTAACTAGG GAACCCACTG CTTAAGCCTC AATAAAGCTT GCCTTGAGTG CTTCAAGTAG     1560

TGTGTGCCCG TCTGTTGTGT GACTCTGGTA ACTAGA                              1596

(2) INFORMATION FOR SEQ ID NO:652:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:652:

GCTTTTTGCC                                                              10

(2) INFORMATION FOR SEQ ID NO:653:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:653:

CTTTTTGCCT                                                              10

(2) INFORMATION FOR SEQ ID NO:654:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:654:

TTTTTGCCTG                                                              10

(2) INFORMATION FOR SEQ ID NO:655:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: DNA (genomic)
```

(xi) SEQUENCE DESCRIPTION: SEQ ID NO:655:

TTTTGCCTGT                                                                                          10

(2) INFORMATION FOR SEQ ID NO:656:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:656:

TTTGCCTGTA                                                                                          10

(2) INFORMATION FOR SEQ ID NO:657:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:657:

TTGCCTGTAC                                                                                          10

(2) INFORMATION FOR SEQ ID NO:658:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:658:

TGCCTGTACT                                                                                          10

(2) INFORMATION FOR SEQ ID NO:659:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:659:

GCCTGTACTG                                                                                          10

(2) INFORMATION FOR SEQ ID NO:660:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:660:

CCTGTACTGG                                                                                          10

(2) INFORMATION FOR SEQ ID NO:661:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:661:

CTGTACTGGG                                                            10

(2) INFORMATION FOR SEQ ID NO:662:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:662:

TGTACTGGGT                                                            10

(2) INFORMATION FOR SEQ ID NO:663:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:663:

GTACTGGGTC                                                            10

(2) INFORMATION FOR SEQ ID NO:664:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:664:

TACTGGGTCT                                                            10

(2) INFORMATION FOR SEQ ID NO:665:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:665:

ACTGGGTCTC                                                            10

(2) INFORMATION FOR SEQ ID NO:666:

(i) SEQUENCE CHARACTERISTICS:
        (A) LENGTH: 10 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:666:

CTGGGTCTCT                                                            10

(2) INFORMATION FOR SEQ ID NO:667:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:667:

TGGGTCTCTC                                                            10

(2) INFORMATION FOR SEQ ID NO:668:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:668:

GGGTCTCTCT                                                            10

(2) INFORMATION FOR SEQ ID NO:669:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:669:

GGTCTCTCTG                                                            10

(2) INFORMATION FOR SEQ ID NO:670:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:670:

GTCTCTCTGG                                                            10

(2) INFORMATION FOR SEQ ID NO:671:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:671:

TCTCTCTGGT                                                                 10

(2) INFORMATION FOR SEQ ID NO:672:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:672:

CTCTCTGGTT                                                                 10

(2) INFORMATION FOR SEQ ID NO:673:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:673:

TCTCTGGTTA                                                                 10

(2) INFORMATION FOR SEQ ID NO:674:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:674:

CTCTGGTTAG                                                                 10

(2) INFORMATION FOR SEQ ID NO:675:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:675:

TCTCTGGTTA                                                                 10

(2) INFORMATION FOR SEQ ID NO:676:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:676:

CTGGTTAGAC                                                                 10

(2) INFORMATION FOR SEQ ID NO:677:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:677:

TGGTTAGACC          10

(2) INFORMATION FOR SEQ ID NO:678:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:678:

GGTTAGACCA          10

(2) INFORMATION FOR SEQ ID NO:679:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:679:

GTTAGACCAG          10

(2) INFORMATION FOR SEQ ID NO:680:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:680:

TTAGACCAGA          10

(2) INFORMATION FOR SEQ ID NO:681:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:681:

TAGACCAGAT          10

(2) INFORMATION FOR SEQ ID NO:682:

(i) SEQUENCE CHARACTERISTICS:
        (A) LENGTH: 10 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:682:

AGACCAGATC                                                                    10

(2) INFORMATION FOR SEQ ID NO:683:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:683:

GACCAGATCT                                                                    10

(2) INFORMATION FOR SEQ ID NO:684:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:684:

ACCAGATCTG                                                                    10

(2) INFORMATION FOR SEQ ID NO:685:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:685:

CCAGATCTGA                                                                    10

(2) INFORMATION FOR SEQ ID NO:686:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:686:

CAGATCTGAG                                                                    10

(2) INFORMATION FOR SEQ ID NO:687:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:687:

AGATCTGAGC                                                                          10

(2) INFORMATION FOR SEQ ID NO:688:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:688:

GATCTGAGCC                                                                          10

(2) INFORMATION FOR SEQ ID NO:689:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:689:

ATCTGAGCCT                                                                          10

(2) INFORMATION FOR SEQ ID NO:690:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:690:

TCTGAGCCTG                                                                          10

(2) INFORMATION FOR SEQ ID NO:691:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:691:

CTGAGCCTGG                                                                          10

(2) INFORMATION FOR SEQ ID NO:692:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:692:

TGAGCCTGGG                                                                          10

(2) INFORMATION FOR SEQ ID NO:693:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:693:

GAGCCTGGGA                        10

(2) INFORMATION FOR SEQ ID NO:694:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:694:

AGCCTGGGAG                        10

(2) INFORMATION FOR SEQ ID NO:695:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:695:

GCCTGGGAGC                        10

(2) INFORMATION FOR SEQ ID NO:696:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:696:

CCTGGGAGCT                        10

(2) INFORMATION FOR SEQ ID NO:697:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:697:

CTGGGAGCTC                        10

(2) INFORMATION FOR SEQ ID NO:698:

(i) SEQUENCE CHARACTERISTICS:
        (A) LENGTH: 10 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:698:

TGGGAGCTCT                                                                10

(2) INFORMATION FOR SEQ ID NO:699:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:699:

GGGAGCTCTC                                                                10

(2) INFORMATION FOR SEQ ID NO:700:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:700:

GGAGCTCTCT                                                                10

(2) INFORMATION FOR SEQ ID NO:701:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:701:

GAGCTCTCTG                                                                10

(2) INFORMATION FOR SEQ ID NO:702:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:702:

AGCTCTCTGG                                                                10

(2) INFORMATION FOR SEQ ID NO:703:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:703:

GCTCTCTGGC                                                                              10

(2) INFORMATION FOR SEQ ID NO:704:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:704:

CTCTCTGGCT                                                                              10

(2) INFORMATION FOR SEQ ID NO:705:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:705:

TCTCTGGCTA                                                                              10

(2) INFORMATION FOR SEQ ID NO:706:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:706:

CTCTGGCTAA                                                                              10

(2) INFORMATION FOR SEQ ID NO:707:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:707:

TCTGGCTAAC                                                                              10

(2) INFORMATION FOR SEQ ID NO:708:

(i) SEQUENCE CHARACTERISTICS:
                (A) LENGTH: 10 base pairs
                (B) TYPE: nucleic acid
                (C) STRANDEDNESS: single
                (D) TOPOLOGY: linear (ii) MOLECULE TYPE: DNA (genomic)

(xi) SEQUENCE DESCRIPTION: SEQ ID NO:708:

CTGGCTAACT                                                                              10

(2) INFORMATION FOR SEQ ID NO:709:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:709:

TGGCTAACTA           10

(2) INFORMATION FOR SEQ ID NO:710:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:710:

GGCTAACTAG           10

(2) INFORMATION FOR SEQ ID NO:711:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:711:

GCTAACTAGG           10

(2) INFORMATION FOR SEQ ID NO:712:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:712:

CTAACTAGGG           10

(2) INFORMATION FOR SEQ ID NO:713:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:713:

TAACTAGGGA           10

(2) INFORMATION FOR SEQ ID NO:714:

(i) SEQUENCE CHARACTERISTICS:
        (A) LENGTH: 10 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:714:

AACTAGGGAA                                                                10

(2) INFORMATION FOR SEQ ID NO:715:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:715:

ACTAGGGAAC                                                                10

(2) INFORMATION FOR SEQ ID NO:716:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:716:

CTAGGGAACC                                                                10

(2) INFORMATION FOR SEQ ID NO:717:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:717:

TAGGGAACCC                                                                10

(2) INFORMATION FOR SEQ ID NO:718:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:718:

AGGGAACCCA                                                                10

(2) INFORMATION FOR SEQ ID NO:719:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:719:

GGGAACCCAC                                                                          10

(2) INFORMATION FOR SEQ ID NO:720:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:720:

GGAACCCACT                                                                          10

(2) INFORMATION FOR SEQ ID NO:721:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:721:

GAACCCACTG                                                                          10

(2) INFORMATION FOR SEQ ID NO:722:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:722:

AACCCACTGC                                                                          10

(2) INFORMATION FOR SEQ ID NO:723:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:723:

ACCCACTGCT                                                                          10

(2) INFORMATION FOR SEQ ID NO:724:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:724:

CCCACTGCTT                                                                          10

(2) INFORMATION FOR SEQ ID NO:725:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:725:

CCACTGCTTA    10

(2) INFORMATION FOR SEQ ID NO:726:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:726:

CACTGCTTAA    10

(2) INFORMATION FOR SEQ ID NO:727:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:727:

ACTGCTTAAG    10

(2) INFORMATION FOR SEQ ID NO:728:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:728:

CTGCTTAAGC    10

(2) INFORMATION FOR SEQ ID NO:729:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:729:

TGCTTAAGCC    10

(2) INFORMATION FOR SEQ ID NO:730:

(i) SEQUENCE CHARACTERISTICS:
        (A) LENGTH: 10 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:730:

GCTTAAGCCT                                                              10

(2) INFORMATION FOR SEQ ID NO:731:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:731:

CTTAAGCCTC                                                              10

(2) INFORMATION FOR SEQ ID NO:732:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:732:

TTAAGCCTCA                                                              10

(2) INFORMATION FOR SEQ ID NO:733:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:733:

TAAGCCTCAA                                                              10

(2) INFORMATION FOR SEQ ID NO:734:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:734:

AAGCCTCAAT                                                              10

(2) INFORMATION FOR SEQ ID NO:735:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:735:

AGCCTCAATA                                                                10

(2) INFORMATION FOR SEQ ID NO:736:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:736:

GCCTCAATAA                                                                10

(2) INFORMATION FOR SEQ ID NO:737:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:737:

CCTCAATAAA                                                                10

(2) INFORMATION FOR SEQ ID NO:738:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:738:

CTCAATAAAG                                                                10

(2) INFORMATION FOR SEQ ID NO:739:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:739:

TCAATAAAGC                                                                10

(2) INFORMATION FOR SEQ ID NO:740:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:740:

CAATAAAGCT                                                                10

(2) INFORMATION FOR SEQ ID NO:741:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:741:

AATAAAGCTT    10

(2) INFORMATION FOR SEQ ID NO:742:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:742:

ATAAAGCTTG    10

(2) INFORMATION FOR SEQ ID NO:743:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:743:

TAAAGCTTGC    10

(2) INFORMATION FOR SEQ ID NO:744:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:744:

AAAGCTTGCC    10

(2) INFORMATION FOR SEQ ID NO:745:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:745:

AAGCTTGCCT    10

(2) INFORMATION FOR SEQ ID NO:746:

(i) SEQUENCE CHARACTERISTICS:
        (A) LENGTH: 10 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:746:

AGCTTGCCTT                                                      10

(2) INFORMATION FOR SEQ ID NO:747:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:747:

GCTTGCCTTG                                                      10

(2) INFORMATION FOR SEQ ID NO:748:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:748:

CTTGCCTTGA                                                      10

(2) INFORMATION FOR SEQ ID NO:749:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:749:

TTGCCTTGAG                                                      10

(2) INFORMATION FOR SEQ ID NO:750:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:750:

TGCCTTGAGT                                                      10

(2) INFORMATION FOR SEQ ID NO:751:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:751:

GCCTTGAGTG                                                                                    10

(2) INFORMATION FOR SEQ ID NO:752:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:752:

CCTTGAGTGC                                                                                    10

(2) INFORMATION FOR SEQ ID NO:753:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:753:

CTTGAGTGCT                                                                                    10

(2) INFORMATION FOR SEQ ID NO:754:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:754:

TTGAGTGCTT                                                                                    10

(2) INFORMATION FOR SEQ ID NO:755:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:755:

TGAGTGCTTC                                                                                    10

(2) INFORMATION FOR SEQ ID NO:756:

(i) SEQUENCE CHARACTERISTICS:
             (A) LENGTH: 10 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:756:

GAGTGCTTCA                                                                                    10

(2) INFORMATION FOR SEQ ID NO:757:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:757:

AGTGCTTCAA                                                              10

(2) INFORMATION FOR SEQ ID NO:758:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:758:

GTGCTTCAAG                                                              10

(2) INFORMATION FOR SEQ ID NO:759:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:759:

TGCTTCAAGT                                                              10

(2) INFORMATION FOR SEQ ID NO:760:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:760:

GCTTCAAGTA                                                              10

(2) INFORMATION FOR SEQ ID NO:761:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:761:

CTTCAAGTAG                                                              10

(2) INFORMATION FOR SEQ ID NO:762:

(i) SEQUENCE CHARACTERISTICS:
        (A) LENGTH: 10 base pairs

```
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:762:

TTCAAGTAGT                                                              10

(2) INFORMATION FOR SEQ ID NO:763:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:763:

TCAAGTAGTG                                                              10

(2) INFORMATION FOR SEQ ID NO:764:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:764:

CAAGTAGTGT                                                              10

(2) INFORMATION FOR SEQ ID NO:765:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:765:

AAGTAGTGTG                                                              10

(2) INFORMATION FOR SEQ ID NO:766:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:766:

AGTAGTGTGT                                                              10

(2) INFORMATION FOR SEQ ID NO:767:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:767:

GTAGTGTGTG                                                                      10

(2) INFORMATION FOR SEQ ID NO:768:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:768:

TAGTGTGTGC                                                                      10

(2) INFORMATION FOR SEQ ID NO:769:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:769:

AGTGTGTGCC                                                                      10

(2) INFORMATION FOR SEQ ID NO:770:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:770:

GTGTGTGCCC                                                                      10

(2) INFORMATION FOR SEQ ID NO:771:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:771:

TGTGTGCCCG                                                                      10

(2) INFORMATION FOR SEQ ID NO:772:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:772:

GTGTGCCCGT                                                                      10

(2) INFORMATION FOR SEQ ID NO:773:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:773:

TGTGCCCGTC          10

(2) INFORMATION FOR SEQ ID NO:774:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:774:

GTGCCCGTCT          10

(2) INFORMATION FOR SEQ ID NO:775:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:775:

TGCCCGTCTG          10

(2) INFORMATION FOR SEQ ID NO:776:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:776:

GCCCGTCTGT          10

(2) INFORMATION FOR SEQ ID NO:777:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:777:

CCCGTCTGTT          10

(2) INFORMATION FOR SEQ ID NO:778:

(i) SEQUENCE CHARACTERISTICS:
        (A) LENGTH: 10 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:778:

CCGTCTGTTG                                                              10

(2) INFORMATION FOR SEQ ID NO:779:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:779:

CGTCTGTTGT                                                              10

(2) INFORMATION FOR SEQ ID NO:780:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:780:

GTCTGTTGTG                                                              10

(2) INFORMATION FOR SEQ ID NO:781:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:781:

TCTGTTGTGT                                                              10

(2) INFORMATION FOR SEQ ID NO:782:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:782:

CTGTTGTGTG                                                              10

(2) INFORMATION FOR SEQ ID NO:783:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:783:

TGTTGTGTGA                                                                                      10

(2) INFORMATION FOR SEQ ID NO:784:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:784:

GTTGTGTGAC                                                                                      10

(2) INFORMATION FOR SEQ ID NO:785:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:785:

TTGTGTGACT                                                                                      10

(2) INFORMATION FOR SEQ ID NO:786:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:786:

TGTGTGACTC                                                                                      10

(2) INFORMATION FOR SEQ ID NO:787:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:787:

GTGTGACTCT                                                                                      10

(2) INFORMATION FOR SEQ ID NO:788:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:788:

TGTGTGACTC                                                                                      10

(2) INFORMATION FOR SEQ ID NO:789:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:789:

GTGTGACTCT          10

(2) INFORMATION FOR SEQ ID NO:790:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:790:

TGTGACTCTG          10

(2) INFORMATION FOR SEQ ID NO:791:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:791:

GTGACTCTGG          10

(2) INFORMATION FOR SEQ ID NO:792:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:792:

TGACTCTGGT          10

(2) INFORMATION FOR SEQ ID NO:793:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:793:

GACTCTGGTA          10

(2) INFORMATION FOR SEQ ID NO:794:

(i) SEQUENCE CHARACTERISTICS:
        (A) LENGTH: 10 base pairs (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:794:

ACTCTGGTAA                                                              10

(2) INFORMATION FOR SEQ ID NO:795:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:795:

CTCTGGTAAC                                                              10

(2) INFORMATION FOR SEQ ID NO:796:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:796:

TCTGGTAACT                                                              10

(2) INFORMATION FOR SEQ ID NO:797:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:797:

CTGGTAACTA                                                              10

(2) INFORMATION FOR SEQ ID NO:798:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:798:

TGGTAACTAG                                                              10

(2) INFORMATION FOR SEQ ID NO:799:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:799:

GGTAACTAGA                                                                    10

(2) INFORMATION FOR SEQ ID NO:800:

(i) SEQUENCE CHARACTERISTICS:
        (A) LENGTH: 9207 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:800:

| | | | | | |
|---|---|---|---|---|---|
| TGGAAGGGCT | AATTCACTCA | CGGAAAAGAC | CAGTTGAACC | AGAAGAAGAT | AGAAGAGGCC | 60 |
| ATGAAGAAGA | AAACAACAGA | TTGTTCTGCT | TGCTCAGCTG | GGGACTTTCC | AGAAGGCGCG | 120 |
| GCCTGAGTGA | CTAAGCCCCG | TTGGGGACTT | TCCGAAGAGG | CATGAAGGGA | CTTTCCAAGG | 180 |
| CAGGCGTGGC | CTGGGCGGGA | CTGGGGAGTG | GCGAGCCCTC | AGATGCTGCA | TATAAGCAGC | 240 |
| TGCTTTCTGC | CTGTACTGGG | TCTCTCTGGT | TAGACCAGAT | CTGAGCCTGG | GAGCTCTCTG | 300 |
| GCTAGCTAGG | GAACCCACTG | CTTAAGCCTC | AATAAAGCTT | GCCTTGAGTG | CTTCAAGTAG | 360 |
| TGTGTGCCCG | TCTGTTGTGT | GACTCTGGTA | TCTAGAGATC | CCTCAGACCA | TTTTAGTCCG | 420 |
| TGTGGAAAAT | CTCTAGCAGT | GGCGCCCGAA | CAGGGACTTG | AAAGCGAAAG | GAAAACCAGA | 480 |
| GGAGCTCTCT | CGACGCAGGA | CTCGGCTTGC | TGAAGCGCGC | ACGGCAAGAG | GCGAGGGGCG | 540 |
| GCGACTGGTG | AGTACGCCGA | AAATTTTGAC | TAGCGGAGGC | TAGAAGGAGA | GAGATGGGTG | 600 |
| CGAGAGCGTC | AATATTAAGC | GGGGGAAAAT | TAGATAGATG | GGAGAAAATT | CGGTTAAGGC | 660 |
| CAGGAGGAAA | GAAAAAGTAT | AAATTAAAAC | ATATAGTATG | GGCAAGCAGG | GAGCTAGAAC | 720 |
| GATTCGCAGT | CAATCCTGGC | CTGTTGGAAA | CATCAGAAGG | CTGTAGACAA | ATACTGGGAC | 780 |
| AGTTACACCC | GTCCCTTCAG | ACAGGATCAG | AAGAACTTAA | ATCAGTATAT | AATGCAGTAG | 840 |
| CAGTCCTCTA | TTGTGTGCAT | CAAAACATAG | ACATAAAGGA | CACCAAGGAA | GCTTTAGAAA | 900 |
| AGATAGAGGA | AGAGCAAAAC | AAATGTAAGA | AAAAAGCACA | GCAAGCAGCA | GCACAGCAAG | 960 |
| CAGCAGCTGG | CACAGGAAAC | AGCAACCCGG | TCAGCCAAAA | TTACCCTATA | GTACAGAACA | 1020 |
| TGCAGGGCA | AATGGTACAT | CAGGCCATAT | CACCTAGAAC | TTTAAATGCA | TGGGTAAAAG | 1080 |
| TAATAGAAGA | GAAGGCTTTC | AGCCCAGAGG | TAATACCCAT | GTTTTCAGCA | TTATCAGAAG | 1140 |
| GAGCCACCCC | ACAAGATTTA | AACACCATGC | TAAACACAGT | GGGGGGACAT | CAAGCAGCTA | 1200 |
| TGCAAATGTT | AAAAGAGACC | ATCAATGAGG | AAGCTGCAGA | ATGGGATAGA | TTACATCCAG | 1260 |
| CGCAGGCAGG | GCCTGTTGCA | CCAGGCCAGA | TGAGAGACCC | AAGGGGAAGT | GACATAGCAG | 1320 |
| GAACTACTAG | TACCCTTCAG | GAACAAATAG | GATGGATGAC | AGGTAATCCA | GCTATCCCAG | 1380 |
| TAGGAGAAAT | CTATAAAAGA | TGGATAATCC | TGGGATTAAA | TAAAATAGTA | AGGATGTATA | 1440 |
| GCCCTATCAG | CATTCTGGAC | ATAAAACAAG | GACCAAAGGA | ACCCTTTAGA | GACTATGTAG | 1500 |
| ACCGGTTCTA | TAAAACTCTA | AGAGCCGAGC | AAGCTACACA | GGAGGTAAAA | AATTGGATGA | 1560 |
| CAGAAACCTT | GTTGGTCCAA | AATGCAAACC | CAGATTGTAA | GACTATTTTA | AAAGCATTGG | 1620 |
| GACCAGCAGC | TACACTAGAA | GAAATGATGA | CAGCATGTCA | GGGAGTGGGA | GGACCCAGCC | 1680 |
| ATAAAGCAAG | AGTTTTGGCA | GAAGCAATGA | GCCAAGCAAC | AAATGCAGCT | ACTGTAATGA | 1740 |
| TGCAGAGAAG | CAATTTTAGA | AACCAAAGAA | AGAATGTTAA | GTGTTTCAAT | TGTGGCAAAG | 1800 |
| AAGGGCACAT | AGCCAGAAAT | TGCAGGGCTC | CTAGGAAAAG | GGGCTGTTGG | AAATGTGGAA | 1860 |

```
AGGAAGGACA CCAAATGAAA GATTGTACTG AGAGACAGGC TAATTTTTTA GGGAAAATCT    1920

GGCCTTCCCA CAAGGGGAGG CCAGGGAACT TTCTTCAGAG CAGGCCAGAA CCAACAGCCC    1980

CTCTCCAGGG CAGGCCGGAG CCATCAGCCC CGCCAGAAGA GAGCTTCAGG TTTGGGGAGG    2040

AGACAACAAC TCCCTCTCAG AAGCAGGAGC CGATAGACAG GGACAGGGAT CTGTATCCTT    2100

TAGCTTCCCT CAGATCACTC TTTGGCAACG ACCCCTCGTC ACAATAAAGA TAGGGGGCA     2160

GCTGAAGGAA GCTCTATTAG ATACAGGAGC AGATGATACA GTATTAGAAG ACATGCATTT    2220

GCCAGGAAAA TGGAAACCAA AAATGATAGG GGGAATTGGA GGTTTTATCA AAGTAAAACA    2280

ATATGATGAA ATTCTTGTAG AAATCTGTGG ACATAAAGCT ATAGGTACAG TATTAGTAGG    2340

ACCTACACCT GTCAACATAA TTGGAAGAAA TCTGTTGACT CAGATTGGTT GCACTTTAAA    2400

TTTTCCCATT AGTCCTATTG AAACTGTACC AGTACAATTA AAGCCAGGAA TGGATGGCCC    2460

AAAGGTTAAA CAATGGCCAT TGACAGAAGA GAAAATAAAA GCATTAGTAG AAATTTGTAC    2520

AGAAATGGAA AAGGAAGGAA AGATTTCAAA AATTGGGCCT GAAAATCCAT ACAATACTCC    2580

AGTATTTGCC ATAAAGAAAA AAGATGGTAC TAAATGGAGA AAATTAGTAG ATTTCAGAGA    2640

CCTTAATAAG AGAACTCAAG ACTTCTGGGA AGTTCAATTA GGAATACCAC ATCCCTCAGG    2700

ATTAAAAAAG AAAAAATCAG TAACAGTACT GGATGTGGGT GATGCATACT TTTCAGTTCC    2760

CTTAGATGAA AACTTCAGGA AGTATACTGC ATTTACCATA CCTAGTATAA ATAATGAGAC    2820

ACCAGGGATT AGATATCAGT ACAATGTGCT TCCACAGGGA TGGAAAGGAT CACCAGCAAT    2880

ATTCCAAAGT AGCATGACAA GAATCTTAGA GCCTTTTAGA AGACAAAATC CAGACATAGT    2940

TATCTATCAA TACATGGATG ACTTGTATGT AGGATCTGAT TTAGAAATAG GACAGCATAG    3000

AATAAAAATA GAGGAACTGA GACAACATCT GTTGAAGTGG GGATTTACCA CACCAGACAA    3060

AAAGCATCAG AAAGAACCCC CATTCCTTTG GATGGGTTAT GAACTCCATC CTGATAAATG    3120

GACAGTGCAA CCTATAGTAC TGCCAGAAAA AGACAGCTGG ACTGTCAATG ACATACAGAA    3180

GTTAGTGGGT AAATTAAATT GGGCAAGTCA GATTTACCCA GGAATTAAAG TAAGGCAATT    3240

ATGTAAACTC CTTAGGGGAA CCAAAGCACT AACAGAAGTA ATACCACTAA CAGAAGAAGC    3300

AGAGCTAGAA CTGGCAGAAA ACAGGGAAAT TCTAAGAGAA CCAGTACATG GAGTGTATTA    3360

TGACCCATCA AAAGACTTAA TAGCAGAAAT ACAGAAGCAG GAGCAAGGCC AATGGACATA    3420

TCAAATTTAT CAAGATCAAT TTAAAAATCT AAAAACAGGA AAGTATGCAA GATTGAGGGG    3480

TGCCCACACT AATGATGTAA AACAATTTCC AGAGGCAGTG CAAAAAATAG CCACAGAAAG    3540

CATAGTAATA TGGGGAAAGA CTCCTAAATT TAGACTACCC ATACAAAAAG AAACATGGGA    3600

CGCATGGTGG ACAGAGTATT GGCAAGCCAC CTGGATTCCT GAGTGGGAGT TTGTCAATAC    3660

CCCTCCCCTA GTAAAATTAT GGTACCAGTT AGAAAAAGAA CCCATAATAG GAGCAGAAAC    3720

TTTCTATGTA GATGGGGCAG CTAACAGAGA GACTAAATTA GGAAAAGCAG GATATGTTAC    3780

TGACAGAGGA AGACAAAAAG TTGTCTCCCT AACTGACACA ACAAATCAGA AGACTGAGTT    3840

ACAAGCAATT CATCTAGCTT TGCAGGATTC AGGATTAGAA GTAAACATAG TAACAGACTC    3900

ACAGTATGCA TTAGGAATCA TTCAAGCACA ACCAGATAAA AGTGAATCAG AAATAGTCAA    3960

TCAAATAATA GAGCAATTAA TAAAAAAGGA AAAGGTCTAC CTGGCATGGG TACCAGCACA    4020

CAAAGGAATT GGAGGGAATG AACAAGTAGA TAAATTAGTC AGTGCTGGAA TCAGGAAAAT    4080

ACTATTTTTA GATGGAATAG ATAAGGCACA AGAAGGCCAT GAGAAATATC ACAGTAATTG    4140

GAGAGCAATG GCTAGTGGTT TTAACCTGCC ACCTATAGTA GCAAAAGAAA TAGTAGCCAG    4200

CTGTGATAAA TGTCAGCTAA AAGGAGAAGC CATGCATGGA CAAGTAGACT GTAGTCCAGG    4260
```

```
AATATGGCAA CTAGATTGTA CACATCTAGA AGGAAAAATT ATCCTGGTAG CAGTTCATGT    4320

AGCCAGTGGA TATATAGAAG CAGAAGTTAT TCCAGCAGAG ACAGGGCAGG AAACAGCATA    4380

CTTTATCTTA AAATTAGCAG GAAGGTGGCC AGTAAACACA ATACATACAG ACAATGGCGG    4440

CAATTTCATC AGTACCACGG TTAAGGCCGC CTGTTGGTGG GCAGGGATCA AGCAGGAATT    4500

TGGCATTCCC TACAATCCCC AAAGCCAAGG AGTAGTGGAA TCTATGAATA GAGAATTAAA    4560

GAAAATTATA GGACAGGTAA GAGATCAGGC TGAACATCTT AAGACAGCAG TACAAATGGC    4620

AGTATTCATC CACAATTTTA AAAGAAAAGG GGGGATTGGG GGATACAGTG CAGGGGAAAG    4680

AATAGTAGAC ATAATAGCAA CAGACATACA AACTAAAGAA TTACAAAAGC AAATTACAAA    4740

AATTCAAAAT TTTCGGGTTT ATTACAGGGA CAGCAGAGAT CCACTTTGGA AAGGACCAGC    4800

AAAACTTCTC TGGAAAGGCG AAGGGGCAGT AGTAATACAA GATAATAGTG ACATAAAAGT    4860

AGTGCCAAGA AGAAAAGTAA AGATCATTAG GGATTATGGA AAACAGATGG CAGGTGATGA    4920

TTGTGTGGCA AGTAGACAGG ATGAGGATTA GAACATGGAA CAGTTTAGTG AAACACCATA    4980

TGTATGTTTC AAAGAAAGCT AAGGGATGGA TTTATAGACA TCACTATGAA AACACTCATC    5040

CAAAAATAAG CTCAGAAGTA CACATCCCAC TAGGGGAAGC TAGATTGGTA ATAACAACAT    5100

ATTGGGGTCT ACATACAGGA GAAAGAGACT GGCATTTGGG TCAGGGAGTC TCCATAGAAT    5160

GGAGGGAAAG GACATATAGA ACACAAGTAG ACCCCGAACT AGCAGACCAA CTAATTCATA    5220

TACATTACTT TGATTGTTTT TCAGAATCTG CCATAAGAAG TGCCATATTA GGATATAGAG    5280

TTAGGCATAG GTGTGAATAT CAAGCAGGAC ATAACAAGGT AGGATCTCTA CAGTACTTGG    5340

CACTAACAGC ATTAATAACA CCAAAGAAGA TAAAGCCACC TTTGCCTAGT GTTGCGAAAC    5400

TGACAGAGGA TAGATGGAAC AAGCCCCAGA AGACCAAGGG CCACAGAGGC AGCCATACAA    5460

TGAATGGACA CTAGAACTTT TAGAGGAGCT TAAGAATGAA GCTGTTAGGC ATTTTCCTAG    5520

GGTATGGCTC CATGGCTTAG GGCAACATAT CTATGAAACT TATGGGGATA CTTGGGAAGG    5580

AGTGGAGGCC ATAACAAGAA CTCTGCAACA ACTGCTGTTT ATTCATTTCA GAATTGGGTG    5640

TCAACATAGC AGAATAGGCA TTATTCGACA GAGGAGAGCA AGAAATGGAG CCAGTAGATC    5700

CTAGACTAGA GCCCTGGAAG CATCCAGGAA GTCAGCCTAA GACTGCGTGT ACCACTTGCT    5760

ATTGTAAAAA GTGCTGCTTT CATTGCCAAG TTTGTTTTAT GACAAAAGGC TTAGGCATCT    5820

CCTATGGCAG GAAGAAGCGG AGACAGCGAC GAAGAGCTCC TCAAGACAGT CAGACTCATC    5880

AAGCTTATCT ATCAAAGCAG TAAGTAATAT ATGTAATGCA ACCTTTACAA ATAGTAGCAA    5940

TAGTAGCATT AGTAGTAGCA GGAATAATAG CAATAGTTGT GTGGACCATA GTATTCATAG    6000

AATATAAGAA AATATTAAGA CAAAGAAAAA TAGACAGGTT GATTGATAGA ATAAGAGAAA    6060

GAGCAGAAGA CAGTGGCAAT GACAGTGAAG GGGATCAGGA AGAATTATCG GCACTTGTGG    6120

ACATGGGGCA CCATGATCCT TGGGATATTA ATGATCTGTA GAGCTGCAAA CAATTTGTGG    6180

GTCACAGTCT ATTATGGGGT ACCTGTGTGG AGAGAAGCAA CCACCACTCT ATTTTGTGCA    6240

TCAGATGCCA AGGCATATGA TGCAGAGGTA CATAATGTTT GGGCCACACA TGCCTGTGTA    6300

CCCACAGACC CTAACCCACA AGAAGTAGAA TTGAAAAATG TGACAGAAAA TTTTAACATG    6360

TGGAAAAATA ACATGGTAGA ACAGATGCAT GAGGATATAA TCAGTTTATG GGATCAAAGC    6420

CTGAAGCCAT GTGTAAAATT AACCCCACTC TGTGTTTCTT TAAATTGCAC TGATGCTACT    6480

AATACCACTA ATAGTAATAC CACTAGCAGC AGCGAGAAAC CGAAGGGGAC AGGGGAAATA    6540

AAAAACTGCT CTTTCAATAT CACCACAAGC ATAAGAGATA AGGTGCAGAA ACAATATGCA    6600

CTTTTTTATA GCCTTGATGT AGTACCAATG GATGATAATG ATAATAGTAC AAGCTATAGG    6660
```

```
TTAATAAGTT GTAACACCTC AATCATTACA CAGGCCTGTC CAAAGATATC CTTTGAGCCA    6720

ATTCCCATAC ATTATTGTGC CCCGGCTGGT TTTGCGATTC TAAAGTGTAA AGATAAAAGG    6780

TTCAATGGAA AAGGACCATG TACAAGTGTC AGCACAGTAC AGTGTACACA TGGAATTAGG    6840

CCAGTAGTAT CAACTCAACT GTTGTTAAAT GGCAGTCTAG CAGAAGAAGA GGTAGTAATT    6900

AGATCTGACA ATTTTACGAA CAATGCTAAA ACCATAATAG TACAGCTGAG CAAATCTGTA    6960

GAAATTACTT GTGTAAGACC CAACAACAAT ACAAGAAAAA GTATAAGTAT GGGACCAGGG    7020

AGAGCATTTT ATACAACAGA AATAATAGGA GATATAAGAC AAGCATATTG TAACATTAGT    7080

AAAGCAAACT GGACTGACAC TTTAGAACAG ATAGCTAGAA AATTAAGAGA ACAATTTGAG    7140

AATAAAACAA TAGTCTTTAA GCCATCCTCA GGAGGGGACC CAGAAATTGT AACACAGTTT    7200

TACAGTTTTA ATTGTGGAGG GGAATTTTTC TACTGTAATT CAACACAACT GTTTAATGGT    7260

ACTTGGAATG GTACTTGGGT TAATGGTACT TGGAGTAGTA ATAATACGAC TGATACTGCA    7320

AATATCACAC TCCCATGCAG AATAAAACAA TTTATAAACA TGTGGCAGGA AGTAGGAAAA    7380

GCAATGTATG CCCCTCCCAT CAAAGGACAA ATTAAATGTA CATCAAATAT TACAGGGCTG    7440

ATATTAACAA GAGATGGTGG TAACAATAAC ACCACGAACG ACAACGAGAC CGAGACCTTC    7500

AGACCTGGAG GAGGAGATAT GAGGGACAAT TGGAGAAGTG AATTATATAA ATATAAAGTA    7560

GTACAAGTTG AACCATTAGG AGTAGCACCC ACCAAGGCAA AGAGAAGAGT GGTGCAAAGA    7620

GAAAAAAGAG CAGTGGGAAT AGGAGCTATG TTCCTTGGGT TCTTAGGAGC AGCAGGAAGC    7680

ACTATGGGCG CAGCGTCAGT GACGCTGACG GTACAAGCCA GACAATTATT GTCTGGTATA    7740

GTGCAGCAGC AGAACAATCT GCTGAGGGCT ATTGAGGCGC AACAGCATCT GTTGCAACTC    7800

ACAGTCTGGG GCATCAAACA GCTCCAGGCA AGAGTCCTGG CTGTGGAAAG ATACCTAAGG    7860

GATCAACAGC TCCTGGGACT TTGGGGTTGC TCTGGAAAAC TCATTTGCAC CACTACTGTG    7920

CCTTGGAACA ATAGCTGGAG TAATAAATCT CTGGAAACAA TTTGGGATAA CATGACCTGG    7980

ATGCAGTGGG AAAGAGAAAT TGACAATTAC ACAAACATAA TATACACCTT AATTGAAGAA    8040

TCGCAGAACC AACAAGAAAA AAATGAACTA GAATTATTGG AATTGGATAA ATGGGCAAAT    8100

TTGTGGAATT GGTTTAGTAT ATCAAACTGG CTATGGTATA TAAAATTATT CATAATGGTA    8160

GTAGGAGGCT TGGTAGGTTT AAGAATAGTT TTTACTGTAC TTTCTATAGT TAATAGAGTT    8220

AGGCAGGGAT ACTCACCATT ATCGTTTCAG ACCCACCTCC CAACCCCGAA GGGACCCGAC    8280

AGGCCAGAAG GAATCGAAGA AGAAGGTGGA GAGAGAGACA GAGGCAGCTC CACTCGATTA    8340

GTGCACGGAT TCTTAGCACT TTTCTGGGAC GACCTGAGGA GTCTGTGCCT CTTCAGCTAC    8400

CACCACTTGA GAGACTTACT CTTGATTGTA ACGAGGATTG TGGAACTTCT GGGACGCAGG    8460

GGATGGGAAG CCCTCAAATA CTGGTGGAAT CTCCTGCAGT ATTGGAGGCA GGAACTACAG    8520

AAGAGTGCTG TTAGCTTGTT CAATGGCACG GCCATAGCAG TAGCTGAGGG GACAGATAGA    8580

GTTATAGAAG CTTTACGAAG GGCTTATAGA GCTATTCTCC ACATACCTAG AAGAATAAGA    8640

CAGGGCTTAG AAAGGCTTTT GCTATAAAAT GGGTGGCAAG TGGTCAGAAA GTAGTGTGGT    8700

TAGAAGGCAT GTACCTTTAA GACAAGGCAG CTATAGATCT TAGCCGCTTT TTAAAAGAAA    8760

AGGGGGGACT GGAAGGGCTA ATTCACTCAC GGAAAAGACC AGTTGAACCA GAAGAAGATA    8820

GAAGAGGCCA TGAAGAAGAA AACAACAGAT TGTTCTGCTT GCTCAGCTGG GGACTTTCCA    8880

GAAGGCGCGG CCTGAGTGAC TAAGCCCCGT TGGGGACTTT CCGAAGAGGC ATGAAGGGAC    8940

TTTCCAAGGC AGGCGTGGCC TGGGCGGGAC TGGGGAGTGG CGAGCCCTCA GATGCTGCAT    9000

ATAAGCAGCT GCTTTCTGCC TGTACTGGGT CTCTCTGGTT AGACCAGATC TGAGCCTGGG    9060
```

```
AGCTCTCTGG CTAGCTAGGG AACCCACTGC TTAAGCCTCA ATAAAGCTTG CCTTGAGTGC    9120

TTCAAGTAGT GTGTGCCCGT CTGTTGTGTG ACTCTGGTAT CTAGAGATCC CTCAGACCAT    9180

TTTAGTCCGT GTGGAAAATC TCTAGCA                                        9207
```